(12) United States Patent
Wilson

(10) Patent No.: US 10,293,020 B2
(45) Date of Patent: May 21, 2019

(54) PEPTIDE THERAPEUTICS AND METHODS FOR USING SAME

(71) Applicant: Stealth BioTherapeutics Corp, Monaco (MC)

(72) Inventor: D. Travis Wilson, Newton, MA (US)

(73) Assignee: STEALTH BIOTHERAPEUTICS CORP., Monaco (MC)

( * ) Notice: Subject to any disclaimer, the term of this patent is extended or adjusted under 35 U.S.C. 154(b) by 0 days.

(21) Appl. No.: 14/899,439

(22) PCT Filed: Jun. 24, 2014

(86) PCT No.: PCT/US2014/043944
§ 371 (c)(1),
(2) Date: Dec. 17, 2015

(87) PCT Pub. No.: WO2014/210056
PCT Pub. Date: Dec. 31, 2014

(65) Prior Publication Data
US 2016/0151446 A1    Jun. 2, 2016

Related U.S. Application Data

(60) Provisional application No. 61/840,317, filed on Jun. 27, 2013.

(51) Int. Cl.
*A61K 38/08*    (2006.01)
*A61K 38/07*    (2006.01)
*A61K 38/05*    (2006.01)
*A61K 38/06*    (2006.01)
*A61K 38/10*    (2006.01)
*A61K 38/13*    (2006.01)

(52) U.S. Cl.
CPC ............ *A61K 38/07* (2013.01); *A61K 38/05* (2013.01); *A61K 38/06* (2013.01); *A61K 38/08* (2013.01); *A61K 38/10* (2013.01); *A61K 38/13* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,674,534 A | 10/1997 | Zale et al. |
| 5,716,644 A | 2/1998 | Zale et al. |
| 5,994,372 A | 11/1999 | Yaksh |
| 6,468,798 B1 | 10/2002 | Debs et al. |
| 2007/0027070 A1 | 2/2007 | Szeto et al. |
| 2010/0317571 A1 | 12/2010 | Szeto et al. |
| 2012/0329730 A1 | 12/2012 | Szeto et al. |

FOREIGN PATENT DOCUMENTS

| | | | |
|---|---|---|---|
| CA | 2800741 | 12/2011 | |
| WO | WO-96/40073 | 12/1996 | |
| WO | WO-99/15154 | 4/1999 | |
| WO | WO-2011/106717 | 9/2011 | |
| WO | WO-2011/116007 A1 | 9/2011 | |
| WO | WO 2011150493 A1 * | 12/2011 | ....... A61K 47/48246 |
| WO | WO-2012/006569 | 1/2012 | |
| WO | WO-2013/049697 | 4/2013 | |
| WO | WO-2013/086020 | 6/2013 | |

OTHER PUBLICATIONS

Szeto, "Mitochondria-targeted cytoprotective peptides for ischemia-reperfusion injury," Antioxid. Redox Signal. 10:601-619 (2008).*
Park et al., "Microwave-assisted solid-phase synthesis of pseudopeptides containing reduced amine bond," Tetra. Lett. 48:1053-57 (2007).*
Marbella et al., "Observing the translocation of a mitochondria-penetrating peptide with solid-state NMR," Biochim. Biophys. Acta 1828:1674-1682 (available online Apr. 6, 2013).*
Horton et al., "Mitochondria-Penetrating Peptides," Chem. Biol. 15: 375-382 (2008).*
Horton et al. Supplemental Data Chem. Biol. 15: 1-5 (2008).*
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss: AREDS Report No. 8," Arch. Ophthalmol. (Oct. 2001), vol. 119, No. 10, pp. 1417-1436.
Agmon, Yoram et al., "Nitric Oxide and Prostanoids Protect the Renal Outer Medulla from Radiocontrast Toxicity in the Rat," J. Clin. Invest., (Sep. 1994), vol. 94, Issue 3, pp. 1069-1075.
Allikmets, Rando et al., "Mutation of the Stargardt Disease Gene (ABCR) in Age-Related Macular Degeneration," Science, (Sep. 19, 1997), vol. 277, pp. 1805-1807.
Allikmets, Rando, "Simple and Complex ABCR: Genetic Predisposition to Retinal Disease," Am. J Hum. Genet., (2000), vol. 67, pp. 793-799.
Amselem, S., "Liposome Technology," (1993), vol. 1, 2nd Ed. CRC Press, (26 pages).
Anderson, Ethan J. et al., "Mitochondrial H2O2 emission and cellular redox state link excess fat intake to insulin resistance in both rodents and humans," J. Clin. Invest., (Mar. 2009), vol. 119, No. 3, pp. 573-581.
Anderson, Ethan J. et al., "Type II skeletal myofibers possess unique properties that potentiate mitochondrial H2O2 generation," Am J Physiol Cell Physiol, (Mar. 2006), vol. 290, pp. C844-C851.
Beauchamp, Martin H. et al., "Role of thromboxane in retinal microvascular degeneration in oxygen-induced retinopathy," J. Appl. Physiol., (2001), vol. 90, pp. 2279-2288.

(Continued)

*Primary Examiner* — Julie Ha
*Assistant Examiner* — Kristina M Hellman
(74) *Attorney, Agent, or Firm* — Foley & Lardner LLP

(57) ABSTRACT

Disclosed herein are methods and compositions for the treatment and/or prevention of diseases or conditions comprising administration of an MPP, and/or naturally or artificially occurring variants or analogs of an MPP, or pharmaceutically acceptable salts thereof, alone or in combination with one or more active agents (e.g., an aromatic-cationic peptide such as D-Arg-2'6'-Dmt-Lys-Phe-NH$_2$).

5 Claims, No Drawings

(56) References Cited

OTHER PUBLICATIONS

Chonn, Arcadio et al., "Recent Advances in Liposomal Drug-Delivery Systems," Current Opinion in Biotechnology, (1995), vol. 6, pp. 698-708.
Duan, S.-B. et al., "Nephrotoxicity of high- and low-osmolar contrast media: The protective role of amlodipine in a rat model," Acta Radiol, (Sep. 2000), 41, pp. 503-507.
Fadok et al., "Exposure of Phosphatidylserine on the Surface of Apoptotic Lymphocytes Triggers Specific Recognition and Removal by Macrophages," Journal of Immunology, (1992), vol. 148, pp. 2207-2216.
Gregoriadis, G., "Engineering Liposomes for Drug Delivery: Progress and Problems," Trends in Biotechnology, (Dec. 1995), vol. 13, No. 12, pp. 527-537.
Heckenlively, John R. et al., "Clinical Findings and Common Symptoms in Retinitis Pigmentosa," Am. J. Ophthalmol., (May 1988), vol. 105, pp. 504-511.
Homburg, Christa H.E. et al., "Human neutrophils lose their surface FcyRiii and acquire Annexin V binding sites during apoptosis in vitro," Blood, (Jan. 1995), vol. 85, No. 2, pp. 532-540.
Ignarro, Louis J. et al., "Endothelium-derived relaxing factor produced and released from artery vein is nitric oxide," Proc. Natl. Acad. Sci. USA, (Dec. 1987), vol. 84, pp. 9265-9269.
International Search Report and written Opinion of the International Searching Authority for Application No. PCT/US2014/043944 dated Nov. 4, 2014, 11 pages.
Karan, G. et al., "Lipofuscin accumulation, abnormal electrophysiology, and photoreceptor degeneration in mutant ELOVL4 transgenic mice: A model for macular degeneration," Pro. Natl. Acad. Sci., (Mar. 15, 2005), vol. 102, No. 11, pp. 4164-4169.
Klevering, B. Jeroen et al. "Three Families Displaying the Combination of Stargardt's Disease with Cone-Rod Dystrophy or Retinitis Pigmentosa," Ophthalmology, (Mar. 2004), vol. 111, No. 3, pp. 546-553.
Koopman, G. et al., "Annexin V for Flow Cytometric Detection of Phosphatidylserine Expression on B Cells Undergoing Apoptosis," Blood, (Sep. 1994), vol. 84, No. 5, pp. 1415-1420.
Korshunov, Sergey S. et al., "High protonic potential actuates a mechanism of production of reactive oxygen species in mitochondria," FEBS Letters, (Oct. 1997), vol. 416, Issue 1, pp. 15-18.
Kozarich, John W. et al., "Next generation therapeutics: Looking to the horizon: Editorial overview," Current Opinion in Chemical Biology, (1998), vol. 2, Issue 4, pp. 439-440.
Kruse, Shane E. et al., "Mice with Mitochondrial Complex I Deficiency Develop a Fatal Encephalomyopathy," Cell Metabolism, (Apr. 2008), vol. 7, pp. 312-320.
Lewis, Richard Alan et al., "Genotype/Phenotype Analysis of a Photoreceptor-Specific ATP-Binding Cassette Transporter Gene, ABCR, in Stargardt Disease," Am. J. Hum. Genet., (1999); vol. 64, pp. 422-434.
Li, Bin et al., "Culture and Characterization of Human Retinal Capillary Endothelial Cell," Chin Ophthal Res, (2005), vol. 23, No. 1, pp. 20-22.
Li, Yunbo et al., "Detection of mitochondria-derived reactive oxygen species production by the chemilumigenic probes lucigenin and luminol," Biochim. Bioiphys. Acta., (Jun. 28, 1999), vol. 1428, Issue 1, pp. 1-12.
Lichtenberg, Dov et al., "Liposomes: Preparation, Characterization, and Preservation," Methods Biochem. Anal., (1998), vol. 33, pp. 337-462.
Lim, Kelvin H.H. et al., "The effects of ischaemic preconditioning, diazoxide and 5-hydroxydecanoate on rat heart mitochondrial volume and respiration," J Physiol, (2002), vol. 545, Issue 3, pp. 961-974.
Liu, Yuanbin et al., "Generation of reactive oxygen species by the mitochondrial electron transport chain," J. Neurochem., (2002), vol. 80, Issue 5, pp. 780-787.
Longoni, Biancamaria et al., "Inhibition of Lipid Peroxidation by N-Acetylserotonin and Its Role in Retinal Physiology," Biochem. Biophys. Res. Commun., (Apr. 28, 1997), vol. 233, Issue 3, pp. 778-780.
McCombs, Peter R. et al., "Acute renal failure following resection of abdominal aortic aneurysm," Surg. Gynecol. Obstet., (1979), vol. 148, pp. 175-178.
McCullough, Peter A., "Contrast-Induced Acute Kidney Injury," J. Am. Coll. Cardio., (2008), vol. 51, No. 15, pp. 1419-1428.
McGwin Jr., Gerald et al., "The association between statin use and age related maculopathy," Br J Ophthalmol, (2003), 87, pp. 1121-1125.
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Nijtmans, Leo G.J. et al., "Blue Native electrophoresis to study mitochondrial and other protein complexes," Methods, (Apr. 2002), vol. 26, Issue 4, pp. 327-334.
Ozturk, Feral et al., "Carbon tetrachloride-induced nephrotoxicity and protective effect of betaine in Sprague-Dawley rats," Urology, (Aug. 2003), vol. 62, Issue 2, pp. 353-356.
Palmer, R.M.J. et al., "Nitric oxide release accounts for the biological activity of endothelium-derived relaxing factor," Letters to Nature, (Jun. 1987), vol. 327, pp. 524-526.
Parvez, Zaheer et al., "Contrast Media-Induced Lipid Peroxidation in the Rat Kidney," Invest. Radiol., (Sep. 1989), vol. 24, No. 9, pp. 697-702.
Petri, Susanne et al., "Cell-permeable peptide antioxidants as a novel therapeutic approach in a mouse model of amyotrophic lateral sclerosis", Journal of Neurochemistry, (2006), vol. 98, pp. 1141-1148.
Premanand, Chinnaraj et al., "Effect of Curcumin on Proliferation of Human Retinal Endothelial Cells under In Vitro Conditions," Invest. Ophthalmol. Vis. Sci., (May 2006), vol. 47, No. 5, pp. 2179-2184.
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Saks, et al., "Permeabilized cell and skinned fiber techniques in studies of mitochondrial function in vivo," Mol Cell Biochem., (Jul. 1998), vol. 184(1-2), pp. 81-100.
Schafer, Freya Q. et al., "Redox environment of the cell as viewed through the redox state of the glutathione disulfide/glutathione couple", Free Radical Biology and Medicine, (2001), vol. 30, Issue 11, pp. 1191-1212.
Shaban, Hamdy et al, "Phosphatidylglycerol Potently Protects Human Retinal Pigment Epithelial Cells Against Apoptosis Induced by A2E, a Compound Suspected to Cause Age-related Macular Degeneration," Experimental Eye Research, (Jul. 2002), vol. 75, Issue 1, pp. 99-108.
Shaban, Hamdy et al., "A2E and Blue Light in the Retina: The Paradigm of Age-Related Macular Degeneration," Biol. Chem., (Mar./Apr. 2002), vol. 383, pp. 537-545.
Sparrow, Janet R. et al., "A2E-epoxides Damage DNA in Retinal Pigment Epithelial Cells: Vitamin E and Other Antioxidants Inhibit A2E-Epoxide Formation," J. Biol. Chem., (May 2003), vol. 278, No. 20, pp. 18207-18213.
Srinivasan, K. et al., "Combination of high-fat diet-fed and low-dose streptozotocin-treated rat: A model for type 2 diabetes and pharmacological screening," Pharmacological Research, (2005), vol. 52, pp. 313-320.
Stone, Edwin M. et al., "Allelic variation in ABCR associated with Stargardt disease but not age-related macular degeneration," Nature Genetics, (Dec. 1998), vol. 20, pp. 328-329.
St-Pierre, Julie et al., "Topology of Superoxide Production from Different Sites in the Mitochondrial Electron Transport Chain," J. Biol. Chem., (Nov. 2002), vol. 277, No. 47, pp. 44784-44790.
Szeto, Hazel H. "Mitochondria-targeted peptide antioxidants: Novel Neuroprotective Agents," The AAPS Journal, (2006), 8(3), Article 62, pp. E521-E531.
Szeto, Hazel H., "Development of Mitochondria-targeted Aromatic-cationic Peptides for Neurodegenerative Diseases," Mitochondira and Oxidative Stress in Neurodegenerative Disorders: Ann. N.Y. Acad. Sci., 2008, vol. 1147, pp. 112-121.

(56) References Cited

OTHER PUBLICATIONS

Thomas, Merlin C. et al., "Interactions between Renin Angiotension System and Advanced Glycation in the Kidney," J Am Soc Nephrol, (2005), vol. 16, pp. 2976-2984.

Tonkonogi, et al., "Reduced oxidative power but unchanged antioxidative capacity in skeletal muscle from aged humans," Pflügers Arch, (2003), vol. 446, pp. 261-269.

Tsutsui, Hiroyuki et al., "Mitochondrial Oxidative Stress, DNA Damage, and Heart Failure," Antioxidants & Redox Signaling, (Sep. 2006), vol. 8, No. 9-10, pp. 1737-1744.

Turrens, Julio F. et al., "Generation of superoxide anion by the NADH dehydrogenase of bovine heart mitochondria," Biochem J., (Oct. 15, 1980), vol. 191, Part 2, pp. 421-427.

Vermes, Istvan et al., "A novel assay for apoptosis Flow cytometric detection of phosphatidylserine expression on early apoptotic cells unsing fluorescein labelled Annexin V," J. Immunol. Meth., (Jul. 17, 1995), vol. 184, Issue 1, pp. 39-51.

Walsh, et al., "The role of phosphorylcreatine and creatine in the regulation of mitochondrial respiration in human skeletal muscle," Journal of Physiology, (2001), vol. 537, No. 3, pp. 971-978.

Weiner, Alan L., "Liposomes for Protein Delivery: Selecting Manufacture and Development Processes," Immunomethods, (1994), 4(3), pp. 201-209.

Whittaker, Mark et al., "Design and Therapeutic Application of Matrix Metalloproteinase Inhibitors," Chemical Reviews, (1999), vol. 99(9), pp. 2735-2776.

Zhao, Kesheng et. al., "Cell-permeable Peptide Antioxidants Targeted to Inner Mitochondrial Membrane inhibit Mitochondrial Swelling, Oxidative Cell Death, and Reperfusion Injury," J Biol Chem., (Aug. 2004), vol. 279, No. 33, pp. 34682-34690.

\* cited by examiner

PEPTIDE THERAPEUTICS AND METHODS FOR USING SAME

CROSS-REFERENCE TO RELATED APPLICATIONS

This Application is the U.S. 371 National Stage Application of International Application No.: PCT/US2014/043944, filed Jun. 24, 2014, which claims the benefit of and priority to U.S. Application No. 61/840,317, filed Jun. 27, 2013, the entire contents of which are incorporated herein by reference in their entireties.

TECHNICAL FIELD

Disclosed herein are methods and compositions related to the treatment and/or amelioration of diseases and conditions utilizing mitochondria penetrating peptides (MPP), such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$).

BACKGROUND

Mitochondria are an interesting target for drug delivery due to their role in energy production, reactive oxygen species production, and apoptosis. Drug delivery to the mitochondria is difficult due to the intricacies involved in crossing three diverse membranes: the plasma membrane, and the outer and inner mitochondrial membranes (OMM and IMM, respectively). Overcoming these challenges, a new class of synthetically designed peptides was recently discovered to penetrate the plasma membrane and target the mitochondria with high specificity, coined mitochondria-penetrating peptides (MPPs). By targeting the mitochondria directly, MPPs become a valuable vehicle for drug delivery. For instance, methotrexate is a powerful antibacterial agent, but accumulation in the cytosol of human cells renders it highly toxic and limits its therapeutic capabilities. By conjugating methotrexate to MPPs, the drug specifically targeted the mitochondria, decreasing the toxicity three orders of magnitude, while maintaining antibacterial activity. Recent studies have shown that membrane composition, specifically headgroup functionality, and transmembrane potential play important roles in membrane-peptide activity by controlling peptide binding and subsequent bilayer disruption or alteration.

SUMMARY

In one aspect, the present disclosure provides a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$. In some embodiments, the composition further comprises one or more additional active agents such as cyclosporine, a cardiac drug, an anti-inflammatory, an anti-hypertensive drug, an antibody, an ophthalmic drug, an antioxidant, a metal complexer, and an antihistamine.

In some embodiments, the composition comprises an MPP analog comprising a modification selected from inclusion of one or more D-amino acids, inclusion of one or more sites of N-methylation, and inclusion of one or more reduced amide bonds (P[CH$_2$—NH]).

In some embodiments, the composition further comprises one or more of at least one pharmaceutically acceptable pH-lowering agent; and at least one absorption enhancer effective to promote bioavailability of the active agent, and one or more lamination layers. In some embodiments, the pH-lowering agent is selected from the group consisting of citric acid, tartaric acid and, an acid salt of an amino acid.

In another aspect, the present disclosure provides a method for treating or preventing mitochondrial dysfunction in a subject, comprising administering to the subject a therapeutically effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method of treating a disease or condition characterized by mitochondrial dysfunction, comprising administering a therapeutically effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In some embodiments, the disease or condition comprises a neurological or neurodegenerative disease or condition, ischemia, reperfusion, hypoxia, atherosclerosis, ureteral obstruction, diabetes, complications of diabetes, arthritis, liver damage, insulin resistance, diabetic nephropathy, acute renal injury, chronic renal injury, acute or chronic renal injury due to exposure to nephrotoxic agents and/or radiocontrast dyes, hypertension, metabolic syndrome, an ophthalmic disease or condition such as dry eye, diabetic retinopathy, cataracts, retinitis pigmentosa, glaucoma, macular degeneration, choroidal neovascularization, retinal degeneration, oxygen-induced retinopathy, cardiomyopathy, ischemic heart disease, heart failure, hypertensive cardiomyopathy, vessel occlusion, vessel occlusion injury, myocardial infarction, coronary artery disease, oxidative damage.

In some embodiments, the mitochondrial dysfunction comprises mitochondrial permeability transition.

In some embodiments, the neurological or neurodegenerative disease or condition comprises Alzheimer's disease, Amyotrophic Lateral Sclerosis (ALS), Parkinson's disease, Huntington's disease or Multiple Sclerosis.

In some embodiments, the subject is suffering from ischemia or has an anatomic zone of no-reflow in one or more of cardiovascular tissue, skeletal muscle tissue, cerebral tissue and renal tissue.

In another aspect, the present disclosure provides a method for reducing CD36 expression in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for treating or preventing a disease or condition characterized by CD36 elevation in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In some embodiments, the subject is diagnosed as having, suspected of having, or at risk of having atherosclerosis, inflammation, abnormal angiogenesis, abnormal lipid metabolism, abnormal removal of apoptotic cells, ischemia such as cerebral ischemia and myocardial ischemia, ischemia-reperfusion, ureteral obstruction, stroke, Alzheimer's Disease, diabetes, diabetic nephropathy, or obesity.

In another aspect, the present disclosure provides a method for reducing oxidative damage in a removed organ or tissue, comprising administering to the removed organ or tissue an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In some embodiments, the removed organ comprises a heart, lung, pancreas, kidney, liver, or skin.

In another aspect, the present disclosure provides a method for preventing the loss of dopamine-producing neurons in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In some embodiments, the subject is diagnosed as having, suspected of having, or at risk of having Parkinson's disease or ALS.

In another aspect, the present disclosure provides a method of reducing oxidative damage associated with a neurodegenerative disease in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In some embodiments, the neurodegenerative disease comprises Alzheimer's disease, Parkinson's disease, or ALS.

In another aspect, the present disclosure provides a method for preventing or treating a burn injury in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for treating or preventing mechanical ventilation-induced diaphragm dysfunction in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for treating or preventing no reflow following ischemia-reperfusion injury in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for preventing norepinephrine uptake in a mammal in need of analgesia, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for treating or preventing drug-induced peripheral neuropathy or hyperalgesia in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for inhibiting or suppressing pain in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

In another aspect, the present disclosure provides a method for treating atherosclerotic renal vascular disease (ARVD) in a subject in need thereof, comprising administering to the subject an effective amount of a composition comprising an MPP alone or in combination with one or more active agents. In some embodiments, the active agents include any one or more of the aromatic-cationic peptides shown in Section II and/or Table 1. In some embodiments, the aromatic-cationic peptide is D-Arg-2'6'-Dmt-Lys-Phe-NH$_2$.

DETAILED DESCRIPTION

I. Mitochondria Penetrating Peptides

The present disclosure provides mitochondria penetrating peptides (MPPs) and methods for using the same.

As used herein, the term "mitochondria penetrating peptides" or "MPPs" refer to small, water soluble peptides with many cationic and hydrophobic residues.

In one embodiment, the MPP is defined by formula I:

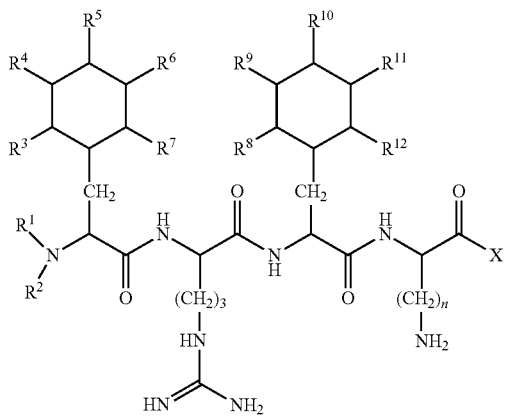

wherein $R^1$ and $R^2$ are each independently selected from
(i) hydrogen; or
(ii) linear or branched $C_1$-$C_6$ alkyl, optionally substituted with an amino, carboxyl, carboxamide, or hydroxyl group;
(iii) HC(O)—;
(iv) $R^{13}$C(O)—; or
(v) $R^{13}$OC(O)—;
$R^3$, $R^4$, $R^5$, $R^6$, $R^7$, $R^8$, $R^9$, $R^{10}$, $R^{11}$, and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_6$ alkylamino;
(vi) $C_1$-$C_6$ dialkylamino;
(vii) nitro;
(viii) hydroxyl; or
(ix) halogen, where "halogen" encompasses chloro, fluoro, bromo, and iodo;
$R^{13}$ is $C_1$-$C_6$ alkyl, benzyl or fluorenylmethyl;
X is $NHR^{14}$ or $OR^{14}$ wherein $R^{14}$ is H or $C_1$-$C_6$ alkyl; and n is an integer from 1 to 5.

In some embodiments, $R^1$ and $R^2$ are independently selected from hydrogen, linear or branched $C_1$-$C_6$ alkyl, or

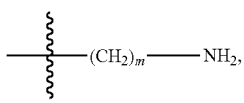

where m=2-4

In a particular embodiment, $R^1$ and $R^2$ are hydrogen; $R^3$, $R^4$, $R^5$, $R^6$, $R^7$, $R^8$, $R^9$, $R^{10}$, $R^{11}$, and $R^{12}$ are all hydrogen; and n is 4.

In certain embodiments, X is amino (i.e., $NH_2$). In some such embodiments, $R^1$ and $R^2$ are hydrogen; $R^3$, $R^4$, $R^5$, $R^6$, $R^7$, $R^8$, $R^9$, $R^{10}$, $R^{11}$, and $R^{12}$ are all hydrogen; and n is 4.

In certain embodiments, X is hydroxyl. In some such embodiments, $R^1$ and $R^2$ are hydrogen; $R^3$, $R^4$, $R^5$, $R^6$, $R^7$, $R^8$, $R^9$, $R^{10}$, $R^{11}$, and $R^{12}$ are all hydrogen; and n is 4.

In a some embodiments, the Arg residue of formula I is D-Arg. In other embodiments, the Arg residue is L-Arg.

In general, penetrating peptides are small, water soluble peptides with many cationic and hydrophobic residues. These peptides are able to cross membranes in a highly efficient, non-lytic fashion to deliver cargo to the interior of cells, but the mechanism of translocation remains unknown. Several proposed models exist to describe the apparent energyindependent mode of membrane penetration, including the inverse micelle model, the electroporation model, and the guanidinum-phosphate complexation model, all of which show distinct spectroscopic signatures. By utilizing static $^{31}$P and paramagnetic relaxation enhancement (PRE) ssNMR techniques, it is possible to gain information on lamellar integrity, bilayer sidedness, and peptide insertion depth, in order to differentiate between each model. The peptide-lipid interaction is believed to be a vital step in the translocation. The favorable interaction between cationic peptides and negatively charged phospholipid headgroups is thought to be the first step in translocation, and is shared by penetrating peptides, antimicrobial peptides, and voltage gated channel-forming peptides. In the inverse micelle model, the peptide remains bound at the membrane-water interface throughout translocation and the formation of inverse micelles permits passage to the membrane interior. The presence of an inverse micelle phase produces an isotropic peak in $^{31}$P powder pattern which is consistent with a disruption of the native lamellar character and the rapid tumbling of micelles.

In the electroporation and guanidinium-phosphate complexation models, the cationic peptide charge and anionic lipid charge are believed to play a role in both initial peptide-lipid interaction, as well as the translocation mechanism. In the electroporation model, the negatively charged phospholipid headgroup on the outer leaflet of the bilayer binds the cationic penetrating peptide, until the remaining anionic surface change reaches a critical value. When the peptide concentration exceeds this threshold, the asymmetrically bound peptides on the outer leaflet create an electric field between the differently charged outer and inner monolayers. The transbilayer electric field destabilizes the membrane and the peptide crosses the hydrophobic core in an electroporation-like fashion to bind to the inner leaflet of the bilayer. Therefore, if the peptide is internalized via the electroporation model, it is expected that binding will be limited to the outer leaflet at low peptide concentrations, with binding to both the inner and outer leaflets at high peptide concentrations.

The guanidinium-phosphate complexation model proposes that the cationic arginine residues on the peptide bind electrostatically to the anionic phosphate groups present on the lipid headgroups. By neutralizing the highly cationic charge, the peptides are able to cross the bilayer without a high free-energy penalty. Since this mechanism does not require charge accumulation to destabilize the membrane, it is expected that at both high and low concentrations, the peptide will bind to both the inner and outer leaflet of the bilayer. To determine the mode of MPP translocation, $^{13}$C magic angle spinning (MAS) PRE NMR is used to create a system that can distinguish bilayer sidedness and probe peptide insertion depth, which in turn, will differentiate between the electroporation and guanidinium-phosphate complexation models. To assess bilayer lamellarity during peptide insertion, variable temperature static $^{31}$P NMR measurements are used. Both static $^{31}$P and $^{2}$H NMR measurements are sensitive to alterations in membrane integrity. In the $^{13}$C PRE method, paramagnetic ions bind to membranes and cause line broadening and subsequent signal reduction in the NMR spectra by enhancing the T2 relaxation rate. The PRE effect is distance dependent and can distinguish each leaflet of the bilayer so the signal attenuation serves as a spectroscopic ruler for molecular location in the membrane. The NMR relaxation enhancement due to the addition of paramagnetic ions and tags has been exploited to provide long distance measurements for protein structure determination, rapid acquisition of membrane-bound protein spectra, probe protein-biomolecule and small molecule interactions, distinguish between inner and outer leaflets of lipid bilayers, manipulate bicelle orientation, and measure immersion depth in membrane systems.

II. Aromatic-Cationic Peptides

The aromatic-cationic peptides of the present technology are water-soluble, highly polar, and can readily penetrate cell membranes.

The aromatic-cationic peptides of the present technology include a minimum of three amino acids, covalently joined by peptide bonds.

The maximum number of amino acids present in the aromatic-cationic peptides of the present invention is about twenty amino acids covalently joined by peptide bonds. In some embodiments, the maximum number of amino acids is about twelve. In some embodiments, the maximum number of amino acids is about nine. In some embodiments, the maximum number of amino acids is about six. In some embodiments, the maximum number of amino acids is four.

The amino acids of the aromatic-cationic peptides of the present technology can be any amino acid. As used herein, the term "amino acid" is used to refer to any organic molecule that contains at least one amino group and at least one carboxyl group. In some embodiments, at least one amino group is at the α position relative to the carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present invention can contain one or more non-naturally occurring amino acids. The non-naturally occurring amino acids may be L-, dextrorotatory (D), or mixtures thereof. In some embodiments, the peptide has no amino acids that are naturally occurring.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenyl acetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the present methods is the derivatization of a carboxyl group of an aspartic acid or a glutamic acid residue of the peptide. One example of derivatization is amidation with ammonia or with a primary or secondary amine, e.g., methylamine, ethylamine, dimethylamine or dethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are in some embodiments resistant, and in some embodiments insensitive, to common proteases. Examples of non-naturally occurring amino acids that are resistant or insensitive to proteases include the dextrorotatory (D-) form of any of the above-mentioned naturally occurring L-amino acids, as well as L- and/or D non-naturally occurring amino acids. The D-amino acids do not normally occur in proteins, although they are found in certain peptide antibiotics that are synthesized by means other than the normal ribosomal protein synthetic machinery of the cell, as used herein, the D-amino acids are considered to be non-naturally occurring amino acids.

In order to minimize protease sensitivity, the peptides useful in the methods of the invention should have less than five, less than four, less than three, or less than two contiguous L-amino acids recognized by common proteases, irrespective of whether the amino acids are naturally or non-naturally occurring. In some embodiments, the peptide has only D-amino acids, and no L-amino acids.

If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that the aromatic-cationic peptides have a minimum number of net positive charges at physiological pH in comparison to the total number of amino acid residues in the peptide. The minimum number of net positive charges at physiological pH is referred to below as $(p_m)$. The total number of amino acid residues in the peptide is referred to below as $(r)$.

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-Arg has one negatively charged amino acid (i.e., Glu) and four positively charged amino acids (i.e., two Arg residues, one Lys, and one His). Therefore, the above peptide has a net positive charge of three.

In one embodiment of the present invention, the aromatic-cationic peptides have a relationship between the minimum number of net positive charges at physiological pH $(p_m)$ and the total number of amino acid residues (r) wherein 3 $p_m$ is the largest number that is less than or equal to r+1. In this embodiment, the relationship between the minimum number of net positive charges $(p_m)$ and the total number of amino acid residues (r) is as follows:

| (r)     | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|----|----|----|----|----|----|----|----|----|----|----|
| $(p_m)$ | 1 | 1 | 2 | 2 | 2 | 3 | 3 | 3  | 4  | 4  | 4  | 5  | 5  | 5  | 6  | 6  | 6  | 7  |

In another embodiment, the aromatic-cationic peptides have a relationship between the minimum number of net positive charges $(p_m)$ and the total number of amino acid residues (r) wherein 2 $p_m$ is the largest number that is less than or equal to r+1. In this embodiment, the relationship between the minimum number of net positive charges $(p_m)$ and the total number of amino acid residues (r) is as follows:

| (r)     | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|----|----|----|----|----|----|----|----|----|----|----|
| $(p_m)$ | 2 | 2 | 3 | 3 | 4 | 4 | 5 | 5  | 6  | 6  | 7  | 7  | 8  | 8  | 9  | 9  | 10 | 10 |

In one embodiment, the minimum number of net positive charges $(p_m)$ and the total number of amino acid residues (r) are equal. In another embodiment, the peptides have three or four amino acid residues and a minimum of one net positive charge, a minimum of two net positive charges, or a minimum of three net positive charges.

It is also important that the aromatic-cationic peptides have a minimum number of aromatic groups in comparison to the total number of net positive charges $(p_t)$. The minimum number of aromatic groups is referred to below as (a).

Naturally occurring amino acids that have an aromatic group include the amino acids histidine, tryptophan, tyrosine, and phenylalanine. For example, the hexapeptide Lys-Gln-Tyr-Arg-Phe-Trp has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present technology have a relationship between the minimum number of aromatic groups (a) and the total number of net positive charges at physiological pH $(p_t)$ wherein 3a is the largest number that is less than or equal to $p_t$+1, except that when $p_t$ is 1, a may also be 1. In this embodiment, the relationship between the minimum number of aromatic groups (a) and the total number of net positive charges $(p_t)$ is as follows:

| $(p_t)$ | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment the aromatic-cationic peptides have a relationship between the minimum number of aromatic groups (a) and the total number of net positive charges $(p_t)$ wherein 2a is the largest number that is less than or equal to $p_t+1$. In this embodiment, the relationship between the minimum number of aromatic amino acid residues (a) and the total number of net positive charges $(p_t)$ is as follows:

| $(p_t)$ | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges $(p_t)$ are equal.

Carboxyl groups, especially the terminal carboxyl group of a C-terminal amino acid, are preferably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-dethyl amido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described herein.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

TABLE 1

2'6'-Dmp-D-Arg-2'6'-Dmt-Lys-NH₂

2'6'-Dmp-D-Arg-Phe-Lys-NH₂

2'6'-Dmt-D-Arg-Phe Orn-NH₂

2'6'-Dmt-D-Arg-Phe-Ahp(2-aminoheptanoic acid)-NH₂

2'6'-Dmt-D-Arg-Phe-Lys-NH₂

2'6'-Dmt-D-Cit-Phe Lys-NH₂

Ala-D-Phe-D-Arg-Tyr-Lys-D-Trp-His-D-Tyr-Gly-Phe

Arg-D-Leu-D-Tyr-Phe-Lys-Glu-D-Lys-Arg-D-Trp-Lys-D-Phe-Tyr-D-Arg-Gly

TABLE 1-continued

Asp-Arg-D-Phe-Cys-Phe-D-Arg-D-Lys-Tyr-Arg-D-Tyr-Trp-D-His-Tyr-D-Phe-Lys-Phe

TABLE 1-continued

Asp-D-Trp-Lys-Tyr-D-His-Phe-Arg-D-Gly-Lys-NH₂

D-Arg-2'6'-Dmt-Lys-Phe-NH₂

D-Glu-Asp-Lys-D-Arg-D-His-Phe-Phe-D-Val-Tyr-Arg-Tyr-D-Tyr-Arg-His-Phe-NH₂

D-His-Glu-Lys-Tyr-D-Phe-Arg

D-His-Lys-Tyr-D-Phe-Glu-D-Asp-D-Asp-D-His-D-Lys-Arg-Trp-NH₂

D-Tyr-Trp-Lys-NH₂

Glu-Arg-D-Lys-Tyr-D-Val-Phe-D-His-Trp-Arg-D-Gly-Tyr-Arg-D-Met-NH₂

Gly-Ala-Lys-Phe-D-Lys-Glu-Arg-Tyr-His-D-Arg-D-Arg-Asp-Tyr-Trp-D-His-Trp-His-D-Lys-Asp

Gly-D-Phe-Lys-His-D-Arg-Tyr-NH₂

His-Tyr-D-Arg-Trp-Lys-Phe-D-Asp-Ala-Arg-Cys-D-Tyr-His-Phe-D-Lys-Tyr-His-Ser-NH₂

Lys-D-Arg-Tyr-NH₂

Lys-D-Gln-Tyr-Arg-D-Phe-Trp-NH₂

Lys-Trp-D-Tyr-Arg-Asn-Phe-Tyr-D-His-NH₂

Met-Tyr-D-Arg-Phe-Arg-NH₂

Met-Tyr-D-Lys-Phe-Arg

Phe-Arg-D-His-Asp

Phe-D-Arg-2'6'-Dmt-Lys-NH₂

Phe-D-Arg-His

Phe-D-Arg-Lys-Trp-Tyr-D-Arg-His

Phe-D-Arg-Phe-Lys-NH₂

Phe-Phe-D-Tyr-Arg-Glu-Asp-D-Lys-Arg-D-Arg-His-Phe-NH₂

Phe-Tyr-Lys-D-Arg-Trp-His-D-Lys-D-Lys-Glu-Arg-D-Tyr-Thr

Thr-Gly-Tyr-Arg-D-His-Phe-Trp-D-His-Lys

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂

TABLE 1-continued

Trp-D-Lys-Tyr-Arg-NH₂

Trp-Lys-Phe-D-Asp-Arg-Tyr-D-His-Lys

Tyr-Asp-D-Lys-Tyr-Phe-D-Lys-D-Arg-Phe-Pro-D-Tyr-His-Lys

Tyr-D-Arg-Phe-Lys-Glu-NH₂

Tyr-D-Arg-Phe-Lys-NH₂

Tyr-D-His-Phe-D-Arg-Asp-Lys-D-Arg-His-Trp-D-His-Phe

Tyr-His-D-Gly-Met

Val-D-Lys-His-Tyr-D-Phe-Ser-Tyr-Arg-NH₂

D-Arg-Dmt-Lys-Trp-NH₂

D-Arg-Trp-Lys-Trp-NH₂

D-Arg-Dmt-Lys-Phe-Met-NH₂

H-D-Arg-Dmt-Lys(NαMe)-Phe-NH₂

H-D-Arg-Dmt-Lys-Phe(NMe)-NH₂

H-D-Arg-Dmt-Lys(NαMe)-Phe(NMe)-NH₂

H-D-Arg(NαMe)-Dmt(NMe)-Lys(NαMe)-Phe(NMe)-NH₂

D-Arg-Dmt-Lys-Phe-Lys-Trp-NH₂

D-Arg-Dmt-Lys-Dmt-Lys-Trp-NH₂

D-Arg-Dmt-Lys-Phe-Lys-Met-NH₂

D-Arg-Dmt-Lys-Dmt-Lys-Met-NH₂

H-D-Arg-Dmt-Lys-Phe-Sar-Gly-Cys-NH₂

H-D-Arg-Ψ[CH2-NH]Dmt-Lys-Phe-NH₂

H-D-Arg-Dmt-Ψ[CH2-NH]Lys-Phe-NH₂

H-D-Arg-Dmt-LysΨ[CH2-NH]Phe-NH₂

H-D-Arg-Dmt-Ψ[CH2-NH]Lys-Ψ[CH2-NH]Phe-NH₂

D-Arg-Tyr-Lys-Phe-NH₂

D-Arg-Dmt-D-Lys-Phe-NH₂

D-Arg-Dmt-Lys-D-Phe-NH₂

Phe-D-Arg-D-Phe-Lys-NH₂

Phe-D-Arg-Phe-D-Lys-NH₂

D-Phe-D-Arg-D-Phe-D-Lys-NH₂

Lys-D-Phe-Arg-Dmt-NH₂

D-Arg-Arg-Dmt-Phe-NH₂

Dmt-D-Phe-Arg-Lys-NH₂

Phe-D-Dmt-Arg-Lys-NH₂

D-Arg-Dmt-Lys-NH₂

Arg-D-Dmt-Lys-NH₂

D-Arg-Dmt-Phe-NH₂

Arg-D-Dmt-Arg-NH₂

Dmt-D-Arg-NH₂

D-Arg-Dmt-NH₂

D-Dmt-Arg-NH₂

Arg-D-Dmt-NH₂

D-Arg-D-Dmt-NH₂

D-Arg-D-Tyr-Lys-Phe-NH₂

D-Arg-Tyr-D-Lys-Phe-NH₂

D-Arg-Tyr-Lys-D-Phe-NH₂

D-Arg-D-Tyr-D-Lys-D-Phe-NH₂

Lys-D-Phe-Arg-Tyr-NH₂

D-Arg-Arg-Tyr-Phe-NH₂

Tyr-D-Phe-Arg-Lys-NH₂

Phe-D-Tyr-Arg-Lys-NH₂

D-Arg-Tyr-Lys-NH₂

Arg-D-Tyr-Lys-NH₂

D-Arg-Tyr-Phe-NH₂

Arg-D-Tyr-Arg-NH₂

Tyr-D-Arg-NH₂

D-Arg-Tyr-NH₂

D-Tyr-Arg-NH₂

Arg-D-Tyr-NH₂

D-Arg-D-Tyr-NH₂

Dmt-Lys-Phe-NH₂

Lys-Dmt-D-Arg-NH₂

Phe-Lys-Dmt-NH₂

D-Arg-Phe-Lys-NH₂

D-Arg-Cha-Lys-NH₂

D-Arg-Trp-Lys-NH₂

Dmt-Lys-D-Phe-NH₂

Dmt-Lys-NH₂

Lys-Phe-NH₂

D-Arg-Cha-Lys-Cha-NH₂

D-Nle-Dmt-Ahe-Phe-NH₂

D-Nle-Cha-Ahe-Cha-NH₂

Cyclohexylalanine (Cha); Norleucine (Nle); 2-amino-heptanoic acid (Ahe)

In some embodiments, the aromatic-cationic peptide is a peptide having:
at least one net positive charge;
a minimum of four amino acids;
a maximum of about twenty amino acids;
a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t+1$, except that when a is 1, $p_t$ may also be 1.

In one embodiment, $2p_m$ is the largest number that is less than or equal to r+1, and a may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide has opioid receptor agonist activity. In other embodiments, the peptide does not have opioid receptor agonist activity.

In one embodiment, the peptide comprises a tyrosine or a 2',6'-dimethyltyrosine (Dmt or 2'6'-Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine (Dmp) residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2'6'Dmt-Lys-Phe-NH$_2$.

In one embodiment, the peptide is defined by formula II:

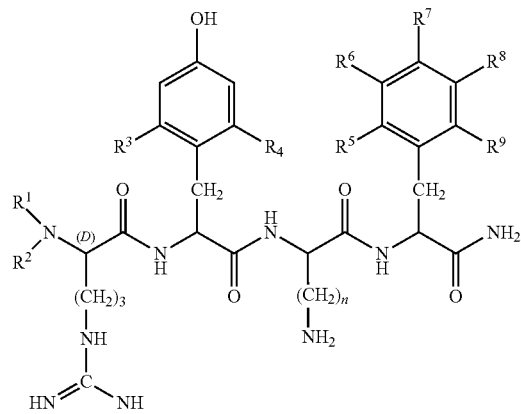

wherein $R^1$ and $R^2$ are each independently selected from
(i) hydrogen;
(ii) linear or branched $C_1$-$C_6$ alkyl;

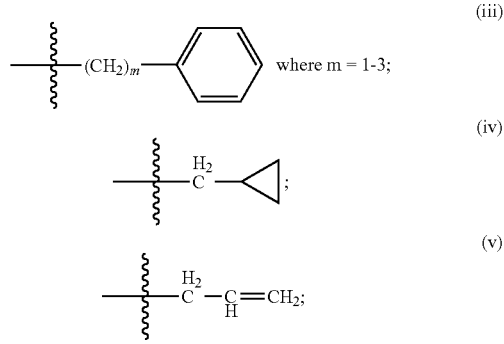

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

III. MPP Uses

Disclosed herein are methods of treating and/or ameliorating diseases and conditions by administering a therapeutically effective amount of a mitochondria penetrating peptide (MPP), such as Cha-Arg-Cha-Lys-NH$_2$, and/or naturally or artificially occurring variants or analogues, or pharmaceutically acceptable salts thereof, alone or in conjunction with one or more additional active agents. In some embodiments, the one or more additional active agents include an aromatic-cationic peptide, e.g., D-Arg-2'6'-Dmt-Lys-Phe-NH$_2$ or a pharmaceutically acceptable salt thereof such as acetate or trifluoroacetate salt.

Provided below are exemplary, non-limiting examples of MPP function, e.g., function with respect to treatment of a disease, disease state, or condition. In some embodiments, the disease, disease state or condition is associated with mitochondrial dysfunction (e.g., mitochondria permeability transition). In some embodiments, the administration of an MPP alone or in combination with one or more additional active agents (e.g., an aromatic-cationic peptide) serves to prevent, treat or ameliorate a disease, conditions or signs and symptoms of a disease or condition.

As used herein, "neuropathy" or "peripheral neuropathy" refers generally to damage to nerves of the peripheral nervous system. The term encompasses neuropathy of various etiologies, including but not limited to neuropathy caused by, resulting from, or associated with genetic disorders, metabolic/endocrine complications, inflammatory diseases, vitamin deficiencies, malignant diseases, and toxicity, such as alcohol, organic metal, heavy metal, radiation, and drug toxicity. As used herein, the term encompasses motor, sensory, mixed sensorimotor, chronic, and acute neuropathy. As used herein the term encompasses mononeuropathy, multiple mononeuropathy, and polyneuropathy.

In some embodiments, the present disclosure provides compositions for the treatment or prevention of peripheral neuropathy or the symptoms of peripheral neuropathy. In some embodiments, the peripheral neuropathy is drug-induced peripheral neuropathy. In some embodiments, the peripheral neuropathy is induced by a chemotherapeutic agent. In some embodiments, the chemotherapeutic agent is a vinca alkaloid. In some embodiments, the vinca alkaloid is vincristine. In some embodiments, the symptoms of peripheral neuropathy include hyperalgesia.

As used herein, "hyperalgesia" refers to an increased sensitivity to pain, which may be caused by damage to nociceptors or peripheral nerves (i.e. neuropathy). The term refers to temporary and permanent hyperalgesia, and encompasses both primary hyperalgesia (i.e. pain sensitivity occurring directly in damaged tissues) and secondary hyperalgesia (i.e. pain sensitivity occurring in undamaged tissues surrounding damaged tissues). The term encompasses hyperalgesia caused by but not limited to neuropathy caused by, resulting from, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. In some embodiments hyperalgesia is caused by drug-induced peripheral neuropathy.

In some embodiments, the present disclosure provides compositions for the treatment or prevention of hyperalgesia. In some embodiments, the hyperalgesia is drug-induced. In some embodiments, the hyperalgesia is induced by a chemotherapeutic agent. In some embodiments, the chemotherapeutic agent is a vinca alkaloid. In some embodiments, the vinca alkaloid is vincristine.

The mitochondria penetrating peptides (MPPs), such as Cha-Arg-Cha-Lys-NH$_2$, and/or naturally or artificially occurring variants or analogues, or pharmaceutically acceptable salts thereof, described herein are useful in treating or preventing neuropathy or hyperalgesia. In some embodiments, the peptides may be administered to a subject following the onset of neuropathy or hyperalgesia. Thus, the term "treatment" is used herein in its broadest sense and refers to use of one or more peptides for a partial or complete cure of the neuropathy or hyperalgesia.

In other embodiments, the a mitochondria penetrating peptide (MPP), such as Cha-Arg-Cha-Lys-NH$_2$, and/or naturally or artificially occurring variants or analogues, or pharmaceutically acceptable salts thereof, of the present technology is administered to a subject before the onset of neuropathy or hyperalgesia in order to protect against or provide prophylaxis for neuropathy or hyperalgesia. Thus, the term "prevention" is used herein in its broadest sense and refers to a prophylactic use which completely or partially prevents neuropathy or hyperalgesia. It is also contemplated that the peptide compounds may be administered to a subject at risk of developing neuropathy or hyperalgesia.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce oxLDL-induced CD36 mRNA and protein levels, and foam cell formation in mouse peritoneal macrophages.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce infarct volume and hemispheric swelling in a subject suffering from acute cerebral ischemia.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce the decrease in reduced glutathione (GSH) in post-ischemic brain in a subject in need thereof.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce CD36 expression in post-ischemic brain in a subject in need thereof.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce CD36 expression in renal tubular cells after unilateral ureteral obstruction (UUO) in a subject in need thereof.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce lipid peroxidation in a kidney after UUO.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce tubular cell apoptosis in an obstructed kidney after UUO.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce macrophage infiltration in an obstructed kidney induced by UUO.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce interstitial fibrosis in an obstructed kidney after UUO.

Cold storage of isolated hearts with MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is anticipated to reduce up-regulation of CD36 expression.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to reduce lipid peroxidation in cardiac tissue (e.g., heart) subjected to warm reperfusion after prolonged cold ischemia.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to abolish endothelial apoptosis in cardiac tissue (e.g., heart) subjected to warm reperfusion after prolonged cold ischemia.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to preserve coronary flow in cardiac tissue (e.g., heart) subjected to warm reperfusion after prolonged cold ischemia.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to prevent damage to renal proximal tubules in diabetic subjects.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are anticipated to prevent renal tubular epithelial cell apoptosis in diabetic subjects.

Mammals in need of a method for reducing CD36 expression include, for example, mammals that have increased CD36 expression. The increased expression of CD36 is associated with various diseases and conditions for which administration of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is therapeutic. Examples of diseases and conditions characterized by increased CD36 expression include, but is not limited to atherosclerosis, inflammation, abnormal angiogenesis, abnormal lipid metabolism, abnormal removal of apoptotic cells, ischemia such as cerebral ischemia and myocardial ischemia, ischemia-reperfusion, ureteral obstruction, stroke, Alzheimer's Disease, diabetes, diabetic nephropathy and obesity.

Mammals in need of reducing CD36 expression also include mammals suffering from complications of diabetes. Administration of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is therapeutic to such patient populations. Complications of diabetes include, but are not limited to, nephropathy, neuropathy, retinopathy, coronary artery disease, and peripheral vascular disease.

In some embodiments, the methods disclosed herein are methods for reducing CD36 expression in removed organs and tissues by administering an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$). The method comprises contacting the removed organ or tissue with an effective amount of a peptide(s) described herein. An organ or tissue may, for example, be removed from a donor for autologous or heterologous transplantation. Examples of organs and tissues amenable to methods of the present technology include, but are not limited to, heart, lungs, pancreas, kidney, liver, skin, etc.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will translocate to and accumulate within mitochondria.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will protect against mitochondrial permeability transition (MPT) induced by $Ca^{2+}$ overload and 3-nitroproprionic acid (3NP).

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will inhibit mitochondrial swelling and cytochrome c release.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will protect myocardial contractile force during ischemia-reperfusion in cardiac tissue.

It is anticipated that the addition of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to a cardioplegic solution will significantly enhance contractile function after prolonged ischemia in isolated cardiac tissue (e.g., heart) perfused with the solution.

The peptides described herein (e.g., MPPs, such as Cha-Arg-Cha-Lys-NH$_2$, and/or naturally or artificially occurring variants or analogues, or pharmaceutically acceptable salts thereof, alone or in combination with one or more aromatic-cationic peptides) are useful in treating any disease or condition that is associated with MPT. Such diseases and conditions include, but are not limited to, ischemia and/or reperfusion of a tissue or organ, hypoxia and any of a number of neurodegenerative diseases. Mammals in need of treatment or prevention of MPT are those mammals suffering from these diseases or conditions.

The methods and compositions of the present disclosure can also be used in the treatment or prophylaxis of neurodegenerative diseases associated with MPT. Neurodegenerative diseases associated with MPT include, for example, Parkinson's disease, Alzheimer's disease, Huntington's disease and Amyotrophic Lateral Sclerosis (ALS). The methods and compositions disclosed herein can be used to delay the onset or slow the progression of these and other neurodegenerative diseases associated with MPT. The methods and compositions disclosed herein are particularly useful in the treatment of humans suffering from the early stages of neurodegenerative diseases associated with MPT and in humans predisposed to these diseases.

The peptides disclosed herein (e.g., MPPs, such as Cha-Arg-Cha-Lys-NH$_2$, and/or naturally or artificially occurring variants or analogues, or pharmaceutically acceptable salts thereof, alone or in combination with an aromatic-cationic peptide such as D-Arg-2'6'-Dmt-Lys-Phe-NH$_2$) may be used to preserve an organ of a mammal prior to transplantation. A removed organ is susceptible to MPT due to lack of blood flow. Therefore, methods comprising contacting the organ with peptides of the present technology can be used to prevent MPT in the removed organ.

The removed organ may be placed in a standard buffered solution, such as those commonly used in the art. For example, a removed heart may be placed in a cardioplegic solution containing the peptides described herein. The concentration of peptides in the standard buffered solution can be easily determined by those skilled in the art. Such concentrations may be, for example, between about 0.1 nM to about 10 μM.

The peptides (e.g., MPPs, such as Cha-Arg-Cha-Lys-NH$_2$, and/or naturally or artificially occurring variants or analogues, or pharmaceutically acceptable salts thereof, alone or in combination with an aromatic-cationic peptide such as D-Arg-2'6'-Dmt-Lys-Phe-NH$_2$) may also be administered to a mammal taking a drug to treat a condition or disease. If a side effect of the drug includes MPT, mammals taking such drugs would greatly benefit from administration of the peptides disclosed herein.

An example of a drug which induces cell toxicity by effecting MPT is the chemotherapy drug Adriamycin. Administration of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is anticipated to ameliorate, diminish, or prevent the side effects of such drugs.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will dose-dependently scavenge H$_2$O$_2$.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will dose-dependently inhibit linoleic acid peroxidation induced by ABAP and reduced the rate of linoleic acid peroxidation induced by ABAP.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will dose-dependently inhibit LDL oxidation induced by 10 mM CuSO$_4$ and reduced rate of LDL oxidation.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will inhibit mitochondrial production of hydrogen peroxide as measured by luminol chemiluminescence under basal conditions and upon stimulation by antimycin.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduce spontaneous generation of hydrogen peroxide by mitochondria in certain stress or disease states.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will inhibit spontaneous production of hydrogen peroxide in mitochondria and hydrogen peroxide production stimulated by antimycin.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease intracellular ROS (reactive oxygen species) and increase survival in cells of a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent loss of cell viability in subjects suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decreased the percent of cells showing increased caspase activity in a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduced the rate of ROS accumulation in a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will inhibit lipid peroxidation in a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent mitochondrial depolarization and ROS accumulation in a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys- Phe-NH$_2$) will prevent apoptosis in a subject in need thereof, e.g., a subject suffering from a disease or condition characterized by mitochondrial dysfunction.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will significantly improve coronary flow in cardiac tissue (e.g., heart) subjected to warm reperfusion after prolonged (e.g., 18 hours) cold ischemia.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent apoptosis in endothelial cells and myocytes in cardiac tissue (e.g., heart) subjected to warm reperfusion after prolonged (e.g., 18 hours) cold ischemia.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will improve survival of pancreatic cells in a subject in need thereof.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduce apoptosis and increase viability in islet cells of pancreas in subjects in need thereof.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduce oxidative damage in pancreatic islet cells in subjects in need thereof.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will protect dopaminergic cells against MPP+ toxicity in subjects in need thereof.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent loss of dopaminergic neurons in subject in need thereof.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will increase striatal dopamine, DOPAC (3,4-dihydroxyphenylacetic acid) and HVA (homovanillic acid) levels in subjects in need thereof.

The peptides described herein (e.g., MPPs, such as Cha-Arg-Cha-Lys-NH$_2$, and/or naturally or artificially occurring variants or analogues, or pharmaceutically acceptable salts thereof, alone or in combination with an aromatic-cationic peptide such as D-Arg-2'6'-Dmt-Lys-Phe-NH$_2$) are useful in reducing oxidative damage in a mammal in need thereof. Mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO.), superoxide anion radical ($O_2.^-$), nitric oxide (NO.), hydrogen peroxide ($H_2O_2$), hypochlorous acid (HOCl), and peroxynitrite anion ($ONOO^-$).

In some embodiments, a mammal in need thereof may be a mammal undergoing a treatment associated with oxidative damage. For example, the mammal may be undergoing reperfusion. "Reperfusion" refers to the restoration of blood flow to any organ or tissue in which the flow of blood is decreased or blocked. The restoration of blood flow during reperfusion leads to respiratory burst and formation of free radicals.

In some embodiments, a mammal in need thereof is a mammal suffering from a disease or condition associated with oxidative damage. The oxidative damage can occur in any cell, tissue or organ of the mammal. Examples of cells, tissues or organs affected by oxidative damage include, but are not limited to, endothelial cells, epithelial cells, nervous system cells, skin, heart, lung, kidney, and liver. For example, lipid peroxidation and an inflammatory process are associated with oxidative damage for a disease or condition.

"Lipid peroxidation" refers to oxidative modification of lipids. The lipids can be present in the membrane of a cell. This modification of membrane lipids typically results in change and/or damage to the membrane function of a cell. In addition, lipid peroxidation can also occur in lipids or lipoproteins exogenous to a cell. For example, low-density lipoproteins are susceptible to lipid peroxidation. An example of a condition associated with lipid peroxidation is atherosclerosis. Reducing oxidative damage associated with atherosclerosis is important because atherosclerosis is implicated in, for example, heart attacks and coronary artery disease.

"Inflammatory process" refers to the activation of the immune system. Typically, the immune system is activated by an antigenic substance. The antigenic substance can be any substance recognized by the immune system, and include self-derived and foreign-derived substances. Examples of diseases or conditions resulting from an inflammatory response to self-derived substances include arthritis and multiple sclerosis. Examples of foreign substances include viruses and bacteria.

The virus can be any virus which activates an inflammatory process, and associated with oxidative damage. Examples of viruses include, hepatitis A, B or C virus, human immunodeficiency virus, influenza virus, and bovine diarrhea virus. For example, hepatitis virus can elicit an inflammatory process and formation of free radicals, thereby damaging the liver.

The bacteria can be any bacteria, and include gram-negative and gram-positive bacteria. Gram-negative bacteria contain lipopolysaccharide in the bacteria wall. Examples of gram-negative bacteria include *Escherichia coli, Klebsiella pneumoniae, Proteus* species, *Pseudomonas aeruginosa, Serratia*, and *Bacteroides*. Examples of gram-positive bacteria include pneumococci and streptococci.

The methods and compositions disclosed herein can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes and microglia.

The neurodegenerative condition can be an acute condition, such as a stroke or a traumatic brain or spinal cord injury. In one embodiment, the neurodegenerative disease or condition is a chronic neurodegenerative condition. In a chronic neurodegenerative condition, the free radicals can, for example, cause damage to a protein. An example of such a protein is amyloid p-protein. Examples of chronic neurodegenerative diseases associated with damage by free radicals include Parkinson's disease, Alzheimer's disease, Huntington's disease and Amyotrophic Lateral Sclerosis (ALS).

Other conditions which can be treated in accordance with the disclosed methods and compositions include preeclampsia, diabetes, and symptoms of and conditions associated with aging, such as macular degeneration, and wrinkles.

In some embodiments, the peptides disclosed herein (e.g., MPPs, such as Cha-Arg-Cha-Lys-$NH_2$, and/or naturally or artificially occurring variants or analogues, or pharmaceutically acceptable salts thereof, alone or in combination with an aromatic-cationic peptide such as D-Arg-2'6'-Dmt-Lys-Phe-$NH_2$) are used for reducing oxidative damage in an organ of a mammal prior to transplantation. For example, a removed organ, when subjected to reperfusion after transplantation can be susceptible to oxidative damage. Therefore, the peptides can be used to reduce oxidative damage from reperfusion of the transplanted organ.

The removed organ can be any organ suitable for transplantation. Examples of such organs include, the heart, liver, kidney, lung, and pancreatic islets. The removed organ is placed in a suitable medium, such as in a standard buffered solution commonly used in the art.

For example, a removed heart can be placed in a cardioplegic solution containing the peptides described herein (e.g., MPPs, such as Cha-Arg-Cha-Lys-$NH_2$, and/or naturally or artificially occurring variants or analogues, or pharmaceutically acceptable salts thereof, alone or in combination with an aromatic-cationic peptide such as D-Arg-2'6'-Dmt-Lys-Phe-$NH_2$). The concentration of peptides in the standard buffered solution can be easily determined by those skilled in the art. Such concentrations may be, for example, between about 0.01 µM to about 10 µM, between about 0.1 nM to about 10 µM, between about 1 µM to about 5 µM, between about 1 nM to about 100 nM.

In some embodiments, the present technology encompasses methods and compositions for reducing oxidative damage in a cell in need thereof. In some embodiments, the methods include administering a therapeutically effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$). Cells in need of reducing oxidative damage are generally those cells in which the cell membrane or DNA has been damaged by free radicals, for example, ROS and/or RNS. Examples of cells capable of sustaining oxidative damage include, but are not limited to, pancreatic islet cells, myocytes, endothelial cells, neuronal cells, stem cells, and other cell types discussed herein.

The cells can be tissue culture cells. Alternatively, the cells may be obtained from a mammal. In one instance, the cells can be damaged by oxidative damage as a result of a cellular insult. Cellular insults include, for example, a disease or condition (e.g., diabetes, etc.) or ultraviolet radiation (e.g., sun, etc.). For example, pancreatic islet cells damaged by oxidative damage as a result of diabetes can be obtained from a mammal.

The peptides described herein (e.g., MPPs, such as Cha-Arg-Cha-Lys-$NH_2$, and/or naturally or artificially occurring variants or analogues, or pharmaceutically acceptable salts thereof, alone or in combination with an aromatic-cationic peptide such as D-Arg-2'6'-Dmt-Lys-Phe-$NH_2$) can be administered to cells by any method known to those skilled in the art. For example, the peptides can be incubated with the cells under suitable conditions. Such conditions can be readily determined by those skilled in the art.

Due to reduction of oxidative damage, the treated cells may be capable of regenerating. Such regenerated cells may be re-introduced into the mammal from which they were derived as a therapeutic treatment for a disease or condition. As mentioned above, one such condition is diabetes.

Oxidative damage is considered to be "reduced" if the amount of oxidative damage in a mammal, a removed organ, or a cell is decreased after administration of an effective amount of the peptides described herein. Typically, oxidative damage is considered to be reduced if the oxidative damage is decreased by at least about 10%, at least about 25%, at least about 50%, at least about 75%, or at least about 90%.

It is anticipated that MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) will have an effect on the oxidation state of muscle tissue.

It is anticipated that MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) will have an effect on the oxidation state of muscle tissue in lean and obese human subjects.

It is anticipated that MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) will have an effect on insulin resistance in muscle tissue.

In some embodiments, insulin resistance induced by obesity or a high-fat diet affects mitochondrial bioenergetics. Without wishing to be bound by theory, it is thought that the oversupply of metabolic substrates causes a reduction on the function of the mitochondrial respiratory system, and an increase in ROS production and shift in the overall redox environment to a more oxidized state. If persistent, this leads to development of insulin resistance. Linking mitochondrial bioenergetics to the etiology of insulin resistance has a number of clinical implications. For example, it is known that insulin resistance (NIDDM) in humans often results in weight gain and, in selected individuals, increased variability of blood sugar with resulting metabolic and clinical consequences. The examples shown herein demonstrate that treatment of mitochondrial defects with a mitochondrial-targeted antioxidant (e.g., an MPP) provides a new and surprising approach to treating or preventing insulin resistance without the metabolic side-effects of increased insulin.

The present methods and compositions are anticipated to reduce insulin resistance by administration of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$).

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) as disclosed herein are useful to prevent or treat disease. Specifically, the peptides are useful for prophylactic and therapeutic methods of treating a subject at risk of (or susceptible to) a disorder, or a subject having a disorder associated with insulin resistance. Insulin resistance is generally associated with type II diabetes, coronary artery disease, renal dysfunction, atherosclerosis, obesity, hyperlipidemia, and essential hypertension. Insulin resistance is also associated with fatty liver, which can progress to chronic inflammation (NASH; "non-alcoholic steatohepatitis"), fibrosis, and cirrhosis. Cumulatively, insulin resistance syndromes, including, but not limited to diabetes, underlie many of the major causes of morbidity and death of people over age 40. Accordingly, the present invention provides methods for the prevention and/or treatment of insulin resistance and associated syndromes in a subject in need thereof comprising administering an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to the subject. For example, a subject may be administered a composition comprising an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to improve the sensitivity of mammalian skeletal muscle tissues to insulin. In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used to prevent drug-induced obesity, insulin resistance, and/or diabetes, wherein the peptide is administered with a drug that shows the side-effect of causing one or more of these conditions (e.g., olanzapine, Zyprexa®).

In various embodiments, suitable in vitro or in vivo assays are performed to determine the effect of a specific MPP-based therapeutic and whether its administration is indicated for treatment of the affected tissue in a subject. In various embodiments, in vitro assays are performed with representative cells of the type(s) involved in the subject's disorder, to determine if a given MPP-based therapeutic exerts the desired effect upon the cell type(s). Compounds for use in therapy can be tested in suitable animal model systems including, but not limited to, rats, mice, chicken, cows, monkeys, rabbits, and the like, prior to testing in human subjects. Similarly, for in vivo testing, any animal model system known in the art can be used prior to administration to human subjects. Increased or decreased insulin resistance or sensitivity can be readily detected by quantifying body weight, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity), or mitochondrial enzyme activity.

In one aspect, the methods disclosed herein are methods for preventing, in a subject, a disease or condition associated with insulin resistance in skeletal muscle tissues, by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to modulate one or more signs or markers of insulin resistance, e.g., body weight, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity), or mitochondrial enzyme activity.

Subjects at risk for a disease that is caused or contributed to by aberrant mitochondrial function or insulin resistance can be identified by, e.g., any or a combination of diagnostic or prognostic assays as described herein. In prophylactic applications, pharmaceutical compositions or medicaments including an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are administered to a subject susceptible to, or otherwise at risk of a disease or condition in an amount sufficient to eliminate or reduce the risk, lessen the severity of, or delay the onset of the disease, including biochemical, histological and/or behavioral symptoms of the disease, its complications and intermediate pathological phenotypes presenting during development of the disease. Administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can occur prior to the manifestation of symptoms characteristic of the aberrancy, such that a disease or disorder is prevented or, alternatively, delayed in its progression. Depending upon the type of aberrancy, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$), will act to enhance or improve mitochondrial function, and can be used for treating the subject. The appropriate compound can be determined based on screening assays described herein.

Another aspect disclosed herein includes methods of modulating insulin resistance or sensitivity in a subject for therapeutic purposes. In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject suffering from insulin resistance or sensitivity. In therapeutic applications, compositions or medicaments are administered to a subject suspected of, or already suffering from such a disease in an amount sufficient to cure, or partially arrest, the symptoms of the disease (biochemical, histological and/or behavioral), including its complications and intermediate pathological phenotypes in development of the disease. An amount adequate to accomplish therapeutic or prophylactic treatment is defined as a therapeutically- or prophylactically-effective dose. These modulatory methods can be performed in vitro (e.g., by culturing the cell with the MPP) or, alternatively, in vivo (e.g., by administering the MPP alone or in combination with one or more active agents (e.g., an aromatic-cationic peptide such as D-Arg-2'6'-Dmt-Lys-Phe-NH$_2$) to a subject). As such, the invention provides methods of treating an individual afflicted with a insulin resistance-associated disease or disorder.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will improve the histopathological score resulting from ischemia and reperfusion.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will increase the rate of ATP production after reperfusion in renal tissue following ischemia.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will improve renal mitochondrial respiration following ischemia.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease medullary fibrosis in unilateral ureteral obstruction (UUO).

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease interstitial fibrosis in UUO.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease tubular apoptosis in UUO.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease macrophage infiltration in UUO.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will increase tubular proliferation in UUO.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will decrease oxidative damage in UUO.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduce renal dysfunction caused by a radiocontrast dye.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will protect renal tubules from radiocontrast dye injury.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent renal tubular apoptosis induced by radiocontrast dye injury.

MPPs, such as Cha-Arg-Cha-Lys-NH$_2$, and/or naturally or artificially occurring variants or analogues, or pharmaceutically acceptable salts thereof, alone or in combination with one or more active agents described herein (e.g., an aromatic-cationic peptide such as D-Arg-2'6'-Dmt-Lys-Phe-NH$_2$) are useful in protecting a subject's kidney from renal injury. Acute renal injury (ARI) refers to a reduction of renal function and filtration of waste products from a patient's blood. ARI is typically characterized as including a decline of glomerular filtration rate (GFR) to a level so low that little or no urine is formed. Therefore, substances usually eliminated by the kidney remain in the body.

The causes of ARI may be caused by various factors, falling into three categories: (1) pre-renal ARI, in which the kidneys fail to receive adequate blood supply, e.g., due to reduced systemic blood pressure as in shock/cardiac arrest, or subsequent to hemorrhage; (2) intrinsic ARI, in which the failure occurs within the kidney, e.g., due to drug-induced toxicity; and (3) post-renal ARI, caused by impairment of urine flow out of the kidney, as in ureteral obstruction due to kidney stones or bladder/prostate cancer. ARI may be associated with any one or a combination of these categories.

An example of a condition in which kidneys fail to receive adequate blood supply to the kidney is ischemia. Ischemia is a major cause of ARI. Ischemia of one or both kidneys is a common problem experienced during aortic surgery, renal transplantation, or during cardiovascular anesthesia. Surgical procedures involving clamping of the aorta and/or renal arteries, e.g., surgery for supra- and juxta-renal abdominal aortic aneurysms and renal transplantation, are also particularly liable to produce renal ischemia, leading to significant postoperative complications and early allograft rejection. In high-risk patients undergoing these surgeries, the incidence of renal dysfunction has been reported to be as high as 50%.

Renal ischemia may be caused by loss of blood, loss of fluid from the body as a result of severe diarrhea or burns, shock, and ischemia associated with storage of the donor kidney prior to transplantation. In these situations, the blood flow to the kidney may be reduced to a dangerously low level for a time period great enough to cause ischemic injury to the tubular epithelial cells, sloughing off of the epithelial cells into the tubular lumen, obstruction of tubular flow that leads to loss of glomerular filtration and acute renal injury.

Subjects may also become vulnerable to ARI after receiving anesthesia, surgery, or α-adrenergic agonists because of related systemic or renal vasoconstriction. Additionally, systemic vasodilation caused by anaphylaxis, and antihypertensive drugs, sepsis or drug overdose may also cause ARI because the body's natural defense is to shut down, i.e., vasoconstriction of non-essential organs such as the kidneys.

Accordingly, in some embodiments, a subject at risk for ARI may be a subject undergoing an interruption or reduction of blood supply or blood pressure to the kidney. These subjects may be administered an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) of the present technology prior to or simultaneously with such interruption or reduction of blood supply. Likewise, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) may be administered after the therapeutic agent to treat ischemia.

Another cause of ARI includes drug-induced toxicity. For example, nephrotoxins can cause direct toxicity on tubular epithelial cells. Nephrotoxins include, but are not limited to, therapeutic drugs, e.g., cisplatin, gentamicin, cephaloridine, cyclosporin, amphotericin, radiocontrast dye (described in further detail below), pesticides (e.g., paraquat), and environmental contaminants (e.g., trichloriethylene and dichloroacetylene). Other examples include puromycin aminonucleoside (PAN); aminoglycosides, such as gentamicin; cephalosporins, such as cephaloridine; caleineurin inhibitors, such as tacrolimus or sirolimus. Drug-induced nephrotoxicity may also be caused by non-steroidal anti-inflammatories, antiretrovirals, anticytokines, immunosuppressants, oncological drugs, or angiotensin-converting-enzyme (ACE) inhibitors. The drug-induced nephrotoxicity may further be caused by analgesic abuse, ciprofloxacin, clopidogrel, cocaine, cox-2 inhibitors, diuretics, foscamet, gold, ifosfamide, immunoglobin, Chinese herbs, interferon, lithium, mannitol, mesalamine, mitomycin, nitrosoureas, penicillamine, penicillins, pentamidine, quinine, rifampin, streptozocin, sulfonamides, ticlopidine, triamterene, valproic acid, doxorubicin, glycerol, cidofovir, tobramycin, neomycin sulfate, colistimethate, vancomycin, amikacin, cefotaxime, cisplatin, acyclovir, lithium, interleukin-2, cyclosporin, or indinavir.

In addition to direct toxicity on tubular epithelial cells, some nephrotoxins also reduce renal perfusion, causing injury to zones known to have limited oxygen availability (inner medullary region). Such nephrotoxins include amphotericin and radiocontrast dyes. Renal failure can result even from clinically relevant doses of these drugs when combined with ischemia, volume depletion, obstruction, or infection. An example is the use of radiocontrast dye in patients with impaired renal function. The incidence of contrast dye-induced nephropathy (CIN) is 3-8% in the normal patient, but increases to 25% for patients with diabetes mellitus. Most cases of ARI occur in patients with predisposing co-morbidities (McCombs, P. R. & Roberts, B., *Surg Gynecol. Obstet.*, 148:175-178 (1979)).

Accordingly, in one embodiment, a subject at risk for ARI is receiving one or more therapeutic drugs that have a nephrotoxic effect. The subject is administered the MPPs of the present technology prior to or simultaneously with such therapeutic agents. Likewise, MPPs may be administered after the therapeutic agent to treat nephrotoxicity.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to a subject at risk for CIN, in order to prevent the condition. CIN is an important cause of acute renal failure. CIN is defined as acute renal failure occurring within 48 hours of exposure to intravascular radiographic contrast material, and remains a common complication of radiographic procedures.

CIN arises when a subject is exposed to radiocontrast dye, such as during coronary, cardiac, or neuro-angiography procedures. Contrast dye is essential for many diagnostic and interventional procedures because it enables doctors to visualize blocked body tissues. A creatinine test can be used to monitor the onset of CIN, treatment of the condition, and efficacy of MPPs of the present invention in treating or preventing CIN.

In some embodiments, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to a subject prior to or simultaneously with the administration of a contrast agent in order to provide protection against CIN. For example, the subject may receive the peptides from about 1 to 2 hours, about 1 to 6 hours, about 1 to 12 hours, about 1 to 24 hours, or about 1 to 48 hours prior to receiving the contrast agent. Likewise, the subject may be administered the peptides at about the same time as the contrast agent. Moreover, administration of the peptides to the subject may continue following administration of the contrast agent. In some embodiments, the subject continues to receive the peptide at intervals of about 1, 2, 3, 4, 5, 6, 7, 8, 12, 24, and 48 hours following administration of the contrast agent, in order to provide a protective or prophylactic effect against CIN.

In some embodiments, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to a subject after administration of a contrast agent in order to treat CIN. For example, the subject receives the peptides from about 1 to 2 hours, about 1 to 6 hours, about 1 to 12 hours, about 1 to 24 hours, about 1 to 48 hours, or about 1 to 72 hours after receiving the contrast agent. For instance, the subject may exhibit one or more signs or symptoms of CIN prior to receiving the peptides of the invention, such as increased serum creatinine levels and/or decreased urine volume. Administration of the peptides of the invention improves one or more of these indicators of kidney function in the subject compared to a control subject not administered the peptides.

In one embodiment, a subject in need thereof may be a subject having impairment of urine flow. Obstruction of the flow of urine can occur anywhere in the urinary tract and has many possible causes, including but not limited to, kidney stones or bladder/prostate cancer. Unilateral ureteral obstruction (UUO) is a common clinical disorder associated with obstructed urine flow. It is also associated with tubular cell apoptosis, macrophage infiltration, and interstitial fibrosis. Interstitial fibrosis leads to a hypoxic environment and contributes to progressive decline in renal function despite surgical correction. Thus, a subject having or at risk for UUO may be administered an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to prevent or treat ARI.

In yet another aspect of the invention, a method for protecting a kidney from renal fibrosis in a mammal in need thereof is provided. The method comprises administering to the mammal an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) as described herein. The peptides described herein can be administered to a mammal in need thereof, as described herein, by any method known to those skilled in the art.

In another aspect of the invention, a method for treating acute renal injury in a mammal in need thereof is provided. The method comprises administering to the mammal an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) as described herein. The peptides described herein can be administered to a mammal in need thereof, as described herein, by any method known to those skilled in the art.

The methods of the invention may be particularly useful in patients with renal insufficiency, renal failure, or end-stage renal disease attributable at least in part to a nephrotoxicity of an drug or chemical. Other indications may include creatinine clearance levels of lower than 97 (men) and 88 (women) mL/min, or a blood urea level of 20-25 mg/dl or higher. Furthermore, the treatment are useful in patients with microalbuminuria, macroalbuminuria, and/or proteinuria levels of over 1, 2, 3, 4, 5, 6, 7, 8, 9, or 10 g or more per a 24 hour period, and/or serum creatinine levels of about 1.0, 1.5, 2.0, 2.5, 3, 3.5, 4.0, 4.5, 5, 5.5, 6, 7, 8, 9, 10 mg/dl or higher.

The methods of the invention can be used to slow or reverse the progression of renal disease in patients whose renal function is below normal by 25%, 40%, 50%, 60%, 75%, 80%, 90% or more, relative to control subjects. In some embodiments, the methods of the invention slow the loss of renal function by at least 10%, 20%, 30%, 40%, 50%, 60%, 70%, 80%, 90%, 100% or more, relative to control subjects. In other embodiments, the methods of the invention improve the patient's serum creatinine levels, proteinuria, and/or urinary albumin excretion by at least 10%, 20%, 30%, 40%, 50%, 60%, 70%, or more, relative to control subjects. Non-limiting illustrative methods for assessing renal function are described herein and, for example, in WO 01/66140.

In one embodiment, the peptides disclosed herein, e.g., MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may also be used in protecting a subject's kidney from acute renal injury prior to transplantation. For example, a removed kidney can be placed in a solution containing the peptides described herein. The concentration of peptides in the standard buffered solution can be easily determined by those skilled in the art. Such concentrations may be, for example, between about 0.01 nM to about 10 μM, about 0.1 nM to about 10 μM, about 1 μM to about 5 μM, or about 1 nM to about 100 nM.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are useful in preventing or treating ARI and is also applicable to tissue injury and organ failure in other systems besides the kidney. For instance, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are predicted to minimize mitochondrial dysfunction, cell death, inflammation, and fibrosis. In some embodiments, the present invention provides a method of treating a subject having a tissue injury, e.g., noninfectious pathological conditions such as pancreatitis, ischemia, multiple trauma, hemorrhagic shock, and immune-mediated organ injury.

The tissue injury can be associated with, for example, aortic aneurysm repair, multiple trauma, peripheral vascular disease, renal vascular disease, myocardial infarction, stroke, sepsis, and multi-organ failure. In one aspect, the invention relates to a method of treating a subject having a tissue such as from heart, brain, vasculature, gut, liver, kidney and eye that is subject to an injury and/or ischemic event. The method includes administering to the subject a therapeutically effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to provide a therapeutic or prophylactic effect. Another embodiment of the present invention provides the administration of the peptides of the present invention to improve a function of one or more organs selected from the group consisting of: renal, lung, heart, liver, brain, pancreas, and the like. In a particular embodiment, the improvement in lung function is selected from the group consisting of lower levels of edema, improved histological injury score, and lower levels of inflammation.

In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used for the prevention and/or treatment of acute hepatic injury caused by ischemia, drugs (e.g., acetaminophen, alcohol), viruses, obesity (e.g., non-alcoholic steatohepatitis), and obstruction (e.g., bile duct obstruction, tumors). In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to prevent or treat acute liver failure (ALF). ALF is a clinical condition that results from severe and extensive damage of liver cells leading to failure of the liver to function normally. ALF results from massive necrosis of liver cells leading to hepatic encephalopathy and severe impairment of hepatic function. It has various causes, such as viral hepatitis (A, B, C), drug toxicity, frequent alcohol intoxication, and autoimmune hepatitis. ALF is a very severe clinical condition with high mortality rate. Drug-related hepatotoxicity is the leading cause of ALF in the United States.

In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject prior to or simultaneously with the administration of an drug or agent known or suspected to induced hepatotoxicity, e.g., acetaminophen, in order to provide protection against ALF. For example, the subject may receive the peptides from about 1 to 2 hours, about 1 to 6 hours, about 1 to 12 hours, about 1 to 24 hours, or about 1 to 48 hours prior to receiving the drug or agent. Likewise, the subject may be administered the peptides at about the same time as the drug or agent to provide a prophylactic effect against ALF caused by the drug or agent. Moreover, administration of the peptides to the subject may continue following administration of the drug or agent. In some embodiments, the subject may continue to receive the peptide at intervals of about 1, 2, 3, 4, 5, 6, 7, 8, 12, 24, and 48 hours following administration of the drug or agent, in order to provide a protective or prophylactic effect.

In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject exhibiting one or more signs or symptoms of ALF, including, but not limited to, elevated levels of hepatic enzymes (transaminases, alkaline phosphatase), elevated serum bilirubin, ammonia, glucose, lactate, or creatinine. Administration of the peptides of the present technology improves one or more of these indicators of liver function in the subject compared to a control subject not administered the peptides. The subject may receive the peptides from about 1 to 2 hours, about 1 to 6 hours, about 1 to 12 hours, about 1 to 24 hours, about 1 to 48 hours, or about 1 to 72 hours after the first signs or symptoms of ALF.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used to treat or ameliorate the local and distant pathophysiological effects of burn injury, including, but not limited to, hypermetabolism and organ damage. It is to be appreciated that certain aspects, modes, embodiments, variations, and features of the invention are described herein in various levels of detail in order to provide a substantial understanding of the present invention.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) as described herein are useful in treating or preventing burn injuries and systemic conditions associated with a burn injury. In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject following a burn and after the onset of detectable symptoms of systemic injury. Thus, the term "treatment" is used herein in its broadest sense and refers to use of an MPP for a partial or complete cure of the burn and/or secondary complications, such as organ dysfunction and hypermetabolism.

In other embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject following a burn, but before the onset of detectable symptoms of systemic injury in order to protect against or provide prophylaxis for the systemic injury, such as organ damage or hypermetabolism. Thus the term "prevention" is used herein in its broadest sense and refers to a prophylactic use which completely or partially prevents local injury to the skin or systemic injury, such as organ dysfunction or hypermetabolism following burns. It is also contemplated that the compounds may be administered to a subject at risk of receiving burns.

Burns are generally classified according to their severity and extent. First degree burns are the mildest and typically affect only the epidermis. The burn site appears red, and is painful, dry, devoid of blisters, and may be slightly moist due to fluid leakage. Mild sunburn is typical of a first degree burn. In second degree burns, both the epidermis and dermis are affected. Blisters usually appear on the skin, with damage to nerves and sebaceous glands. Third degree burns are the most serious, with damage to all layers of the skin, including subcutaneous tissue. Typically there are no blisters, with the burned surface appearing white or black due to charring, or bright red due to blood in the bottom of the wound. In most cases, the burn penetrates the superficial fascia, extending into the muscle layers where arteries and veins are affected. Because of nerve damage, it is possible for them to be painless.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are effective for the treatment of burns from any cause, including dry heat or cold burns, scalds, sunburn, electrical burns, chemical agents such as acids and alkalis, including hydrofluoric acid, formic acid, anhydrous ammonia, cement, and phenol, or radiation burns. Burns resulting from exposure to either high or low temperature are within the scope of the invention. The severity and extent of the burn may vary, but secondary organ damage or hypermetabolism will usually arise when the burns are very extensive or very severe (second or third degree burns). The development of secondary organ dysfunction or failure is dependent on the extent of the burn, the response of the patient's immune system and other factors, such as infection and sepsis.

In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used to treat or prevent organ dysfunction secondary to a burn. The chain of physiological processes which lead to organ dysfunction following burns is complex. In subjects with serious burns, release of catecholamines, vasopressin, and angiotensin causes peripheral and splanchnic bed vasoconstriction that can compromise the perfusion of organs remote to the injury. Myocardial contractility also may be reduced by the release of TNF-α. Activated neutrophils are sequestered in dermal and distant organs, such as the lung, within hours following a burn injury, resulting in the release of toxic reactive oxygen species and proteases and producing vascular endothelial cell damage. When the integrity of pulmonary capillary and alveolar epithelia is compromised, plasma and blood leak into the interstitial and intra-alveolar spaces, resulting in pulmonary edema. A decrease in pulmonary function can occur in severely burned patients, as a result of bronchoconstriction caused by humoral factors, such as histamine, serotonin, and thromboxane A2.

Subjects suffering from a burn injury are also at risk for skeletal muscle dysfunction. While not wishing to be limited by theory, burn-induced mitochondrial skeletal muscle dysfunction is thought to result from defects in oxidative phosphorylation (OXPHOS) via stimulation of mitochondrial production of reactive oxygen species (ROS) and the resulting damage to the mitochondrial DNA (mtDNA). In some embodiments, it is anticipated that the MPPs will induce ATP synthesis via a recovery of the mitochondrial redox status or via the peroxisome proliferator activated receptor-gamma coactivator-1β, which is down-regulated as early as 6 hours after a burn. Thus, it is anticipated that the mitochondrial dysfunction caused by a burn injury will recover with the administration of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$).

In one aspect, the present methods relate to treating a wound resulting from a burn injury by administering to a subject an effective amount an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$). The peptides may be administered systemically or topically to the wound. Burn wounds are typically uneven in depth and severity. There are typically significant area around the coagulated tissue where injury may be reversible and damage mediated by the inflammatory and immune cells to the microvasculature of the skin could be prevented. In one embodiment, the administration of the peptides will slow or ameliorate the effects of wound contraction. Wound contraction is the process which diminishes the size of a full-thickness open wound, especially a full-thickness burn. The tensions developed during contracture and the formation of subcutaneous fibrous tissue can result in deformity, and in particular to fixed flexure or fixed extension of a joint where the wound involves an area over the joint. Such complications are especially relevant in burn healing. No wound contraction will occur when there is no injury to the tissue, and maximum contraction will occur when the burn is full thickness and no viable tissue remains in the wound. In one embodiment, it is anticipated that the administration of the peptides will prevent progression of a burn injury from a second degree burn to a third degree burn.

It is also anticipated that the method for the treatment of burn injury may also be effective for decreasing scarring or the formation of scar tissue attendant the healing process at a burn site. Scarring is the formation of fibrous tissue at sites where normal tissue has been destroyed. The present disclosure thus also includes a method for decreasing scarring following a second or third degree burn. This method comprises treating an animal with a second or third degree burn with an effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$).

In a particular embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to a subject suffering from a burn in order to treat or prevent damage to distant organs or tissues. In particular, dysfunction or failure of the lung, liver, kidneys, and/or bowel following burns to the skin or other sites of the body has a significant impact on morbidity and mortality. While not wishing to be limited by theory, it is believed that systemic inflammatory responses arise in subjects following burn injury, and that it is this generalized inflammation which leads to remote tissue injury which is expressed as the dysfunction and failure of organs remote from the injury site. Systemic injury, including organ dysfunction and hypermetabolism, is typically associated with second and third degree burns. A characteristic of the systemic injury, i.e., organ dysfunction or hypermetabolism, is that the burn which provokes the subsequent injury or condition does not directly affect the organ in question, i.e., the injury is secondary to the burn.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to treat or protect damage to liver tissues secondary to a burn. Methods for assessing liver function are well known in the art and include, but are not limited to, using blood tests for serum alanine aminotransferase (ALT) levels, alkaline phosphatase (AP), or bilirubin levels. Methods for assessing deterioration of liver structure are also well known. Such methods include liver imaging (e.g., MRT, ultrasound), or histological evaluation of liver biopsy.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to treat or protect damage to liver tissues secondary to a burn. Methods for assessing liver function are well known in the art and include, but are not limited to, using blood tests for serum creatinine, or glomerular filtration rate. Methods for assessing deterioration of kidney structure are also well known. Such methods include kidney imaging (e.g., MRI, ultrasound), or histological evaluation of kidney biopsy.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered to prevent or treat hypermetabolism associated with a burn injury. A hypermetabolic state may be associated with hyperglycemia, protein loss, and a significant reduction of lean body mass. Reversal of the hypermetabolic response may be accomplished by administering an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and by manipulating the subject's physiologic and biochemical environment through the administration of specific nutrients, growth factors, or other agents. As demonstrated in the examples, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be administered to a subject suffering from a burn in order to treat or prevent hypermetabolism.

In one aspect, the disclosure provides method for preventing in a subject, a burn injury or a condition associated with a burn injury, by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$). MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be administered to a subject at risk of receiving burns. In prophylactic applications, pharmaceutical compositions or medicaments of MPPs are administered to a subject susceptible to, or otherwise at risk of a burn injury to eliminate or reduce the risk, lessen the severity of, or delay the onset of the burn injury and its complications.

Another aspect of the disclosure includes methods of treating burn injuries and associated complications in a subject for therapeutic purposes. In therapeutic applications, compositions or medicaments are administered to a subject already suffering from a burn injury in an amount sufficient to cure, or partially arrest, the symptoms of the injury, including its complications and intermediate pathological phenotypes in development of the disease. An MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be administered to a subject following a burn, but before the development of detectable symptoms of a systemic injury, such as organ dysfunction or failure, and thus the term "treatment" as used herein in its broadest sense and refers to a prophylactic use which completely or partially prevents systemic injury, such as organ dysfunction or failure or hypermetabolism following burns. As such, the disclosure provides methods of treating an individual afflicted with a burn injury.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can prevent or treat metabolic syndrome in mammalian subjects. In some cases, the metabolic syndrome may be due to a high-fat diet or, more generally, over-nutrition and lack of exercise. MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may reduce one or more signs or symptoms of metabolic syndrome, including, but not limited to, dyslipidemia, central obesity, blood fat disorders, and insulin resistance.

Without wishing to be bound by theory, it is thought that loss of mitochondrial integrity and insulin sensitivity stem from a common metabolic disturbance, i.e., oxidative stress. Over-nutrition, particularly from high-fat diets may increase mitochondrial reactive oxygen species (ROS) production and overall oxidative stress, leading to both acute and chronic mitochondrial dysfunction and the development of metabolic syndrome. MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) mitigates these effects, thereby improving mitochondrial function in various body tissues, and improving one or more of the risk factors associated with metabolic syndrome.

The present technology also relates to the reduction of the symptoms of metabolic syndrome by administration of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$).

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is useful to prevent or treat disease. Specifically, the disclosure provides for both prophylactic and therapeutic methods of treating a subject at risk of (or susceptible to) metabolic syndrome. Metabolic syndrome is generally associated with type II diabetes, coronary artery disease, renal dysfunction, atherosclerosis, obesity, dyslipidemia, and essential hypertension. Accordingly, the present methods provide for the prevention and/or treatment of metabolic syndrome or associated conditions in a subject by administering an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to a subject in need thereof. For example, a subject may be administered an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to improve one or more of the factors contributing to metabolic syndrome.

In one aspect, the technology may provide a method of treating or preventing the specific disorders associated with metabolic syndrome, such as obesity, diabetes, hypertension, and hyperlipidemia, in a mammal by administering an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$). In certain embodiments, the specific disorder may be obesity. In certain embodiments, the specific disorder may be dyslipidemia (i.e., hyperlipidemia).

In one embodiment, administration of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to a subject exhibiting one or more conditions associated with metabolic syndrome is anticipated to cause an improvement in one or more of those conditions. For instance, a subject may exhibit at least about 5%, at least about 10%, at least about 20%, or at least about 50% reduction in body weight compared to the subject prior to receiving the MPP composition. In one embodiment, a subject may exhibit at least about 5%, at least about 10%, at least about 20%, or at least about 50% reduction in HDL cholesterol and/or at least about 5%, at least about 10%, at least about 20%, or at least about 50% increase in LDL cholesterol compared to the subject prior to receiving the MPP composition. In one embodiment, a subject may exhibit at least about 5%, at least about 10%, at least about 20%, or at least about 50% reduction in some triglycerides. In one embodiment, a subject may exhibit at least about 5%, at least about 10%, at least about 20%, or at least about 50% improvement in oral glucose tolerance (OGTT). In some embodiments, the subject may show observable improvement in more than one condition associated with metabolic syndrome.

In one aspect, the invention may provide a method for preventing, in a subject, a disease or condition associated with metabolic syndrome in skeletal muscle tissues, by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) that modulates one or more signs or markers of metabolic syndrome, e.g., body weight, serum triglycerides or cholesterol, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity) or mitochondrial enzyme activity. The fasting glucose/insulin/free fatty acid, oral glucose tolerance (OGTT), cholesterol and triglyceride levels, etc. may be measured using standard clinical laboratory techniques well-known in the art.

Subjects at risk for metabolic syndrome can be identified by, e.g., any or a combination of diagnostic or prognostic assays as described herein. In prophylactic applications, pharmaceutical compositions or medicaments of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are administered to a subject susceptible to, or otherwise at risk for a disease or condition in an amount sufficient to eliminate or reduce the risk, lessen the severity of, or delay the onset of the disease, including biochemical, histologic and/or behavioral symptoms of the disease, its complications and intermediate pathological phenotypes presenting during development of the disease. Administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can occur prior to the manifestation of symptoms characteristic of the aberrancy, such that a disease or disorder is prevented or, alternatively, delayed in its progression. Depending upon the type of aberrancy, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$), which acts to enhance or improve mitochondrial function, can be used for treating the subject. The appropriate compound can be determined based on screening assays described herein.

Another aspect of the technology includes methods of reducing the symptoms associated with metabolic syndrome in a subject for therapeutic purposes. In therapeutic applications, compositions or medicaments are administered to a subject suspected of, or already suffering from such a disease in an amount sufficient to cure, or partially arrest, the symptoms of the disease, including its complications and intermediate pathological phenotypes in development of the disease. As such, the invention provides methods of treating an individual afflicted with metabolic syndrome or a metabolic syndrome-associated disease or disorder.

The present disclosure contemplates combination therapies of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) with one or more agents for the treatment of blood pressure, blood triglyceride levels, or high cholesterol. Treatment for metabolic syndrome, obesity, insulin resistance, high blood pressure, dyslipidemia, etc., can also include a variety of other approaches, including weight loss and exercise, and dietary changes. These dietary changes include: maintaining a diet that limits carbohydrates to 50 percent or less of total calories; eating foods defined as complex carbohydrates, such as whole grain bread (instead of white), brown rice (instead of white), sugars that are unrefined, increasing fiber consumption by eating legumes (for example, beans), whole grains, fruits and vegetables, reducing intake of red meats and poultry, consumption of "healthy" fats, such as those in olive oil, flaxseed oil and nuts, limiting alcohol intake, etc. In addition, treatment of blood pressure, and blood triglyceride levels can be controlled by a variety of available drugs (e.g., cholesterol modulating drugs), as can clotting disorders (e.g., via aspirin therapy) and in general, prothrombotic or proinflammatory states. If metabolic syndrome leads to diabetes, there are, of course, many treatments available for this disease.

The present technology relates to the treatment or prevention of an ophthalmic condition by administration of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$). Without wishing to be limited by theory, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may treat or prevent ophthalmic diseases or conditions by reducing the severity or occurrence of oxidative damage in the eye. In one embodiment, the ophthalmic condition is selected from the group consisting of: dry eye, diabetic retinopathy, cataracts, retinitis pigmentosa, glaucoma, macular degeneration, choroidal neovascularization, retinal degeneration, and oxygen-induced retinopathy.

It is anticipated that treatment with MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will reduce intracellular reactive oxygen species (ROS) in human retinal epithelial cells (HRECs).

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will prevent the mitochondrial potential loss of human retinal epithelial cells (HREC)s treated with high-glucose. The AWm of HRECs will be measured by flow cytometry after JC-1 fluorescent probe staining. It is anticipated that high glucose (30 mM) treatment will result in a rapid loss of mitochondrial membrane potential of the cultured HRECs. In contrast, it is anticipated that flow cytometric analysis will show that 30 mM glucose co-treated with an MPP composition will increased AWm compared with the high glucose alone group.

It is anticipated that increased expression of caspase-3 in HRECs treated with high glucose (HG) will be reduced by MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) treatment. Caspase-3 expression will be normalized to the expression of f3-actin. It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will increase the expression of Trx2 in the high glucose-treated HRECs.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will have no adverse effects on the viability of primary human retinal pigment epithelial (RPE) cells.

It is anticipated that MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) as described herein will be useful to prevent or treat disease. Specifically, the disclosure provides for both prophylactic and therapeutic methods of treating a subject at risk of (or susceptible to) an ophthalmic disease or condition. Accordingly, the present methods provide for the prevention and/or treatment of an ophthalmic condition in a subject by administering an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to a subject in need thereof. For example, a subject can be administered compositions comprising MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to improve one or more of the factors contributing to an ophthalmic disease or condition.

One aspect of the present technology includes methods of reducing an ophthalmic condition in a subject for therapeutic purposes. In therapeutic applications, compositions or medicaments are administered to a subject known to have or suspected of having a disease, in an amount sufficient to cure, or at partially arrest/reduce, the symptoms of the disease, including complications and intermediate pathological phenotypes in development of the disease. As such, the disclosure provides methods of treating an individual afflicted with an ophthalmic condition. In some embodiments, the technology provides a method of treating or preventing specific ophthalmic disorders, such as diabetic retinopathy, cataracts, retinitis pigmentosa, glaucoma, choroidal neovascularization, retinal degeneration, and oxygen-induced retinopathy, in a mammal by administering MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$).

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent diabetic retinopathy. Diabetic retinopathy is characterized by capillary microaneurysms and dot hemorrhaging. Thereafter, microvascular obstructions cause cotton wool patches to form on the retina. Moreover, retinal edema and/or hard exudates may form in individuals with diabetic retinopathy due to increased vascular hyperpermeability. Subsequently, neovascularization appears and retinal detachment is caused by traction of the connective tissue grown in the vitreous body. Iris rubeosis and neovascular glaucoma may also occur which, in turn, can lead to blindness. The symptoms of diabetic retinopathy include, but are not limited to, difficulty reading, blurred vision, sudden loss of vision in one eye, seeing rings around lights, seeing dark spots, and/or seeing flashing lights.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent cataracts. Cataracts are a congenital or acquired disease characterized by a reduction in natural lens clarity. Individuals with cataracts may exhibit one or more symptoms, including, but not limited to, cloudiness on the surface of the lens, cloudiness on the inside of the lens, and/or swelling of the lens. Typical examples of congenital cataract-associated diseases are pseudo-cataracts, membrane cataracts, coronary cataracts, lamellar cataracts, punctuate cataracts, and filamentary cataracts. Typical examples of acquired cataract-associated diseases are geriatric cataracts, secondary cataracts, browning cataracts, complicated cataracts, diabetic cataracts, and traumatic cataracts. Acquired cataracts are also inducible by electric shock, radiation, ultrasound, drugs, systemic diseases, and nutritional disorders. Acquired cataracts further includes postoperative cataracts.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent retinitis pigmentosa. Retinitis pigmentosa is a disorder that is characterized by rod and/or cone cell damage. The presence of dark lines in the retina is typical in individuals suffering from retinitis pigmentosa. Individuals with retinitis pigmentosa also present with a variety of symptoms including, but not limited to, headaches, numbness or tingling in the extremities, light flashes, and/or visual changes. See, e.g., Heckenlively, et al., *Am. J. Ophthalmol.* 105(5):504-511 (1988).

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent glaucoma. Glaucoma is a genetic disease characterized by an increase in intraocular pressure, which leads to a decrease in vision. Glaucoma may emanate from various ophthalmologic conditions that are already present in an individual, such as, wounds, surgery, and other structural malformations. Although glaucoma can occur at any age, it frequently develops in elderly individuals and leads to blindness. Glaucoma patients typically have an intraocular pressure in excess of 21 mm Hg. However, normal tension glaucoma, where glaucomatous alterations are found in the visual field and optic papilla, can occur in the absence of such increased intraocular pressures, i.e., greater than 21 mm Hg. Symptoms of glaucoma include, but are not limited to, blurred vision, severe eye pain, headache, seeing haloes around lights, nausea, and/or vomiting.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent macular degeneration. Macular degeneration is typically an age-related disease. The general categories of macular degeneration include wet, dry, and non-aged related macular degeneration. Dry macular degeneration, which accounts for about 80-90 percent of all cases, is also known as atrophic, nonexudative, or drusenoid macular degeneration. With dry macular degeneration, drusen typically accumulate beneath the retinal pigment epithelium tissue. Vision loss subsequently occurs when drusen interfere with the function of photoreceptors in the macula. Symptoms of dry macular generation include, but are not limited to, distorted vision, center-vision distortion, light or dark distortion, and/or changes in color perception. Dry macular degeneration can result in the gradual loss of vision.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent choroidal neovascularization. Choroidal neovascularization (CNV) is a disease characterized by the development of new blood vessels in the choroid layer of the eye. The newly formed blood vessels grow in the choroid, through the Bruch membrane, and invade the sub-retinal space. CNV can lead to the impairment of sight or complete loss of vision. Symptoms of CNV include, but are not limited to, seeing flickering, blinking lights, or gray spots in the affected eye or eyes, blurred vision, distorted vision, and/or loss of vision.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent retinal degeneration. Retinal degeneration is a genetic disease that relates to the break-down of the retina. Retinal tissue may degenerate for various reasons, such as, artery or vein occlusion, diabetic retinopathy, retinopathy of prematurity, and/or retrolental fibroplasia. Retinal degradation generally includes retinoschisis, lattice degeneration, and is related to progressive macular degeneration. The symptoms of retina degradation include, but are not limited to, impaired vision, loss of vision, night blindness, tunnel vision, loss of peripheral vision, retinal detachment, and/or light sensitivity.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject to treat or prevent oxygen-induced retinopathy. Oxygen-induced retinopathy (OIR) is a disease characterized by microvascular degeneration. OIR is an established model for studying retinopathy of prematurity. OIR is associated with vascular cell damage that culminates in abnormal neovascularization. Microvascular degeneration leads to ischemia which contributes to the physical changes associated with OIR. Oxidative stress also plays an important role in the development of OIR where endothelial cells are prone to peroxidative damage. Pericytes, smooth muscle cells, and perivascular astrocytes, however, are generally resistant to peroxidative injury. See, e.g., Beauchamp, et al., *J. Appl. Physiol.* 90:2279-2288 (2001). OIR, including retinopathy of prematurity, is generally asymptomatic. However, abnormal eye movements, crossed eyes, severe nearsightedness, and/or leukocoria, can be a sign of OIR or retinopathy of prematurity.

In one aspect, the present technology is anticipated to provide a method for preventing, an ophthalmic condition in a subject by administering to the subject an MPP, such as Cha-Arg-Cha-Lys-NH$_2$, and/or naturally or artificially occurring variants or analogues, or pharmaceutically acceptable or in combination with one or more active agents (e.g., an aromatic-cationic peptide such as D-Arg-2'6'-Dmt-Lys-Phe-NH$_2$) that modulates one or more signs or markers of an ophthalmic condition. Subjects at risk for an ophthalmic condition can be identified by, e.g., any or a combination of diagnostic or prognostic assays as described herein. In prophylactic applications, pharmaceutical compositions or medicaments of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are administered to a subject susceptible to, or otherwise at risk of a disease or condition in an amount sufficient to eliminate or reduce the risk, lessen the severity of, or delay the onset of the disease, including biochemical, histologic and/or behavioral symptoms of the disease, its complications and intermediate pathological phenotypes presenting during development of the disease. Administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can occur prior to the manifestation of symptoms characteristic of the aberrancy, such that a disease or disorder is prevented or, alternatively, delayed in its progression. Depending upon the type of aberrancy MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) act to enhance or improve mitochondrial function or reduce oxidative damage, and can be used for treating the subject. The appropriate compound can be determined based on screening assays described herein.

The MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) described herein are useful to prevent or treat disease. Specifically, the disclosure provides for both prophylactic and therapeutic methods of treating a subject having or at risk of (susceptible to) heart failure. Accordingly, the present methods provide for the prevention and/or treatment of heart failure in a subject by administering an effective amount of an MPP to a subject in need thereof. See Tsutsui, et al., *Antiox. Redox Sig.* 8(9):1737-1744 (2006). In particular embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used to treat or prevent heart failure by enhancing mitochondrial function in cardiac tissues.

One aspect of the technology includes methods of treating heart failure in a subject for therapeutic purposes. In therapeutic applications, compositions or medicaments are administered to a subject suspected of, or already suffering from such a disease in an amount sufficient to cure, or partially arrest, the symptoms of the disease, including its complications and intermediate pathological phenotypes in development of the disease. As such, the invention provides methods of treating an individual afflicted with heart failure.

Subjects suffering from heart failure can be identified by any or a combination of diagnostic or prognostic assays known in the art. For example, typical symptoms of heart failure include shortness of breath (dyspnea), fatigue, weakness, difficulty breathing when lying flat, and swelling of the legs, ankles, or abdomen (edema). The subject may also be suffering from other disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are: cardiomegaly (enlarged heart), tachypnea (rapid breathing; occurs in the case of left side failure) and hepatomegaly (enlarged liver; occurs in the case of right side failure). Acute myocardial infarction ("AMI") due to obstruction of a coronary artery is a common initiating event that can lead ultimately to heart failure. However, a subject that has AMI does not necessarily develop heart failure. Likewise, subjects that suffer from heart failure do not necessarily suffer from an AMI.

In one aspect, the present technology provides a method of treating hypertensive cardiomyopathy by administering an effective amount of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) to a subject in need thereof. As hypertensive cardiomyopathy worsens, it can lead to congestive heart failure. Subjects suffering from hypertensive cardiomyopathy can be identified by any or a combination of diagnostic or prognostic assays known in the art. For example, typical symptoms of hypertensive cardiomyopathy include hypertension (high blood pressure), cough, weakness, and fatigue. Additional symptoms of hypertensive cardiomyopathy include leg swelling, weight gain, difficulty breathing when lying flat, increasing shortness of breath with activity, and waking in the middle of the night short of breath.

In one aspect, the present technology provides a method for preventing heart failure in a subject by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) that prevents the initiation or progression of the infarction. Subjects at risk for heart failure can be identified by, e.g., any or a combination of diagnostic or prognostic assays as described herein. In prophylactic applications, pharmaceutical compositions or medicaments of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are administered to a subject susceptible to, or otherwise at risk of a disease or condition in an amount sufficient to eliminate or reduce the risk, lessen the severity of, or delay the onset of the disease, including biochemical, histologic and/or behavioral symptoms of the disease, its complications and intermediate pathological phenotypes presenting during development of the disease. It is anticipated that administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can occur prior to the manifestation of symptoms characteristic of the aberrancy, such that a disease or disorder is prevented or, alternatively, delayed in its progression. The appropriate compound can be determined based on screening assays described herein.

In various embodiments, suitable in vitro or in vivo assays will be performed to determine the effect of a specific MPP-based therapeutic (or variants, analogues, or pharmaceutically acceptable salts thereof) alone or in combination with one or more active agents (e.g., an aromatic-cationic peptide such as D-Arg-2'6'-Dmt-Lys-Phe-NH$_2$), and whether its administration is indicated for treatment. In various embodiments, in vitro assays can be performed with representative animal models, to determine if a given MPP-based therapeutic (or variants, analogues, or pharmaceutically acceptable salts thereof) alone or in combination with one or more active agents (e.g., an aromatic-cationic peptide such as D-Arg-2'6'-Dmt-Lys-Phe-NH$_2$) exerts the desired effect in preventing or treating heart failure. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

It is anticipated that MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) can act downstream of NAOPH oxidase and reduce activation of p38 MAPK and apoptosis in response to Ang II.

It is anticipated that worsening of myocardial performance index (MPI) in Gaq mice will be significantly ameliorated by MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$). It is anticipated that an increase in normalized heart weight in Gaq mice will be substantially prevented by MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$), and that increased normalized lung weight will be displayed as an effect from MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) treatment.

MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) described herein are predicted to be useful to prevent or treat disease. Specifically, the disclosure provides for both prophylactic and therapeutic methods of treating a subject at risk of (or susceptible to) vessel occlusion injury, ischemia-reperfusion injury, or cardiac ischemia-reperfusion injury. Accordingly, the present methods provide for the prevention and/or treatment of vessel occlusion injury, ischemia-reperfusion injury, or cardiac ischemia-reperfusion injury in a subject by administering an effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) to a subject in need thereof or of a subject having a coronary artery bypass graft (CABG) procedure.

In one aspect, the present technology provides a method for preventing, in a subject, vessel occlusion injury by administering to the subject an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) that prevents the initiation or progression of the condition. Subjects at risk for vessel occlusion injury can be identified by, e.g., any or a combination of diagnostic or prognostic assays as described herein. In prophylactic applications, pharmaceutical compositions or medicaments of MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) are administered to a subject susceptible to, or otherwise at risk of a disease or condition in an amount sufficient to eliminate or reduce the risk, lessen the severity of, or delay the onset of the disease, including biochemical, histologic and/or behavioral symptoms of the disease, its complications and intermediate pathological phenotypes presenting during development of the disease. Administration of a prophylactic MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) can occur prior to the manifestation of symptoms characteristic of the aberrancy, such that a disease or disorder is prevented or, alternatively, delayed in its progression. The appropriate compound can be determined based on screening assays described herein. In some embodiments, the peptides are administered in sufficient amounts to prevent renal or cerebral complications from CABG.

Another aspect of the present technology includes methods of treating vessel occlusion injury or ischemia-reperfusion injury in a subject. In therapeutic applications, compositions or medicaments are administered to a subject suspected of, or already suffering from such a disease in an amount sufficient to cure, or partially arrest, the symptoms of the disease, including its complications and intermediate pathological phenotypes in development of the disease. As such, the technology provides methods of treating an individual afflicted with ischemia-reperfusion injury or treating an individual afflicted with cardiac ischemia-reperfusion injury by administering an effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) and performing a CABG procedure.

The present technology also potentially relates to compositions and methods for the treatment or prevention of ischemia-reperfusion injury associated with acute myocardial infarction and organ transplantation in mammals. In general, the methods and compositions include one or more MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) or pharmaceutically acceptable salts thereof.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is used in methods for treating acute myocardial infarction injury in mammals.

In one embodiment, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is used in methods for ischemia and/or reperfusion injury mammals.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used in methods for the treatment, prevention or alleviation of symptoms of cyclosporine-induced nephrotoxicity injury mammals.

In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used in methods for performing revascularization procedures in mammals.

In one embodiment, the revascularization procedure is selected from the group consisting of: percutaneous coronary intervention; balloon angioplasty; insertion of a bypass graft; insertion of a stent; and directional coronary atherectomy. In some embodiments, the revascularization procedure comprises removal of the occlusion. In some embodiments, the revascularization procedure comprises administration of one or more thrombolytic agents. In some embodiments, the one or more thrombolytic agents are selected from the group consisting of: tissue plasminogen activator; urokinase; prourokinase; streptokinase; an acylated form of plasminogen; acylated form of plasmin; and acylated streptokinase-plasminogen complex.

In another aspect, the present disclosure provides a method of coronary revascularization comprising: (a) administering simultaneously, separately or sequentially an effective amount of (i) an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt and (ii) an additional active agent; and (b) performing a coronary artery bypass graft procedure on the subject. In some embodiments, the additional active agent comprises cyclosporine or a cyclosporine derivative or analogue.

In another aspect, the present disclosure provides a method of coronary revascularization comprising: (a) administering to a mammalian subject a therapeutically effective amount an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof; (b) administering to the subject a therapeutically effective amount of cyclosporine or a cyclosporine derivative or analogue; and (c) performing a coronary artery bypass graft procedure on the subject.

In one aspect, the invention provides a method for preventing, in a subject, acute myocardial infarction injury by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and cyclosporine that prevents the initiation or progression of the condition. In prophylactic applications, pharmaceutical compositions or medicaments of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and cyclosporine are administered to a subject susceptible to, or otherwise at risk of a disease or condition in an amount sufficient to eliminate or reduce the risk, lessen the severity of, or delay the onset of the disease, including biochemical, histologic and/or behavioral symptoms of the disease, its complications and intermediate pathological phenotypes presenting during development of the disease. Administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and cyclosporine can occur prior to the manifestation of symptoms characteristic of the aberrancy, such that a disease or disorder is prevented or, alternatively, delayed in its progression.

Treatment with an MPP, such as Cha-Arg-Cha-Lys-NH$_2$, and/or naturally or artificially occurring variants or analogues, or pharmaceutically acceptable salts thereof, such as acetate or trifluoroacetate, alone or in combination with one or more active agents (e.g., an aromatic-cationic peptide such as D-Arg-2'6'-Dmt-Lys-Phe-NH$_2$) disclosed herein, is anticipated to protect kidneys from acute renal injury (ARI). Another aspect of the technology includes methods of treating ischemia in any organ or tissue. For example, the methods relate to the treatment of a condition in which kidneys (or other organs) fail to receive adequate blood supply (ischemia). Ischemia is a major cause of acute renal injury (ARI). Ischemia of one or both kidneys is a common problem experienced during aortic surgery, renal transplantation, or during cardiovascular anesthesia. Surgical procedures involving clamping of the aorta and/or renal arteries, e.g., surgery for supra- and juxtarenal abdominal aortic aneurysms and renal transplantation, are also particularly liable to produce renal ischemia, leading to significant postoperative complications and early allograft rejection. In high-risk patients undergoing these surgeries, the incidence of renal dysfunction has been reported to be as high as 50%. The skilled artisan will understand that the above described causes of ischemia are not limited to the kidney, but may occur in other organs during surgical procedures. Accordingly, in some embodiments, such ischemia can be treated, prevented, ameliorated (e.g., the severity of ischemia is decreased) by the administration of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate or trifluoroacetate salt, and an active agent, such as cyclosporine or a derivative or analogue thereof.

Another aspect of the present technology includes methods for preventing or ameliorating cyclosporine-induced nephrotoxicity. For example, in some embodiments, a pharmaceutical composition or medicament comprising an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject presenting with or at risk of cyclosporine-induced nephrotoxicity. For example, in some embodiments, a subject receiving cyclosporine, e.g., as an immunosuppressant after an organ or tissue transplant, is also administered a therapeutically effective amount of an MPP, such as Cha- Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$). In some embodiments, the peptide is administered to the subject prior to organ or tissue transplant, during organ or tissue transplant and/or after an organ or tissue transplant. In some embodiments, the subject would receive a combination of an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and cyclosporine before, during and/or after an organ or tissue transplant. The composition or medicament including the MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and optionally, cyclosporine, would be administered in an amount sufficient to cure, or partially arrest, the symptoms of nephrotoxicity, including its complications and intermediate pathological phenotypes. For example, in some embodiments, the compositions or medicaments are administered in an amount sufficient to eliminate the risk of, reduce the risk of, lessen the severity of, or delay the onset of nephrotoxicity, including biochemical, histologic and/or behavioral symptoms of the condition, its complications and intermediate pathological phenotypes. Administration of prophylactic MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) and cyclosporine can occur prior to the manifestation of symptoms characteristic of the aberrancy, such that the condition is prevented or, alternatively, delayed in its progression. Typically, subjects who receive the peptide will have a healthier transplanted organ or tissue, and/or are able to maintain a higher and/or more consistent cyclosporine dosage or regimen for longer periods of time compared to subjects who do not receive the peptide. In some embodiments, patients receiving an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or pharmaceutically acceptable salt thereof such as an acetate salt or a trifluoroacetate salt, in conjunction with cyclosporine are able to tolerate longer and/or more consistent cyclosporine treatment regimens, and/or higher doses of cyclosporine. In some embodiments, patients receiving an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof such as an acetate salt or a trifluoroacetate salt, in conjunction with cyclosporine, will have an increased tolerance for cyclosporine as compared to a patient who is not receiving the peptide.

Treatment with an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is useful in decreasing islet cell apoptosis and enhance viability of islet cells after transplantation.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) described herein are useful in reducing oxidative damage in a mammal in need thereof. Mammals in need of reducing oxidative damage are those mammals suffering from a disease, condition or treatment associated with oxidative damage. Typically, tic oxidative damage is caused by free radicals, such as reactive oxygen species (ROS) and/or reactive nitrogen species (RNS). Examples of ROS and RNS include hydroxyl radical, superoxide anion radical, nitric oxide, hydrogen, hypochlorous acid (HOCl) and peroxynitrite anion. Oxidative damage is considered to be "reduced" if the amount of oxidative damage in a mammal, a removed organ, or a cell is decreased after administration of an effective amount of the MPPs described herein.

In some embodiments, a mammal to be treated can be a mammal with a disease or condition associated with oxidative damage. The oxidative damage can occur in any cell, tissue or organ of the mammal. In humans, oxidative stress is involved in many diseases. Examples include atherosclerosis, Parkinson's disease, heart failure, myocardial infarction, Alzheimer's disease, schizophrenia, bipolar disorder, fragile X syndrome, and chronic fatigue syndrome.

In one embodiment, a mammal may be undergoing a treatment associated with oxidative damage. For example, the mammal may be undergoing reperfusion. Reperfusion refers to the restoration of blood flow to any organ or tissue in which the flow of blood is decreased or blocked. The restoration of blood flow during reperfusion leads to respiratory burst and formation of free radicals.

In one embodiment, the mammal may have decreased or blocked blood flow due to hypoxia or ischemia. The loss or severe reduction in blood supply during hypoxia or ischemia may, for example, be due to thromboembolic stroke, coronary atherosclerosis, or peripheral vascular disease. Numerous organs and tissues are subject to ischemia or hypoxia. Examples of such organs include brain, heart, kidney, intestine and prostate. The tissue affected is typically muscle, such as cardiac, skeletal, or smooth muscle. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

The methods can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes, and microglia. The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid p-protein. Examples of chronic neurodegenerative diseases associated with damage by free radicals include Parkinson's disease, Alzheimer's disease, Huntington's disease and Amyotrophic Lateral Sclerosis (ALS).

Other conditions which can be treated include preeclampsia, diabetes, and symptoms of and conditions associated with aging, such as macular degeneration, wrinkles.

MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) described herein are useful in treating any disease or condition that is associated with mitochondria permeability transitioning (MPT). Such diseases and conditions include, but are not limited to, ischemia and/or reperfusion of a tissue or organ, hypoxia and any of a number of neurodegenerative diseases. Mammals in need of inhibiting or preventing of MPT are those mammals suffering from these diseases or conditions.

Accordingly, the present disclosure describes methods and compositions including mitochondria-targeted, antioxidant, MPPs capable of reducing mitochondrial ROS production in the diaphragm during prolonged MV, or in other skeletal muscles, e.g., soleus or plantaris muscle, during limb immobilization, or muscle disuse in general.

In one aspect, the present disclosure provides a mitochondria-targeted antioxidant, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate salt or trifluoroacetate salt. For example, in some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used as a therapeutic and/or a prophylactic agent in subjects suffering from, or at risk of suffering from muscle infirmities such as weakness, atrophy, dysfunction, etc. caused by mitochondrial derived ROS. In some embodiments, MPP (or variants, analogues, or pharmaceutically acceptable salts thereof) alone or in combination with one or more active agents (e.g., an aromatic-cationic peptide such as D-Arg-2'6'-Dmt-Lys-Phe-NH$_2$) is anticipated to decrease mitochondrial ROS production in muscle. Additionally or alternatively, in some embodiments it is anticipated that an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) will selectively concentrate in the mitochondria of skeletal muscle and provides radical scavenging of H$_2$O$_2$, OH—, and ONOO—, and in some embodiments, radical scavenging occurs on a dose-dependent basis.

In some embodiments, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is used in methods for treating muscle infirmities (e.g., weakness, atrophy, dysfunction, etc.). In such therapeutic applications, compositions or medicaments including MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate salt or trifluoroacetate salt, can be administered to a subject suspected of, or already suffering from, muscle infirmity, in an amount sufficient to prevent, reduce, alleviate, or partially arrest, the symptoms of muscle infirmity, including its complications and intermediate pathological phenotypes in development of the infirmity. As such, the invention provides methods of treating an individual afflicted, or suspected of suffering from muscle infirmities described herein. In one embodiment, an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate salt or trifluoroacetate salt, is administered.

In another aspect, the disclosure provides methods for preventing, or reducing the likelihood of muscle infirmity, as described herein, by administering to the subject an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) that prevents or reduces the likelihood of the initiation or progression of the infirmity. Subjects at risk for developing muscle infirmity can be readily identified, e.g., a subject preparing for or about to undergo MV or related diaphragmatic muscles disuse or any other skeletal muscle disuse that may be envisaged by a medical professional (e.g., casting a limb).

In prophylactic applications, a pharmaceutical composition or medicament comprising one or more MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate salt or trifluoroacetate salt, are administered to a subject susceptible to, or otherwise at risk of muscle infirmity in an amount sufficient to eliminate or reduce the risk, lessen the severity of, or delay the onset of muscle infirmity, including biochemical, histologic and/or behavioral symptoms of the infirmity, its complications and intermediate pathological phenotypes presenting during development of the infirmity. Administration of one or more of the MPPs, such as Cha-Arg-Cha-Lys-NH$_2$, and/or naturally or artificially occurring variants or analogues, or pharmaceutically acceptable salts thereof, alone or in combination with one or more active agents disclosed herein (e.g., an aromatic-cationic peptide such as D-Arg-2'6'-Dmt-Lys-Phe-NH$_2$) can occur prior to the manifestation of symptoms characteristic of the aberrancy, such that the disorder is prevented or, alternatively, delayed in its progression. The appropriate compound can be determined based on screening assays described herein or as well known in the art. In one embodiment, the pharmaceutical composition includes an MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) or a pharmaceutically acceptable salt thereof, such as acetate salt or trifluoroacetate salt.

In some embodiments, subjects in need of protection from or treatment of muscle infirmity also include subjects suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO.), superoxide anion radical ($O_2.^-$), nitric oxide (NO.), hydrogen peroxide ($H_2O_2$), hypochlorous acid (HOCl), and peroxynitrite anion ($ONOO^-$).

A composition comprising an MPP disclosed herein to treat or prevent muscle infirmity associated with muscle immobilization e.g., due to casting or other disuse can be administered at any time before, during or after the immobilization or disuse. For example, in some embodiments, one or more doses of a composition comprising an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) can be administered before muscle immobilization or disuse, immediately after muscle immobilization or disuse, during the course of muscle immobilization or disuse, and/or after muscle immobilization or disuse (e.g., after cast removal). By way of example, and not by way of limitation, in some embodiments, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered once per day, twice per day, three times per day, four times per day six times per day or more, for the duration of the immobilization or disuse. In other embodiments, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is administered daily, every other day, twice, three times, or for times per week, or once, twice three, four, five or six times per month for the duration of the immobilization or disuse.

In some embodiments, an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is used in methods to treat or prevent muscle infirmity due to muscle disuse or disuse atrophy, associated with loss of muscle mass and strength. Atrophy is a physiological process relating to the reabsorption and degradation of tissues, e.g., fibrous muscle tissue, which involves apoptosis at the cellular level. When atrophy occurs from loss of trophic support or other disease, it is known as pathological atrophy. Such atrophy or pathological atrophy may result from, or is related to, limb immobilization, prolonged limb immobilization, casting limb immobilization, mechanical ventilation (MV), prolonged MV, extended bed rest cachexia, congestive heart failure, liver disease, sarcopenia, wasting, poor nourishment, poor circulation, hormonal irregularities, loss of nerve function, and the like. Accordingly, the present methods relate to the prevention and/or treatment of muscle infirmities in a subject, including skeletal muscle atrophy, comprising administering an effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) or a pharmaceutically acceptable salt thereof, such as acetate salt or trifluoroacetate salt, to a subject in need thereof.

Additional examples of muscle infirmities which can be treated, prevented, or alleviated by administering the compositions and formulations disclosed herein include, without limitation, age-related muscle infirmities, muscle infirmities associated with prolonged bed rest, muscle infirmities such as weakness and atrophy associated with microgravity, as in space flight, muscle infirmities associated with effects of certain drugs (e.g., statins, antiretrovirals, and thiazolidinediones (TZDs)), and muscle infirmities such as cachexia, for example cachexia caused by cancer or other diseases.

In one aspect, the present technology relates to the treatment or prevention of an anatomic zone of no re-flow by administration of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) to a subject in need thereof. In one embodiment, administration of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) to a subject is done before the formation of the anatomic zone of no re-flow. In another embodiment, administration of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) to a subject is done after the formation of an anatomic zone of no re-flow. In one embodiment, the method is performed in conjunction with a revascularization procedure. Also provided is a method for the treatment or prevention of cardiac ischemia-reperfusion injury. Also provided is a method of treating a myocardial infarction in a subject to prevent injury to the heart upon reperfusion. In one aspect, the present technology relates to a method of coronary revascularization comprising administering to a mammalian subject a therapeutically effective amount of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) and performing a coronary artery bypass graft (CABG) procedure on the subject.

In one aspect, the invention provides a method for preventing an anatomic zone of no re-flow in a subject, comprising administering to the subject an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) that prevent the initiation or progression of the condition. Subjects at risk for an anatomic zone of no re-flow can be identified by, e.g., any or a combination of diagnostic or prognostic assays as described herein. In prophylactic applications, pharmaceutical compositions or medicaments of an MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) are administered to a subject susceptible to, or otherwise at risk of a disease or condition in an amount sufficient to eliminate or reduce the risk, lessen the severity of, or delay the onset of the disease or condition, including biochemical, histologic and/or behavioral symptoms of the disease or condition, its complications and intermediate pathological phenotypes presenting during development of the disease or condition. Administration of a prophylactic MPP, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) can occur prior to the manifestation of symptoms characteristic of the aberrancy, such that a disease or disorder is prevented or, alternatively, delayed in its progression.

Another aspect of the technology includes methods of treating vessel occlusion injury, an anatomic zone of no re-flow, or cardiac ischemia-reperfusion injury in a subject for therapeutic purposes. In therapeutic applications, compositions or medicaments are administered to a subject suspected of, or already suffering from such a disease or condition in an amount sufficient to cure, or partially arrest, the symptoms of the disease or condition, including its complications and intermediate pathological phenotypes in development of the disease or condition. As such, the invention provides methods of treating an individual afflicted with an anatomic zone of no re-flow.

IV. Peptide Synthesis

The peptides useful in the methods of the present disclosure (e.g., MPPs, variants, analogues, or pharmaceutically acceptable salts thereof and an aromatic-cationic peptide such as D-Arg-2'6'-Dmt-Lys-Phe-NH$_2$) may be synthesized by any method known in the art. Exemplary, non-limiting methods for chemically synthesizing the protein include those described by Stuart and Young in "Solid Phase Peptide Synthesis," Second Edition, Pierce Chemical Company (1984), and in "Solid Phase Peptide Synthesis," Methods Enzymol. 289, Academic Press, Inc, New York (1997).

V. Modes of Administration and Dosage

Any method known to those in the art for contacting a cell, organ or tissue with a peptide (e.g., an aromatic-cationic peptide such as D-Arg-2'6'-Dmt-Lys-Phe-NH$_2$) or pharmaceutically acceptable salt thereof, may be employed. Suitable methods include in vitro, ex vivo, or in vivo methods.

In vitro methods typically include cultured samples. For example, a cell can be placed in a reservoir (e.g., tissue culture plate), and incubated with a peptide under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the peptide under appropriate conditions. The contacted cells, organs or tissues are typically returned to the donor, placed in a recipient, or stored for future use. Thus, the peptide is generally in a pharmaceutically acceptable carrier.

In vivo methods typically include the administration of a peptide, such as those described herein, to a mammal such as a human. The peptides useful in the present methods are administered to a mammal in an amount effective in obtaining the desired result or treating the mammal. The effective amount is determined during pre-clinical trials and clinical trials by methods familiar to physicians and clinicians.

An effective amount of a peptide useful in the present methods, such as in a pharmaceutical composition, may be administered to a mammal in need thereof by any of a number of well-known methods for administering pharmaceutical compounds. The peptide may be administered systemically or locally.

In one embodiment, the peptide is administered intravenously. For example, MPPs (or variants, analogues, or pharmaceutically acceptable salts thereof) alone or in combination with one or more active agents (e.g., an aromatic-cationic peptide such as D-Arg-2'6'-Dmt-Lys-Phe-NH$_2$) may be administered via rapid intravenous bolus injection. In some embodiments, the peptide is administered as a constant-rate intravenous infusion.

The peptide may also be administered orally, topically, intranasally, intramuscularly, subcutaneously, or transdermally. In one embodiment, transdermal administration is by iontophoresis, in which the charged peptide is delivered across the skin by an electric current.

Other routes of administration include intracerebroventricularly or intrathecally. Intracerebroventricularly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system.

The peptides useful in the methods of the invention may also be administered to mammals by sustained release, as is known in the art. Sustained release administration is a method of drug delivery to achieve a certain level of the drug over a particular period of time. The level is typically measured by serum or plasma concentration. A description of methods for delivering a compound by controlled release can be found in international PCT Application No. WO 02/083106, which is incorporated herein by reference in its entirety.

Any formulation known in the art of pharmacy is suitable for administration of the MPP (or variants, analogues, or pharmaceutically acceptable salts thereof) alone or in combination with one or more active agents (e.g., an aromatic-cationic peptide such as D-Arg-2'6'-Dmt-Lys-Phe-NH$_2$) useful in the present methods. For oral administration, liquid or solid formulations may be used. Examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the peptide useful in the present methods may utilize conventional diluents, carriers, or excipients etc., such as those known in the art to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may comprise, for example, an amino acid, such as for instance, glycine; or an oligosaccharide, such as, sucrose, tetralose, lactose; or a dextran. Alternatively, the stabilizer may comprise a sugar alcohol, such as, mannitol.

In some embodiments, the stabilizer or combination of stabilizers constitutes from about 0.1% to about 10% weight for weight of the peptide.

In some embodiments, the surfactant is a nonionic surfactant, such as a polysorbate. Examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. In some embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

Formulations of the peptides useful in the present methods may additionally contain one or more conventional additives. Examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; an anesthetic agent such as for example a morphine derivative; and an isotonic agent etc., such as described herein. As a further precaution against oxidation or other spoilage, the pharmaceutical compositions may be stored under nitrogen gas in vials sealed with impermeable stoppers.

The mammal treated in accordance with the invention may be any mammal, including, for example, farm animals, such as sheep, pigs, cows, and horses; pet animals, such as dogs and cats; and laboratory animals, such as rats, mice and rabbits. In one embodiment, the mammal is a human.

In some embodiments, MPPs, such as Cha-Arg-Cha-Lys-NH$_2$, and/or naturally or artificially occurring variants or analogues, or pharmaceutically acceptable salts thereof, are administered to a mammal in an amount effective in reducing the number of mitochondria undergoing, or preventing, MPT. The effective amount is determined during pre-clinical trials and clinical trials by methods familiar to physicians and clinicians.

The peptide may be administered systemically or locally. In one embodiment, the peptide is administered intravenously. For example, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$), may be administered via rapid intravenous bolus injection. In one embodiment, the peptide is administered as a constant-rate intravenous infusion.

The peptide can be injected directly into a coronary artery during, for example, angioplasty or coronary bypass surgery, or applied onto coronary stents.

The dose and dosage regimen will depend upon the severity of disease, the characteristics of the particular MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) used, e.g., its therapeutic index, the characteristics of the subject, and the subject's medical history.

The peptides described herein (e.g., MPPs alone or in combination with an aromatic-cationic peptide such as D-Arg-2'6'-Dmt-Lys-Phe-NH$_2$) can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Routes of administration include, for example, parenteral (e.g., intravenous, intradermal, intraperitoneal or subcutaneous), oral, respiratory (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity, such as sodium chloride or dextrose. The pH can be adjusted with acids or bases, such as hydrochloric acid or sodium hydroxide. The preparation can be enclosed in ampoules, disposable syringes or multiple-dose vials made of glass or plastic. For convenience of the patient or treating physician, the dosing formulation can be provided in a kit containing all necessary equipment (e.g., vials of drug, vials of diluent, syringes and needles) for a course of treatment (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J., USA) or phosphate buffered saline (PBS). In all cases, a composition for parenteral administration must be sterile and should formulated for ease of syringeability. The composition should be stable under the conditions of manufacture and storage, and must be shielded from contamination by microorganisms such as bacteria and fungi.

MPP compositions may include a carrier, which can be a solvent or dispersion medium containing, for example, water, ethanol, polyol (for example, glycerol, propylene glycol, and liquid polyetheylene glycol, and the like), or suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included in the composition to prevent oxidation. In many cases, it is desirable to include isotonic agents, for example, sugars, polyalcohols such as mannitol, sorbitol, or sodium chloride. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials may be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic protein or peptide can be formulated in a carrier system. The carrier can be a colloidal system. The colloidal system can be a liposome, a phospholipid bilayer vehicle. In one embodiment, the therapeutic protein is encapsulated in a liposome while maintaining protein integrity. As one skilled in the art will appreciate, there are a variety of methods to prepare liposomes. (See Lichtenberg, et al., *Methods Biochem. Anal.* 33:337-462 (1988); Anselem, et al., *Liposome Technology, CRC Press* (1993)). Liposomal formulations can delay clearance and increase cellular uptake (See Reddy, *Ann. Pharmacother.* 34 (78):915-923 (2000)).

The carrier can also be a polymer, e.g., a biodegradable, biocompatible polymer matrix. In one embodiment, the therapeutic protein can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.* 34:915-923 (2000)). A polymer formulation for human growth hormone (hGH) has been used in clinical trials. (See Kozarich and Rich, *Chemical Biology* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation (Mountain View, Calif., USA) and Nova Pharmaceuticals, Inc. (Sydney, AU). Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art. See, e.g., Chonn and Cullis, *Curr. Opin. in Biotech.* 6:698-708 (1995); Weiner, *Immunometh.* 4(3):201-9 (1994); Gregoriadis, *Trends Biotechnol.* 13(12):527-37 (1995). Mizguchi, et al., *Cancer Lett.* 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) disclosed herein sufficient for achieving a therapeutic or prophylactic effect, range from about 0.000001 mg per kilogram body weight per day to about 10,000 mg per kilogram body weight per day. In some embodiments, the dosage ranges will be from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, MPP concentrations in a carrier range from 0.2 to 2000 micrograms per delivered milliliter. An exemplary treatment regimen entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is defined as a concentration of peptide at the target tissue of $10^{-11}$ to $10^{-6}$ molar, e.g., approximately 10-molar. This concentration may be delivered by systemic doses of 0.01 to 100 mg/kg or equivalent dose by body surface area. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

In some embodiments, the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to a subject in an amount effective to protect the subject from acute renal injury (ARI) or acute liver failure (ALF). Also, the peptides useful in the present methods may be administered to a subject in an amount effective in treating ARI or ALF.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with ARI or ALF. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the present methods, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be administered to a subject having one or more signs of ARI caused by a disease or condition. Administration of an effective amount of the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may improve at least one sign or symptom of ARI in the subject, e.g., metabolic acidosis (acidification of the blood), hyperkalaemia (elevated potassium levels), oliguria, or anuria (decrease or cessation of urine production), changes in body fluid balance, and effects on other organ systems. For example, a "therapeutically effective amount" of the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) means a level at which the physiological effects of acute renal failure will be kept at a minimum. Typically, the efficacy of the biological effect is measured in comparison to a subject or class of subjects not administered the peptides.

Any method known to those in the art for contacting a cell, organ or tissue with a peptide may be employed. Suitable methods include in vitro, ex vivo, or in vivo methods. In vivo methods typically include the administration of MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$), such as those described herein, to a mammal, such as a human. When used in vivo for therapy, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is administered to the subject in effective amounts (i.e., amounts that have desired therapeutic effect). Peptides will normally be administered parenteral, topically, or orally. The dose and dosage regimen will depend upon the type and severity of disease or injury, the characteristics of the particular MPP used, and any aromatic-cationic peptides such as D-Arg-2'6'-Dmt-Lys-Phe-NH$_2$ e.g., its therapeutic index, the characteristics of the subject, and the subject's medical history.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regimen). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic, and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic, and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, acetate, trifluoroacetate, and the like.

In some embodiments, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) is provided at a "low," "mid," or "high" dose level. In some embodiments, the low dose is from about 0.001 to about 0.5 mg/kg/h, or from about 0.01 to about 0.1 mg/kg/h. In some embodiments, the mid-dose is from about 0.1 to about 1.0 mg/kg/h, or from about 0.1 to about 0.5 mg/kg/h. In some embodiments, the high dose is from about 0.5 to about 10 mg/kg/h, or from about 0.5 to about 2 mg/kg/h.

In some embodiments, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) described herein (or a pharmaceutically acceptable salt, ester, amide, prodrug, or solvate) is administered in combination with another therapeutic agent. By way of example, a patient receiving MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) who experiences inflammation may be co-administered an anti-inflammatory agent. By way of example, the therapeutic effectiveness of the compounds described herein may be enhanced by co-administration of an adjuvant. By way of example, the therapeutic benefit to a patient may be increased by administering the compounds described herein in combination with another therapeutic agent known or suspected to aid in the prevention or treatment of a particular condition.

Non-limiting examples of combination therapies include use of one or more MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) together with nitric oxide (NO) inducers, statins, negatively charged phospholipids, antioxidants, minerals, anti-inflammatory agents, anti-angiogenic agents, matrix metalloproteinase inhibitors, or carotenoids. In some embodiments, agents used in combination with compositions described herein may fall within multiple categories (for example, lutein is both an antioxidant and a carotenoid). Further, the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be administered with additional agents that may provide benefit to the patient, including by way of example only cyclosporin A.

In addition, the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may also be used in combination with procedures that may provide additional or synergistic benefit to the patient, including, for example, extracorporeal rheopheresis (membrane differential filtration), implantable miniature telescopes, laser photocoagulation of drusen, and microstimulation therapy.

The use of antioxidants has been shown to benefit patients with macular degenerations and dystrophies. See, e.g., *Arch. Ophthalmol.* 119:1417-36 (2001); Sparrow, et al., *J. Biol. Chem.* 278:18207-13 (2003). Non-limiting examples of antioxidants suitable for use in combination with at least one MPP include vitamin C, vitamin E, beta-carotene and other carotenoids, coenzyme Q, 4-hydroxy-2,2,6,6-tetramethylpiperidineN-oxyl (Tempol), lutein, butylated hydroxytoluene, resveratrol, a trolox analogue (PNU-83836-E), and bilberry extract.

The use of certain minerals has also been shown to benefit patients with macular degenerations and dystrophies. See, e.g., Arch. Ophthalmol., 119:1417-36 (2001). Non-limiting examples of minerals for use in combination with at least one MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) include copper-containing minerals (e.g., cupric oxide), zinc-containing minerals (e.g., zinc oxide), and selenium-containing compounds.

The use of certain negatively-charged phospholipids has also been shown to benefit patients with macular degenerations and dystrophies. See, e.g., Shaban & Richter, Biol., Chem. 383:537-45 (2002); Shaban, et al., Exp. Eye Res. 75:99-108 (2002). Non-limiting examples of negatively charged phospholipids suitable for use in combination with at least one MPP include cardiolipin and phosphatidylglycerol. Positively-charged and/or neutral phospholipids may also provide benefit for patients with macular degenerations and dystrophies when used in combination with MPPs.

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring species have been identified. Carotenoids include hydrocarbons (carotenes) and their oxygenated, alcoholic derivatives (xanthophylls). They include actinioerythrol, astaxanthin, canthaxanthin, capsanthin, capsorubin, p-8'-apocarotenal (apo-carotenal), p-12'-apo-carotenal, a-carotene, p-carotene, "carotene" (a mixture of a- and p-carotenes), y-carotenes, p-cyrptoxanthin, lutein, lycopene, violerythrin, zeaxanthin, and esters of hydroxyl- or carboxyl-containing members. Many of the carotenoids occur in nature as cis- and trans-isomeric forms, while synthetic compounds frequently exist as racemic mixtures.

In humans, the retina selectively accumulates mainly two carotenoids: zeaxanthin and lutein. These two carotenoids are thought to aid in protecting the retina because they are powerful antioxidants and absorb blue light. Studies with quails have established that animals raised on carotenoid-deficient diets develop retinas with low concentrations of zeaxanthin and suffer severe light damage, as evidenced by a very high number of apoptotic photoreceptor cells. By contrast, animals raised on high-carotenoid diets develop retinas with high zeaxanthin concentrations that sustain minimal light damage. Non-limiting examples of carotenoids suitable for use in combination with at least one MPP, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) include lutein and zeaxanthin, as well as any of the aforementioned carotenoids.

Nitric oxide inducers include compounds that stimulate endogenous NO or elevate levels of endogenous endothelium-derived relaxing factor (EDRF) in vivo, or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide or a closely related derivative thereof (Palmer, et al., Nature 327:524-526 (1987); Ignarro, et al., Proc. Natl. Acad. Sci. 84:9265-9269 (1987)).

Statins serve as lipid-lowering agents and/or suitable nitric oxide inducers. In addition, a relationship has been demonstrated between statin use and delayed onset or development of macular degeneration. G. McGwin, et al., Br. J. Ophthalmol. 87:1121-25 (2003). Statins can thus provide benefit to a patient suffering from an ophthalmic condition (such as the macular degenerations and dystrophies, and the retinal dystrophies) when administered in combination with MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$). Suitable statins include, by way of example only, rosuvastatin, pitivastatin, simvastatin, pravastatin, cerivastatin, mevastatin, vclostatin, fluvastatin, compactin, lovastatin, dalvastatin, fluindostatin, atorvastatin, atorvastatin calcium (which is the hemicalcium salt of atorvastatin), and dihydrocompactin.

Suitable anti-inflammatory agents for use in combination with MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) include, by way of example only, aspirin and other salicylates, cromolyn, nedocromil, theophylline, zileuton, zafirlukast, montelukast, pranlukast, indomethacin, lipoxygenase inhibitors, non-steroidal anti-inflammatory drugs (NSAIDs) (e.g., ibuprofen and naproxin), prednisone, dexamethasone, cyclooxygenase inhibitors (i.e., COX-1 and/or COX-2 inhibitors such as Naproxen™, and Celebrex™), statins (e.g., rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (hemicalcium salt of atorvastatin), dihydrocompactin), and disassociated steroids.

Matrix metalloproteinase (MMP) inhibitors may also be administered in combination with compositions described herein for the treatment of ophthalmic conditions or symptoms associated with macular or retinal degeneration. MMPs are known to hydrolyze most components of the extracellular matrix. These proteinases play a central role in many biological processes such as normal tissue remodeling, embryogenesis, wound healing, and angiogenesis. However, high levels of MMPs are associated with many disease states, including macular degeneration. Many MMPs have been identified, most of which are multi-domain zinc endopeptidases. A number of metalloproteinase inhibitors are known (see, e.g., Whittaker, et al., Chem. Rev. 99(9):2735-2776 (1999)). Representative examples of MMP inhibitors include tissue inhibitors of metalloproteinases (TIMPs) (e.g., TIMP-1, TIMP-2, TIMP-3, TIMP-4), α-2-macroglobulin, tetracyclines (e.g., tetracycline, minocycline, doxycycline), hydroxamates (e.g., BATIMASTAT™, MARIMISTAT™ and TROCADE™), chelators (e.g., EDTA, cysteine, acetylcysteine, D-penicillamine, gold salts), synthetic MMP fragments, succinyl mercaptopurines, phosphonamidates, and hydroxaminic acids. Non-limiting examples of MMP inhibitors suitable for use in combination with compositions described herein include any of the aforementioned inhibitors.

The use of anti-angiogenic or anti-VEGF drugs has also been shown to provide benefit for patients with macular degenerations and dystrophies. Examples of suitable anti-angiogenic or anti-VEGF drugs for use in combination with at least one MPP include rhufab V2 (Luccntis™), rrypto-phanyl-tRNA synthetase (TrpRS), eye001 (anti-VEGF pegylated aptamer), squalamine, Retaane™ (anecortave acetate for depot suspension), combretastatin A4 prodrug (CA4P), Macugen™, Mifeprex™ (mifepristone-ru486), subtenon triamcinolone acetonide, intravitreal crystalline triamcinolone acetonide, prinomastat (AG3340), fluocinolone acetonide (including fluocinolone intraocular implant), VEGFR inhibitors, and VEGF-Trap.

Other pharmaceutical therapies that have been used to relieve visual impairment can be used in combination with at least one MPP. Such treatments include but are not limited to agents such as Visudyne™ with use of a non-thermal laser, PKC 412, endovion, neurotrophic factors (e.g., glial derived neurotrophic factor, ciliary neurotrophic factor), diatazem, dorzolamide, phototrop, 9-cis-retinal, eye medication (including Echo Therapy) including phospholine iodide or echothiophate or carbonic anhydrase inhibitors, AE-941, Sima-027, pegaptanib, neurotrophins (e.g., NT-4/5), cand5, ranibizumab, INS-37217, integrin antagonists, EG-3306, BDM-E, thalidomide, cardiotrophin-1,2-methoxyestradiol, DL8234, NTC-200, tetrathiomolybdate, LYN-002, microalgal compound, D-9120, ATX-S10, TGF-beta 2, tyrosine kinase inhibitors, NX-278-L, Opt-24, retinal cell ganglion neuroprotectants, N-nitropyrazole derivatives, KP-I02, and cyclosporin A.

Multiple therapeutic agents may be administered in any order or simultaneously. If simultaneously, the agents may be provided in a single, unified form, or in multiple forms (i.e. as a single solution or as two separate solutions). One of the therapeutic agents may be given in multiple doses, or both may be given as multiple doses. If not simultaneous, the timing between the multiple doses may vary from more than zero weeks to less than about four weeks, less than about six weeks, less than about 2 months, less than about 4 months, less than about 6 months, or less than about one year. In addition, the combination methods, compositions, and formulations are not limited to the use of only two agents. By way of example, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be provided with at least one antioxidant and at least one negatively charged phospholipid. By way of example, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be provided with at least one antioxidant and at least one inducer of nitric oxide production. By way of example, MPPs, such as Cha-Arg-Cha-Lys-NH$_2$, and/or naturally or artificially occurring variants or analogues, or pharmaceu-tically acceptable salts thereof, alone or in combination with one or more active agents (e.g., an aromatic-cationic peptide such as D-Arg-2'6'-Dmt-Lys-Phe-NH$_2$) may be provided with at least one inducer of nitric oxide productions and at least one negatively charged phospholipid.

In addition, MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) may be used in combination with procedures that may provide additional or synergistic benefits to the patient. For example, procedures known, proposed, or considered to relieve visual impairment include but are not limited to "limited retinal translocation," photodynamic therapy (e.g., receptor-targeted PDT, porfimer sodium for injection with PDT, verteporfin, rostaporfin with PDT, talaporfin sodium with PDT, motexafin lutetium), antisense oligonucleotides (e.g., products ofNovagali Pharma SA, ISIS-13650), laser photocoagulation, drusen lasering, macular hole surgery, macular translocation surgery, implantable miniature telescopes, phi-motion angiography (micro-laser therapy and feeder vessel treatment), proton beam therapy, microstimulation therapy, retinal detachment and vitreous surgery, scleral buckle, submacular surgery, transpupillary thermotherapy, photo-system I therapy, use of RNA interference (RNAi), extracorporeal rheopheresis (membrane differential filtration and rheotherapy), microchip implantation, stem cell therapy, gene replacement therapy, ribozyme gene therapy (including gene therapy for hypoxia response element, LENTIPAC™, PDEF gene therapy), photoreceptor/retinal cell transplantation (including transplantable retinal epithelial cells, retinal cell transplant), and acupuncture.

Further combinations that may be used to benefit an individual include using genetic testing to determine whether that individual is a carrier of a mutant gene that is known to be correlated with certain ophthalmic conditions. By way of example only, defects in the human ABCA4 gene are thought to be associated with five distinct retinal phenotypes including Stargardt disease, cone-rod dystrophy, age-related macular degeneration and retinitis pigmentosa. See e.g., Allikmets, et al., *Science* 277:1805-07 (1997); Lewis, et al., *Am. J. Hum. Genet.* 64:422-34 (1999); Stone, et al., *Nature Genetics* 20:328-29 (1998); Allikmets, *Am. J Hum. Gen.* 67:793-799 (2000); Klevering, et al., *Ophthalmology* 11 1:546-553 (2004). In addition, an autosomal dominant form of Stargardt Disease is caused by mutations in the ELOV4 gene. See Karan, et al., *Proc. Natl. Acad. Sci.* (2005). Patients possessing any of these mutations are expected to benefit from the therapeutic and/or prophylactic methods described herein.

In some embodiments, the MPPs, such as Cha-Arg-Cha-Lys-NH$_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-NH$_2$) are combined with one or more additional agents for the prevention or treatment of heart failure. Drug treatment for heart failure typically involves diuretics, angiotensin-converting-enzyme (ACE) inhibitors, digoxin (digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of heart failure. Typical doses of ACE inhibitors include captopril at 2550 mg/day and quinapril at 10 mg/day.

In one embodiment, MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is combined with an adrenergic beta-2 agonist. An "adrenergic beta-2 agonist" refers to adrenergic beta-2 agonists and analogues and derivatives thereof, including, for example, natural or synthetic functional variants which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having heart failure. Commonly known adrenergic beta-2 agonists include, but are not limited to, clenbuterol, albuterol, formeoterol, levalbuterol, metaproterenol, pirbuterol, salmeterol, and terbutaline.

In one embodiment, MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta receptors. Commonly known adrenergic beta-1 antagonists include, but are not limited to, acebutolol, atenolol, betaxolol, bisoprolol, esmolol, and metoprolol.

Clenbuterol, for example, is available under numerous brand names including Spiropent, Broncodil®, Broneoterol®, Cesbron, and Clenbuter. Similarly, methods of preparing adrenergic beta-1 antagonists such as metoprolol and their analogues and derivatives are well-known in the art. Metoprolol, in particular, is commercially available under the brand names Lopressor® (metoprolol tartate) manufactured by Novartis Pharmaceuticals Corporation (East Hanover, N.J., USA). Generic versions of Lopressor® are also available from Mylan Laboratories Inc. (Canonsburg, Pa., USA); and Watson Pharmaceuticals, Inc. (Morristown, N.J., USA). Metoprolol is also commercially available under the brand name Toprol XL®, manufactured by Astra Zeneca, LP (London, G.B.).

In one embodiment, an additional therapeutic agent is administered to a subject in combination with MPPs, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$), such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. Therefore, lower doses of one or both of the therapeutic agents may be used in treating a particular condition, resulting in increased therapeutic efficacy and decreased side-effects.

In one embodiment, the subject is administered a composition described herein prior to ischemia. In one embodiment, the subject is administered the composition prior to the reperfusion of ischemic tissue. In one embodiment, the subject is administered the composition at about the time of reperfusion of ischemic tissue. In one embodiment, the subject is administered the composition after reperfusion of ischemic tissue.

In one embodiment, the subject is administered a composition described herein prior to the CABG or revascularization procedure. In another embodiment, the subject is administered the composition after the CABG or revascularization procedure. In another embodiment, the subject is administered the composition during and after the CABG or revascularization procedure. In another embodiment, the subject is administered the composition continuously before, during, and after the CABG or revascularization procedure.

In one embodiment, the subject is administered a composition described herein starting at least 5 minutes, at least 10 minutes, at least 30 minutes, at least 1 hour, at least 3 hours, at least 5 hours, at least 8 hours, at least 12 hours, or at least 24 hours prior to CABG or revascularization, i.e., reperfusion of ischemic tissue. In one embodiment, the subject is administered the peptide from about 5-30 minutes, from about 10-60 minutes, from about 10-90 minutes, or from about 10-120 minutes prior to the CABG or revascularization procedure. In one embodiment, the subject is administered the peptide until about 5-30 minutes, until about 10-60 minutes, until about 10-90 minutes, until about 10-120 minutes, or until about 10-180 minutes after the CABG or revascularization procedure.

In one embodiment, the subject is administered the composition for at least 30 min, at least 1 hour, at least 3 hours, at least 5 hours, at least 8 hours, at least 12 hours, or at least 24 hours after the CABG procedure or revascularization procedure, i.e., reperfusion of ischemic tissue. In one embodiment, the composition is administered until about 30 minutes, about 1 hour, about 2 hours, about 3 hours, about 4 hours, about 5 hours, about 8 hours, about 12 hours, or about 24 hours after the CABG procedure or revascularization procedure i.e., reperfusion of ischemic tissue.

In one embodiment, the subject is administered the peptide composition as an IV infusion starting at about 1 minute to 30 minutes prior to reperfusion (i.e. about 5 minutes, about 10 minutes, about 20 minutes, or about 30 minutes prior to reperfusion) and continuing for about 1 hour to about 24 hours after reperfusion (i.e., about 1 hour, about 2 hours, about 3 hours, about 4 hours, etc. after reperfusion). In one embodiment, the subject receives an IV bolus injection prior to reperfusion of the tissue. In one embodiment, the subject continues to receive the composition chronically after the reperfusion period, i.e., for about 1-7 days, about 1-14 days, or about 1-30 days after the reperfusion period. During this period, the composition may be administered by any route, e.g., subcutaneously or intravenously.

In one embodiment, the peptide composition is administered by a systemic intravenous infusion commencing about 5-60 minutes, about 10-45 minutes, or about 30 minutes before the induction of anesthesia. In one embodiment, the peptide composition is administered in conjunction with a cardioplegic solution. In one embodiment, the peptide is administered as part of the priming solution in a heart lung machine during cardiopulmonary bypass.

In various embodiments, the subject is suffering from a myocardial infarction, a stroke, or is in need of angioplasty. In one embodiment, a revascularization procedure is selected from the group consisting of balloon angioplasty, insertion of a stent, percutaneous coronary intervention (PCI), percutaneous transluminal coronary angioplasty, or directional coronary atherectomy. In one embodiment, the revascularization procedure comprises the removal of the occlusion. In one embodiment, the revascularization procedure comprises the administration of one or more thrombolytic agents. In one embodiment, the one or more thrombolytic agents is selected from the group consisting of: tissue plasminogen activator, urokinase, prourokinase, streptokinase, acylated form of plasminogen, acylated form of plasmin, and acylated streptokinase-plasminogen complex.

In one embodiment the vessel occlusion comprises a cardiac vessel occlusion. In another embodiment, the vessel occlusion is an intracranial vessel occlusion. In yet other embodiments, the vessel occlusion is selected from the group consisting of: deep venous thrombosis; peripheral thrombosis; embolic thrombosis; hepatic vein thrombosis; sinus thrombosis: venous thrombosis; an occluded arteriovenal shunt; and an occluded catheter device.

In one aspect, the present technology relates to the treatment of atherosclerotic vascular disease (ARVD) comprising administering to a subject in need thereof therapeutically effective amounts of MPPs, such as Cha-Arg-Cha-Lys-NH$_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-NH$_2$ or any one or more of the peptides shown in Section II and/or Table 1). In some embodiments, the treatment is chronic treatment, administered for a period of greater than 1 week.

In another aspect, the present technology relates to the treatment or prevention of ischemic injury in the absence of tissue reperfusion. For example, peptides may be administered to patients experiencing acute ischemia in one or more tissues or organs who, for example, are not suitable candidates for revascularization procedures or for whom revascularization procedures are not readily available. Additionally or alternatively, the peptides may be administered to patients with chronic ischemia in one or more tissues in order to forestall the need for a revascularization procedure. Patients administered peptides for the treatment or prevention of ischemic injury in the absence of tissue reperfusion may additionally be administered peptides prior to, during, and subsequent to revascularization procedures according to the methods described herein.

In one embodiment, the treatment of renal reperfusion injury includes increasing the amount or area of tissue perfusion in a subject compared to a similar subject not administered the peptide. In one embodiment, the prevention of renal reperfusion injury includes reducing the amount or area of microvascular damage caused by reperfusion in a subject compared to a similar subject not administered the peptide. In some embodiments, treatment or prevention of renal reperfusion injury includes reducing injury to the affected vessel upon reperfusion, reducing the effect of plugging by blood cells, and/or reducing endothelial cell swelling in a subject compared to a similar subject not administered the peptide. The extent of the prevention or treatment can be measured by any technique known in the art, including but not limited to measurement of renal volume, renal arterial pressure, renal blood flow (RBF), and glomerular filtration rate (GFR), as well as by imaging techniques known in the art, including, but not limited to CT and micro-CT. Successful prevention or treatment can be determined by comparing the extent of renal reperfusion injury in the subject observed by any of these imaging techniques compared to a control subject or a population of control subjects that are not administered the peptide.

In one embodiment, the administration of the peptide(s) to a subject is before the occurrence of renal reperfusion injury. For example, in some embodiments, the peptide is administered to inhibit, prevent or treat ischemic injury in a subject in need thereof, and/or to forestall reperfusion treatment and/or alleviate or ameliorate reperfusion injury. Additionally or alternatively, in some embodiments, the administration of the peptide(s) to a subject is after the occurrence of renal reperfusion injury. In one embodiment, the method is performed in conjunction with a revascularization procedure. In one embodiment, the revascularization procedure is percutaneous transluminal renal angioplasty (PTRA). In one aspect, the present technology relates to a method of renal revascularization comprising administering to a mammalian subject a therapeutically effective amount of the aromatic cationic peptide and performing PTRA on the subject.

In one embodiment, the subject is administered a peptide such as D-Arg-2',6'-Dmt-Lys-Phe-NH$_2$, or pharmaceutically acceptable salts thereof, such as acetate salt or trifluoroacetate salt, prior to a revascularization procedure. In another embodiment, the subject is administered the peptide after the revascularization procedure. In another embodiment, the subject is administered the peptide during and after the revascularization procedure. In yet another embodiment, the subject is administered the peptide continuously before, during, and after the revascularization procedure. In another embodiment, the subject is administered the peptide regularly (i.e., chronically) following renal artery stenosis and/or a renal revascularization procedure.

In some embodiments, the subject is administered the peptide after the revascularization procedure. In one embodiment, the subject is administered the peptide for at least 3 hours, at least 5 hours, at least 8 hours, at least 12 hours, or at least 24 hours after the revascularization procedure. In some embodiments, the subject is administered the peptide prior to the revascularization procedure. In one embodiment, the subject is administered the peptide starting at least 8 hours, at least 4 hours, at least 2 hours, at least 1 hour, or at least 10 minutes prior to the revascularization procedure. In one embodiment, the subject is administered for at least one week, at least one month or at least one year after the revascularization procedure. In some embodiments, the subject is administered the peptide prior to and after the revascularization procedure. In some embodiments, the subject is administered the peptide as an infusion over a specified period of time. In some embodiments, the peptide is administered to the subject as a bolus.

In some embodiments, the present methods comprise administration of peptide in conjunction with one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

MPP Analogs

In some aspects, the present disclosure provides MPPs, such as Cha-Arg-Cha-Lys-NH$_2$, and/or naturally or artificially occurring variants or analogues, or pharmaceutically acceptable salts thereof, in combination with one or more active agents. In some embodiments, the active agents include any one or more of the aromatic-cationic peptides shown in Section II and/or Table 1. In some embodiments, the aromatic-cationic peptide is D-Arg-2' 6'-Dmt-Lys-Phe-NH$_2$.

In some embodiments, the MPPs are modified so as to increase resistance to enzymatic degradation. One way of stabilizing peptides against enzymatic degradation is the replacement of an L-amino acid with a D-amino acid at the peptide bond undergoing cleavage. MPP analogs are prepared containing one or more D-amino acid residues in addition to the D-Arg residue already present. Another way to prevent enzymatic degradation is N-methylation of the α-amino group at one or more amino acid residues of the peptides. This will prevent peptide bond cleavage by any peptidase. Examples include: H-D-Arg-Dmt-Lys(N$^\alpha$Me)-Phe-NH$_2$; H-D-Arg-Dmt-Lys-Phe(NMe)-NH$_2$; H-D-Arg-Dmt-Lys(N$^\alpha$Me)-Phe(NMe)-NH$_2$; and H-D-Arg(N$^\alpha$Me)-Dmt(NMe)-Lys(N$^\alpha$Me)-Phe(NMe)-NH$_2$. N$^\alpha$-methylated analogues have lower hydrogen bonding capacity and can be expected to have improved intestinal permeability. In some embodiments, MPPs are modified by N-methylation of the α-amino group at one or more amino acid residues of the peptide.

An alternative way to stabilize a peptide amide bond (—CO—NH—) against enzymatic degradation is its replacement with a reduced amide bond (Ψ[CH$_2$—NH]). This can be achieved with a reductive alkylation reaction between a Boc-amino acid-aldehyde and the amino group of the N-terminal amino acid residue of the growing peptide chain in solid-phase peptide synthesis. The reduced peptide bond is predicted to result in improved cellular permeability because of reduced hydrogen-bonding capacity. Examples include: H-D-Arg-Ψ[CH$_2$—NH]Dmt-Lys-Phe-NH$_2$, H-D-Arg-Dmt-Ψ[CH$_2$—NH]Lys-Phe-NH$_2$, H-D-Arg-Dmt-LysΨ[CH$_2$—NH]Phe-NH$_2$, H-D-Arg-Dmt-Ψ[CH$_2$—NH]Lys-Ψ[CH$_2$—NH]Phe-NH$_2$, etc. In some embodiments, MPPs are modified to include a reduced amide bond (Ψ[CH$_2$—NH]).

Stabilized MPP analogs may be screened for stability in plasma, simulated gastric fluid (SGF) and simulated intestinal fluid (SIF). An amount of peptide is added to 10 ml of SGF with pepsin (Cole-Palmer) or SIF with pancreatin (Cole-Palmer), mixed and incubated for 0, 30, 60, 90 and 120 min. The samples are analyzed by HPLC following solid-phase extraction. New analogs that are stable in both SGF and SIF are then be evaluated for their distribution across the Caco-2 monolayer. Analogs with apparent permeability coefficient determined to be >10$^{-6}$ cm/s (predictable of good intestinal absorption) will then have their activity in reducing mitochondrial oxidative stress determined in cell cultures. Mitochondrial ROS is quantified by FACS using MitoSox for superoxide, and HyPer-mito (a genetically encoded fluorescent indicator targeted to mitochondria for sensing H$_2$O$_2$). Mitochondrial oxidative stressors can include t-butylhydroperoxide, antimycin and angiotensin. MPP analogs that satisfy all these criteria can then undergo large-scale synthesis.

It is predicted that the proposed strategies will produce an MPP analog that would have oral bioavailability. The Caco-2 model is regarded as a good predictor of intestinal absorption by the drug industry.

VI. Formulations

In some aspects, the present disclosure provide pharmaceutical formulations for the delivery of MPPs, such as Cha-Arg-Cha-Lys-NH$_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-NH$_2$ or any one or more of the peptides shown in Section II and/or Table 1).

In one aspect, the present technology relates to a finished pharmaceutical product adapted for oral delivery of MPPs, the product comprising: (a) a therapeutically effective amount of the active peptide; (b) at least one pharmaceutically acceptable pH-lowering agent; and (c) at least one absorption enhancer effective to promote bioavailability of the active agent, wherein the pH-lowering agent is present in the finished pharmaceutical product in a quantity which, if the product were added to 10 milliliters of 0.1M aqueous sodium bicarbonate solution, would be sufficient to lower the pH of the solution to no higher than 5.5, and wherein an outer surface of the product is substantially free of an acid-resistant protective vehicle.

In some embodiments, the pH-lowering agent is present in a quantity which, if the product were added to 10 milliliters of 0.1M sodium bicarbonate solution, would be sufficient to lower the pH of the solution to no higher than 3.5. In some embodiments, the absorption enhancer is an absorbable or biodegradable surface active agent. In some embodiments, the surface active agent is selected from the group consisting of acylcarnitines, phospholipids, bile acids and sucrose esters. In some embodiments, the absorption enhancer is a surface active agent selected from the group consisting of: (a) an anionic agent that is a cholesterol derivative, (b) a mixture of a negative charge neutralizer and an anionic surface active agent, (c) non-ionic surface active agents, and (d) cationic surface active agents.

In some embodiments, the finished pharmaceutical product further comprises an amount of a second peptide that is not a physiologically active peptide effective to enhance bioavailability of the MPP. In some embodiments, the finished pharmaceutical product comprises at least one pH-lowering agent with a solubility in water of at least 30 grams per 100 milliliters of water at room temperature. In some embodiments, the finished pharmaceutical product comprises granules containing a pharmaceutical binder and, uniformly dispersed in the binder, the pH-lowering agent, the absorption enhancer and the MPP.

In some embodiments, the finished pharmaceutical product comprises a lamination having a first layer comprising the at least one pharmaceutically acceptable pH-lowering agent and a second layer comprising the therapeutically effective amount of the active peptide; the product further comprising the at least one absorption enhancer effective to promote bioavailability of the active agent, wherein the first and second layers are united with each other, but the at least one pH-lowering agent and the peptide are substantially separated within the lamination such that less than about 0.1% of the peptide contacts the pH-lowering agent to prevent substantial mixing between the first layer material and the second layer material and thus to avoid interaction in the lamination between the pH-lowering agent and the peptide.

In some embodiments, the finished pharmaceutical product comprises a pH-lowering agent selected from the group consisting of citric acid, tartaric acid and an acid salt of an amino acid. In some embodiments, the pH-lowering agent is selected from the group consisting of dicarboxylic acids and tricarboxylic acids. In some embodiments, the pH-lowering agent is present in an amount not less than 300 milligrams.

VII. Pain Management/Analgesia

In one aspect, the present disclosure provides a method for stimulating a mu-opioid receptor in a mammal in need thereof. The method comprises administering systemically to the mammal an effective amount of MPPs, such as Cha-Arg-Cha-Lys-$NH_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-$NH_2$ or any one or more of the peptides shown in Section II and/or Table 1). In one embodiment, the method comprises inhibiting norepinephrine in the mammal.

The term "peripheral neuropathy" refers generally to damage to nerves of the peripheral nervous system. The term encompasses neuropathy of various etiologies, including but not limited to acquired neuropathies, hereditary neuropathies, and idiopathic neuropathies. Illustrative acquired neuropathies include but are not limited to neuropathies caused by, resulting from, or otherwise associated with trauma, metabolic/endocrine disorders (e.g., diabetes), inflammatory diseases, infectious diseases, vitamin deficiencies, malignant diseases, and toxicity, such as alcohol, organic metal, heavy metal, radiation, and drug toxicity. As used herein, the "peripheral neuropathy" encompasses motor, sensory, mixed sensorimotor, chronic, and acute neuropathy. As used herein the term encompasses mononeuropathy, multiple mononeuropathy, and polyneuropathy.

Drug toxicity causes multiple forms of peripheral neuropathy, with the most common being axonal degeneration. A notable exception is that of perhexiline, a prophylactic anti-anginal agent that can cause segmental demyelination, a localized degeneration of the insulating layer around some nerves.

Peripheral neuropathies usually present sensory symptoms initially, and often progress to motor disorders. Most drug-induced peripheral neuropathies are purely sensory or mixed sensorimotor defects. A notable exception here is that of Dapzone, which causes an almost exclusively motor neuropathy.

Drug-induced peripheral neuropathy, including, for example, chemotherapy-induced peripheral neuropathy can cause a variety of dose-limiting neuropathic conditions, including 1) myalgias, 2) painful burning paresthesis, 3) glove-and-stocking sensory neuropathy, and 4) hyperalgia and allodynia. Hyperalgia refers to hypersensitivity and pain caused by stimuli that is normally only mildly painful or irritating. Allodynia refers to hypersensitivity and pain caused by stimuli that is normally not painful or irritating.

The term "hyperalgesia" refers to an increased sensitivity to pain, which may be caused by damage to nociceptors or peripheral nerves (i.e. neuropathy). The term refers to temporary and permanent hyperalgesia, and encompasses both primary hyperalgesia (i.e. pain sensitivity occurring directly in damaged tissues) and secondary hyperalgesia (i.e. pain sensitivity occurring in undamaged tissues surrounding damaged tissues). The term encompasses hyperalgesia caused by peripheral neuropathy, including but not limited to neuropathy caused by, resulting from, or associated with genetic disorders, metabolic/endocrine complications, inflammatory diseases, vitamin deficiencies, malignant diseases, and toxicity, such as alcohol, organic metal, heavy metal, radiation, and drug toxicity. In some embodiments hyperalgesia is caused by drug-induced peripheral neuropathy.

In some embodiments, the present disclosure provides compositions for the treatment or prevention of hyperalgesia. In some embodiments, the hyperalgesia is drug-induced. In some embodiments, the hyperalgesia is induced by a chemotherapeutic agent. In some embodiments, the chemotherapeutic agent is a vinca alkaloid. In some embodiments, the vinca alkaloid is vincristine.

A wide variety of pharmaceuticals are known to cause drug-induced neuropathy, including but not limited to anti-microbials, anti-neoplastic agents, cardiovascular drugs, hypnotics and psychotropics, anti-rheumatics, and anti-convulsants.

Illustrative anti-microbials known to cause neuropathy include but are not limited to isoniazid, ethambutol, ethionamide, nitrofurantoin, metronidazole, ciprofloxacin, chloramphenicol, thiamphenicol, diamines, colistin, streptomycin, nalidixic acid, clioquinol, sulphonamides, amphotericin, penicillin.

Illustrative anti-neoplastic agents known to cause neuropathy include but are not limited to procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, and thioguanine. Vinca alkaloids, such as vincristine, are known to be particularly neurotoxic.

Illustrative cardiovascular drugs known to cause neuropathy include but are not limited to propranolol, perhexiline, hydrallazine, amiodarone, disopyramide, and clofibrate.

Illustrative hypnotics and psychotropics known to cause neuropathy include but are not limited to phenelzine, thalidomide, methaqualone, glutethimide, amitriptyline, and imipramine.

Illustrative anti-rheumatics known to cause neuropathy include but are not limited to gold, indomethacin, colchicine, chloroquine, and phenyl butazone.

Illustrative anti-convulsants known to cause neuropathy include but are not limited to phenytoin.

Other drugs known to cause neuropathy include but are not limited to calcium carbimide, sulfoxone, ergotamine, propylthiouracil, sulthaime, chlorpropamide, methysergide, phenytoin, disulfiram, carbutamide, tolbutamide, methimazole, dapsone, and anti-coagulants.

The present disclosure contemplates combination therapies comprising the administration of MPPs, such as Cha-Arg-Cha-Lys-$NH_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-$NH_2$ or any one or more of the peptides shown in Section II and/or Table 1) with one or more additional therapeutic regimens. In some embodiments, the additional therapeutic regimens are directed to the treatment or prevention of neuropathy or hyperalgesia or symptoms associated with neuropathy or hyperalgesia. In some embodiments, the additional therapeutic regimens are directed to the treatment or prevention of diseases or conditions unrelated to neuropathy or hyperalgesia. In some embodiments, the additional therapeutic regimens include regimens directed to the treatment or prevention of neuropathy or hyperalgesia or symptoms associated with neuropathy or hyperalgesia, in addition to diseases, conditions, or symptoms unrelated to neuropathy or hyperalgesia or symptoms associated with neuropathy or hyperalgesia. In some embodiments, the additional therapeutic regimens comprise administration of one or more drugs, including but not limited to anti-microbials, anti-neoplastic agents, cardiovascular drugs, hypnotics and psychotropics, anti-rheumatics, and anti-convulsants. In embodiments, the additional therapeutic regimens comprise non-pharmaceutical therapies, including but not limited to dietary and lifestyle management.

In one aspect, the present disclosure provides a method for inhibiting or suppressing pain in a subject in need thereof, comprising administering to the subject an effective amount of MPPs, such as Cha-Arg-Cha-Lys-NH$_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-NH$_2$ or any one or more of the peptides shown in Section II and/or Table 1). In some embodiments, the MPP suppresses pain throught the binding and inhibition of mu-opioid receptors.

EXAMPLES

The following examples demonstrate select embodiments described herein. It is to be understood that compositions including MPPs, such as Cha-Arg-Cha-Lys-NH$_2$, and/or naturally or artificially occurring variants or analogues, or pharmaceutically acceptable salts thereof, in combination with one or more active agents (e.g., an aromatic-cationic peptide such as D-Arg-2'6'-Dmt-Lys-Phe-NH$_2$ or any one or more of the peptides shown in Section II and/or Table 1) could also be used according to the examples to achieve the same or similar results.

Example 1: MPP-Mediated Suppression of Oxidized Low-Density Lipoprotein (oxLDL)-Induced CD36 Expression and Foam Cell Formation in Mouse Peritoneal Macrophages Atherosclerosis is thought to develop as a result of lipid uptake by vascular-wall macrophages leading to the development of foam cells and the elaboration of cytokines and chemokines resulting in smooth muscle-cell proliferation. CD36 is a scavenger receptor that mediates uptake of oxLDL into macrophages and subsequent foam-cell development. CD36 knockout mice showed reduced uptake of oxLDL and reduced atherosclerosis. CD36 expression is regulated at the transcriptional level by various cellular stimuli, including glucose and oxLDL.

Macrophages are harvested from mice peritoneal cavity cultured overnight in the absence or presence of oxLDL (50 μg/ml) for 48 hours. Incubation with oxLDL is anticipated to significantly increase CD36 mRNA. Inclusion of MPPs (e.g., 10 nM or 1 μM) alone or in combination with aromatic-cationic peptides to the culture medium is anticipated to abolish the up-regulation of CD36.

Expression of CD36 protein, as determined by western blot, is also anticipated to significantly increase after a 48 hour incubation with 25 μg/ml of oxLDL (oxLDL) when compared to vehicle control (V). Other controls will include CD36 expression from mouse heart (H) and macrophages obtained from CD36 knockout mice (KO). The amount of CD36 protein will be normalized to β-actin. Incubation with MPPs (e.g., 1 μM) alone or in combination with aromatic-cationic peptides is anticipated to significantly reduce CD36 protein levels compared to macrophages exposed to vehicle control (V). Concurrent incubation with MPPs (1 μM) alone or in combination with aromatic-cationic peptides is anticipated to also significantly inhibit the up-regulation of CD36 protein levels in macrophages exposed to 25 μg/ml oxLDL for 48 hours (oxLDL/S).

Incubation of macrophages with oxLDL for 48 hours is also anticipated to increase foam cell formation. Foam cell will be visualized by oil red O, which stains lipid droplets red. Inclusion of MPPs (1 μM) alone or in combination with aromatic-cationic peptides is anticipated to prevent oxLDL-induced foam cell formation.

Incubation of macrophages with oxLDL is anticipated to increase the percentage of apoptotic cells. Concurrent treatment with MPPs (1 nM) alone or in combination with aromatic-cationic peptides is anticipated to significantly reduce the percentage of apoptotic cells induced by oxLDL.

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for treating or preventing atherosclerosis in mammalian subjects.

Example 2: MPP-Mediated Protection from the Effects of Acute Cerebral Ischemia Cerebral ischemia initiates a cascade of cellular and molecular events that lead to brain damage. One such event is post-ischemic inflammation. Using a mouse model of cerebral ischemia-reperfusion (20 minute occlusion of the middle cerebral artery), it has been found that CD36 is up-regulated in microglia and macrophages in the post-ischemic brain, with increased reactive oxygen species production. CD36 knockout mice have a profound reduction in reactive oxygen species after ischemia and improved neurological function compared to wild type mice.

Cerebral ischemia will be induced by occlusion of the right middle cerebral artery for 30 min. Wild-type (WT) mice will be given either saline vehicle (Veh) (i.p., n=9) or MPPs alone or in combination with aromatic-cationic peptides (2 mg/kg or 5 mg/kg, i.p., n=6) at 0, 6, 24 and 48 hours after ischemia. Mice will be sacrificed 3 days after ischemia. Brains will be frozen, sectioned, and stained using Nissl stain. Infarct volume and hemispheric swelling will be determined using an image analyzer. Data will be analyzed by one-way ANOVA with posthoc analysis.

It is anticipated that treatment of wild type mice with MPPs alone or in combination with aromatic-cationic peptides (2 mg/kg or 5 mg/kg, i.p., n=6) at 0, 6, 24 and 48 hours after a 30 minute occlusion of the middle cerebral artery will result in a significant reduction in infarct volume and hemispheric swelling compared to saline controls. It has previously been shown that thirty minutes of cerebral ischemia in WT mice results in significant depletion in reduced glutathione (GSH) in the ipsilateral cortex and striatum compared to the contralateral side in vehicle-treated animals. The depletion of GSH in the ipsilateral cortex is anticipated to significantly be reduced when the mice are treated with MPPs alone or in combination with aromatic-cationic peptides (2 mg/kg i.p. at 0, 6, 24 and 48 hours).

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for treating or preventing the effects of acute cerebral ischemia in mammalian subjects.

Example 3: MPPs Protect Against CD36-Mediated Acute Cerebral Ischemia

CD36 knockout (CD36 KO) mice will be subjected to acute cerebral ischemia as described in Example 2. CD36 KO mice will be given either saline vehicle (Veh) (i.p., n=5) or MPPs alone or in combination with aromatic-cationic peptides (2 mg/kg, i.p. n=5) at 0, 6, 24 and 48 hours following a 30 minute period of ischemia. Infarct volume and hemispheric swelling in CD36 KO mice are expected to be similar in subjects receiving saline and MPPs. It is expected that treatment of CD36 KO mice with MPPs alone or in combination with aromatic-cationic peptides (2 mg/kg, i.p., n=5) will fail to further prevent GSH depletion in the ipsilateral cortex caused by the ischemia. The data will show that the protective action of MPPs alone or in combination with aromatic-cationic peptides in acute cerebral ischemia is a function of inhibition of CD36 up-regulation.

These results will show that MPPs of the present technology or pharmaceutically acceptable salts thereof, such as acetate, tartrate, or trifluoroacetate salts, alone or in combination with aromatic-cationic peptides, are useful in methods for preventing or treating the effects of CD36-mediated acute cerebral ischemia in mammalian subjects.

Example 4: MPP-Mediated Suppression of CD36 Expression in Post-Ischemic Brain

Transient occlusion of the middle cerebral artery has been shown to significantly increase the expression of CD36 mRNA in microglia and macrophages in the post-ischemic brain. Wild-type mice will be given saline vehicle (Veh, i.p., n=6) or MPPs alone or in combination with aromatic-cationic peptides (5 mg/kg, i.p., n=6) at 0 and 6 hours after a 30 minute period of ischemia. Levels of CD36 mRNA in post-ischemic brain will be determined using real time PCR. It is anticipated that CD36 expression will be up-regulated as much as 6-fold in the ipsilateral brain compared to the contralateral brain of mice receiving saline, with CD36 mRNA significantly reduced in the ipsilateral brain of mice receiving MPPs either alone or in combination with aromatic-cationic peptides.

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for suppressing CD36 expression in post-ischemic brain in mammalian subjects.

Example 5: MPP-Mediated Suppression CD36 Up-Regulation in Renal Tubular Cells Following Unilateral Ureteral Obstruction Unilateral ureteral obstruction (UUO) is a common clinical disorder associated with tubular cell apoptosis, macrophage infiltration, and interstitial fibrosis. Interstitial fibrosis leads to a hypoxic environment and contributes to progressive decline in renal function despite surgical correction. CD36 has been shown to be expressed in renal tubular cells.

UUO will be induced in Sprague-Dawley rats. The rats will be treated with saline (i.p., n=6) or MPPs alone or in combination with aromatic-cationic peptides (1 mg/kg i.p., n=6) one day prior to induction of UUO, and once daily for 14 days after UUO induction. Rats will be sacrificed and the kidneys removed, embedded in paraffin, and sectioned. The sections will be treated with an anti-CD36 polyclonal IgG (Santa Cruz, sc-9154; diluted 1:100 with blocking serum) at room temperature for 1.5 hours. The slides will then be incubated with the second antibody conjugated with biotin (anti-rabbit IgG-B 1; ABC kit, PK-6101) at room temperature for 30 min. The slides will then be treated with avidin, developed with DAB and counterstained with 10% hematoxylin. The contralateral unobstructed kidney will serve as the control for each animal.

It is anticipated that UUO will result in tubular dilation and significant increase in expression of CD36 in the tubular cells of saline-treated subjects. Tubular dilation is also anticipated in rats treated with MPPs. But it is anticipated that treatment with MPPs alone or in combination with aromatic-cationic peptides will result in a significant reduction in CD36 expression.

To demonstrate that MPPs reduce lipid peroxidation in kidney after UUO, rats will be treated with either saline (n=6) or MPPs alone or in combination with aromatic-cationic peptides (1 mg/kg i.p., n=6) one day prior to induction of UUO, and once daily for 14 days after UUO. Rats will then be sacrificed, kidneys removed, embedded in paraffin and sectioned. Slides will be incubated with anti-HNE rabbit IgG and a biotin-linked anti-rabbit IgG will be used as secondary antibody. The slides will be developed with DAB. Lipid peroxidation, which is increased by UUO, is anticipated to be reduced by treatment with MPPs either alone or in combination with aromatic-cationic peptides. It is anticipated that HNE stain (brown) will be significantly increased in tubular cells in the obstructed kidney compared to the contralateral control. It is anticipated that obstructed kidneys from rats treated with MPPs alone or in combination with aromatic-cationic peptides will show significantly less HNE stain compared to saline-treated rats.

To demonstrate that MPPs reduce tubular cell apoptosis in obstructed kidney after UUO, rats will be treated with either saline (n=6) or MPPs alone or in combination with aromatic-cationic peptides (1 mg/kg i.p., n=6) one day prior to induction of UUO, and once daily for 14 days after UUO. Rats will then be sacrificed, kidneys removed, embedded in paraffin and sectioned. To quantify nuclei with fragmented DNA, TUNEL assay will be performed with in situ TUNEL kit. Slides will be developed with DAB and counterstained with 10% hematoxylin. The up-regulation of CD36 in saline-treated controls associated with tubular cell apoptosis is anticipated to be significantly inhibited by treatment with MPPs alone or in combination with aromatic-cationic peptides. It is anticipated that there will be a significant increase in apoptotic cells observed in the obstructed kidney from saline-treated animals when compared to the contralateral unobstructed control. The number of apoptotic cells is anticipated to be significantly reduced in obstructed kidney from animals treated with MPPs alone or in combination with aromatic-cationic peptides.

Macrophage infiltration and interstitial fibrosis are anticipated to be prevented by treatment with MPPs alone or in combination with aromatic-cationic peptides. Rats will be treated with either saline (n=6) or MPPs alone or in combination with aromatic-cationic peptides (1 mg/kg i.p., n=6)

one day prior to induction of UUO, and once daily for 14 days after UUO. Rats will then be sacrificed, the kidneys removed, embedded in paraffin and sectioned. Slides will be treated with monoclonal antibody for ED1 macrophage (1:75; Serotec). Horseradish peroxidase-linked rabbit anti-mouse secondary antibody (Dako) will be used for macrophage detection. Sections will then be counterstained with 10% hematoxylin. The number of macrophages in the obstructed kidney in saline-treated rats is anticipated to be significantly increased compared to the contralateral unobstructed control. Macrophage infiltration is anticipated to be significantly reduced in rats treated with MPPs alone or in combination with aromatic-cationic peptides.

Rats will be treated with either saline (11=6) or MPPs alone or in combination with aromatic-cationic peptides (1 mg/kg i.p., n=6) one day prior to induction of UUO, and once daily for 14 days after UUO. Rats will then be sacrificed, kidneys removed, embedded in paraffin and sectioned. Slides will be stained with hematoxylin and eosin and Masson's trichrome for interstitial fibrosis (blue stain). It is anticipated that obstructed kidneys from saline-treated rats will show increased fibrosis compared to the contralateral unobstructed control, while obstructed kidneys from rats treated with MPPs alone or in combination with aromatic-cationic peptides will show significantly less fibrosis.

It is further anticipated that treatment with the MPP along with the aromatic-cationic peptide will show a synergistic effect.

These results will show that MPPs alone or in combination with aromatic-cationic peptides suppress the up-regulation of CD36 in renal tubular cells induced by UUO. These results will further show that MPPs of the present technology or pharmaceutically acceptable salts thereof, such as acetate, tartrate, or trifluoroacetate salts, are useful in methods for suppressing the up-regulation of CD36 in renal tubular cells induced by UUO in mammalian subjects.

Example 6: MPP-Mediated Suppression of CD36 Up-Regulation in Isolated Hearts Upon Reperfusion after Prolonged Cold Ischemic Storage Organ transplantation requires hypothermic storage of the isolated organ for transport to the recipient. Currently, cardiac transplantation is limited by the short time of cold ischemic storage that can be tolerated before coronary blood flow is severely compromised (<4 hours). The expression of CD36 in coronary endothelium and cardiac muscles is up-regulated in isolated hearts subjected to prolonged cold ischemic storage and warm reperfusion.

Isolated guinea pig hearts will be perfused with St. Thomas solution alone or St. Thomas solution containing 1-100 nM MPPs alone or in combination with aromatic-cationic peptides, for 3 minutes and then stored in the same solution at 4° C. for 18 hours. After ischemic storage, hearts will be re-perfused with 34° C. Krebs-Henseleit solution for 90 min. Hearts freshly isolated from guinea pigs will be used as controls.

The hearts will be fixed in paraffin and sliced for immunostaining with an anti-CD36 rabbit polyclonal antibody. It is anticipated that the sections from a representative heart stored in St. Thomas solution for 18 hours at 4° C. will show increased CD36 staining compared to controls. CD36 staining is anticipated to be significantly reduced in hearts stored with 1-100 nM MPPs (either alone or in combination with aromatic-cationic peptides) in St. Thomas solution for 18 hours.

It is also anticipated that there will be a decrease in lipid peroxidation in the hearts treated with MPPs alone or in combination with aromatic-cationic peptides. Guinea pig hearts will be perfused with a cardioplegic solution (St. Thomas solution) alone or St. Thomas solution containing 1-100 nM MPPs alone or in combination with aromatic-cationic peptides for 3 minutes and then subjected to 18 hours of cold ischemia (4° C.). The hearts will be then re-perfused with Krebs Henseleit buffer at 34° C. for 90 minutes. Immunohistochemical analysis of 4-hydroxynonenol (HNE)-modified proteins in paraffin sections from tissue slices will be performed by incubation with an anti-HNE antibody (Santa Cruz) and a fluorescent secondary antibody. HNE staining is anticipated to significantly increase in hearts subjected to 18 hours of cold storage in St. Thomas solution compared to non-ischemic hearts. HNE staining is anticipated to be reduced in hearts stored in MPPs, either alone or in combination with aromatic-cationic peptides compared to controls.

Further, it is anticipated that MPPs alone or in combination with aromatic-cationic peptides will dramatically reduce endothelial apoptosis. Guinea pig hearts will be perfused with St. Thomas solution alone or St. Thomas solution containing 1-100 nM MPPs (alone or in combination with aromatic-cationic peptides) for 3 minutes and then subjected to 18 hours of cold ischemia (4° C.). The hearts will then be re-perfused with Krebs-Henseleit buffer at 34° C. for 90 min. After deparaffinization, sections will be incubated with deoxynucleotidyl transferase (Tdt) with digoxigenin-dNTP for 1 hour. The reaction will be stopped with terminating buffer. A fluorescent anti-digoxigenin antibody will then be applied.

It is anticipated that hearts subjected to 18 hours of cold storage in St. Thomas solution will show prominent endothelial apoptosis, whereas no endothelial apoptosis will be observed in non-ischemic control hearts. It is anticipated that apoptotic cells will not be observed in hearts stored in MPPs alone or in combination with aromatic-cationic peptides. It is anticipated that a significant improvement of coronary blood flow after prolonged cold ischemic storage and warm reperfusion will occur when hearts are preserved in MPPs alone or in combination with aromatic-cationic peptides.

It is further anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for suppressing CD36 up-regulation in isolated organs upon reperfusion following prolonged cold ischemic storage.

Example 7: MPP-Mediated Prevention of Renal Damage in Diabetic Mice

CD36 expression is up-regulated in a variety of tissues of diabetic patients, including monocytes, heart, kidneys, and blood. High glucose is known to up-regulate the expression of CD36 by improving the translational efficiency of CD36 mRNA. Diabetic nephropathy is a common complication of type 1 and type 2 diabetes, and is associated with tubular epithelial degeneration and interstitial fibrosis. CD36 has been identified as a mediator of tubular epithelial apoptosis in diabetic nephropathy. High glucose stimulates CD36 expression and apoptosis in proximal tubular epithelial cells.

Streptozotocin (STZ) will be used to induce diabetes in mice. Four groups of CD-1 mice will be studied: Group I—no STZ treatment; Group II—STZ (50 mg/kg, i.p.) will be given once daily for 5 days; Group III—STZ (50 mg/kg, i.p.) will be given once daily for 5 days, and MPPs (3 mg/kg, i.p.) will be given once daily for 16 days; Group IV—STZ (50 mg/kg, i.p.) will be given once daily for 5 days, and MPPs along with aromatic-cationic peptides (3 mg/kg, i.p.) will be given once daily for 16 days. It is anticipated that STZ treatment will result in a progressive increase in blood glucose. Animals will be sacrificed after 3 weeks and kidney tissues preserved for histopathology. Kidney sections will be examined by Periodic Schiff (PAS) staining for renal tubular brush border.

It is anticipated that STZ treatment will cause a dramatic loss of brush border in proximal tubules of the renal cortex, with tubular epithelial cells showing small condensed nuclei. It is anticipated that daily treatment with MPPs alone or in combination with aromatic-cationic peptides (3 mg/kg, i.p.) will prevent the loss of brush border in the STZ-treated mice, and the tubular epithelial nuclei will appear normal.

It is anticipated that STZ treatment will induce significant apoptosis in tubular epithelial cells. Kidney sections will be examined for apoptosis using a TUNEL assay as described above. It is anticipated that kidney sections from mice treated with STZ will show a large number of apoptotic nuclei in the proximal tubules, compared to non-treated controls. It is anticipated that treatment with MPPs alone or in combination with aromatic-cationic peptides will dramatically reduce apoptotic cells in the proximal tubule CD36 expression in proximal tubular epithelial cells. It is anticipated that by reducing CD36 expression, MPPs alone or in combination with aromatic-cationic peptides will inhibit tubular cell apoptosis and the loss of brush border in mice treated with STZ, without affecting blood glucose levels.

It is further anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for treating or preventing renal damage in diabetic mammals.

Example 8: Penetration of Cell Membranes by MPPs

The cellular uptake of [$^3$H]MPPs will be studied using Caco-2 cells (human intestinal epithelial cells), and confirmed using SH-SY5Y (human neuroblastoma), HEK293 (human embryonic kidney) and CRFK (kidney epithelial) cells. Monolayers of cells will be cultured in 12-well plates ($5 \times 10^5$ cells/well) coated with collagen for 3 days. On day 4, the cells will be washed twice with pre-warmed HBSS, and incubated with 0.2 ml of HBSS containing 250 nM [$^3$H]MPPs at 37° C. or 4° C. for various times up to 1 hour.

It is anticipated that [$^3$H]MPPs will be observed in cell lysate and steady state levels will be achieved within 1 hour. It is anticipated that the rate of [$^3$H]MPP uptake will be slower at 4° C. compared to 37° C., but that uptake will reach a high level of saturation by 45 minutes (e.g., 76.5%) and a higher level of saturation by 1 hour (e.g., 86.3%). It is anticipated that the internalization of [$^3$H]MPPs will not be limited to Caco-2 cells, and that similar results will be achieved with SH-SY5Y, HEK293 and CRFK cells. The intracellular concentration of MPPs is anticipated to be approximately 50 times higher than the extracellular concentration following 1 hour of incubation. It is further anticipated that treatment with the MPP along with the aromatic-cationic peptide will show a synergistic effect with respect to cell entry.

In a separate experiment, cells will be incubated with a range of MPP concentrations (1 μM-3 mM) for 1 hour at 37° C. At the end of the incubation period, cells will be washed 4 times with HBSS, and 0.2 ml of 0.1N NaOH with 1% SDS will be added to each well. The cell lysates will then be transferred to scintillation vials and radioactivity will be counted. To distinguish between internalized radioactivity and surface-associated radioactivity, an acid-wash step will be included. Prior to cell lysis, cells will be incubated with 0.2 ml of 0.2 M acetic acid/0.05 M NaCl for 5 minutes on ice.

The uptake of MPPs into Caco-2 cells will be confirmed by confocal laser scanning microscopy (CLSM) using a fluorescent analog of MPPs. Cells will be grown as described above and will be plated on (35 mm) glass dishes (MatTek Corp., Ashland, Mass.) for 2 days. The medium will then be removed and cells will be incubated with 1 ml of HBSS containing 0.1 μM to 1.0 μM of the fluorescent analog at 37° C. for 1 hour. Cells will be washed three times with ice-cold HBSS and covered with 200 μL of PBS. Microscopy will be performed within 10 minutes at room temperature using a Nikon confocal laser scanning microscope with a C-Apochromat 63x/1.2 W corr objective. Excitation will be performed at 340 nm by means of a UV laser, and emission will be measured at 520 nm. For optical sectioning in z-direction, 5-10 frames with 2.0 μz-steps will be collected.

CLSM will be used to confirm the uptake of fluorescent MPPs into Caco-2 cells after incubation with 0.1 μM fluorescent analog for 1 h at 37° C. It is anticipated that the uptake of the fluorescent analog will be similar at 37° C. and 4° C. It is anticipated that the fluorescence will appear diffuse throughout the cytoplasm but will be completely excluded from the nucleus.

These results will show that MPPs of the present technology or pharmaceutically acceptable salts thereof, such as acetate, tartrate, or trifluoroacetate salts, alone or in combination with aromatic-cationic peptides, are useful in methods comprising the entry of MPPs into cells.

Example 9: Targeting of MPPs to Mitochondria In Vivo

A fluorescent analog of MPPs will be prepared. The cells will be grown as described above and will be plated on (35 mm) glass dishes (MatTek Corp., Ashland, Mass.) for 2 days. The medium will be then removed and cells will be incubated with 1 ml of HBSS containing 0.1 μM fluorescent analog at 37° C. for 15 minutes to 1 hour.

Cells will also incubated with tetramethylrhodamine methyl ester (TMRM, 25 nM), a dye for staining mitochondria, for 15 minutes at 37° C. Cells will be washed three times with ice-cold HBSS and covered with 200 μL of PBS. Microscopy will be performed within 10 minutes at room temperature using a Nikon confocal laser scanning microscope with a C-Apochromat 63x/1.2 W corr objective.

For fluorescent analog, excitation will be performed at 350 nm using a UV laser, and emission will be measured at 520 nm. For TMRM, excitation will be performed at 536 nm, and emission will be measured at 560 nm.

It is anticipated that CLSM will show the uptake of fluorescent analog into Caco-2 cells after incubation for as little as 15 minutes at 37° C., and that staining will be excluded from the nucleus. Mitochondrial localization of fluorescent analog will be demonstrated by the overlap of the fluorescent analog and TMRM.

It is further anticipated that concurrent treatment with the MPP and an aromatic-cationic peptide will show a synergistic effect with respect to mitochondrial targeting.

These results will show that MPPs of the present technology or pharmaceutically acceptable salts thereof, such as acetate, tartrate, or trifluoroacetate salts, alone or in combination with aromatic-cationic peptides, are useful in methods comprising the targeting of the MPP to mitochondria in vivo.

Example 10: Targeting of MPPs to Isolated Mitochondria

To isolate mitochondria from mouse liver, mice will be sacrificed by decapitation. The liver will be removed and rapidly placed into chilled liver homogenization medium. The liver will be finely minced using scissors and then homogenized by hand using a glass homogenizer.

The homogenate will be centrifuged for 10 minutes at 1000×g at 4° C. The supernatant will be aspirated and transferred to polycarbonate tubes and centrifuged again for 10 minutes at 3000×g, 4° C. The resulting supernatant will be removed, and the fatty lipids on the side-wall of the tube will be removed.

The pellet will be resuspended in liver homogenate medium and the homogenization repeated twice. The final purified mitochondrial pellet will be resuspended in medium. Protein concentration in the mitochondrial preparation will be determined by the Bradford procedure.

Approximately 1.5 mg mitochondria in 400 μl buffer will be incubated with [$^3$H]MPPs for 5-30 minutes at 37° C. The mitochondria will then be centrifuged and the amount of radioactivity will be determined in the mitochondrial fraction and buffer fraction. Assuming a mitochondrial matrix volume of 0.7 μl/mg protein (Lim, et al., *J. Physiol.* 545: 961-974 (2002)), it is anticipated that the concentration of [$^3$H]MPPs in mitochondria will be higher than in the buffer, indicating that MPPs are concentrated in mitochondria.

To demonstrate that MPPs are selectively distributed to mitochondria, we will examine the uptake of fluorescent MPPs and [$^3$H]MPPs into isolated mouse liver mitochondria. The rapid uptake of fluorescent MPPs is anticipated. Pre-treatment of mitochondria with carbonyl cyanide p-(trifluoromethoxy)-phenylhydrazone (FCCP), an uncoupler that results in immediate depolarization of mitochondria, is anticipated to reduce the uptake of fluorescent MPPs, demonstrating that the uptake is membrane potential-dependent.

To demonstrate that the mitochondrial targeting is not an artifact of the fluorophore, we will also examine mitochondrial uptake of [$^3$H]MPPs. Isolated mitochondria will be incubated with [$^3$H] MPPs and radioactivity will be determined in the mitochondrial pellet and supernatant. It is anticipated that the amount of radioactivity in the pellet will not change from 2 minutes to 8 minutes, and that treatment of mitochondria with FCCP will decrease the amount of [$^3$H] MPPs associated with the mitochondrial pellet.

The minimal effect of FCCP on mitochondrial uptake of MPPs will show that [$^3$H] MPPs are likely associated with mitochondrial membranes or in the inter-membrane, space rather than in the mitochondrial matrix. We will also demonstrate the effect of mitochondrial swelling on the mitochondrial localization of fluorescent MPPs using alamethicin to induce swelling and rupture of the outer mitochondrial membrane. It is anticipated that the uptake of fluorescent MPPs will be only partially reversed by mitochondrial swelling. This result will confirm that MPPs are associated with mitochondrial membranes.

It is further anticipated that concurrent treatment with the MPP and an aromatic-cationic peptide will show a synergistic effect with respect to mitochondrial targeting.

These results will show that MPPs of the present technology or pharmaceutically acceptable salts thereof, such as acetate, tartrate, or trifluoroacetate salts, alone or in combination with aromatic-cationic peptides, are useful in methods comprising the targeting of the MPPs to isolated mitochondria.

Example 11: MPPs do not Alter Mitochondrial Respiration or Membrane Potential

This example will demonstrate that MPPs do not alter mitochondrial function, as measured by oxygen consumption and mitochondrial membrane potential.

Isolated mouse liver mitochondria will be incubated with 100 μM of MPPs, and oxygen consumption will be measured. It is anticipated that MPPs will not alter oxygen consumption during state 3 or state 4, or the respiratory ratio (state 3/state 4) (6.2 versus 6.0). Mitochondrial membrane potential will be measured using TMRM. It is anticipated that addition of mitochondria will result in immediate quenching of the TMRM signal, which will be readily reversible by the addition of FCCP, indicating mitochondrial depolarization. It is anticipated that the addition of $Ca^{2+}$ (150 μM) will result in immediate mitochondrial depolarization followed by progressive loss of quenching indicative of MPT. It is anticipated that the addition of MPPs alone, even at 200 μM, will not cause mitochondrial depolarization or MPT.

These results will show that MPPs of the present technology or pharmaceutically acceptable salts thereof, such as acetate, tartrate, or trifluoroacetate salts, do not alter mitochondrial function, as measured by oxygen consumption and mitochondrial membrane potential.

Example 12: MPP-Mediated Protection Against MPT Induced by $Ca^{2+}$ and 3NP

This example will demonstrate that MPPs alone or in combination with aromatic-cationic peptides protect against MPT induced by $Ca^{2+}$ overload and 3-nitropropionic acid (3NP).

It is anticipated that the pre-treatment of isolated mitochondria with 10 μM MPPs alone or in combination with aromatic-cationic peptides for 2 minutes prior to addition of $Ca^{2+}$ will result only in transient depolarization and will prevent the onset of MPT. It is further anticipated that MPPs alone or in combination with aromatic-cationic peptides will dose-dependently increase the tolerance of mitochondria to cumulative $Ca^{2+}$ challenges.

3-Nitropropionic acid (3NP) is an irreversible inhibitor of succinate dehydrogenase in complex II of the electron transport chain. It is anticipated that the addition of 3NP (1 mM) to isolated mitochondria will cause the loss of mitochondrial membrane potential and the onset of MPT. It is further anticipated that the pre-treatment of mitochondria with MPPs alone or in combination with aromatic-cationic peptides will dose-dependently delay the onset of MPT induced by 3NP.

Caco-2 cells will be treated with 3NP (10 mM) in the absence or presence of MPPs with or without aromatic-cationic peptides (0.1 µM) for 4 hours, and then incubated with TMRM and examined by LSCM. It is expected that 3NP-treated cells will display reduced fluorescence compared to control cells, which indicates mitochondrial depolarization. By contrast, it is anticipated that concurrent treatment with MPPs alone or in combination with aromatic-cationic peptides will protect against mitochondrial depolarization caused by 3NP.

It is further anticipated that concurrent treatment with the MPP and an aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for protecting mitochondria against MPT in vitro or in vivo.

Example 13: MPPs Protect Against Mitochondrial Swelling and Cytochrome c Release MPT pore opening results in mitochondrial swelling. We will demonstrate the effects of MPPs alone or in combination with aromatic-cationic peptides on mitochondrial swelling by measuring reduction in absorbance at 540 nm ($A_{540}$). Mitochondrial suspensions will be centrifuged and the amount of cytochrome c in the pellet and supernatant will be determined using a commercially available ELISA kit. It is anticipated that the pre-treatment of isolated mitochondria with MPPs alone or in combination with aromatic-cationic peptides will inhibit swelling and cytochrome c release induced by $Ca^{2+}$ overload. It is further anticipated that in addition to preventing MPT induced by $Ca^{2+}$ overload, MPPs alone or in combination with aromatic-cationic peptides will also prevent mitochondrial swelling induced by 1-methyl-4-phenylpyridium ions ($MPP^+$), an inhibitor of complex I of the mitochondrial electron transport chain.

It is further anticipated that concurrent treatment with the MPP and an aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for protecting mitochondria against mitochondrial swelling and cytochrome c release in vitro or in vivo.

Example 14: MPPs Protect Against Ischemia-Reperfusion-Induced Myocardial Stunning Guinea pig hearts will be rapidly isolated, and the aorta will be cannulated in situ and perfused in a retrograde fashion with an oxygenated Krebs-Henseleit at constant pressure (40 cm $H_2O$). Contractile force will be measured with a small hook inserted into the apex of the left ventricle and a silk ligature connected to a force-displacement transducer. Coronary flow will be measured by timing the collection of pulmonary artery effluent.

Hearts will be perfused with MPPs (1-100 nM) alone or in combination with aromatic-cationic peptides for 30 minutes and then subjected to 30 minutes of global ischemia. Reperfusion will not be performed using perfusion buffer lacking MPPs.

It is anticipated that two-way ANOVA will demonstrate significant differences in contractile force, heart rate, and coronary flow in hearts treated with MPPs alone or in combination with aromatic-cationic peptides compared to controls. In control hearts, it is anticipated that contractile force will be significantly lower during the reperfusion period compared to the pre-ischemic period. In hearts treated with MPPs alone or in combination with aromatic-cationic peptides, it is anticipated that contractile force during the reperfusion period will be improved compared to controls. It is further anticipated that MPPs alone or in combination with aromatic-cationic peptides will provide complete inhibition of cardiac stunning. In addition, it is anticipated that coronary flow will be well-sustained throughout the reperfusion period and that there will be no decrease in heart rate in hearts treated with MPP (either alone or in combination with aromatic-cationic peptides).

It is further anticipated that treatment with the MPP along with the aromatic-cationic peptide will show a synergistic effect.

These results will show that MPPs of the present technology, or pharmaceutically acceptable salts thereof, such as acetate, tartrate, or trifluoroacetate salts, alone or in combination with aromatic-cationic peptides, are useful in methods for treating or preventing the effects of ischemia-reperfusion induced myocardial stunning.

Example 15: MPPs Enhance Organ Preservation

For transplantation, the donor hearts are preserved in a cardioplegic solution during transport. The preservation solution contains high potassium which effectively stops the heart from beating and conserves energy. However, the survival time of the isolated heart is quite limited.

This example will demonstrate that MPPs alone or in combination with aromatic-cationic peptides prolong survival of organs stored for transplant. Isolated guinea pig hearts will be perfused in a retrograde fashion with an oxygenated Krebs-Henseleit solution at 34° C. After 30 minutes of stabilization, the hearts will be perfused with a cardioplegic solution (CPS; St. Thomas) with or without MPPs (alone or in combination with aromatic-cationic peptides) (100 nM) for 3 minutes. Global ischemia will then be induced by complete interruption of coronary flow and maintained for 90 minutes. Reperfusion will be performed for 60 minutes with oxygenated Krebs-Henseleit solution. Contractile force, heart rate, and coronary flow will be monitored continuously throughout the procedure.

It is anticipated that the addition of MPPs alone or in combination with aromatic-cationic peptides to cardioplegic solution will significantly enhance contractile function after prolonged ischemia. It is further anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for enhancing organ preservation.

Example 16: MPPs Scavenge Hydrogen Peroxide

The effect of MPPs alone or in combination with aromatic-cationic peptides on $H_2O_2$ will be measured by luminol-induced chemiluminescence. Luminol (25 µM) and horseradish peroxidase (0.7 IU) will be added to a solution of $H_2O_2$ (4.4 nmol) and MPPs with or without aromatic-cationic peptides, and chemiluminescence will be monitored with a Chronolog Model 560 aggregometer (Havertown, Pa.) for 20 minutes at 37° C.

It is anticipated that MPPs alone or in combination with aromatic-cationic peptides will dose-dependently inhibit the luminol response, demonstrating that MPPs can scavenge $H_2O_2$. It is further anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for $H_2O_2$ scavenging.

Example 17: MPPs Inhibit Lipid Peroxidation

Linoleic acid peroxidation will be induced using the water-soluble initiator 2,2'-azobis(2-amidinopropane) (ABAP), and lipid peroxidation will be detected by the formation of conjugated dienes, monitored spectrophotometrically at 236 nm (E. Longoni, W. A. Pryor, P. Marchiafava, *Biochem. Biophys. Res. Commun.* 233, 778-780 (1997)).

5 ml of 0.5 M ABAP and varying concentrations of MPPs will be incubated in 2.4 ml linoleic acid suspension until autoxidation rate becomes constant. It is anticipated that MPPs will dose-dependently inhibit the peroxidation of linoleic acid.

Various peptides described herein will be tested at a concentration of 100 µM, alone and in conjunction with MPPs. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for inhibiting lipid peroxidation.

Example 18: MPPs Inhibit LDL Oxidation

Human low density lipoprotein (LDL) will be prepared fresh from stored plasma. LDL oxidation will be induced catalytically by the addition of 10 mM $Cu_8O_4$, and the formation of conjugated dienes will be monitored at 234 nm for 5 hours at 37° C. (B. Moosmann and C. Behl, *Mol. Pharmacol.* 61:260-268 (2002).

It is anticipated that MPPs will dose-dependently inhibit the rate of LDL oxidation.

Various peptides described herein will be tested at a concentration of 100 µM, alone and in conjunction with MPPs. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for inhibiting LDL oxidation.

Example 19: MPPs Suppress Hydrogen Peroxide Production by Isolated Mouse Liver Mitochondria This Example will demonstrate the effect of MPPs alone or in combination with aromatic-cationic peptides on $H_2O_2$ formation in isolated mitochondria. Livers will be harvested from mice, homogenized in ice-cold buffer, and centrifuged at 13800×g for 10 min. The pellet will be washed once, re-suspended in 0.3 ml of wash buffer, and placed on ice until use. $H_2O_2$ will be measured using luminol chemiluminescence as described previously (Li, et al., *Biochim. Biophys. Acta* 1428:1-12 (1999). 0.1 mg mitochondrial protein will be added to 0.5 ml potassium phosphate buffer (100 mM, pH 8.0) in the absence or presence of MPPs (either alone or in combination with aromatic-cationic peptides) (100 µM). 25 mM luminol and 0.7 IU horseradish peroxidase will be added, and chemiluminescence will be monitored with a Chronolog Model 560 aggregometer (Havertown, Pa.) for 20 minutes at 37° C. The amount of $H_2O_2$ produced will be quantified as the area under the curve (AUC) over 20 min, and all data will be normalized to AUC produced by mitochondria alone.

It is anticipated that the amount of $H_2O_2$ production will be significantly reduced in the presence of MPPs alone or in combination with aromatic-cationic peptides. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for suppressing $H_2O_2$ production in mitochondria.

Example 20: MPPs Suppress Antimycin-Induced Hydrogen Peroxide Production by Isolated Mouse Liver Mitochondria Livers will be harvested from mice, homogenized in ice-cold buffer, and centrifuged at 13800×g for 10 min. The pellet will be washed once, re-suspended in 0.3 ml of wash buffer, and placed on ice until use. $H_2O_2$ will be measured using luminol chemiluminescence as described previously (Li, et al., *Biochim. Biophys. Acta* 1428, 1-12 (1999). 0.1 mg mitochondrial protein will be added to 0.5 ml potassium phosphate buffer (100 mM, pH 8.0) in the absence or presence of MPPs (either alone or in combination with aromatic-cationic peptides). 25 mM luminol and 0.7 IU horseradish peroxidase will be added, and chemiluminescence will be monitored with a Chronolog Model 560 aggregometer (Havertown, Pa.) for 20 minutes at 37° C. The amount of $H_2O_2$ produced will be quantified as the area under the curve (AUC) over 20 min, and all data will be normalized to AUC produced by mitochondria alone.

It is anticipated that MPPs alone or in combination with aromatic-cationic peptides will dose-dependently reduce the spontaneous production of $H_2O_2$ by isolated mitochondria.

It is anticipated that MPPs alone or in combination with aromatic-cationic peptides will dose-dependently reduce the production of $H_2O_2$ induced by antimycin in isolated mitochondria. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for suppressing antimycin-induced $H_2O_2$ production in mitochondria.

Example 21: MPPs Reduce Intracellular Reactive Oxygen Species (ROS) and Increases Cell Survival To demonstrate that peptides described herein are effective when applied to whole cells, neuronal N2A cells will be plated in 96-well plates at a density of $1\times10^4$/well and allowed to grow for 2 days before treatment with tBHP (0.5 or 1 mM) for 40 min. Cells will be washed twice and incubated in medium alone or medium containing varying concentrations of MPPs (alone or in combination with aromatic-cationic peptides) for 4 hours. Intracellular ROS will be measured using carboxy-H2DCFDA (Molecular Probes, Portland, Oreg., U.S.A.). Cell death will be measured using an MTS cell proliferation assay (Promega, Madison, Wis.).

It is anticipated that incubation with tBHP will result in a dose-dependent increase in intracellular ROS and a decrease in cell viability. It is anticipated that incubation with MPPs alone or in combination with aromatic-cationic peptides will dose-dependently reduce intracellular ROS and increase cell survival with an $EC_{50}$ in the nM range. It is anticipated that treatment with the MPP along with the aromatic-cationic peptide will show a synergistic effect.

These results will show that MPPs of the present technology, or pharmaceutically acceptable salts thereof, such as acetate, tartrate, or trifluoroacetate salts, alone or in combination with aromatic-cationic peptides, are useful in methods comprising reducing intracellular ROS levels/production and increasing cell survival.

Example 22: MPPs Prevent Loss of Cell Viability

Neuronal N2A and SH-SY5Y cells will be plated in 96-well plate at a density of $1\times10^4$/well and allowed to grow for 2 days before treatment with t-butyl hydroperoxide (tBHP) (0.05-0.1 mM) with or without MPPs (alone or in combination with aromatic-cationic peptides) for 24 hours. Cell death will be assessed using an MTS cell proliferation assay (Promega, Madison, Wis.).

It is anticipated that treatment of N2A and SH-SY5Y cells with low doses of t-BHP (0.05-0.1 mM) for 24 hours will result in a decrease in cell viability. It is anticipated that concurrent treatment of cells with MPPs alone or in combination with aromatic-cationic peptides will result in a dose-dependent reduction of t-BHP-induced cytotoxicity. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for reducing the loss of cell viability.

Example 23: MPPs Decrease Caspase Activity

N2A cells will be grown on 96-well plates, treated with t-BHP (0.05 mM) in the absence or presence of MPPs (either alone or in combination with aromatic-cationic peptides) at 37° C. for 12-24 hours. All treatments will be carried out in quadruplicate. N2A cells will be incubated with t-BHP (50 mM) with or without MPPs (either alone or in combination with aromatic-cationic peptides) at 37° C. for 12 hours. Cells will be gently lifted from the plates with a cell detachment solution (Accutase, Innovative Cell Technologies, Inc., San Diego, Calif., U.S.A.) and will be washed twice in PBS. Caspase activity will be assayed using a FLICA kit (Immunochemistry Technologies LLC, Bloomington, Minn.). According to the manufacturer's recommendation, cells will be resuspended (approx. $5\times10^6$ cells/ml) in PBS and labeled with pan-caspase inhibitor FAM-VAD-FMK for 1 hour at 37° C. under 5% $CO_2$ while protected from light. Cells will then be rinsed to remove the unbound reagent and fixed. Fluorescence intensity in the cells will be measured by a laser scanning cytometer (Beckman-Coulter XL, Beckman Coulter, Inc., Fullerton, Calif., U.S.A.) using the standard emission filters for green (FL1). For each run, 10,000 individual events will be collected and stored in list-mode files for off-line analysis.

Caspase activation is the initiating trigger of the apoptotic cascade, and it is anticipated that there will be a significant increase in caspase activity after incubation of the cells with 50 mM t-BHP for 12 hours, which will be dose-dependently inhibited by MPPs alone or in combination with aromatic-cationic peptides. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for decreasing caspase activity.

Example 24: MPPs Inhibit Lipid Peroxidation in Cells Exposed to Oxidative Damage Lipid peroxidation will be evaluated by measuring 4-HNE Michael adducts. 4-HNE is one of the major products of the peroxidation of membrane polyunsaturated fatty acids. N2A cells will be seeded on a glass dish 1 day before t-BHP treatment (1 mM, 3 hours, 37° C., 5% $CO_2$) in the presence or absence of MPPs ($10^{-8}$ to $10^{-10}$ M) either alone or in combination with aromatic-cationic peptides. Cells will be washed twice with PBS, fixed 30 minutes with 4% paraformaldehyde in PBS at RT, and washed 3 additional times with PBS. Cells will then be permeabilized and treated with rabbit anti-HNE antibody followed by a secondary antibody (goat anti-rabbit IgG conjugated to biotin). Cells will be mounted in Vectashield and imaged using a Zeiss fluorescence microscope using an excitation wavelength of 460±20 nm and a longpass filter of 505 nm for emission.

It is anticipated that MPPs alone or in combination with aromatic-cationic peptides will inhibit lipid peroxidation in N2A cells treated with t-BHP. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for inhibiting lipid peroxidation in cells exposed to oxidative damage.

Example 25: MPPs Inhibit Loss of Mitochondrial Membrane Potential in Cells Exposed to Hydrogen Peroxide Caco-2 cells will be treated with tBHP (1 mM) in the absence or presence of MPPs (0.1 μM) either alone or in combination with aromatic-cationic peptides for 4 hours, and then incubated with TMRM and examined under LSCM. In cells treated with tBHP, it is anticipated that TMRM fluorescence will be much reduced compared to control cells, suggesting generalized mitochondrial depolarization. In contrast, it is anticipated that concurrent treatment with MPPs alone or in combination with aromatic-cationic peptides will protect against mitochondrial depolarization caused by t-BHP. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for inhibiting the loss of mitochondrial membrane potential in cells exposed to hydrogen peroxide.

Example 26: MPPs Prevent Loss of Mitochondrial Membrane Potential and Increased ROS Accumulation in N2A Cells Exposed to t-BHP N2A cells cultured in a glass dish will be treated with 0.1 mM t-BHP with or without MPPs (either alone or in combination with aromatic-cationic peptides) (1 nM), for 6 hours. Cells will then be loaded with 10 M dichlorofluorescin (ex/em=485/530) for 30 minutes at 37° C., 5% $CO_2$. Cells will be washed 3 times with HBSS, stained with 20 nM of Mitotracker TMRM (ex/em=550/575 nm) for 15 minutes at 37° C., and examined by confocal laser scanning microscopy.

It is anticipated that the treatment of N2A cells with t-BHP will result in a loss of TMRM fluorescence, indicating mitochondrial depolarization, and a concomitant increase in DCF fluorescence, indicating an increase in intracellular ROS. It is further anticipated that concurrent treatment with MPPs alone or in combination with aromatic-cationic peptides will prevent mitochondrial depolarization and reduce ROS accumulation. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for inhibiting the loss of mitochondrial membrane potential and increased ROS accumulation in cells exposed to t-BHP.

Example 27: MPPs Prevent Apoptosis Caused by Oxidative Stress

SH-SY5Y cells will be grown in 96-well plates and treated with t-BHP (0.025 mM) in the absence or presence of MPPs (either alone or in combination with aromatic-cationic peptides) at 37° C. for 24 hours. All treatments will be carried out in quadruplicate. Cells will then be stained with 2 mg/ml Hoechst 33342 for 20 minutes, fixed with 4% paraformaldehyde, and imaged using a Zeiss fluorescent microscope (Axiovert 200M) equipped with the Zeiss Acroplan 20× objective. Nuclear morphology will be evaluated using an excitation wavelength of 350±100 m and a longpass filter of 400 nm for emission. All images will be processed and analyzed using MetaMorph software (Universal Imaging Corp., West Chester, Pa., U.S.A.). Uniformly stained nuclei will be scored as healthy, viable neurons. Cells with condensed or fragmented nuclei will be scored as apoptotic. It is anticipated that MPPs alone or in combination with aromatic-cationic peptides will prevent SH-SY5Y cell apoptosis induced by 0.025 mM t-BHP. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for preventing apoptosis caused by oxidative stress.

Example 28: MPPs Prevent Lipid Peroxidation in Hearts Subjected to Ischemia and Reperfusion Isolated guinea pig hearts will be perfused in a retrograde manner in a Langendorff apparatus and subjected to various intervals of ischemia-reperfusion. Hearts will be fixed immediately, embedded in paraffin, and sectioned. Immunohistochemical analysis of 4-hydroxy-2-nonenol (HNE)-modified proteins will be carried out using an anti-HNE antibody.

It is anticipated that treatment with MPPs alone or in combination with aromatic-cationic peptides will prevent lipid peroxidation in hearts subjected to brief intervals of ischemia and reperfusion compared to untreated controls. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for preventing lipid peroxidation in organs subjected to ischemia and reperfusion.

Example 29: MPPs Improve Viability of Isolated Pancreatic Islet Cells

Islet cells will be isolated from mouse pancreas according to standard procedures. MPPs (either alone or in combination with aromatic-cationic peptides) or control vehicle will be added to isolation buffers used throughout the isolation procedure. Mitochondrial membrane potential will be measured using TMRM (red) and visualized by confocal microscopy, and apoptosis will be measured by flow cytometry using annexin V and necrosis by propidium iodide.

It is anticipated that MPPs alone or in combination with aromatic-cationic peptides will reduce apoptosis and increase islet cell viability, as measured by mitochondrial membrane potential. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for improving the viability of isolated pancreatic islet cells.

Example 30: MPPs Protect Against Oxidative Damage in Pancreatic Islet Cells

Isolated mouse pancreatic islet cells will be treated with 25 µM tBHP, without or with MPPs (either alone or in combination with aromatic-cationic peptides). Mitochondrial membrane potential will be measured by TMRM (red) and reactive oxygen species will be measured by DCF (green) using confocal microscopy. It is anticipated that MPPs alone or in combination with aromatic-cationic peptides will protect against oxidative damage in isolated pancreatic islet cells. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for preventing oxidative damage in pancreatic islet cells.

Example 31: MPPs Protect Against Parkinson's Disease 1-methyl-4-phenyl-1,2,3,6-tetrahydropyridine ($M_{tox}$) is a neurotoxin that selectively destroys striatal dopaminergic neurons and is an accepted animal model of Parkinson's Disease. 1-methyl-4-phenylpyridinium ($MPP^+$), a metabolite of $M_{tox}$, targets mitochondria, inhibits complex I of the electron transport chain, and increases ROS production. $MPP^+$ is used for in vitro studies because cells are unable to metabolize $M_{tox}$ to the active metabolite, while $M_{tox}$ is used for in vivo (i.e., animal) studies.

SN-4741 cells will be treated with buffer, 50 µM $MPP^+$, or 50 µM $MPP^+$ and MPPs, or 50 µM $MPP^+$ and MPPs with aromatic-cationic peptides for 48 hours. Apoptosis will be measured by fluorescent microscopy with Hoechst 33342. It is anticipated that the number of condensed, fragmented nuclei will be significantly increased by $MPP^+$ treatment in control cells, and that concurrent treatment with MPPs alone or in combination with aromatic-cationic peptides will reduce the number of apoptotic cells.

It is further anticipated that MPPs will dose-dependently prevent the loss of dopaminergic neurons in mice treated with $M_{tox}$. Three doses of $M_{tox}$ (10 mg/kg) will be given to mice (n=12) 2 hours apart. MPPs either alone or in combination with aromatic-cationic peptides will be administered 30 minutes before each $M_{tox}$ injection, and at 1 and 12 hours after the last $M_{tox}$ injection. Animals will be sacrificed one week later and striatal brain regions will be immunostained for tyrosine hydroxylase activity. Levels of dopamine, DOPAC and HVA levels will be quantified by high pressure liquid chromatography.

It is anticipated that dopamine, DOPAC and HVA levels will be significantly reduced by $M_{tox}$ exposure in untreated control mice. It is anticipated that MPPs alone or in combination with aromatic-cationic peptides will dose-dependently increase striatal dopamine, DOPAC (3,4 dihydroxyphenylacetic acid), and HVA (homovanillic acid) levels in mice treated with $M_{tox}$.

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for treating or preventing Parkinson's disease in mammalian subjects.

Example 32: MPPs Reduce Mitochondrial Dysfunction in Rats Fed a High-Fat Diet To determine the potential impact of diet-induced obesity on the control of cellular redox balance in skeletal muscle, a novel approach to measure the rate of mitochondrial $H_2O_2$ production in permeabilized skeletal muscle fiber bundles will be developed. See Anderson, et al., *J. Clin. Invest.* (doi: 10.1 172/J C137048). During basal (state 4) respiration supported by NADH-linked complex I substrates, the rate of superoxide formation is low, representing 0.1-0.5% of total $O_2$ utilization (Anderson & Neufer, *Am. J. Physiol. Cell Physiol.* 290: C844-851 (2006); St-Pierre, et al., *J. Biol. Chem.* 277:44784-44790 (2002)). However, respiration supported exclusively by succinate, an FADH-linked complex II substrate, promotes high rates of superoxide production by generating reverse electron flow back into complex I (Anderson & Neufer, *Am J Physiol Cell Physiol* 290:C844-851 (2006); St-Pierre, et al., *J. Biol. Chem.* 277:44784-44790 (2002); Liu, et al., *J. Neurochem.* 80:780-787 (2002); Turrens, et al., *Biochem. J.* 191:421-427 (1980)). This Example describes methods for measuring mitochondrial function in permeabilized muscle tissues and examines the effects of a high-fat diet on mitochondrial function.

Animals and Reagents.

Thirty male Sprague-Dawley rats will be obtained from Charles River Laboratory (Wilmington, Mass.) and housed in a temperature (22° C.) and light controlled room with free access to food and water. Twenty of the animals will be maintained on a high (60%) fat diet (Research Dyets, Bethlehem, Pa.). Skeletal muscle will be obtained from anesthetized animals (100 mg/kg i.p. ketamine-xylazine). After surgery, animals will be sacrificed by cervical dislocation while anesthetized. Amplex Red Ultra reagent will be obtained from Molecular Probes (Eugene, Oreg.). Stigmatellin and horseradish peroxidase (HRP) will be obtained from Fluka Biochemika (Buchs, Switzerland). All other chemicals will be purchased from Sigma-Aldrich (St. Louis, Mo.). All animal studies will be approved by the East Carolina University Institutional Animal Care and Use Committee.

Preparation Ofpermeabilized Muscle Fiber Bundles.

Briefly, small portions (25 mg) of soleus, red gastrocnemius (RG), and white gastrocnemius (WG) muscle will be dissected and placed in ice-cold buffer X, containing 60 mM K-MES, 35 mM KCl, 7.23 mM $K_2EGTA$, 2.77 mM $CaK_2EGTA$, 20 mM imidazole, 0.5 mM DTT, 20 mM taurine, 5.7 mM ATP, 15 mM PCr, and 6.56 mM $MgCl_2.6H_2O$ (pH 7.1, 295 mosmol/kg $H_2O$). The muscle will be trimmed of connective tissue and cut down to fiber bundles (2×7 mm, 4-8 mg wet wt). Using a pair of needle-tipped forceps under a dissecting microscope, fibers will be gently separated from one another to maximize surface area of the fiber bundle, leaving only small regions of contact. To permeabilize the myofibers, each fiber bundle will be placed in ice-cold buffer X containing 50 µg/ml saponin and incubated on a rotator for 30 minutes at 4° C. Permeabilized fiber bundles (PmFBs) will be washed in ice-cold buffer Z containing 110 mM K-MES, 35 mM KCl, 1 mM EGTA, 10 mM $K_2HPO_4$, 3 mM $MgCl_2.6\ H_2O$, 5 mg/ml BSA, 0.1 mM glutamate, and 0.05 mM malate (pH 7.4, 295 mOsm), and incubated in buffer Z on a rotator at 4° C. until analysis (<2 hours).

Mitochondrial Respiration and $H_2O_2$ Production Measurements.

High resolution respirometric measurements will be obtained at 30° C. in buffer Z using the Oroboros $O_2K$ Oxygraph (Innsbruck, Austria). Mitochondrial $H_2O_2$ production will be measured at 30° C. during state 4 respiration in buffer Z (10 µg/ml oligomycin) by continuously monitoring oxidation of Amplex Red using a Spex Fluoromax 3 (Jobin Yvon, Ltd.) spectrofluorometer with temperature control and magnetic stirring at >1000 rpm. Amplex Red reagent reacts with $H_2O_2$ in a 1:1 stoichiometry catalyzed by HRP to yield the fluorescent compound resorufin and molar equivalent $O_2$. Resorufin has excitation/emission characteristics of 563 nm/587 nm and is extremely stable once formed. After baseline fluorescence (reactants only) is established, the reaction will be initiated by addition of a permeabilized fiber bundle to 300 µl of buffer Z containing 5 µM Amplex Red and 0.5 U/ml HRP, with succinate at 37° C. For the succinate experiments, the fiber bundle will be washed briefly in buffer Z without substrate to eliminate residual pyruvate and malate. Where indicated, 10 µg/ml oligomycin will be included in the reaction buffer to block ATP synthase and ensure state 4 respiration. At the conclusion of each experiment, PmFBs will be washed in double-distilled (dd) $H_2O$ to remove salts, and freeze-dried in a lyophilizer (LabConco). The rate of respiration will be expressed as pmol per second per mg dry weight, and mitochondrial $H_2O_2$ production expressed as pmol per minute per dry weight.

Statistical Analyses.

Data will be presented as means±SE. Statistical analyses will be performed using a one-way ANOVA with Student-Newman-Keuls method for analysis of significance among groups. The level of significance will be set at $p<0.05$.

It is anticipated that maintaining animals on a 60% fat diet for a period of 3 weeks will cause an increase in the maximal rate of mitochondrial $H_2O_2$ production. It is anticipated that the addition of rotenone at the conclusion of succinate titration will eliminate $H_2O_2$ production, confirming complex I as the source of superoxide production in both control animals and those fed high-fat diets. Mitochondrial $H_2O_2$ production will also be measured by titrating pyruvate/malate in the presence of antimycin (complex III inhibitor), with the expectation that animals fed a high-fat diet will have a higher maximal rate of $H_2O_2$ production than control animals.

It is anticipated that MPPs alone or in combination with aromatic-cationic peptides will reduce mitochondrial dysfunction in mammalian subjects exposed to a high-fat diet. It is anticipated that treatment with the MPP along with the aromatic-cationic peptide will show a synergistic effect.

These results will show that MPPs of the present technology, or pharmaceutically acceptable salts thereof, such as acetate, tartrate, or trifluoroacetate salts, alone or in combination with aromatic-cationic peptides, are useful in methods for reducing mitochondrial dysfunction in mammalian subjects exposed to a high-fat diet.

Example 33: MPPs Reduce ROS Production in Rats Fed a High-Fat Diet

Superoxide production is higher during basal respiration supported by fatty acid versus carbohydrate metabolism, raising the possibility that the increase in mitochondrial $H_2O_2$ production caused by a high-fat diet may be a result of elevations in cellular $H_2O_2$ levels (e.g., ROS by a ROS-induced ROS release mechanism). To test this hypothesis, the effects of the MPPs alone or in combination with aromatic-cationic peptides on mitochondrial function in high-fat fed rats will be examined. Some antioxidants have been shown to effectively reduce ROS in hearts subjected to myocardial stunning, in pancreatic islet cells after transplantation, and in animal models of Parkinson's disease and amyotrophic lateral sclerosis (Zhao, et al., *J. Biol. Chem.* 279:34682-34690 (2004); Thomas, et al., *J. Am. Soc. Nephr.* 16, TH-FC067 (2005); Petri, et al., *J. Neurochem.* 98, 1141-1148 (2006); Szeto, et al., *AAPS J.* 8: E521-531 (2006)).

Ten rats maintained on a high-fat diet will receive daily intraperitoneal injections of MPPs either alone or in combination with aromatic-cationic peptides dissolved in phosphate-buffered saline (1.5 mg/kg). Dose response curves for MPPs with or without aromatic-cationic peptides will be established in vitro and in vivo. Mitochondrial function will be measured according to the methods described in Example 1. It is anticipated that both dose response curves will reflect a reduction in mitochondrial $H_2O_2$ production during succinate-supported respiration.

Next, rats will be placed on a high-fat diet (60%) for six weeks with or without daily administration of MPPs (either alone or in combination with aromatic-cationic peptides). It is anticipated that succinate titration experiments conducted on permeabilized fibers will reveal an increase in the maximal rate of $H_2O_2$ production in high-fat fed rats. It is further anticipated that permeabilized fibers from high-fat fed rats will display a higher rate of $H_2O_2$ production during basal respiration supported by palmitoyl-carnitine. It is anticipated that high-fat fed rats treated with MPPs alone or in combination with aromatic-cationic peptides, will show a reduction in mitochondrial $H_2O_2$ production during both succinate and palmitoyl-carnitine supported respiration. It is anticipated that treatment with the MPP along with the aromatic-cationic peptide will show a synergistic effect.

It is further anticipated that basal respiration supported by pyruvate/malate will be slightly increased in fibers from high-fat fed rats, suggesting some degree of uncoupling. However, it is also anticipated that in high-fat fed rats, basal rates of pyruvate/malate- or palmitoyl-carnitine-supported respiration will be unaffected by MPP-treatment, indicating that the normalization of $H_2O_2$ production with MPP-treatment is not mediated by an increase in proton leak. It is also anticipated that treatment with MPPs will not affect body weight gain in high-fat fed rats.

Collectively, these findings will demonstrate that administration of a mitochondrial targeted antioxidant, such as the MPPs of the present technology alone or in combination with aromatic-cationic peptides, prevents or compensates for the increase in mitochondrial $H_2O_2$ production induced by a high-fat diet. As such, the MPPs of the present technology are useful in methods for preventing or treating insulin resistance caused by mitochondrial dysfunction in mammalian subjects.

It is increasingly recognized that the intracellular localization and activity of many proteins (e.g., receptors, kinases/phosphatases, transcription factors, etc.) is controlled by the oxidation state of thiol (—SH)-containing residues, suggesting that shifts in the intracellular redox environment can affect a wide variety of cellular functions (Schafer and Buetner, *Free Radic Biol Med* 30, 1191-1212 (2001). Glutathione (GSH), the most abundant redox buffer in cells, is reversibly oxidized to GSSG by glutathione peroxidase in the presence of $H_2O_2$, and reduced to GSH by glutathione reductase with electrons donated by NADPH. The ratio of GSH/GSSG is typically very dynamic, and reflects the overall redox environment of the cell.

Protein homogenates will be prepared by homogenizing 100 mg of frozen muscle in a buffer containing 10 mM Tris, 1 mM EDTA, 1 mM EGTA, 2 mM NaOrthovanadate, 2 mM NaPyrophosphate, 5 mM NaF, and protease inhibitor cocktail (Complete), at pH 7.2. After homogenization, 1% Triton X-100 will be added to the protein suspension, which will be vortexed and incubated on ice for 5 minutes. Samples will be centrifuged at 10,000 rpm for 10 minutes to pellet the insoluble debris. For GSSG measurement, tissue will be homogenized in a solution containing 20 mM Methyl-2-vinylpyridinium triflate to scavenge all reduced thiols in the sample. Total GSH and GSSG will be measured using a commercially available GSH/GSSG assay (Oxis Research Products, Percipio Biosciences, Foster City, Calif., U.S.A).

It is anticipated that high-fat feeding will cause a reduction in total cellular glutathione content ($GSH_t$) irrespective of treatment with MPPs, demonstrating that high-fat intake compromises GSH-mediated redox buffering capacity in skeletal muscle. To establish a link between the increased mitochondrial $H_2O_2$ production brought about by high-fat diet and its effect on overall redox environment of skeletal muscle, both GSH and GSSG will be measured in skeletal muscle from standard chow-fed and high-fat fed rats 1) following a 10 hour fast, and 2) 1 hour after administration of a standard glucose load (oral gavage, 10 hour fasted). In standard chow-fed controls, it is anticipated that glucose ingestion will cause a reduction in the GSH/GSSG ratio (normalized to $GSH_t$), presumably reflecting a shift to a more oxidized state in response to the increase in insulin-stimulated glucose metabolism. In high-fat fed rats, it is anticipated that the GSH/GSSG ratio will be reduced in the 10 hour fasted state relative to standard chow-fed controls and will decrease further in response to the glucose ingestion. It is anticipated that treatment with MPPs alone or in combination with aromatic-cationic peptides will preserve the GSH/GSSG ratio near control levels, even following glucose ingestion. It is anticipated that treatment with the MPP along with the aromatic-cationic peptide will show a synergistic effect.

These findings will demonstrate that a high-fat diet shifts the intracellular redox environment in skeletal muscle to a more oxidized state, as compared to controls. It is anticipated that treatment with MPPs alone or in combination with aromatic-cationic peptides will preserve the intracellular redox state in skeletal muscle, presumably by scavenging primary oxidants, thereby compensating for the reduction in total GSH-mediated redox buffering capacity induced by a high-fat diet. Thus, it is anticipated that the administration of a mitochondrial-targeted antioxidant, such as the MPPs of the present technology, will prevent or compensate for the metabolic dysfunction that develops in rats fed a high-fat diet.

These results will show that MPPs of the present technology or pharmaceutically acceptable salts thereof, such as acetate, tartrate, or trifluoroacetate salts, alone or in combination with aromatic-cationic peptides, are useful in methods for reducing ROS production in mammalian subjects exposed to a high-fat diet.

Example 34: MPPs Prevent Insulin Resistance in Rats Fed a High-Fat Diet

To demonstrate that mitochondria-driven changes in the intracellular redox environment may be linked to the etiology of high-fat diet-induced insulin resistance, oral glucose tolerance tests will be performed in rats following six weeks of a high-fat diet. On the day of testing, food will be removed 10 hours prior to administration of a 2 g/kg glucose solution via oral gavage. Glucose levels will be determined on whole blood samples (Lifescan, Milpitas, Calif., U.S.A.). Serum insulin levels will be determined using a rat/mouse ELISA kit (Linco Research, St. Charles, Mo., U.S.A.). Fasting data will be used to determine homeostatic model assessment (HOMA)-calculated as fasting insulin (mU/ml)× fasting glucose (mM)/22.5.

Blood glucose and insulin responses to the oral glucose challenge are anticipated to be higher and more sustained in high-fat fed rats compared with standard chow-fed rats. Treatment of high-fat fed rats with MPPs alone or in combination with aromatic-cationic peptides is expected to normalize blood glucose and insulin responses to the oral glucose challenge.

It is anticipated that homeostatic model assessment (HOMA) will confirm the development of insulin resistance in high-fat fed rats, and that treatment of high-fat fed rats with MPPs alone or in combination with aromatic-cationic peptides will suppress the development of insulin resistance.

To further assess insulin sensitivity, the phosphorylation state of the insulin signaling protein Akt in skeletal muscle will be measured 1) following a 10 hour fast, and 2) 1 hour after receiving an oral glucose load. It is anticipated that in response to glucose ingestion, Akt phosphorylation will increase in skeletal muscle of standard chow-fed controls but will remain essentially unchanged in high-fat fed rats, confirming the presence of insulin resistance at the level of insulin signaling. It is further anticipated that the treatment of high-fat fed rats with MPPs alone or in combination with aromatic-cationic peptides will increase Akt phosphorylation in response to glucose ingestion, which indicates insulin sensitivity.

It is anticipated that treatment with the MPP along with the aromatic-cationic peptide will show a synergistic effect.

These results will show that administration of a mitochondrial-targeted antioxidant, such as the MPPs of the present technology, prevents insulin resistance that develops in rats fed a high-fat diet. As such, the MPPs of the present technology or pharmaceutically acceptable salts thereof, such as acetate, tartrate, or trifluoroacetate salts, alone or in combination with aromatic-cationic peptides, are useful in methods of preventing or treating insulin resistance in mammalian subjects.

Example 35: MPPs Prevent Mitochondrial Dysfunction in Human Subjects

This example will illustrate the link between mitochondria-driven changes in the intracellular redox environment and insulin resistance in human subjects.

Mitochondrial $H_2O_2$ production and respiration in permeabilized skeletal myofiber bundles from lean, insulin sensitive (BMI=21.6±1.2 kg·m$^{-2}$, HOMA=1.2±0.4), and obese/insulin resistant (BMI=43.0∓4.1 kg·m$^{-2}$, HOMA=2.5±0.7) male subjects will be measured. On the day of the experiment, subjects will report to the laboratory following an overnight fast (approximately 12 hours). A fasting blood sample will be obtained for determination of glucose and insulin. Height and body weight will be recorded and skeletal muscle biopsies will be obtained from lateral aspect of vastus lateralis by the percutaneous needle biopsy technique under local subcutaneous anesthesia (1% lidocaine). A portion of the biopsy samples will be flash frozen in liquid $N_2$ for protein analysis, and another portion will be used to prepare permeabilized fiber bundles.

Mitochondrial $H_2O_2$ production is anticipated to be higher in obese subjects than in lean subjects in response to titration of succinate, and to be higher during basal respiration supported by fatty acid. Basal $O_2$ utilization is anticipated to be similar in lean and obese subjects, with the rate of mitochondrial free radical leak higher during glutamate/malate/succinate and palmitoyl-carnitine supported basal respiration higher in obese subjects. Finally, it is anticipated that both total cellular GSH content and the GSH/GSSG ratio will be lower in the skeletal muscle of obese subjects, indicating an overall lower redox buffer capacity and a more oxidized intracellular redox environment.

These results will show that mitochondrial ROS production and the resulting shift to a more oxidized skeletal muscle redox environment is an underlying cause of high-fat diet-induced insulin resistance. The anticipated increase in mitochondrial $H_2O_2$ production is expected to be a primary factor contributing to the shift in overall cellular redox environment. Thus, administration of a mitochondrial-targeted antioxidant, such as the MPPs of the present technology alone or in combination with aromatic-cationic peptides, is expected to prevent or compensate for the metabolic dysfunction caused by a high-fat diet. It is anticipated that treatment with the MPP along with the aromatic-cationic peptide will show a synergistic effect.

As such, the MPPs of the present technology or pharmaceutically acceptable salts thereof, such as acetate, tartrate, or trifluoroacetate salts, alone or in combination with aromatic-cationic peptides, are useful in methods for preventing or treating insulin resistance in human subjects.

Example 36: MPPs in the Prevention and Treatment of Insulin Resistance

To demonstrate the prevention and treatment of insulin resistance, the MPPs of the present technology will be administered alone or in combination with aromatic-cationic peptides to fatty (fa/fa) Zucker rats, which are an accepted model of diet-induced insulin resistance. As compared to high-fat fed Sprague-Dawley rats (as used in Examples 32-34), fatty Zucker rats are anticipated to develop a greater degree of obesity and insulin resistance under similar conditions. As in Examples 32-34, it is anticipated that mitochondrial dysfunction (e.g., increased $H_2O_2$ production) will be evident in permeabilized fibers from the Zucker rats.

To demonstrate the effects of MPPs on the prevention of insulin resistance, young Zucker rats (~3-4 weeks of age) will be administered MPPs alone or in combination with aromatic-cationic peptides for approximately 6 weeks. As these young rats do not yet exhibit signs or symptoms of insulin resistance, they provide a useful model for assessing the efficacy of methods of preventing insulin resistance. MPPs alone or in combination with aromatic-cationic peptides (1.0-5.0 mg/kg body wt) will be administered to the rats intraperitoneally (i.p.) or orally (drinking water or oral gavage).

It is predicted that administration of MPPs alone or in combination with aromatic-cationic peptides will attenuate or prevent the development of whole body and muscle insulin resistance that normally develops in fatty Zucker rats. Physiological parameters measured will include body weight, fasting glucose/insulin/free fatty acid, oral glucose tolerance (OGTT), in vitro muscle insulin sensitivity (in vitro incubation), biomarkers of insulin signaling (Akt-P, IRS-P), mitochondrial function studies on permeabilized fibers (respiration, $H_2O_2$ production), biomarkers of intracellular oxidative stress (lipid peroxidation, GSH/GSSG ratio, aconitase activity), and mitochondrial enzyme activity. Control animals will include wild-type and fatty rats not administered MPPs. Successful prevention of insulin resistance by the MPPs of the present technology will be indicated by a reduction in one or more of the markers associated with insulin resistance or mitochondrial dysfunction enumerated above.

It is anticipated that treatment with the MPP along with the aromatic-cationic peptide will show a synergistic effect.

To demonstrate the effects of the MPPs on treatment of insulin resistance, Zucker rats (~12 weeks of age) will be administered MPPs alone or in combination with aromatic-cationic peptides for approximately 6 weeks. As these rats show signs of obesity and insulin resistance, they will provide a useful model for assessing the efficacy of methods of treating insulin resistance. MPPs alone or in combination with aromatic-cationic peptides (1.0-5.0 mg/kg body wt) will be administered to the rats intraperitoneally (i.p.) or orally (drinking water or oral gavage).

It is predicted that administration of MPPs alone or in combination with aromatic-cationic peptides will reduce the whole body and muscle insulin resistance that normally develops in fatty Zucker rats. Parameters measured will include body weight, fasting glucose/insulin/free fatty acid, oral glucose tolerance (OGTT), in vitro muscle insulin sensitivity (in vitro incubation), biomarkers of insulin signaling (Akt-P, IRS-P), mitochondrial function studies on permeabilized fibers (respiration, $H_2O_2$ production), biomarkers of intracellular oxidative stress (lipid peroxidation, GSH/GSSG ratio, aconitase activity), and mitochondrial enzyme activity. Controls will include wild-type and fatty rats not administered MPPs. Successful treatment of insulin resistance by the MPPs of the present technology will be indicated by a reduction in one or more of the markers associated with insulin resistance or mitochondrial dysfunction enumerated above.

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for treating or preventing insulin resistance in mammalian subjects.

Example 37: MPPs Protect Against Prerenal ARI Caused by Ischemia-Reperfusion

This example will demonstrate the effects of MPPs of the present technology in protecting a subject from acute renal injury (ARI) caused by ischemia-reperfusion (I/R).

Eight Sprague Dawley rats (250-300 g) will be assigned to one of the following groups: (1) sham surgery (no I/R); (2) I/R+saline vehicle; (3) I/R+MPPs; (4) I/R+MPPs+aromatic-cationic peptides. MPPs with or without aromatic-cationic peptides (3 mg/kg in saline) will be administered 30 minutes before ischemia and immediately before reperfusion. Control animals will be given saline alone according to the same schedule.

Rats will be anesthetized with a mixture of ketamine (90 mg/kg, i.p.) and xylazine (4 mg/kg, i.p.). The left renal vascular pedicle will be occluded using a micro-clamp for 30-45 min. At the end of the ischemic period, reperfusion will be established by removing the clamp. At that time, the contralateral kidney will be removed. After 24 hours of reperfusion, animals will be sacrificed and blood samples will be obtained by cardiac puncture. Renal function will be determined by measuring levels of blood urea nitrogen (BUN) and serum creatinine (BioAssay Systems DIUR-500 and DICT-500).

Renal Morphologic Examination:

Kidneys will be fixed in 10% neutral-buffered formalin and embedded in paraffin wax for sectioning. Three-micron sections will be stained with hematoxylin-eosin (H&E) and periodic acid-Schiff (PAS), and analyzed by light microscopy. Lesions will be scored based on 1) mitosis and necrosis of individual cells, 2) necrosis of all cells in adjacent proximal convoluted tubules with survival of surrounding tubules, 3) necrosis confined to the distal third of the proximal convoluted tubule with a band of necrosis extending across the inner cortex, and 4) necrosis affecting all three segments of the proximal convoluted tubule.

TUNEL Assay for Apoptosis:

Renal tissue sections will be deparaffinized and rehydrated with xylenes, a graded alcohol series, and deionized $H_2O$, and incubated in 20 jtg/ml proteinase K for 20 minutes at RT An in situ cell death detection POD kit (Roche, Ind., USA) will be used according to the manufacturer's instructions. Briefly, endogenous peroxidase activity in the kidney sections will be blocked by incubation for 10 minutes with 0.3% $H_2O_2$ in methanol. The sections will be then incubated in a humidified chamber in the dark for 30 minutes at 37° C. with TUNEL reaction mixture. After washing, the slides will be incubated with 50-100 µl Converter-POD in a humidified chamber for 30 minutes at RT. The slides will be incubated in DAB solution (1-3 min), counterstained with hemotoxylin, dehydrated through a graded series of alcohol, and mounted in Permount for microscopy.

Immunohistochemistry:

Renal sections will be cut from paraffin blocks and mounted on slides. After removal of paraffin with xylene, the slides will be rehydrated using graded alcohol series and deionized $H_2O$. Slides will be heated in citrate buffer (10 mM Citric Acid, 0.05% Tween 20, pH 6.0) for antigen retrieval. Endogenous peroxidase will be blocked with hydrogen peroxide 0.3% in methanol. Immunohistochemistry will be then performed using a primary antibody against heme oxygenase-I (HO-1) (rat anti-HO-1/HMOX1/HSP32 monoclonal antibody (R&D Systems, MN, USA) at 1:200 dilution, and secondary antibody (HRP conjugated goat anti-rat IgG, VECTASTAIN ABC (VECTOR Lab Inc. MI, USA)). Substrate reagent 3-amino-9-ethylcarbazole (AEC, Sigma, MO, USA) will be used to develop the slides, with hematoxylin used for counterstaining.

Western Blotting:

Kidney tissue will be homogenized in 2 ml of RIPA lysis buffer (Santa Cruz, Calif., USA) on ice and centrifuged at 500×g for 30 minutes to remove cell debris. Aliquots of the supernatants will be stored at −80° C. An aliquot comprising 30 µg of protein from each sample will be suspended in loading buffer, boiled for 5 minutes, and subjected to 10% SDS-PAGE gel electrophoresis. Proteins will be transferred to a PVDF membrane, blocked in 5% non-fat dry milk with 1% bovine serum albumin for 1 hour, and incubated with a 1:2000 dilution of anti-HO1/HMOX1/HSP32 or a 1:1000 diluted anti-AMPKα-1, monoclonal antibody (R&D Systems, MN, USA). Specific binding will be detected using horseradish peroxidase-conjugated secondary antibodies, which will be developed using Enhanced Chemi Luminescence detection system (Cell Signaling, MA, USA).

ATP Content Assay:

Immediately following harvesting, kidney tissue will be placed into 10 ml 5% trichloroacetic acid with 10 mM DTT, 2 mM EDTA, homogenized on ice, incubated on ice for 10 min, centrifuged for 10 minutes at 2000×g, and neutralized with pH 7.6 using 10 N KOH. Following centrifugation for 10 minutes at 2000×g, aliquots of the resulting supernatant will be stored at −80° C. ATP will be measured by bioluminescence using a commercially available kit (ATP bioluminescent kit, Sigma, MO, USA).

Mitochondrial Function:

Renal mitochondria will be isolated and oxygen consumption measured in accordance with the procedures described herein.

It is anticipated that treatment with MPPs alone or in combination with aromatic-cationic peptides will improve BUN and serum creatinine values in rats after ischemia and reperfusion, and will prevent tubular cell apoptosis after ischemia and reperfusion. It is further anticipated that MPPs alone or in combination with aromatic-cationic peptides will prevent tubular cell injury after ischemia and reperfusion.

It is anticipated that treatment with the MPP along with the aromatic-cationic peptide will show a synergistic effect. These results will show that the MPPs of the present technology are effective in reducing the incidence of ARI caused by ischemia-reperfusion.

These results will show that MPPs of the present technology or pharmaceutically acceptable salts thereof, such as acetate, tartrate, or trifluoroacetate salts, alone or in combination with aromatic-cationic peptides, are useful in methods for protecting a subject from ARI caused by ischemia.

Example 38: MPPs Protect Against Postrenal ARI Caused by Ureteral Obstruction

The effects of the MPPs of the present technology in protecting a subject from ARI caused by ureteral obstruction will be demonstrated in an animal model of unilateral ureteral obstruction (UUO).

Sprague-Dawley rats will undergo unilateral ureteral ligation with a 4-0 silk suture through a midline abdominal incision under sterile conditions. Ureteral obstruction will be carried out by ligating the lower end of the left ureter, just above the ureterovesical junction. MPPs with or without aromatic-cationic peptides (1 mg/kg or 3 mg/kg; n=16) or control vehicle (n=16) will be administered intraperitoneally, one day prior to UUO and continuing for 14 days following UUO.

Renal Histology:

Trichrome sections of paraffin embedded specimens will be examined by a board-certified pathologist (SVS, renal pathology specialist), and fibrosis scored on a scale of 0-+++.

Immunohistochemical Analysis:

Immunohistochemical staining for macrophages will be carried out using a monoclonal antibody to ED-1 as previously described. Macrophages will be counted in 10 high-power fields (×400) by two independent investigators in a blinded fashion. Apoptosis will be measured by TUNEL assay as described in Example 37. The presence of fibroblasts will be examined using immunohistochemistry, as described above, using the DAKO #S100-A4 antibody (1:100 dilution). Antigen will be retrieved by incubating cells with Proteinase K for 20 minutes. The remaining immunoperoxidase protocol will be carried out according to routine procedures.

It is expected that S100-A4 staining will be present in spindle-shaped interstitial cells and round, inflammatory cells. Only spindle-shaped cells will be quantified. Staining for 8-OH dG will be done using Proteinase K for antigen retrieval and an antibody provided by the Japan Institute Control of Aging at a dilution of 1:200-1:500.

Polymerase Chain Reaction Analysis:

Renal expression of heme oxygenase-1 (HO-1) will be measured by RT-PCR according to the following: Rat kidneys will be harvested and stored at −80° C. until use. Total RNA will be extracted using the Trizol (R)-Chloroform extraction procedure, and mRNA will be purified using the Oligotex mRNA extraction kit (Qiagen, Valencia, Calif., U.S.A.) according to manufacturer instructions. mRNA concentration and purity will be determined by measuring absorbance at 260 nm. RT-PCR will be performed using Qiagen One-step PCR kit (Qiagen, Valencia, Calif., U.S.A.) and an automated thermal cycler (ThermoHybrid, PX2). Thermal cycling will be carried out as follows: initial activation step for 15 minutes at 95° C. followed by 35 cycles of denaturation for 45 seconds at 94° C., annealing for 30 seconds at 60° C., extension for 60 seconds at 72° C. Amplification products will be separated on a 2% agarose gel electrophoresis, visualized by ethidium bromide staining, and quantified using Image J densitometric analysis software. GAPDH will be used as an internal control.

It is anticipated that the unobstructed contralateral kidneys will show very little, if any, inflammation or fibrosis in tubules, glomeruli or interstitium, and that obstructed kidneys of control animals will show moderate (1 2+) medullary trichrome staining and areas of focal peripelvic 1+ staining. It is anticipated that the cortex will show less fibrosis than the medulla. It is also anticipated that control obstructed kidneys will show moderate inflammation, generally scored as 1+ in the cortex and 2+ in the medulla. MPP or MPP+aromatic-cationic peptide treated obstructed kidneys are expected to show significantly less trichrome staining, with 0-trace in the cortex and tr-1+ in the medulla. Thus, it is anticipated that treatment with MPPs alone or in combination with aromatic-cationic peptides will decrease medullary fibrosis in a UUO model.

Fibroblasts will be visualized by immunoperoxidase for fibroblast-specific protein (FSP-1; aka S100-A4). It is anticipated that increased expression of FSP-1 will be found in obstructed kidneys. It is also anticipated that MPPs alone or in combination with aromatic-cationic peptides (1 mg/kg) will significantly decrease the amount of fibroblast infiltration in obstructed kidneys. Thus, it anticipated that MPPs will decrease fibroblast expression in a UUO model.

It is anticipated that in untreated kidneys, 2 weeks of UUO will result in a significant increase in apoptotic tubular cells as compared to the contralateral kidneys. It is further anticipated that MPPs alone or in combination with aromatic-cationic peptides (1 mg/kg) will significantly decrease tubular apoptosis in obstructed kidneys. Thus, it is anticipated that MPPs will decrease tubular apoptosis in a UUO model.

It is anticipated that there will be a significant increase in macrophage infiltration into obstructed kidneys as compared to contralateral kidneys after 2 weeks of UUO. It is further expected that treatment with 1 mg/kg or 3 mg/kg of MPPs alone or in combination with aromatic-cationic peptides will significantly decrease macrophage infiltration in obstructed kidneys. Thus, it is anticipated that MPPs will decrease macrophage infiltration in a UUO model.

It is anticipated that obstructed kidneys will be associated with increased proliferation of renal tubular cells, as visualized by immunoperoxidase for PCNA. It is anticipated that MPPs alone or in combination with aromatic-cationic peptides will cause a significant decrease in renal tubular proliferation in the obstructed kidneys. It is anticipated that tubular cell proliferation will be decreased at the 1 mg/kg dose, and by as much as 3.5-fold at the 3 mg/kg dose. Thus, it is anticipated that MPPs will suppress renal tubular cell proliferation in a UUO model.

It is anticipated that obstructed kidneys will show elevated oxidative damage compared to contralateral kidneys, as measured by increased expression of heme oxygenase-1 (HO-1) and 8-OH dG. It is anticipated that treatment with MPPs alone or in combination with aromatic-cationic peptides will decrease HO-1 expression in the obstructed kidney. It is anticipated that 8-OH dG staining will be detected in both tubular and interstitial compartments of the obstructed kidney, that the number of 8-OH dG positive cells will be significantly increased in obstructed kidneys compared to contralateral kidneys, and that the number of 8-OH dG positive cells will be significantly reduced by treatment with MPPs either alone or in combination with aromatic-cationic peptides. Thus, it is anticipated that MPPs will decrease oxidative damage in a UUO model.

These results will show that MPPs are effective in reducing interstitial fibrosis, tubular apoptosis, macrophage infiltration, and tubular proliferation in an animal model of ARI caused by UUO. It is anticipated that treatment with the MPP along with the aromatic-cationic peptide will show a synergistic effect. As such, the MPPs of the present technology or pharmaceutically acceptable salts thereof, such as acetate, tartrate, or trifluoroacetate salts, alone or in combination with aromatic-cationic peptides, are useful in methods for protecting a subject from ARI caused by ureteral obstruction.

Example 39: MPPs in the Prevention and Treatment of Contrast-Induced Nephropathy (CIN)

This example will demonstrate the use of MPPs of the present technology in the prevention and treatment of contrast-induced nephropathy (CIN) in an animal model of ARI.

Animal Model:

A rat model of radiocontrast dye-induced renal failure as described by Agmon, et al., *J. Clin. Invest.* 94:1069-1075 (1994) will be used. As in humans, radiocontrast dyes are generally non-toxic when administered to animals with normal renal function. However, radiocontrast dyes can induce ARI in animals with impaired renal function. In this model, impaired renal function will be induced by the administration of indomethacin (10 mg/kg) and L-NAME (10 mg/kg). Animals will be assigned to one of the following groups:
1. Control (n=8)
2. Indomethcin and L-NAME administered 15 minutes apart, followed by iothalamate (6 ml/kg) (n=7)
3. MPPs (3 mg/kg, i.p.) administered 15 minutes prior to indomethacin/L-NAME/iothalamate administration as described in Group 2; second dose of MPPs (3 mg/kg) administered immediately after drug exposure (n=9).
4. MPPs+aromatic-cationic peptides (3 mg/kg, i.p.) administered 15 minutes prior to indomethacin/L-NAME/iothalamate administration as described in Group 2; second dose of MPPs+aromatic-cationic peptides (3 mg/kg) administered immediately after drug exposure (n=9).

Renal Function:

Renal function will be assessed by determining GFR at baseline and 24 hours following dye administration. GFR will be determined by creatinine clearance which will be estimated over a 24 hour interval before and after dye administration. Creatinine clearance will be analyzed by measuring plasma and urinary creatinine levels (Bioassay Systems; DICT-500) and urine volume.

Renal Histology:

Kidneys will be fixed in 10% neutral-buffered formalin and embedded in paraffin wax for sectioning. Three-micron sections will be stained with hematoxylin-eosin (H&E) and periodic acid-Schiff (PAS) and analyzed by light microscopy by a board certified pathologist. Apoptosis will be visualized by TUNEL labeling.

It is anticipated that control animals will not display a significant difference in GFR between the first 24 hour period (approx. 235.0±30.5 µl/min/g) and the second 24 hour period (approx. 223.7±44.0 µl/min/g). It is anticipated that when contrast dye is administered to animals pre-treated with indomethacin and L-NAME, GFR will decline within 24 hours, and that treatment with MPPs alone or in combination with aromatic-cationic peptides before and after dye administration will reduce the decline in renal function.

It is anticipated that PAS staining will illustrate normal morphology in control kidneys, and a loss of renal brush border and vacuolization in contrast dye-exposed kidneys. It is further anticipated that these effects will be attenuated by treatment with MPPs alone or in combination with aromatic-cationic peptides. Thus, it is anticipated that MPPs will prevent renal injury in subjects exposed to radiocontrast dyes.

It is anticipated that control kidneys will show few apoptotic cells, while contrast dye-exposed kidneys will have numerous apoptotic cells. It is further anticipated that treatment with MPPs alone or in combination with aromatic-cationic peptides will reduce the number of apoptotic cells in contrast dye-exposed kidneys.

It is anticipated that treatment with the MPP along with the aromatic-cationic peptide will show a synergistic effect.

These results will show that the MPPs of the present technology are effective in reducing renal injury induced by radiocontrast dye exposure. As such, the MPPs of the present technology or pharmaceutically acceptable salts thereof, such as acetate, tartrate, or trifluoroacetate salts, alone or in combination with aromatic-cationic peptides, are useful in methods for treating or preventing acute renal injury caused by contrast dye exposure.

Example 40: MPPs in the Prevention and Treatment of CIN in Diabetic Subjects

This example will demonstrate the use of MPPs of the present technology in the prevention and treatment of contrast-induced nephropathy (CIN) in diabetic subjects.

Animal Model:

Impaired renal function caused by diabetes is one of the major predisposing factors for contrast induced nephropathy (McCullough, et al., *J. Am. Coll. Cardio.*, 2008, 51, 1419-1428). In this experiment, a total of 57 Sprague-Dawley rats will be fed a high-fat diet for 6 weeks, followed by the administration of low-dose streptozotocin (30 mg/kg) for a period of 9 weeks. Blood glucose, serum creatinine and Cystatin C will be measured. Animals meeting the following criteria (n=20) will advance to CIN studies: Scr>250 µM, Cystatin C>750 ng/ml and blood glucose>=16.7 µM.

Animals will be administered iohexol and MPPs with or without aromatic-cationic peptides, or iohexol and a saline control vehicle.

On day 1, serum samples will be collected and total urine protein will be measured using a Bradford assay. On days 2 and 3, 3 mg/kg MPPs (alone or in combination with aromatic-cationic peptides) or control vehicle will be administered subcutaneously (s.c.) 30 minutes prior to contrast dye injection (6 mL/kg i.v. tail vein). MPPs (alone or in combination with aromatic-cationic peptides) or vehicle administration will be repeated at 2 and 24 hours post-dye administration. Serum and urine samples will be collected at days 4 and 5. Animals will be euthanized on day 5, and the vital organs harvested. Samples will be analyzed by students t-test and differences will be considered significant at p<0.05.

Renal Function:

Renal function will be assessed by determining serum and urinary creatinine at baseline, 48 hours and 72 hours following dye administration. The creatinine clearance will be calculated based on the serum and urinary creatinine and urinary volume. Urinary protein concentration will be determined by Bradford Protein Assay kit (Sigma, St. Louis, Mo., U.S.A.), and Cystatin C will be measured using a Westang Rat Cystatin C kit (Shanghai, P.R.C.).

It is anticipated that control animals will display elevated levels of serum Cystatin C (an AKI biomarker) and reduced creatinine clearance following contrast dye exposure, and that treatment with MPPs alone or in combination with aromatic-cationic peptides will attenuate these effects. It is anticipated that treatment with the MPP along with the aromatic-cationic peptide will show a synergistic effect.

Thus, it is anticipated that MPPs of the present technology reduce renal dysfunction caused by radiocontrast dye in a diabetic animal model. As such, the MPPs of the present technology, or pharmaceutically acceptable salts thereof, such as acetate, tartrate, or trifluoroacetate salts, alone or in combination with aromatic-cationic peptides, are useful in methods for protecting a diabetic subject from acute renal injury caused by contrast agents.

Example 41: MPPs in the Prevention and Treatment of CIN in a Glycerol-Induced Rhabdomyolysis Animal Model This example demonstrates the use of MPPs of the present technology in the prevention and treatment of CIN in a glycerol-induced rhabdomyolysis animal model.

Animal Model:

This example will utilize animals subjected to glycerol-induced rhabdomyolysis, as previously described. Parvez, et al., *Invest. Radiol.*, 24:698-702 (1989); Duan, et al., *Acta Radiologica*, 41:503-507 (2000). Sprague-Dawley rats with body weight of 300-400 g will be dehydrated for 24 hours followed by intramuscular (i.m.) injection of 25% glycerol solution (v/v) at the dose of 10 ml/kg. Twenty-four hours later, the animals will be administered a contrast dye with MPPs (alone or in combination with aromatic-cationic peptides) or control vehicle according to the following: 1) 25% glycerin+Saline+PBS (n=6), 2) 25% glycerin+diatrizoate+PBS (n=7), 3) 25% glycerin+diatrizoate+MPPs (n=7), 4) 25% glycerin+diatrizoate+MPPs+aromatic-cationic peptides (n=7). The effects of MPPs on ARI will be demonstrated by comparing the renal functions in animals from each group. Samples will be analyzed by students t-test and differences will be considered significant at p<0.05.

Renal Function:

Renal function will be assessed by determining serum and urinary creatinine at baseline, 24 hours after dehydration, and 48 hours following contrast dye administration. Creatinine clearance will be calculated based on serum and urinary creatinine levels and urinary volume. Urinary albumin concentration will be determined using a competition ELISA assay.

It is anticipated that creatinine clearance will be reduced when contrast dye is administered to subjects having glycerol-induced rhabdomyolysis. It is further anticipated that treatment with MPPs alone or in combination with aromatic-cationic peptides will attenuate or prevent reduced creatinine clearance.

Albuminuria is an indicator of increased permeability of the glomerular membrane, and can result from exposure to contrast dye. It is anticipated that albuminuria will increase when contrast dye is administered to subjects having glycerol-induced rhabdomyolysis. It is further anticipated that treatment with MPPs alone or in combination with aromatic-cationic peptides will attenuate or prevent albuminuria in such subjects, suggesting that MPPs have a protective effect on the permeability of the glomerular basement membrane in this model.

It is anticipated that PAS staining will illustrate a loss of proximal tubule brush border following administration of contrast dye to subjects having glycerol-induced rhabdomyolysis, as well as glomerular swelling and tubular protein cast deposition. It is further anticipated that treatment with MPPs alone or in combination with aromatic-cationic peptides will attenuate or prevent these effects in such subjects.

It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for the prevention and treatment of CIN in subjects having rhabdomyolysis.

Example 42: MPPs in the Prevention and Treatment of Nephrotoxicity ($CCl_4$-Induced Chronic Kidney Injury)

This Example demonstrates the use of MPPs of the present technology for the prevention and treatment of carbon tetrachloride ($CCl_4$)-induced chronic nephrotoxicity.

Animal Model:

Generation of reactive radicals has been implicated in carbon tetrachloride-induced nephrotoxicity, in which is characterized by lipid peroxidation and accumulation of dysfunctional proteins. Ozturk, et al., *Urology*, 62:353-356 (2003). This Example describes the effect of administration of MPPs for the prevention of carbon tetrachloride ($CCl_4$)-induced chronic nephrotoxicity.

Study Design and Experimental Protocol:

Sprague-Dawley rats with body weight of 250 g will be fed a 0.35 g/L phenobarbital solution (Luminal water) for two weeks, and assigned to one of the following groups: 1) luminal water+olive oil, intragastrointestinal (i.g.), 1 ml/kg, twice per week; PBS subcutaneously (s.c.) 5 days per week; 2) luminal water+50% $CCl_4$ .i.g., 2 ml/kg, twice per week; and PBS s.c 5 days per week; 3) luminal water+50% $CCl_4$ .i.g., 2 ml/kg, twice per week; MPPs (10 mg/kg) s.c. 5 days per week; 4) luminal water+50% $CCl_4$ .i.g., 2 ml/kg, twice per week; MPPs with aromatic-cationic peptides (10 mg/kg) s.c. 5 days per week. Trials will run for a total of 7 weeks.

At the end of fifth week, four subjects from each group will be sacrificed for liver histopathological sectioning and fibrosis examination. At the end of seventh week, all remaining subjects will be sacrificed, and kidney and liver tissues harvested for histopathological examination.

Renal Histology:

Kidneys will be fixed in 10% neutral-buffered formalin and embedded in paraffin wax for sectioning. Three-micron sections will be stained with hematoxylin-eosin (H&E) and analyzed by light microscopy by a certified pathologist.

It is anticipated that MPPs alone or in combination with aromatic-cationic peptides will protect renal tubules from $CCl_4$ nephrotoxicity. H&E staining is anticipated to illustrate that $CCl_4$ exposure results in tubular epithelial cell degeneration and necrosis. It is also anticipated that animals treated with MPPs alone or in combination with aromatic-cationic peptides will show no significant histopathological changes compared to control animals. It is anticipated that treatment with the MPP along with the aromatic-cationic peptide will show a synergistic effect.

Thus, MPPs of the present technology, alone or in combination with aromatic-cationic peptides, are useful in methods for preventing or treating $CCl_4$-induced nephrotoxicity.

Example 43: MPPs in the Prevention of Cisplatin-Induced ARI

This example will demonstrate the use of MPPs of the present technology, or pharmaceutically acceptable salts thereof, such as acetate, tartrate, or trifluoroacetate salts, in the prevention of cisplatin-induced ARI.

Experimental Protocol:

Sprague-Dawley rats (350-400 g) will be given a single dose of cisplatin (7 mg/kg) intraperitoneally (i.p.) on Day 1. Subjects will receive MPPs alone or in combination with aromatic-cationic peptides (3 mg/kg) (n=8) or saline vehicle (n=8) subcutaneously just prior to cisplatin administration, and once daily for 3 additional days. Subjects will be placed in metabolic cages for the final 24 hours of the trial for urine collection. At the end of the trial, blood samples will be withdrawn from tail veins and the kidneys harvested.

Renal Function:

Renal function will be assessed by measuring blood urea nitrogen (BUN), serum creatinine, urine creatinine, and urine protein. GFR will be estimated from creatinine clearance, which will be determined from serum and urinary creatinine, and urinary volume.

Renal Histology:

Kidneys will be fixed in 10% neutral-buffered formalin and embedded in paraffin wax for sectioning. Three-micron sections will be stained with periodic acid-Schiff (PAS) and analyzed by light microscopy.

It is anticipated that vehicle control subjects will display a significant reduction in body weight after cisplatin administration, as compared to body weights prior to cisplatin administration, and that treatment with MPPs alone or in combination with aromatic-cationic peptides will attenuate or prevent this effect. It is further anticipated that serum creatinine will substantially increase in vehicle control subjects, and that treatment with MPPs alone or in combination with aromatic-cationic peptides will attenuate or prevent this effect.

It is anticipated that vehicle control subjects will display a significant increase in BUN after cisplatin treatment, and that treatment with MPPs alone or in combination with aromatic-cationic peptides will attenuate or prevent this effect. These results will show that MPPs protect kidneys from cisplatin-induced nephropathy.

It is anticipated that treatment with the MPP along with the aromatic-cationic peptide will show a synergistic effect.

As such, the MPPs of the present technology or pharmaceutically acceptable salts thereof, such as acetate, tartrate, or trifluoroacetate salts, alone or in combination with aromatic-cationic peptides, are useful in methods for protecting a subject from acute renal injury caused by cisplatin or similar nephrotoxic agents.

Example 44: MPPs in the Prevention and Treatment of Acute Liver Failure (ALF)

This example demonstrates the use of MPPs of the present technology in the prevention and treatment of acute liver failure (ALF).

Suitable animal models of ALF utilize surgical procedures, toxic liver injury, or a combination thereof. See Belanger & Butterworth, *Metabolic Brain Disease*, 20:409-423 (2005). MPPs alone or in combination with aromatic-cationic peptides or control vehicle will be administered prior to or simultaneously with a toxic or surgical insult. Hepatic function will be assessed by measuring serum hepatic enzymes (transaminases, alkaline phosphatase), serum bilirubin, serum ammonia, serum glucose, serum lactate, or serum creatinine. Efficacy of the MPPs of the present technology in preventing ALF will be indicated by a reduction in the occurrence or severity of the ALF as indicated by the above markers, as compared to control subjects.

It is anticipated that toxic or surgical liver insult will cause reduced liver function, and that treatment with MPPs alone or in combination with aromatic-cationic peptides will attenuate or prevent these effects. It is anticipated that treatment with the MPP along with the aromatic-cationic peptide will show a synergistic effect.

These results will show that MPPs of the present technology or pharmaceutically acceptable salts thereof, such as acetate, tartrate, or trifluoroacetate salts, alone or in combination with aromatic-cationic peptides, are useful in methods for preventing or treating ALF.

Example 45: MPPs in the Prevention or Treatment of Hypermetabolism after Burn Injury Hypermetabolism (HYPM) is a hallmark feature of metabolic disturbance after burn injury. Increased energy expenditure (EE) is associated with accelerated substrate oxidation and shifts of fuel utilization, with an increased contribution of lipid oxidation to total energy production. Mitochondria dysfunction is closely related to the development of HYPM. This Example will demonstrate the use of MPPs of the present technology in the prevention and treatment of HYPM.

Sprague Dawley rats will be randomized into the following groups: sham-burn (SB), burn with saline treatment (B), burn with MPP-treatment (BP), burn with MPP and aromatic-cationic peptides (BP2). Catheters will be surgically placed into jugular vein and carotid artery. Band BP and BP2 animals will receive 30% total body surface area full thickness burns by immersing the dorsal part into 100° C. water for 12 seconds with immediate fluid resuscitation. BP and BP2 animals will receive IV injection of MPPs without or with aromatic-cationic peptides (2 mg/kg every 12 hours) respectively for three days. The EE of the animals will be monitored for 12 hours in a TSE Indirect Calorimetry System (TSE Co., Germany).

It is anticipated that animals in the B group will show a significant increase in EE compared to animals in the SB group, and that treatment with MPPs alone or in combination with aromatic-cationic peptides will attenuate or prevent this effect. These results will show that treatment with MPPs prevents or attenuates burn-induced HYPM. It is anticipated that treatment with the MPP along with the aromatic-cationic peptide will show a synergistic effect.

As such, MPPs of the present technology, or pharmaceutically acceptable salts thereof, such as acetate, tartrate, or trifluoroacetate salts, alone or in combination with aromatic-cationic peptides, are useful in methods for treating burn injuries and secondary complications in subjects in need thereof.

Example 46: MPPs Protect Against Burn-Induced Liver Apoptosis

Systemic inflammatory response syndrome (SIRS) and multiple organ failure (MOF) are leading causes of morbidity and mortality in severe burn patients. This Example demonstrates the use of MPPs in preventing these effects.

Six-to-eight week old male C57BL mice will be subjected to 30% total body surface (TBSA) burn injury and subsequently injected daily with saline vehicle or MPPs with or without aromatic-cationic peptides (5 mg/kg body weight). A weight- and time-matched sham-burn group exposed to lukewarm (~37° C.) will serve as controls. Liver tissues will be collected 1, 3, and 7 days after burn injury treatment and analyzed for apoptosis (TUNEL), activated caspase levels (Western blot), and caspase activity (enzymatic assay).

It is anticipated that burn injury will increase the rate of apoptosis in the liver of burned subjects on all days examined, with the most dramatic increase predicted to occur on day 7 post-burn injury. It is further anticipated that treatment with MPPs alone or in combination with aromatic-cationic peptides will attenuate or prevent this effect.

It is anticipated that Western blot analysis will reveal a progressive increase in activated caspase-3 following burn injury, as compared to sham control group. It is further anticipated that treatment with MPPs alone or in combination with aromatic-cationic peptides will attenuate or suppress caspase-3 activation on days 3 and 7 post-burn, resulting in activated caspase-3 levels similar to those of sham control animals. It is anticipated that the caspase activity will increase significantly on post-burn day 7, and the treatment with MPPs alone or in combination with aromatic-cationic peptides will reduce caspase activity to a level not statistically different from that of sham control group. It is further anticipated that there will be a decrease in protein oxidation following burn injury in mice treated with the MPPs alone or in combination with aromatic-cationic peptides, as compared to control subjects.

It is anticipated that treatment with the MPP along with the aromatic-cationic peptide will show a synergistic effect.

These results will show that MPPs prevent burn-induced activation of apoptotic signaling pathways and subsequent liver apoptosis. As such, MPPs of the present technology or pharmaceutically acceptable salts thereof, such as acetate, tartrate, or trifluoroacetate salts, alone or in combination with aromatic-cationic peptides, are useful in methods for preventing or treating systemic organ damage, such as liver damage, secondary to a burn.

Example 47: MPPs in the Prevention of Wound Contraction after Burn Injury

This example will demonstrate the use of MPPs of the present technology in the prevention of wound contraction.

Burn wounds are typically uneven in depth and severity, with significant areas around coagulated tissue where the injury may be reversible, and inflammatory tissue damage could be prevented. Wound contraction is a process which diminishes the size of a full-thickness open wound, and especially of a full-thickness burn. Tensions developed during contraction and the formation of subcutaneous fibrous tissue can result in tissue deformity, fixed flexure, or fixed extension of a joint (where the wound involves an area over the joint). Such complications are especially relevant in burn healing. No wound contraction will occur when there is no injury to the tissue; and maximum contraction will occur when the burn is full thickness with no viable tissue remaining in the wound.

Sprague-Dawley rats (male, 300-350 g) will be pretreated with (1 mg) MPPs administered i.p. (approx. 3 mg/kg) 1 hour prior to burn (65° C. water, 25 seconds, lower back), followed by the topical application of MPPs to the wound (1 mg), and 1 mg MPPs administered i.p. once every 12 hours for 72 hours. Wounds will be observed for up to 3 weeks post-burn. A similar treatment regimen is followed for the group treated with MPPs+aromatic-cationic peptides.

It is anticipated that the wounds will take on the appearance of a hard scab, which will be quantified as a measure of wound size. It is anticipated that a slower rate of wound contraction will be observed in the group treated with MPPs alone or in combination with aromatic-cationic peptides as compared to control subjects, such that the burn injury will be less severe in these subjects compared to controls. It is anticipated that treatment with the MPP along with the aromatic-cationic peptide will show a synergistic effect.

These results will show that the MPPs of the present technology or pharmaceutically acceptable salts thereof, such as acetate, tartrate, or trifluoroacetate salts, alone or in combination with aromatic-cationic peptides, are useful in methods for treating wounds associated with a burn injury.

Example 48: MPPs Alleviate Skeletal Muscle Dysfunction after Burn Injury

This example will demonstrate the use of MPPs in the prevention and treatment of post-burn complications.

It is thought that a major cause of skeletal muscle mitochondrial dysfunction in burns is the result of defects in oxidative phosphorylation (OXPHOS) via stimulation of mitochondrial production of reactive oxygen species (ROS) and the oxidative damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia.

A clinically relevant murine burn injury model will be used to demonstrate the effects of MPPs on burn-induced mitochondrial dysfunction and endoplasmic reticulum (ER) stress. The redox state of the gastrocnemius muscle immediately below a local cutaneous burn (90° C. for 3 sec) will be evaluated by nitroxide EPR. It is anticipated that the redox state in the muscle will be compromised by burn injury, with the most dramatic effect at 6 hours post-burn.

MPPs with or without aromatic-cationic peptides (3 mg/kg) will be administered i.p. 30 minutes before burn, and immediately after burn. It is anticipated that at the 6-hour time point, treatment with MPPs alone or in combination with aromatic-cationic peptides will significantly increase the rate of nitroxide reduction, demonstrating that treatment with MPPs decreases oxidative stress in muscle beneath the burn.

It is anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods of preventing or treating secondary complications of a burn injury, such as skeletal muscle dysfunction.

Example 49: MPPs Attenuate the Progression of Tissue Damage Following a Burn

This example will demonstrate the use of MPPs in the prevention of tissue damage progression following burn injuries. The results will show that MPPs improve wound healing (i.e., accelerates healing or leads to less scarring) in a partial thickness burn wound.

Sprague Dawley rats will be randomized into the following groups; sham-burn (SB), burn with saline treatment (B), burn with MPP-treatment (BP), burn with MPP and aromatic-cationic peptides (BP2). Band BP and BP2 animals will receive a 30% total body surface area full thickness burns by immersing the dorsal body into 100° C. water for 12 seconds with immediate fluid resuscitation. BP and BP2 animals will receive IV injection of MPPs without or with aromatic-cationic peptides respectively (2 mg/kg every 12 hours) for three days. Wound re-epithelialization, contraction, and depth will be assessed via gross morphology and histologically over a period of 21 days. For this purpose, immediately after wounding, dark marks will be applied onto the skin of the animals at the wound edges as well as 1 cm away from the edges. Wounds will be digitally photographed over 21 days, and image analysis software will be used to measure the area of the wound (defined as the scab). Distance distances of the marks from the wound site will be used to assess wound contraction.

At selected time points, wounds will be harvested from the animals. Because the progression from a second to a third degree wound is expected to occur primarily in the first 48 hours post-burn, samples will be harvested at 12, 24, and 48 hours. To monitor the long-term impact on the wound healing process, samples will be harvested at 2, 7, 14, and 21 days. The tissues will be fixed and embedded, and sections across the center of the wounds collected for H&E and trichrome staining.

Apoptosis of hair follicles of the skin will be measured using TUNEL labeling and activated caspase-3 immunostaining using skin samples obtained between 0 and 48 hours post-burn. Quantification of TUNEL and caspase-3 staining will be done on digitally acquired images at high power. The number of positive cells per high power field will be determined, and compared among the groups.

Luminescence mapping will be performed using Doppler imaging to assess wound blood flow. Two hours post-burn, the dorsum of the animal will be imaged on a scanning laser Doppler apparatus to quantify the superficial blood flow distribution in the skin within and outside of the burn area. For luminescence mapping, 100 male Sprague-Dawley rats will be used. Eighty animals will receive a large (covering 30% of the total body surface area) full-thickness burn injury on the dorsum. This is a well-established model. They will be divided into several groups, one treated with MPPs, one treated with MPPs+aromatic-cationic peptides and the other with placebo (saline) treatment. Each group will be further divided into 4 subgroups consisting of 4 time points where animals will be sacrificed for further analysis. Prior to sacrifice, luminescence imaging will be carried out, followed by euthanasia and skin tissue sampling for subsequent histology. The remaining 20 animals will receive a "sham burn" and will be treated with MPPs with or without aromatic-cationic peptides, or saline. Euthanasia will be performed on two animals in each of the corresponding 4 time points. On average, each animal will be housed for 10 days (including the pre-burn days in the animal farm) in separate cages.

It is predicted that administration of MPPs alone or in combination with aromatic-cationic peptides will accelerate wound healing and attenuate the progression of burn injuries in this model. It is further predicted that treatment with MPPs alone or in combination with aromatic-cationic peptides will reduce burn-induced apoptosis and blood flow.

It is anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods for attenuating the progression of tissue damage following a burn injury, as in the progression of a partial thickness burn injury to a full-thickness burn injury.

Example 50: MPPs Protect Against Sunburn and Attenuates Progression of Tissue Damage Following Sunburn This example will demonstrate the use of MPPs to protect against sunburn and attenuate the progression of tissue damage following sunburn in a murine model.

Hairless mice, with skin characteristics similar to humans, will be exposed to excessive UV radiation over the course of a week. Subjects will be randomly divided into the following groups: 1) burn; saline vehicle; 2) burn, MPPs (4 mg/kg per day, low-dose group); 3) burn, MPPs (40 mg/kg per day, high-dose group), 4) burn, MPPs+aromatic-cationic peptides (4 mg/kg per day, low-dose group); 5) burn, MPPs+aromatic-cationic peptides (40 mg/kg per day, high-dose group). MPPs with or without aromatic-cationic peptides will be administered intravenously twice per day for seven days. Parameters measured will include wound contraction, re-epithelialization distance, cellularity, and collagen organization. Ki67 proliferation antigen will be assessed, as well as TUNEL and caspase-3 activation. Blood flow will be measured by luminescence mapping.

It is predicted that administration of MPPs alone or in combination with aromatic-cationic peptides will accelerate wound healing and attenuate the progression of sunburn injuries in this model. It is anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods for protecting against sunburn and attenuating the progression of tissue damage following sunburn.

Example 51: MPPs Attenuate Burn-Induced Hypermetabolism by Down-Regulating UCP-1 Expression in Brown Adipose Tissue Hypermetabolism is the hallmark feature of metabolic disturbance after burn injury. Mitochondrial dysfunction occurs after burns, and is closely related to the development of hypermetabolism (and altered substrate oxidation). Uncoupling protein 1 (UCP-1) is expressed in the brown adipose tissue, and plays a key role in producing heat. This example will show that the MPPs of the present technology down-regulate UCP-1 expression following burn injury.

Methods.

Sprague Dawley rats will be randomly divided into the following groups; sham (S), sham with saline vehicle (SSal), sham with MPP-treatment (SC), burn with saline vehicle (BSal), burn with MPP-treatment (BC) and burn with MPP-treatment+aromatic-cationic peptides (BC2). The dorsal aspect of burn subjects will be immersed into 100° C. water for 12 seconds to produce third degree 30% TBSA burns under general anesthesia. Sham burn will be produced by immersion in lukewarm water. Subjects will receive 40 ml/kg intraperitoneal saline injection for the resuscitation following the injury. A venous catheter will be placed surgically into the right jugular vein subsequent to sham or burn injury. MPPs with or without aromatic-cationic peptides (2 mg/kg) or saline vehicle will be infused for 7 days (4 mg/kg/day) using osmotic pumps (Durect, CA). Indirect calorimetry will be performed for 24 hours at 6 days after burn injury in a TSE Indirect Calorimetry System (TSE Co., Germany), and $VO_2$, $VCO_2$ and energy expenditure will be recorded every six minutes. Interscapullar brown adipose tissue will be collected after the indirect calorimetry, and UCP-1 expression in the brown adipose tissue will be evaluated by Western blot.

It is anticipated that $VO_2$, $VCO_2$, and energy expenditure will be significantly increased in the BSal group, as compared to the SSal group, and that treatment with MPPs alone or in combination with aromatic-cationic peptides will significantly attenuate this effect. It is further anticipated that UCP-1 expression in the BSal group will be higher than in the SSal group, with UCP-1 levels in the BC and BC2 groups lower than in the BSal group.

It is anticipated that treatment with the MPP along with the aromatic-cationic peptide will show a synergistic effect.

These results will show that MPPs attenuate burn-induced hypermetabolism by the down regulation of UCP-1 expression in brown adipose tissue. As such, the MPPs of the present technology, or pharmaceutically acceptable salts thereof, such as acetate, tartrate, or trifluoroacetate salts, alone or in combination with aromatic-cationic peptides, are useful in methods for treating a subject suffering from a burn injury.

Example 52: MPPs Induce ATP Synthesis Following a Burn Injury

This example will demonstrate that MPPs increase the rate of ATP synthesis following a burn injury using $^{31}$P NMR and electron paramagnetic resonance (EPR) in vivo.

It is thought that a major cause of skeletal muscle mitochondrial dysfunction in burns is the result of defects in oxidative phosphorylation (OXPHOS) via stimulation of mitochondrial production of reactive oxygen species (ROS) and the oxidative damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia.

Material and Methods.

Male 6-week-old CD1 mice weighing 20-25 g will be anesthetized by intraperitoneal (i.p.) injection of 40 mg/kg pentobarbital sodium. The left hind limb of all mice in all groups will be shaved. Burn subjects will be subjected to a nonlethal scald injury of 3-5% total body surface area (TBSA) by immersing the left hind limb in 90° C. water for 3 seconds.

NMR spectroscopy is described in detail in Padfield, et al., *Proc. Natl. Acad. Sci.,* 102:5368-5373 (2005). Briefly, mice will be randomized into 1) burn+control vehicle, 2) burn+MPP, 3) non-burn+control vehicle, 4) non-burn+MPP, 5) burn+MPP+aromatic-cationic peptides, and 6) non-burn+MPP+aromatic-cationic peptides groups. The MPPs with or without aromatic-cationic peptides (3 mg/kg) will be injected intraperitoneally 30 minutes prior to the burn and immediately after the burn. NMR experiments will be performed in a horizontal bore magnet (proton frequency 400 MHz, 21 cm diameter, Magnex Scientific) using a Bruker Avanee console. A 90° pulse will be optimized for detection of phosphorus spectra (repetition time 2 s, 400 averages, 4K data points). Saturation 90°-selective pulse trains (duration 36.534 ms, bandwidth 75 Hz) followed by crushing gradients will be used to saturate the γ-ATP peak. The same saturation pulse train will be also applied downfield of the inorganic phosphate (Pi) resonance, symmetrically to the γ-ATP resonance. T1 relaxation times of Pi and phosphocreatine (PCr) will be measured using an inversion recovery pulse sequence in the presence of γ-ATP saturation. An adiabatic pulse (400 scans, sweep with 10 KHz, 4K data) will be used to invert Pi and PCr, with an inversion time between 152 ms and 7651 ms.

EPR spectroscopy is described in detail in Khan, et al., *Mol. Med. Rep.* 1:813-819 (2008). Briefly, mice will be randomized into 1) burn+control vehicle, 2) burn+MPP, 3) non-burn+control vehicle, 4) non-burn+MPP, 5) burn+MPP+aromatic-cationic peptides, and 6) non-burn+MPP+aromatic-cationic peptides groups. The MPP with or without aromatic-cationic peptides (3 mg/kg) will be injected intraperitoneally at 0, 3, 6, 24, and 48 hours post-burn. EPR measurements will be carried out with an I.2-GHz EPR spectrometer equipped with a microwave bridge and external loop resonator designed for in vivo experiments. The optimal spectrometer parameters will be: incident microwave power, 10 mW; magnetic field center, 400 gauss; modulation frequency, 27 kHz. The decay kinetics of intravenously-injected nitroxide (150 mg/kg) will be measured at the various time points, to assess the mitochondrial redox status of the muscle.

It is anticipated that control subjects will display a significantly elevated redox status after a burn injury, and a significant reduction of the ATP synthesis rate. It is further anticipated that treatment with MPPs alone or in combination with aromatic-cationic peptides will induce a significant increase in the ATP synthesis rate in burned mice, as compared to controls.

These results will show that treatment with MPPs alone or in combination with aromatic-cationic peptides induces ATP synthesis rate possibly via a recovery of the mitochondrial redox status or via the peroxisome proliferator activated receptor-gamma coactivator-1β (PGC-1β). Thus, it is predicted that the mitochondrial dysfunction caused by burn injury is attenuated by administration of the MPPs alone or in combination with aromatic-cationic peptides. It is anticipated that treatment with the MPP along with the aromatic-cationic peptide will show a synergistic effect.

It is also predicted that administration of the MPPs will increase ATP synthesis rate substantially even in control healthy mice. These results will show that the MPPs of the present technology, or pharmaceutically acceptable salts thereof, such as acetate, tartrate, or trifluoroacetate salts, alone or in combination with aromatic-cationic peptides, are useful in methods of preventing or treating secondary complications of a burn injury, such as skeletal muscle dysfunction.

Example 53: MPPs Reduce Mitochondrial Aconitase Activity

Mitochondrial aconitase is part of the TCA cycle and its activity has been directly correlated with the TCA flux. Moreover, its activity is inhibited by ROS, such that it is considered an index of oxidative stress. This example will demonstrate the effects of MPPs (alone or in combination with an aromatic-cationic peptide) of the present technology on mitochondrial aconitase activity.

Murine subjects will be subjected to burn injury or sham and administered MPPs (alone or in combination with an aromatic-cationic peptide) or control vehicle as described above. Mitochondria will be isolated from burned and control tissues and mitochondrial aconitase activity assessed using a commercially available kit.

It is anticipated that mitochondrial aconitase activity will be increased in both burned (local burn effect) and contralateral to burned leg (systemic burn effect) in vehicle-treated animals, most probably due to the hypermetabolism induced by the burn injury. Thus, the increased ROS production known to occur in burn injury, which could inhibit mitochondrial aconitase activity, will likely not overcome the hypermetabolic effect with respect to mitochondrial aconitase activity and TCA flux. A similar result has been also shown in the case of exercise/repeated contractions in intact human and isolated mouse skeletal muscle, although an increase in ROS is also observed in this situation.

Thus, it is further anticipated that treatment with MPPs (alone or in combination with an aromatic-cationic peptide) will reduce mitochondrial aconitase activity in subjects receiving a burn injury compared to vehicle only burn controls. It is further anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods for reducing mitochondrial aconitase activity following a burn injury.

Example 54: MPPs in the Prevention or Treatment of Metabolic Syndrome

This example will demonstrate the use of MPPs (alone or in combination with an aromatic-cationic peptide) in the prevention and treatment of metabolic syndrome.

Sprague Dawley rats will be fed with a high-fat diet (HFD) for 6 weeks and then administered a single dose of STZ (30 mg/kg). The rats will be maintained on HFD until 14 weeks after STZ administration. Control subjects fed normal rat chow (NRC) for 6 weeks will be administered citrate buffer without STZ. After 5 months, diabetic subjects will be treated with MPPs (alone or in combination with an aromatic-cationic peptide) (10 mg/kg, 3 mg/kg, or 1 mg/kg s.c. q.d. (subcutaneously, once daily), or control vehicle (saline) 5 days per week for 10 weeks. The study groups will be as follows:

Group A: HFD/STZ+MPPs 10 mg/kg s.c. q.d. (Mon-Fri.), n=12;
Group B: HFD/STZ+MPPs 3 mg/kg s.c. q.d. (Mon-Fri.), n=12;
Group C: HFD/STZ+MPPs 1 mg/kg s.c. q.d. (Mon-Fri.), n=10;
Group D: HFD/STZ+control vehicle s.c. q.d. (Mon-Fri.), n=10;
Group E: NRC+control vehicle s.c. q.d. (Mon-Fri.), n=10;
Group F: HFD/STZ MPP and aromatic-cationic peptide 10 mg/kg s.c.q.d., n=12
Group G: HFD/STZ MPP and aromatic-cationic peptide 3 mg/kg s.c.q.d., n=12
Group H: HFD/STZ MPP and aromatic-cationic peptide 1 mg/kg s.c.q.d., n=12.

It is anticipated that HFD feeding for 6 weeks will produce obvious body weight gain, and that STZ administration will increase blood glucose and hyperlipidemia, indicating a metabolic syndrome-like disorder in these subjects. Hence, the protocol will have induced metabolic syndrome in these subjects.

During the 10-week period of treatment with MPPs, no obvious changes in body weight or blood glucose level are expected in subjects receiving MPPs. The blood glucose of NRC group is expected to stay in normal range, while that of STZ treatment groups is predicted to remain higher than throughout the 10-week period trial period.

It is anticipated that the blood triglyceride level of HFD/STZ rats will be much higher than in NRC rats before treatment with MPPs, and will be reduced to normal levels following 10 weeks of MPP-administration, demonstrating that MPPs have beneficial effects on lipid metabolism. It is further anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods for preventing or treating metabolic syndrome.

Example 55: MPPs Prevent High Glucose-Induced Injury to Human Retinal Epithelial Cells This example will demonstrate the use of MPPs (alone or in combination with an aromatic-cationic peptide) for the prevention of high glucose-induced injury to human retinal epithelial cells (HREC).

Methods of HREC culture useful in the studies of the present technology are known. See generally, Li, et al., *Clin. Ophthal. Res.* 23:20-2 (2005); Premanand, et al., *Invest. Ophthalmol. Vis. Sci.* 47:2179-84 (2006). Briefly, HREC cells will be cultured under one of these conditions: 1) normal control; 2) 30 mM glucose; 3) 30 mM glucose+MPPs; 4) 30 mM glucose+MPP+an aromatic-cationic peptide. Survival of HRECs in high glucose co-treated with various concentrations of MPPs (10 nM, 100 nM, 1 µM, 10 µM) will be measured by flow cytometry using Annexin V. See generally, Koopman, et al., *Blood* 84:1415 (1994); Homburg, et al., *Blood X*5: 532 (1995); Vermes, et al. *J. Immunol. Meth.* 184:39 (1995); Fadok, et al., *J. Immunol.* 148:2207 (1992).

The survival of HRECs in high glucose co-treated with MPPs will be tested at 24 hours and 48 hours. It is predicted that survival of HRECs will be significantly improved with the administration of MPPs (alone or in combination with an aromatic-cationic peptide) as compared to controls, with a reduction in apoptotic and necrotic cells. Treatment with MPPs (alone or in combination with an aromatic-cationic peptide) is also anticipated to reduce the production of ROS.

To demonstrate that a mitochondrial-mediated pathway will be important in MPP-mediated protection against high glucose-induced cell death, mitochondrial membrane potential will be measured by flow cytometry using TMRM. It is anticipated that after treating the HRECs with high-glucose without MPPs for 24 or 48 hours, a rapid loss of mitochondrial membrane potential will be detected, and that treatment with 100 nM of MPPs (alone or in combination with an aromatic-cationic peptide) will prevent or attenuate this effect. These results will show that MPPs (alone or in combination with an aromatic-cationic peptide) prevent the mitochondrial membrane potential loss caused by exposure to a high glucose environment.

It is expected that glucose (30 mmol/L) will induce cytochrome c release from the mitochondria of HRECs. Fixed HRECs will be immunolabeled with a cytochrome c antibody and a mitochondrial specific protein antibody (HSP60). It is predicted that confocal microscopic analysis will show that HRECs in normal culture and in cultures containing MPPs (alone or in combination with an aromatic-cationic peptide) co-treated with glucose have overlapping cytochrome c staining and mitochondria staining, indicating colocalization of cytochrome c and mitochondria. It is anticipated that after treatment with 30 mmol/L glucose for 24 or 48 hours, cytochrome c will be observed in the cytoplasm of HRECs, indicating that glucose induces the release of cytochrome c from the mitochondria to cytoplasm in HREC cells, and that treatment with MPPs (alone or in combination with an aromatic-cationic peptide) will prevent or attenuate this effect.

It is further anticipated that treatment with the MPP along with the aromatic-cationic peptide will show a synergistic effect.

These results will show that MPPs (alone or in combination with an aromatic-cationic peptide) promote the survival of HREC cells in a high glucose environment. As such, the MPPs of the present technology, or pharmaceutically acceptable salts thereof, such as acetate, tartrate, or trifluoroacetate salts, alone or in combination with aromatic-cationic peptides, are useful in methods for the prevention of diabetic retinopathy.

Example 56: MPPs Prevent Diabetic Retinopathy in Rats Fed a High-Fat Diet

This example will demonstrate use of MPPs (alone or in combination with an aromatic-cationic peptide) in the prevention of diabetic retinopathy in rats fed a high-fat diet (HFD).

A rat model of diabetes will be established by combination of 6-week HFD and either 1) a low-dose STZ (30 mg/kg) injection, or 2) a single high dose of STZ (65 mg/kg) in Sprague-Dawley rats. See generally, Srinivasan, et al., *Pharm. Res.* 52(4):313-320 (2005). Controls will be maintained on normal rat chow (NRC). Treatment groups will be as follows:

Group A: 12 HFD/STZ MPPs 10 mg/kg s.c
Group B: 12 HFD/STZ MPPs 3 mg/kg s.c.
Group C: 12 HFD/STZ MPPs 1 mg/kg s.c.
Group D: 10 HFD/STZ control vehicle. s.c.
Group E: 10 NRC control vehicle. s.c.
Group F: 12 HFD/STZ MPP and aromatic-cationic peptide 10 mg/kg s.c.
Group G: 12 HFD/STZ MPP and aromatic-cationic peptide 3 mg/kg s.c.
Group H: 12 HFD/STZ MPP and aromatic-cationic peptide 1 mg/kg s.c.

Eyes will be harvested and subjects assessed for cataract formation, epithelial changes, integrity of the blood-retinal barrier, retinal microvascular structure, and retinal tight junction structure using methods known in the art.

It is anticipated that administration of MPPs (alone or in combination with an aromatic-cationic peptide) will result in a prevention or reversal of cataract formation in the lenses of diabetic rats. It is further anticipated that administration of MPPs (alone or in combination with an aromatic-cationic peptide) will reduce epithelial cellular changes in both STZ rat model and HFD/STZ rat model, and result in improved inner blood-retinal barrier function compared to control subjects.

It is anticipated that administration of MPPs (alone or in combination with an aromatic-cationic peptide) will reduce retinal microvascular changes observed in STZ or HFD/STZ rats. It is further anticipated that the tight junctions, as visualized by claudin-5 localization, will be uniformly distributed along the retinal vessels in control subjects, and non-uniformly in HFD/STZ subjects. It is further anticipated that treatment with MPPs (alone or in combination with an aromatic-cationic peptide) (10 mg/kg) will prevent, reverse, or attenuate this effect.

It is further anticipated that treatment with the MPP along with the aromatic-cationic peptide will show a synergistic effect.

These results will collectively establish that MPPs (alone or in combination with an aromatic-cationic peptide) prevent/compensate for the negative effects of diabetes in the eye, e.g., cataracts and microvasculature damage. As such, the MPPs of the present technology, or pharmaceutically acceptable salts thereof, such as acetate, tartrate, or trifluoroacetate salts, alone or in combination with aromatic-cationic peptides, are useful in methods for preventing or treating ophthalmic conditions associated with diabetes in human subjects.

Example 57: MPPs in the Prevention and Treatment of Heart Failure

This example will demonstrate the use of MPPs (alone or in combination with an aromatic-cationic peptide) in the prevention and treatment of hypertensive cardiomyopathy and heart failure. This example will further demonstrate the role of NADPH and mitochondria in angiotensin II (Ang II)-induced cardiomyopathy, and in cardiomyopathic mice overexpressing the a subunit of the heterotrimeric Gq protein (Gaq).

Ventricles from mouse neonates younger than 72 hours will be dissected, minced, and enzymatically digested with Blendzyme 4 (45 mg/ml, Roche). After enzymatic digestion, cardiomyocytes will be enriched using differential pre-plating for 2 hours, and seeded on fibronectin-coated culture dishes for 24 hours in DMEM (Gibco) with 20% Fetal Bovine Serum (Sigma) and 25 µM Arabinosylcytosine (Sigma). Cardiomyocytes will be stimulated with Angiotensin II (1 µM) for 3 hours in scrum-free DMEM containing 0.5% insulin transferrin-selenium (Sigma), 2 mM glutamine, and 1 mg/ml BSA. Cardiomyocytes are simultaneously treated with either of the following: MPPs (alone or in combination with an aromatic-cationic peptide) (1 nM), N-acetyl cysteine (NAC: 0.5 mM), or PBS control. To measure mitochondrial superoxide concentration, Mitosox (5 pM) will be incubated for 30 minutes at 37° C. to load cardiomyocytes, followed by 2 washes with Hanks Balanced Salt Solution. Samples will be analyzed using excitation/emission of 488/625 nm by flow cytometry. Flow data will be analyzed using FCS Express (De Novo Software, Los Angeles, Calif., U.S.A.), and presented as histogram distributions of Mitosox fluorescence intensity.

Mouse Experiments, Drug Delivery, Echocardiography and Blood Pressure Measurement.

Six to ten mice will be included in each experimental group (Saline, Ang II, Ang II+MPP, WT, Gaq, Gaq+MPP). A pressor dose of Ang II (1.1 mg/kg/d) will be continuously administered for 4 weeks using subcutaneous Alzet 1004 osmotic minipumps, with or without the MPP (alone or in combination with an aromatic-cationic peptide) (3 mg/kg/d). Echocardiography will be performed at baseline and 4 weeks after pump implantation using a Siemens Acuson CV-70 equipped with a 13 MHz probe. Under 0.5% isoflurane to reduce agitation, standard M-mode, conventional and Tissue Doppler images will be taken, and functional calculations will be performed according to American Society of Echocardiography guidelines. MTI will be calculated as the ratio of the sum of isovolemic contraction and relaxation time to LV ejection time. An increase in MPI is an indication that a greater fraction of systole is spent to cope with the pressure changes during the isovolemic phases. As a reference for the effect of the MPP in Ang II treated mice, a genetic mouse model of Rosa-26 inducible-mCAT will be included, in which mitochondrial catalase will be overexpressed for two weeks before Ang II treatment.

Blood pressure will be measured in a separate group of mice by telemetry using an intravascular catheter PA-C 10 (DSI, MN), in which measurement will be performed every three hours starting from 2 days before pump placement until 2 days after Ang pump placement. After this time, a new pump loaded with Ang II+MPP will be inserted, followed by another 2 days of recording to see if the MPP has an effect on blood pressure.

Quantitative Pathology.

Ventricular tissues will be cut into transverse slices, and subsequently embedded with paraffin, sectioned, and subjected to Masson Trichrome staining. Quantitative analysis of fibrosis will be performed by measuring the percentage of blue-staining fibrotic tissue relative to the total cross-sectional area of the ventricles.

Measurement of Mitochondrial Protein Carbonyl Groups.

For mitochondrial protein extraction, ventricular tissues will be homogenized in mitochondrial isolation buffer (1 mM EGTA, 10 mM HEPES, 250 mM sucrose, 10 mM Tris-HCl, pH 7.4). The lysates will be centrifuged for 7 minutes at 800 g in 4° C. The supernatants will be then centrifuged for 30 minutes at 4000 g in 4° C. The crude mitochondria pellets will be resuspended in small volume of mitochondrial isolation buffer, sonicated on ice to disrupt the membrane, and treated with 1% streptomycin sulfate to precipitate mitochondrial nucleic acids. The OxiSelect™ Protein Carbonyl ELISA Kit (Cell Biolabs) will be used to analyze 1 µg of protein sample per assay. The ELISA will be performed according to the instruction manual, with slight modification. Briefly, protein samples will be reacted with dinitrophenylhydrazine (DNPH) and probed with anti-DNPH antibody, followed by HRP conjugated secondary antibody. The anti-DNPH antibody and HRP conjugated secondary antibody concentrations will be 1:2500 and 1:4000, respectively.

Quantitative PCR.

Gene expression will be quantified by quantitative real-time PCR using an Applied Biosystems 7900 thermocycler with Taqman Gene Expression Assays on Demand, which includes: PGCl-a (Mm00731216), TFAM (Mm004474X5), NRF-1 (Mm00447996), NRF-2 (Mm00487471), Collagen 1a2 (Mm00483937), and ANP (Mm01255747). Expression assays will be normalized to 18S RNA.

NADPH Oxidase Activity.

The NADPH oxidase assay will be performed as described elsewhere. In brief, 10 µg of ventricular protein extract will be incubated with dihydroethidium (DHE, 10 µM), sperm DNA (1.25 µg/ml), and NADPH (50 µM) in PBS/DTPA (containing 100 µM DTPA). The assay will be incubated at 37° C. in the dark for 30 minutes and the fluorescence will be detected using excitation/emission of 490/580 nm.

Western Immunoblots.

Cardiac protein extracts will be prepared by homogenization in lysis buffer containing protease and phosphatase inhibitors on ice (1.5 mM KCl, 50 mM Tris HCl, 0.125% Sodium deoxycholate, 0.375% Triton X 100, 0.15% NP40, 3 mM EDTA). The samples will be sonicated and centrifuged at 10,000×g for 15 minutes at 4° C. The supernatant will be collected and the protein concentration determined using a BCA assay (Pierce Thermo Scientific, Rockford, Ill., U.S.A.). Total protein (25 µg) will be separated on NuPAGE 4-12% Bis-Tris gel (Invitrogen) and transferred to 0.45 µm PVDF membrane (Millipore), and then blocked in 5% non-fat dry milk in Tris-buffer solution with 0.1% Tween-20 for 1 hour. Primary antibodies will be incubated overnight, and secondary antibodies will be incubated for 1 hour. The primary antibodies include: rabbit monoclonal anti-cleaved caspase-3 (Cell Signaling), mouse monoclonal anti-GAPDH (Millipore), rabbit polyclonal phospho-p3×MAP kinase (Cell Signaling), and mouse monoclonal anti-p38 (Santa Cruz Biotechnology). The enhanced chemiluminescence method (Thermo Scientific) will be used for detection. Image Quant ver.2.0 will be used to quantified the relative band density as a ratio to GAPDH (internal control). All samples will be normalized to the same cardiac protein sample.

It is anticipated that Ang-II will increase mitochondrial ROS in neonatal cardiomyocytes, which will be alleviated by treatment with MPPs (alone or in combination with an aromatic-cationic peptide). It is predicted that flow cytometry analysis will demonstrate that Angiotensin II increased Mitosox fluorescence (an indicator of mitochondrial superoxide) in neonatal cardiomyocytes. It is predicted that treatment with N-acetyl cysteine (NAC), a non-targeted antioxidant drug, will not show any effect on the level of mitochondrial ROS after Ang II. In contrast, it is anticipated that MPPs (alone or in combination with an aromatic-cationic peptide) will reduce Ang II-induced fluorescence to the level similar to that of saline-treated cardiomyocytes These anticipated results will indicate that Ang II induced mitochondrial oxidative stress in cardiomyocytes can be alleviated by a mitochondrial targeted antioxidant.

Treatment with MPPs (alone or in combination with an aromatic-cationic peptide) is anticipated to ameliorate Ang II-induced cardiomyopathy despite the absence of blood pressure lowering effect. To recapitulate hypertensive cardiomyopathy, a pressor dose of Ang II (1.1 mg/kg/d) will be administered for 4 weeks via subcutaneous continuous delivery with Alzet 1004 osmotic minipumps. It is predicted that intravascular telemetry will reveal that this dose of Ang II will significantly increase systolic and diastolic blood pressure by 25-28 mm Hg above baseline. It is predicted that the simultaneous administration of MPPs (alone or in combination with an aromatic-cationic peptide) (3 mg/kg/d) will not have any effect on blood pressure.

The cardiac pathology will be examined by Masson trichrome staining, which demonstrated perivascular fibrosis and interstitial fibrosis after 4 weeks of Ang II. It is anticipated that quantitative image analysis of ventricular fibrosis (blue staining on trichrome) will show that Ang II significantly increases ventricular fibrosis, which is anticipated to be fully attenuated by MPPs (alone or in combination with an aromatic-cationic peptide). The increase in cardiac fibrosis will be confirmed by quantitative PCR of the procollagen 1a2 gene, the main component of fibrosis.

Consistent with the expectation that Ang II will induce mitochondrial ROS in cardiomyocytes, it is predicted that chronic administration of Ang II for 4 weeks will significantly increase ventricular mitochondrial protein carbonyl content, which is an indicator of protein oxidative damage. It is anticipated that mitochondrial targeted antioxidant MPPs (alone or in combination with an aromatic-cationic peptide) will significantly reduce cardiac mitochondrial protein carbonyls.

It is anticipated that MPPs act downstream of NADPH oxidase and will reduce activation of p38 MAPK and apoptosis in response to Ang II. It is anticipated that consistent with previous reports, 4 weeks of Ang II will significantly increase cardiac NADPH oxidase activity, however, it is predicted this will not be changed by administration of MPPs administration, which suggests that MPPs protection act downstream of NADPH oxidase.

Ang II has been shown to activate several mitogen activated protein kinase (MAPK), such as p38. It is anticipated that administration of Ang II for 4 weeks will increase phosphorylation of p38 MAPK, and this phosphorylation will be significantly and nearly fully attenuated by MPPs (alone or in combination with an aromatic-cationic peptide), which suggests that MAP kinase is activated through mitochondrial-ROS sensitive mechanisms. Mitochondrial ROS, either directly, or indirectly by activating apoptosis signal regulating kinase, may induce apoptosis. It is anticipated that Ang II will induce cardiac apoptosis, which will be shown through an increase in cleaved caspase-3. It is also anticipated that MPPs (alone or in combination with an aromatic-cationic peptide) will completely prevent the activation of caspase-3 caused by Ang II.

It is anticipated that MPPs (alone or in combination with an aromatic-cationic peptide) will partially rescue Gaq overexpression-induced heart failure. Gaq protein is coupled to receptors for catecholamines and Ang II, all of which are known to be key mediators in hypertensive cardiovascular diseases. To extend these observations to a model of chronic catecholamine/Ang II stimulation, a genetic mouse model with cardiac specific overexpression of Gaq will be used, which causes heart failure in mice by 14-16 weeks of age. The Gaq mice in this study will have impairment of systolic function at 16 weeks age, which will be shown by a substantial decline in FS, with enlargement of the LV chamber, impairment of diastolic function indicated by decreased Ea/Aa, and worsening of myocardial performance index (MPI). MPPs (alone or in combination with an aromatic-cationic peptide) will be administered from 12 to 16 weeks of age (3 mg/kg/d), and it is predicted that MPPs will significantly ameliorate systolic function and improve myocardial performance. LV chamber enlargement is anticipated to be slightly reduced from treatment with MPPs.

It is further anticipated that treatment with the MPP along with the aromatic-cationic peptide will show a synergistic effect.

These results will show that the MPPs of the present technology, or pharmaceutically acceptable salts thereof, such as acetate, tartrate, or trifluoroacetate salts, alone or in combination with aromatic-cationic peptides, are useful in methods for preventing or treating cardiomyopathy or heart failure in mammalian subjects.

Example 58: MPPs Protect Against Vessel Occlusion Injuries

This Example will demonstrate that the administration of MPPs (alone or in combination with an aromatic-cationic peptide) at the time of revascularization limits the size of the infarct during acute myocardial infarction.

Men and women, 18 years of age or older, who present after the onset of chest pain, and for whom the clinical decision is made to treat with a revascularization procedure (e.g., PCI or thrombolytics) will be eligible for enrollment. Patients may be STEMI (ST-Elevation Myocardial Infarction) or Non-STEMI. A STEMI patient will present with symptoms suggestive or a cutting off of the blood supply to the myocardium and also if the patient's ECG shows the typical heart attack pattern of ST elevation. The diagnosis is made therefore purely on the basis of symptoms, clinical examination and ECG changes. In the case of a Non-ST elevation heart attack, the symptoms of chest pain can be identical to that of a STEMI but the important difference is that the patient's ECG does not show the typical ST elevation changes traditionally associated with a heart attack. The patient often has a history of having experienced angina, but the ECG at the time of the suspected attack may show no abnormality at all. The diagnosis will be suspected on the history and symptoms and will be confirmed by a blood test which shows a rise in the concentration of substances called cardiac enzymes in the blood.

Left ventricular and coronary angiography will be performed with the use of standard techniques, just before revascularization. Revascularization will be performed by PCI with the use of direct stenting. Alternative revascularization procedures include, but are not limited to, balloon angioplasty; percutaneous transluminal coronary angioplasty; and directional coronary atherectomy.

After coronary angiography is performed but before the stent is implanted, patients who meet the enrollment criteria are randomly assigned to either the control group or the experimental group. Randomization is performed with the use of a computer-generated randomization sequence. Less than 10 minutes before direct stenting, the patients in the experimental group receive an intravenous bolus injection of the MPP (with or without aromatic-cationic peptide). Patients will be equally randomized into any of the following treatment arms (for example, 0, 0.001, 0.005, 0.01, 0.025, 0.05, 0.10, 0.25, 0.5, and 1.0 mg/kg/hour). The peptides will be administered as an IV infusion from about 10 minutes prior to reperfusion to about 3 hours post-PCL. Following the reperfusion period, the subject may be administered the peptides chronically by any means of administration, e.g., subcutaneous or IV injection.

The primary end point is the size of the infarct as assessed by measurements of cardiac biomarkers. Blood samples will be obtained at admission and repeatedly over the next 3 days. Coronary biomarkers will be measured in each patient. For example, the area under the curve (AUC) (expressed in arbitrary units) for creatine kinase and troponin I release (Beckman kit) may be measured in each patient by computerized planimetry. The principal secondary end point is the size of the infarct as measured by the area of delayed hyperenhancement that is seen on cardiac magnetic resonance imaging (MRI), assessed on day 5 after infarction. For the late-enhancement analysis, 0.2 mmol of gadolinium-tetrazacyclododecanetetraacetic acid (Gd.DOTA) per kilogram will be injected at a rate of 4 mL per second and will be flushed with 15 mL of saline. Delayed hyperenhancement is evaluated 10 minutes after the injection of gadolinium Gd.DOTA with the use of a three dimensional inversion-recovery gradient-echo sequence. The images are analyzed in short axis slices covering the entire left ventricle.

Myocardial infarction will be identified by delayed hyperenhancement within the myocardium, defined quantitatively by an intensity of the myocardial postcontrast signal that is more than 2 SD above that in a reference region of remote, non-infarcted myocardium within the same slice. For all slices, the absolute mass of the infracted area will be calculated according to the following formula: infarct mass (in grams of tissue)=Σ (hyperenhanced area [in square centimeters])×slice thickness (in centimeters)×myocardial specific density (1.05 g per cubic centimeter).

It is predicted that administration of MPPs (alone or in combination with an aromatic-cationic peptide) at the time of reperfusion will be associated with a smaller infarct by some measures than that seen with placebo. It is further anticipated that treatment with the MPP along with the aromatic-cationic peptide will show a synergistic effect. These results will show that the MPPs of the present technology, or pharmaceutically acceptable salts thereof, such as acetate, tartrate, or trifluoroacetate salts, alone or in combination with aromatic-cationic peptides, are useful for limiting infarct size during acute myocardial infarction.

Example 59: MPPs Protect Against Acute Myocardial Infarction Injury in a Rabbit Model This example will demonstrate the use of MPPs (alone or in combination with an aromatic-cationic peptide) in protecting against an acute myocardial infarction injury in a rabbit model.

New Zealand white rabbits will be used in this study. The rabbits will be males and >10 weeks in age. Environmental controls in the animal rooms will be set to maintain temperatures of 61 to 72° F. and relative humidity between 30% and 70%. Room temperature and humidity will be recorded hourly, and monitored daily. There will be approximately 10-15 air exchanges per hour in the animal rooms. Photoperiod will be 12-hr light/12-hr dark (via fluorescent lighting) with exceptions as necessary to accommodate dosing and data collection. Routine daily observations will be performed. Harlan Teklad, Certified Diet (2030C), rabbit diet will be provided approximately 180 grams per day from arrival to the facility. In addition, fresh fruits and vegetables will be given to the rabbit 3 times a week.

MPPs (alone or in combination with an aromatic-cationic peptide) will be used as the test article. Dosing solutions will be formulated and will be delivered via continuous infusion (IV) at a constant rate (e.g., 50 µL/kg/min). Normal saline (0.9% NaCl) will be used as a control.

The test/vehicle articles will be given intravenously, under general anesthesia, in order to mimic the expected route of administration in the clinical setting of AMI and PTCA. Intravenous infusion will be administered via a peripheral vein using a Kd Scientific infusion pump (Holliston, Mass. 01746) at a constant volume (e.g., 50 µL/kg/min).

The study followed a predetermined placebo and sham controlled design. In short, 10-20 healthy, acclimatized, male rabbits will be assigned to one of three study arms (approximately 2-10 animals per group). Arm A (n=4, CTRL/PLAC) includes animals treated with vehicle (vehicle; VEH, IV); Arm B (n=7, treated) includes animals treated with the test peptides; Arm C (n=2, SHAM) includes sham operated time-controls treated with vehicle (vehicle; VEH, IV) or test peptides.

In all cases, treatments will be started approximately 30 minutes after the onset of a 30-minute ischemic insult (coronary occlusion) and continued for up to 3 hours following reperfusion. In all cases, cardiovascular function will be monitored both prior to and during ischemia, as well as for up to 180 minutes (3 hours) post-reperfusion. The experiments will be terminated 3 hours post-reperfusion (end of study); irreversible myocardial injury (infarct size by histomorphometery) at this time-point will be evaluated, and will be the primary-endpoint of the study.

It is anticipated that administration of MPPs (alone or in combination with an aromatic-cationic peptide) will result in decreased infarct size compared to the control. It is further anticipated that treatment with the MPP along with the aromatic-cationic peptide will show a synergistic effect. These results will show that MPPs of the present technology, or pharmaceutically acceptable salts thereof, such as acetate, tartrate, or trifluoroacetate salts, alone or in combination with aromatic-cationic peptides, are useful in methods for preventing and treating acute myocardial infarction injury in mammalian subjects.

Example 60: Combined MPPs and Cyclosporine in the Treatment of Acute Myocardial Infarction Injury This Example will demonstrate that the administration of a MPP, or a pharmaceutically acceptable salt thereof such as acetate, tartrate, or trifluoroacetate salt (alone or in combination with an aromatic-cationic peptide), and cyclosporine at the time of revascularization limits the size of the infarct during acute myocardial infarction.

Study Group.

Men and women, 18 years of age or older, who present within 6 hours after the onset of chest pain, who have ST-segment elevation of more than 0.1 mV in two contiguous leads, and for whom the clinical decision is made to treat with percutaneous coronary intervention (PCI) will be eligible for enrollment. Patients are eligible for the study whether they are undergoing primary PCI or rescue PCI. Occlusion of the affected coronary artery (Thrombolysis in Myocardial Infarction (TIMI) flow grade 0) at the time of admission is also a criterion for inclusion.

Angiography and Revascularization.

Left ventricular and coronary angiography will be performed with the use of standard techniques, just before revascularization. Revascularization will be performed by PCI with the use of direct stenting. Alternative revascularization procedures include, but are not limited to, balloon angioplasty; insertion of a bypass graft; percutaneous transluminal coronary angioplasty; and directional coronary atherectomy.

Experimental Protocol.

After coronary angiography is performed but before the stent is implanted, patients who meet the enrollment criteria are randomly assigned to either the control group or the experimental group. Randomization will be performed with the use of a computer-generated randomization sequence. Less than 10 minutes before direct stenting, the patients in the experimental group will receive an intravenous bolus injection of the MPP and cyclosporine. The MPP (alone or in combination with an aromatic-cationic peptide) will be dissolved in normal saline (final concentration, 25 mg/mL) and will be injected through a catheter that is positioned within an antecubital vein. Either separately or simultaneously, cyclosporine (final concentration, 25 mg per milliliter will be injected through the catheter. Normal saline (0.9% NaCl) will be used as a control. The patients in the control group receive an equivalent volume of normal saline.

Infarct Size.

The primary end point will be the size of the infarct as assessed by measurements of cardiac biomarkers. Blood samples are obtained at admission and repeatedly over the next 3 days. The area under the curve (AUC) (expressed in arbitrary units) for creatine kinase and troponin I release (Beckman kit) will be measured in each patient by computerized planimetry. The principal secondary end point will be the size of the infarct as measured by the area of delayed hyperenhancement that is seen on cardiac magnetic resonance imaging (MRI), assessed on day 5 after infarction. For the late-enhancement analysis, 0.2 mmol of gadolinium-tetrazacyclododecanetetraacetic acid (Gd.DOTA) per kilogram is injected at a rate of 4 ml per second and will be flushed with 15 ml of saline. Delayed hyperenhancement will be evaluated 10 minutes after the injection of Gd.DOTA with the use of a three dimensional inversion-recovery gradient-echo sequence. The images are analyzed in short axis slices covering the entire left ventricle.

Myocardial infarction will be identified by delayed hyperenhancement within the myocardium, defined quantitatively by an intensity of the myocardial postcontrast signal that is more than 2 SD above that in a reference region of remote, non-infarcted myocardium within the same slice. For all slices, the absolute mass of the infracted area will be calculated according to the following formula: infarct mass (in grams of tissue)=E (hyperenhanced area [in square centimeters])×slice thickness (in centimeters)×myocardial specific density (1.05 g per cubic centimeter).

Other End Points.

The whole-blood concentration of the MPP is measured immediately prior to PCI as well as at 1, 2, 4, 8 and 12 hours post PCI. Blood pressure and serum concentrations of creatinine and potassium will be measured on admission and 24, 48, and 72 hours after PCI. Serum concentrations of bilirubin, glutamyltransferase, and alkaline phosphatase, as well as white-cell counts, will be measured on admission and 24 hours after PCI.

The cumulative incidence of major adverse events that occur within the first 48 hours after reperfusion are recorded, including death, heart failure, acute myocardial infarction, stroke, recurrent ischemia, the need for repeat revascularization, renal or hepatic insufficiency, vascular complications, and bleeding. The infarct-related adverse events will be assessed, including heart failure and ventricular fibrillation. In addition, 3 months after acute myocardial infarction, cardiac events are recorded, and global left ventricular function will be assessed by echocardiography (Vivid 7 systems; GE Vingmed).

It is predicted that administration of the MPP (alone or in combination with an aromatic-cationic peptide) along with cyclosporine at the time of reperfusion will be associated with a smaller infarct by some measures than that seen with placebo. It is further anticipated that treatment with the MPP along with the aromatic-cationic peptide will show a synergistic effect. These results will show that MPPs of the present technology, or pharmaceutically acceptable salts thereof, such as acetate, tartrate, or trifluoroacetate salts, alone or in combination with aromatic-cationic peptides, are useful in combination with cyclosporine useful in methods for the treatment of myocardial infarction.

Example 61: Combined MPPs and Cyclosporine in the Treatment of Nephrotoxicity in Transplant Patients This example will demonstrate the use of MPPs (alone or in combination with an aromatic-cationic peptide) and cyclosporine to treat nephrotoxicity in transplant patients.

To prevent organ or tissue rejection after transplant, patients often receive a regimen of the immunosuppressive drug cyclosporine. Cyclosporine levels are established and maintained in the subject at levels to effectively suppress the immune system. However, nephrotoxicity is a concern for these subjects, and the level of the drug in the subject's blood is monitored carefully. Cyclosporine doses are adjusted accordingly in order to not only prevent rejection, but also to deter these potentially damaging side effects. Typically, an adult transplant patient receives cyclosporine as follows: IV: 2 to 4 mg/kg/day IV infusion once daily over 4 to 6 hours, or 1 to 2 mg/kg IV infusion twice a day over 4 to 6 hours, or 2 to 4 mg/kg/day as a continuous IV infusion over 24 hours. Capsules: 8 to 12 mg/kg/day orally in 2 divided doses. Solution: 8 to 12 mg/kg orally once daily. In some patients, doses can be titrated downward with time to maintenance doses as low as 3 to 5 mg/kg/day. In some patients, the tolerance for cyclosporine is poor, and cyclosporine therapy must be discontinued, the dosage lowered, or the dosage regimen cycled so as to prevent destruction of the subject's kidney.

This example demonstrates the effects of a MPP, or a pharmaceutically acceptable salt thereof, such as acetate, tartrate, or trifluoroacetate salt, (alone or in combination with an aromatic-cationic peptide) together with cyclosporine on post-transplant organ health (e.g., ischemia-reperfusion injury post transplant and organ rejection), as well as kidney health (e.g., nephrotoxic effects of cyclosporine). It is anticipated that administering a MPP (alone or in combination with an aromatic-cationic peptide) will have a protective effect on the transplant organ or tissue, and on kidney health during cyclosporine treatment.

Transplant subjects receiving cyclosporine pursuant to standard pre- and post-transplant procedures will be divided into groups. A therapeutically effective amount of a MPP or pharmaceutically acceptable salt thereof such as acetate, tartrate, or trifluoroacetate salt, (alone or in combination with an aromatic-cationic peptide) will be administered to subjects prior to, during and/or after transplant. Subjects will be monitored for health and function of the transplanted tissue or organ, as well as the incidence and severity of nephrotoxicity often seen with prolonged cyclosporine administration.

It is predicted that subjects who receive the MPP will have a healthier transplanted organ or tissue, and/or will be able to maintain a higher and/or more consistent cyclosporine dosage for longer periods of time compared to subjects who do not receive the MPP. It is further anticipated that treatment with the MPP along with the aromatic-cationic peptide will show a synergistic effect. These results will show that MPPs of the present technology, or pharmaceutically acceptable salts thereof, such as acetate, tartrate, or trifluoroacetate salts, alone or in combination with aromatic-cationic peptides, are useful in combination with cyclosporine is useful in methods for treating nephrotoxicity in transplant patients.

Example 62: Improved MPP Electron Scavenging Capacity

Certain natural amino acids are redox-active and can undergo one-electron oxidation, including Tyr, Trp, Cys and Met, with Tyr being the most versatile. Tyr can undergo one-electron oxidation by mechanisms that include oxidation by $H_2O_2$ and hydroxyl radicals. Tyrosyl radicals react poorly with $O_2$, but can combine to form the dityrosine dimer. Tyrosyl radicals can be scavenged by GSH to generate the thiyl radical (GS) and superoxide. The reaction of superoxide with phenoxyl radicals can result in either repair of the parent phenol or addition to form a hydroperoxide. The generation of the Tyr hydroperoxide is favored by certain conditions, especially if the Tyr is N-terminal or a free amine is nearby. In the existing peptides, electron scavenging has been provided by Tyr or substituted Tyr, including 2',6'-Dmt. Substitution of Tyr with Phe abolishes scavenging activity.

It is predicted that the electron scavenging capacity of the MPPs can be improved by increasing the number of redox-active amino acids, and that incorporation of methyl groups on Tyr further increased the scavenging activity compared to Tyr. Furthermore, in place of Tyr, Trp or Met can be substituted mitochondrial targeting. Superoxide can react with tryptophan to form a number of different reaction products, and with methionine to form methionine sulfoxide. The ability of these modified MPPs to scavenge $H_2O_2$, hydroxyl radical, superoxide, peroxynitrite, will be determined in vitro, and then confirmed in cell culture.

It is anticipated that that scavenging capacity of the MPPs will increase linearly with increased number of redox-active amino acids. It may be possible to increase the peptide length to 6 residues and achieve 3 times the scavenging capacity while still maintaining cell permeability.

These results will show that MPPs of the present technology, or pharmaceutically acceptable salts thereof, such as acetate salts or trifluoroacetate salts, alone or in combination with aromatic-cationic peptides, are useful in methods comprising electron scavenging.

Example 63: MPPs Facilitate Electron Transfer

ATP synthesis in the electron transport chain (ETC) is driven by electron flow through the protein complexes of the ETC which can be described as a series of oxidation/reduction processes. Rapid shunting of electrons through the ETC is important for preventing short-circuiting that would lead to electron escape and generation of free radical intermediates. The rate of electron transfer (ET) between an electron donor and electron acceptor decreases exponentially with the distance between them, and superexchange ET is limited to 20 angstrom. Long-range ET can be achieved in a multi-step electron hopping process, where the overall distance between donor and acceptor is split into a series of shorter, and therefore faster, ET steps. In the ETC, efficient ET over long distances is assisted by cofactors that are strategically localized along the IMM, including FMN, FeS clusters, and hemes. Aromatic amino acids such as Phe, Tyr and Trp can also facilitate electron transfer to heme through overlapping π clouds, and this was specifically shown for cyt c. Amino acids with suitable oxidation potential (Tyr, Trp, Cys, Met) can act as stepping stones by serving as intermediate electron carriers. In addition, the hydroxyl group of Tyr can lose a proton when it conveys an electron, and the presence of a basic group nearby, such as Lys, can result in proton-coupled ET which is even more efficient.

It is hypothesized that the distribution of MPPs among the protein complexes in the IMM allows it to serve as additional an relay station to facilitate ET. This will be demonstrated using the kinetics of cyt c reduction (monitored by absorbance spectroscopy) as a model system, with the MPP facilitating ET. Addition of N-acetylcysteine (NAC) as a reducing agent is anticipated to result in time-dependent increase in absorbance at 550 nm. It is further anticipated that the addition of the MPP alone at 100 μM concentrations will not reduce cyt c, but will dose-dependently increase the rate of NAC-induced cyt c reduction, suggesting that the peptide does not donate an electron but increases the speed of electron transfer.

This example will further demonstrate the effect of MPPs on the restoration of mitochondrial respiration and ATP synthesis following ischemia-reperfusion (IR) injury in rats. Animals will be subjected to bilateral occlusion of renal artery for 45 minutes followed by 20 minutes or 1 hour of reperfusion. Subjects will receive saline vehicle or a MPP (2.0 mg/kg s.c.) 30 minutes before ischemia and again at the time of reperfusion (n=4-5 in each group). It is anticipated that the MPP will improve oxygen consumption and ATP synthesis. It is further anticipated that treatment with the MPP along with the aromatic-cationic peptide will show a synergistic effect.

These results will show that MPPs of the present technology, or pharmaceutically acceptable salts thereof, such as acetate, tartrate, or trifluoroacetate salts, alone or in combination with aromatic-cationic peptides, are useful in methods comprising electron scavenging electron transfer.

Example 64: MPPs Enhance Mitochondrial Reduction Potential

The redox environment of a cell depends on its reduction potential and reducing capacity. Redox potential is highly compartmentalized within the cell, and the redox couples in the mitochondrial compartment are more reduced than in the other cell compartments and are more susceptible to oxidation. Glutathione (GSH) is present in mM concentrations in mitochondria and is considered the major redox couple. The reduced thiol group —SH can reduce disulfide S—S groups in proteins and restore function. The redox potential of the GSH/GSSG couple is dependent upon two factors: the amounts of GSH and GSSG, and the ratio between GSH and GSSG. As GSH is compartmentalized in the cell and the ratio of GSH/GSSG is regulated independently in each compartment, mitochondrial GSH (mGSH) is the primary defense against mitochondrial oxidative stress. Mitochondrial GSH redox potential becomes more oxidizing with aging, and this is primarily due to increase in GSSG content and decrease in GSH content.

It is anticipated that MPPs of the present technology will enhance mitochondrial reduction potential in vitro in isolated mitochondrial and in vivo in cultured cells and animal subjects. These results will show that MPPs of the present technology, or pharmaceutically acceptable salts thereof, such as acetate, tartrate, or trifluoroacetate salts, alone or in combination with aromatic-cationic peptides, are useful in methods for enhancing mitochondrial reduction potential.

Example 65: MPPs Reduce MV-Induced Mitochondrial Oxidation

This example will show that MPPs (alone or in combination with an aromatic-cationic peptide) of the present technology reduce mechanical ventilation (MV)-induced mitochondrial oxidation.

Experimental Design

Murine subjects will be treated as follows:
1. Normal, mobile mice: Normal, mobile mice will be randomly divided into two groups, A and B, with 8 mice per group. Group A mice will receive an injection of saline vehicle; Group B mice will receive an i.p. injection of the MPP.
2. Hind limb casted mice: Mouse hind limbs will be immobilized by casting for 14 days, thereby inducing hind limb muscle atrophy. Casted mice will receive an i.p. injection of saline vehicle (0.3 ml) or the MPP (0.3 ml). A control group of untreated mice will be also used in this experiment.

To demonstrate that mitochondrial ROS production plays a role in immobilization-induced skeletal muscle atrophy, mice will be randomly assigned to one of three experimental groups (n=24/group): 1) no treatment (control) group; 2) 14 days of hind limb immobilization group (cast); and 3) 14 days of hind-limb immobilization group treated with the mitochondrial-targeted antioxidant MPP (CasHSS). Subjects will receive s.c. injections of saline vehicle (0.3 mL) or the MPP (alone or in combination with an aromatic-cationic peptide) (1.5 mg/kg) administered once daily during the immobilization period.

Immobilization.

Mice will be anesthetized with gaseous isoflurane (3% induction, 0.5-2.5%) maintenance). Anesthetized animals will be cast-immobilized bilaterally with the ankle joint in the plantar-flexed position to induce maximal atrophy of the soleus and plantaris muscle. Both hind limbs and the caudal fourth of the body will be encompassed by a plaster cast. A thin layer of padding will be placed underneath the cast in order to prevent abrasions. In addition, to prevent the animals from chewing on the cast, one strip of fiberglass material will be applied over the plaster. The mice will be monitored on a daily basis for chewed plaster, abrasions, venous occlusion, and problems with ambulation.

Preparation Ofpermeabilized Muscle Fibers.

Permeabilized muscle fibers will be prepared as previously described. Korshunov, et al., *FEBS Lett* 416:15-18, 1997; Tonkonogi, et al., *Pflügers Arch* 446:261-269, 2003. Briefly, the muscle will be trimmed of connective tissue and cut down to fiber bundles (4-8 mg wet wt). Under a microscope and using a pair of extra-sharp forceps, the muscle fibers will be gently separated in ice-cold buffer X containing 60 mM K-MES, 35 mM KCl, 7.23 mM $K_2$EGTA, 2.77 mM Ca$K_2$EGTA, 20 mM imidazole, 0.5 mM DTT, 20 mM taurine, 5.7 mM ATP, 15 mM PCr, and 6.56 mM $MgCl_2$.6 $H_2O$ (pH 7.1, 295 mosmol/kg $H_2O$) to maximize surface area of the fiber bundle. To permeabilize the myofibers, each fiber bundle will be incubated in ice-cold buffer X containing 50 µg/ml saponin on a rotator for 30 minutes at 4° C. The permeabilized bundles will be washed in ice-cold buffer Z, containing 110 mM K-MES, 35 mM KCl, 1 mM EGTA, 5 mM $K_2$HPO4, and 3 mM $MgCl_2$, 0.005 mM glutamate, and 0.02 mM malate and 0.5 mg/ml BSA, pH 7.1.

Mitochondrial Respiration in Permeabilized Fibers.

Respiration will be measured polarographically in a respiration chamber maintained at 37° C. (Hansatech Instruments, United Kingdom). After the respiration chamber will be calibrated, permeabilized fiber bundles will be incubated with 1 ml of respiration buffer Z containing 20 mM creatine to saturate creatine kinase (Saks, et al., *Mol. Cell Biochem.* 184:81-100, 1998; Walsh, et al., *J. Physiol.* 537:971-978, 2001). Flux through complex I will be measured using 5 mM pyruvate and 2 mM malate. The maximal respiration (state 3), defined as the rate of respiration in the presence of ADP, will be initiated by adding 0.25 mM ADP to the respiration chamber. Basal respiration (state 4) will be determined in the presence of 10 µg/ml oligomycin to inhibit ATP synthesis. The respiratory control ratio (RCR) will be calculated by dividing state 3 by state 4 respiration.

Mitochondrial ROS Production.

Mitochondrial ROS production will be determined using Amplex™ Red (Molecular Probes, Eugene, Oreg., U.S.A.). The assay will be performed at 37° C. in 96-well plates using succinate as the substrate. Superoxide dismutase (SOD) will be added at 40 units/ml to convert all superoxide into $H_2O_2$. Resorufin formation (Amplex™ Red oxidation by $H_2O_2$) will be monitored at an excitation wavelength of 545 nm and an emission wavelength of 590 nm using a multi-well plate reader flurometer (SpectraMax, Molecular Devices, Sunnyvale, Calif., U.S.A.). The level of Resorufin formation will be recorded every 5 minutes for 15 minutes, and $H_2O_2$ production will be calculated with a standard curve.

It is anticipated that the MPP will have no effect on normal skeletal muscle size or mitochondrial function, and that the MPP will prevent oxidative damage and associated muscle weakness induced by hind limb immobilization (e.g., atrophy, contractile dysfunction, etc.).

It is anticipated that the MPP will have no effect on normal, soleus muscle weight, the respiratory coupling ratio (RCR), mitochondrial state 3 respiration, or mitochondrial state 4 respiration, in mobile mice. RCR is the respiratory quotient ratio of state 3 to state 4 respiration, as measured by oxygen consumption. Likewise, it is anticipated that the MPP will not cause variable effects on muscle fibers of different size in a normal soleus muscle, or on plantaris muscle weight, the respiratory coupling ratio (RCR), mitochondrial state 3 respiration, or mitochondrial state 4 respiration. Similarly, it is anticipated that the MPP will not have any variable effects to the muscle fibers of different size in normal plantaris muscle fiber tissue.

It is anticipated that hind limb casting for 7 days will cause a significant decrease in soleus muscle weight and mitochondrial state 3 respiration, both of which are anticipated to be reversed by administration of the MPP. It is anticipated that casting for 7 days will significantly increase $H_2O_2$ production by mitochondria isolated from soleus muscle, which is anticipated to be prevented by the MPP. Casting is also anticipated to significantly increase oxidative damage in soleus muscle, as measured by lipid peroxidation via 4-hydroxynonenal (4-HNE). It is anticipated that this effect will be overcome by administration of the MPP. Moreover, it is anticipated that casting will significantly increase protease activity in the soleus muscle, promoting muscle degradation and atrophy, and that this effect will be attenuated or prevented by administration of the MPP. It is anticipated that calpain-1, caspase-3 and caspase-12 proteolytic degradation of muscle, respectively, will be all prevented by treatment with the MPP.

These results will show that administering MPPs to subjects with MV-induced or disuse-induced increases in mitochondrial ROS production reduces protease activity and attenuates skeletal muscle atrophy and contractile dysfunction. The results will further show that treatment of animals with the mitochondrial-targeted antioxidant MPP is useful in preventing the atrophy of type I, IIa, and IIx/b skeletal muscle fibers, and that prevention of MV-induced and disuse-induced increases in mitochondrial ROS production protects the diaphragm from MV-induced decreases in diaphragmatic specific force production at both sub-maximal and maximal stimulation frequencies. It is further anticipated that treatment with the MPP along with the aromatic-cationic peptide will show a synergistic effect. As such, MPPs of the present technology, or pharmaceutically acceptable salts thereof, such as acetate, tartrate, or trifluoroacetate salts, alone or in combination with aromatic-cationic peptides, are useful in methods for treating or preventing MV-induced and disuse-induced mitochondrial ROS production in the diaphragm and other skeletal muscles.

Example 66: MPPs Reduce the Anatomic Zone of No-Reflow Following Ischemia/Reperfusion in the Brain This example will demonstrate the use of MPPs (alone or in combination with an aromatic-cationic peptide) of the present technology in protecting a subject from an anatomic zone of no-reflow caused by ischemia-reperfusion in the brain.

Cerebral ischemia initiates a cascade of cellular and molecular events that lead to brain damage. One such event is an anatomic zone of no-reflow. Cerebral ischemia will be induced by occlusion of the right middle cerebral artery for 30 minutes. Wild-type (WT) mice will be given either saline vehicle (Veh) or the MPP alone or in combination with an aromatic-cationic peptide (2-5 mg/kg) i.p. at 0, 6, 24 and 48 hours after ischemia. Mice will be sacrificed 3 days after ischemia, and the brains sliced transversely into 6-8 sections. Sections will be photographed under ultraviolet light to identify the region of no-reflow. The areas of no-reflow in each slice will be digitized using Image J (supplier Rasband W S, Image J, National Institutes of Health). The areas in each slice will be multiplied by the weight of the slice and the results will be summed in order to obtain the mass of the no-reflow areas.

It is predicted that treatment of wild type mice with the MPP will result in a significant reduction in infarct volume and prevent or reduce the anatomic zone of no-reflow. It is anticipated that treatment with the MPP along with the aromatic-cationic peptide will show a synergistic effect. These results will show that the MPPs of the present technology, or pharmaceutically acceptable salts thereof, such as acetate, tartrate, or trifluoroacetate salts, alone or in combination with aromatic-cationic peptides, are useful in methods for reducing the incidence of no-reflow caused by ischemia-reperfusion in the brain.

Example 67: MPPs Reduce the Anatomic Zone of No-Reflow Following Ischemia/Reperfusion in the Kidney This example will demonstrate the use of MPPs of the present technology in protecting a subject from an anatomic zone of no-reflow caused by ischemia-reperfusion in the kidney. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) in reducing the incidence of no-reflow caused by ischemia-reperfusion in the kidney.

Sprague Dawley rats (250-300 g) will be assigned to the following groups: (1) sham surgery group without I/R; (2) I/R+saline vehicle treatment; (3) I/R+MPP treatment; (4) I/R+MPP and aromatic-cationic peptide treatment. The MPP (3 mg/kg, dissolved in saline) will be administered to rats 30 minutes before ischemia and immediately before onset of reperfusion. The control rats will be given saline vehicle on the same schedule. Rats will be anesthetized with a mixture of ketamine (90 mg/kg, i.p.) and xylazine (4 mg/kg, i.p.). The left renal vascular pedicle will be occluded temporarily using a micro-clamp for 30 or 45 min. At the end of the ischemic period, reperfusion will be established by removing of the clamp. At that time, the contralateral right kidney will be removed. After 24 hours reperfusion, animals will be sacrificed and blood samples will be obtained by cardiac puncture. Renal function will be determined by blood urea nitrogen (BUN) and serum creatinine (BioAssay Systems DIUR-500 and DICT-500).

Analysis of No-Reflow Zones, and Necrosis.

The kidneys will be sliced transversely into 6-8 sections. Sections will be photographed under ultraviolet light to identify the region of no-reflow. The areas of no-reflow in each slice are digitized using Image J (supplier Rasband W S, Image J, National Institutes of Health. The areas in each slice will be multiplied by the weight of the slice and the results will be summed in order to obtain the mass of the no-reflow areas.

It is predicted that treatment with the MPP will prevent or reduce the anatomic zone of no-reflow in the kidney. It is further predicted that one or more of BUN, serum creatinine, and glomerular filtration rate will improve in subjects treated with the MPP as compared to control subjects. It is anticipated that treatment with the MPP along with the aromatic-cationic peptide will show a synergistic effect. As such, the MPPs of the present technology, or pharmaceutically acceptable salts thereof, such as acetate, tartrate, or trifluoroacetate salts, alone or in combination with aromatic-cationic peptides, are useful in methods for reducing the incidence of no-reflow caused by ischemia-reperfusion in the kidney.

Example 68: MPPs Protect Against the No Re-Flow Phenomenon in Humans

This example will demonstrate the use of MPPs at the time of revascularization of ischemic tissue to limit the size of the anatomic zone of no-reflow in human subjects. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH2) in reducing the incidence of no-reflow caused by ischemia-reperfusion in the heart.

For treatment of acute myocardial infarction (AMI), the use of mechanical recanalization of the affected artery restores epicardial coronary blood flow to ischemic myocardium (TIMI Flow Grade 3) in more than 90% of patients. However, these reperfusion methods do not address the important ancillary problem of restoration of blood flow downstream at the level of the capillary bed. During or following primary percutaneous coronary intervention (PCI), microcirculatory dysfunction is observed in 20-40% of patients. The lack of ST-segment elevation resolution after angioplasty with stenting is a marker of microvascular problems and is associated with a poor clinical prognosis. In STEMI, failure to achieve myocardial reperfusion despite the presence of a patent coronary artery has been called the "no-reflow" phenomenon.

Study group. Men and women, 18 years of age or older, who present within 6 hours after the onset of chest pain, who have ST-segment elevation of more than 0.1 mV in two contiguous leads, and for whom the clinical decision is made to treat with PCI will be eligible for enrollment. Patients will be eligible for the study whether they are undergoing primary PCI or rescue PCI. Occlusion of the affected coronary artery (Thrombolysis in Myocardial Infarction [TIMI] flow grade 0) at the time of admission will also be a criterion for inclusion.

Angiography and Revascularization. Left ventricular and coronary angiography will be performed with the use of standard techniques, just before revascularization. Revascularization will be performed by PCI with the use of direct stenting. Alternative revascularization procedures include, but are not limited to, balloon angioplasty; insertion of a bypass graft; percutaneous transluminal coronary angioplasty; and directional coronary atherectomy.

Experimental Protocol. After coronary angiography is performed but before the stent is implanted, patients who meet the enrollment criteria will be randomly assigned to the control group; the MPP treatment group; or the MPP and aromatic-cationic peptide group. Randomization will be performed with the use of a computer-generated randomization sequence. Less than 10 minutes before direct stenting, the patients in the experimental group receive an intravenous bolus injection of the MPP. The peptide will be dissolved in normal saline (final concentration, 25 mg per milliliter) and will be injected through a catheter that is positioned within an antecubital vein. The patients in the control group receive an equivalent volume of normal saline.

No re-flow Zone. The primary end point will be the size of the anatomic zone of no-reflow. No re-flow will be assessed by one or more imaging techniques. Re-flow phenomenon will be assessed using myocardial contrast echocardiography, coronary angiography, myocardial blush, coronary doppler imaging, electrocardiography, nuclear imaging single-photon emission CT, using thallium or technetium-99m, or PET. A 1.5-T body MRI scanner will be used to perform cardiac MRI in order to assess ventricular function, myocardial edema (area at risk), microvascular obstruction and infarct size. Post-contrast delayed enhancement will be used on day 4±1, day 30±3 and 6+1.5 months after successful PCI and stenting to quantify infracted myocardium. This will be defined quantitatively by an intensity of the myocardial post-contrast signal that is more than 2 SD above that in a reference region of remote, non-infarcted myocardium within the same slice. Standard extracellular gadolinium-based contrast agents will be used at a dose of 0.2 mmol/kg. The 2D inversion recovery prepared fast gradient echo sequences will be used at the following time points: (1) early (approximately 2 minutes after contrast injection) for evaluation of microvascular obstruction. Single shot techniques may be considered if available and (2) late (approximately 10 minutes after contrast injection) for evaluation of infarct size.

It is predicted that administration of the MPP at the time of reperfusion will be associated with a smaller anatomic zone of no-reflow than that seen with placebo. It is anticipated that treatment with the MPP along with the aromatic-cationic peptide will show a synergistic effect. As such, the MPPs of the present technology, or pharmaceutically acceptable salts thereof, such as acetate, tartrate, or trifluoroacetate salts, alone or in combination with aromatic-cationic peptides, are useful in methods for reducing the incidence of no-reflow caused by ischemia-reperfusion in the heart.

Example 69: Use of MPPs in the Treatment of Drug-Induced Hyperalgesia in Humans

This example will demonstrate use of the methods and compositions of the present technology in the treatment of hyperalgesia in human subjects. The example will demonstrate the use of MPPs (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH2) in the treatment of vincristine-induced hyperalgesia in humans.

Patients will be recruited to the study as they present in clinic with chronic (>6 months' duration), spontaneous, ongoing, vincristine-related pain. Those enrolled will rate their daily maximum level of pain at 4 or greater on a visual analog scale (VAS). The patients will be screened for their willingness to enroll in the study, and informed consent will be obtained. Healthy subjects will also be recruited for collection of comparison data. No subjects in either the patient or comparison group will have known risk factors for any other cause of peripheral neuropathy, including diabetes, AIDS, chronic alcoholism, or previous radiation exposure.

After a focused interview about the history of the patient's cancer and treatment, the patient will be asked to describe sensory symptoms by choosing from a list of ideal type word descriptors. Ongoing and daily maximum pain intensity will be rated on a VAS with prompts of "no pain" at the bottom and "most imaginable" at the top. The areas of pain and sensory disturbances will be drawn by each patient on a standardized body map. Similar to previous observations in patients treated with paclitaxel, subjects with vincristine-induced peripheral neuropathy are predicted to identify the following three zones of sensation:

a) The painful area: The zone of ongoing pain located on the tips of the fingers and/or toes. The tip of the index finger is expected to be involved in all patients and will be used as the test site in this zone.

b) The border area: Adjacent and proximal to, but distinct from the painful area, represented by nonpainful sensory disturbances and located in the palms and/or soles of the feet. The thenar eminence is expected to be involved in all patients and will be used as the test site in this zone.

c) The nonpainful area: Adjacent and proximal to, but distinct from the border area, reported by the patient to feel "normal." This site is expected to be always proximal to the wrists and/or ankles. Sensory testing will be conducted on the volar surface of the arm.

The tip of the index finger, thenar eminence, and volar forearm, will be tested in normal subjects for comparison. Patients will be specifically queried about the stimuli that provoked pain or caused an exacerbation of ongoing pain in these regions, including the effects that clothing, bed linens, bathing, and normal activities of daily living cause. Each zone will be examined for any physical changes, such as scaling, finger clubbing, and erythema, which will be documented. The areas of sensory disturbance will be physically probed by light touch with a camel hair brush and by manual massage to screen for the presence of allodynia or hyperalgesia.

Touch and Sharpness Detection Thresholds—Touch detection thresholds will be determined with von Frey monofilaments using the up/down method as previously reported. Starting with a bending force of 0.02 g, each monofilament will be applied to a spot on the skin less than 2 mm in diameter for approximately one second. The force of the filament detected four consecutive times will be assigned as the touch detection threshold. Sharpness detection will be determined using weighted 30-gauge metal cylinders. Briefly, the tip of 30-gauge needles (200 mm diameter) will be filed to produce flat, cylindrical ends and the luers will be fitted to calibrated brass weights with the desired force (100, 200, and 400 mN) level for each stimulus. Each loaded needle will be placed inside a separate 10 cc syringe where it will be able to move freely. Each stimulus will be applied for one second perpendicular to the skin 10 times within each area of interest in a pseudorandom order. The subjects will indicate whether the stimulus is perceived as touch, pressure, sharp, or other. The percentages of each reply will be calculated and then combined into group grand means for comparison. The 50% sharpness detection threshold will be calculated as the weighted needle that caused five or more sharp responses after 10 consecutive stimuli.

Grooved Pegboard Test—Manual dexterity will be assessed with the grooved pegboard test. Subjects will be instructed to fill a five-by-five slotted pegboard in an ordered fashion and the times for both dominant and non-dominant hands will be recorded.

Thermal Detection Thresholds—The threshold for heat pain will be determined using the Marstock technique. A radiometer will be used at the outset of testing to ascertain the baseline skin temperature at all testing sites. All tests and measurements will be conducted at room temperature 22° C. Thermal ramps will be applied using a 3.6×3.6 cm Peltier thermode from a baseline temperature of 32° C. Skin heating will be at a ramp of 0.30° C./s, and skin cooling will be at a ramp of −0.5° C./s. Subjects will be instructed to signal when the stimulus is perceived as first becoming warmer and then painfully hot, or as first becoming cooler and then painfully cold. If a subject fails to reach a given threshold before the cutoff temperature of 51.5° C. for the ascending ramp or 3° C. held for 10 seconds in the cooling test, the cutoff values will be assigned for any that are not reached. The final threshold value for each skin sensation in each patient will be determined by averaging the results of three heating and cooling trials.

Statistical Analysis—The thresholds for touch detection will be compared using nonparametric methods (Wilcoxon's test). The sharpness detection, thermal thresholds, and times in the grooved pegboard tests will be compared using analysis of variance and post hoc comparison of the means with Duncan's multiple range tests. Comparisons of mechanical and thermal thresholds will be performed between healthy subjects and patients for the different areas of the tested skin. Further analyses will be performed between glabrous and volar skin within the patient group. For every comparison performed in the present study, $p<0.05$ will be considered significant.

Following initial assessment of the above criteria, subjects will be divided into five groups:
a) Healthy controls
b) No treatment
c) Vehicle-only placebo, administered s.c., once daily for 14 days
d) MPP (or derivatives, analogues, or pharmaceutically acceptable salts thereof) alone, 10 mg/kg, administered s.c., once daily for 14 days
e) MPP (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH$_2$), 10 mg/kg, administered s.c., once daily for 14 days Following the 14 day treatment period, subjects will be re-assessed according to the above criteria, with statistical analysis as described above.

Results—

It is expected that neuropathy subjects administered the MPP for a period of 14 days will report a reduction in hyperalgesia symptoms compared to subjects administered no treatment or a vehicle-only placebo. The reduction in hyperalgesia will be manifested in improved scores for touch and sharpness detection thresholds, grooved pegboard tests, and thermal detection tests compared to control subjects. It is anticipated that treatment with the MPP along with the additional active agent(s) (e.g., an aromatic-cationic peptide) will show a synergistic effect.

These results will show that MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) are useful in the treatment of vincristine-induced hyperalgesia, and drug-induced hyperalgesia generally. The results will show that the methods and compositions described herein are useful in the treatment of drug-induced peripheral neuropathy or hyperalgesia.

Example 70: Use of MPPs in the Treatment of Hyperalgesia in Humans

This example will demonstrate use of the methods and compositions of the present technology in the treatment of hyperalgesia. The example will demonstrate the use of MPPs (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH$_2$) in the treatment of hyperalgesia associated with peripheral neuropathy of various etiologies in humans.

Patients will be recruited to the study as they present in clinic with chronic (>6 months' duration), spontaneous, ongoing, neuropathy-related pain. Independent studies will address neuropathies resulting from, caused by, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. Subjects will be selected such that they have a single type of neuropathy and no known risk factors for neuropathy types outside the scope of the study in which the subject is enrolled. Those enrolled will rate their daily maximum level of pain at 4 or greater on a visual analog scale (VAS). Subjects will be screened for their willingness to enroll in the study, and informed consent will be obtained. Healthy subjects will also be recruited for collection of comparison data.

After a focused interview about the medical history, the patient will be asked to describe sensory symptoms by choosing from a list of ideal type word descriptors. Ongoing and daily maximum pain intensity will be rated on a VAS with prompts of "no pain" at the bottom and "most imaginable" at the top. The areas of pain and sensory disturbances will be drawn by each patient on a standardized body map. Neuropathy subjects are predicted to identify the following three zones of sensation:

a) The painful area: The zone of ongoing pain located on the tips of the fingers and/or toes. The tip of the index finger is expected to be involved in all patients and will be used as the test site in this zone.

b) The border area: Adjacent and proximal to, but distinct from the painful area, represented by nonpainful sensory disturbances and located in the palms and/or soles of the feet. The thenar eminence is expected to be involved in all patients and will be used as the test site in this zone.

c) The nonpainful area: Adjacent and proximal to, but distinct from the border area, reported by the patient to feel "normal." This site is expected to be always proximal to the wrists and/or ankles. Sensory testing will be conducted on the volar surface of the arm.

The tip of the index finger, thenar eminence, and volar forearm, will be tested in normal subjects for comparison. Patients will be specifically queried about the stimuli that provoked pain or caused an exacerbation of ongoing pain in these regions, including the effects that clothing, bed linens, bathing, and normal activities of daily living cause. Each zone will be examined for any physical changes, such as scaling, finger clubbing, and erythema, which will be documented. The areas of sensory disturbance will be physically probed by light touch with a camel hair brush and by manual massage to screen for the presence of allodynia or hyperalgesia.

Touch and Sharpness Detection Thresholds—

Touch detection thresholds will be determined with von Frey monofilaments using the up/down method as previously reported. Starting with a bending force of 0.02 g, each monofilament will be applied to a spot on the skin less than 2 mm in diameter for approximately one second. The force of the filament detected four consecutive times will be assigned as the touch detection threshold. Sharpness detection will be determined using weighted 30-gauge metal cylinders. Briefly, the tip of 30-gauge needles (200 mm diameter) will be filed to produce flat, cylindrical ends and the luers will be fitted to calibrated brass weights with the desired force (100, 200, and 400 mN) level for each stimulus. Each loaded needle will be placed inside a separate 10 cc syringe where it will be able to move freely. Each stimulus will be applied for one second perpendicular to the skin 10 times within each area of interest in a pseudorandom order. The subjects will indicate whether the stimulus is perceived as touch, pressure, sharp, or other. The percentages of each reply will be calculated and then combined into group grand means for comparison. The 50% sharpness detection threshold will be calculated as the weighted needle that caused five or more sharp responses after 10 consecutive stimuli.

Grooved Pegboard Test—

Manual dexterity will be assessed with the grooved pegboard test. Subjects will be instructed to fill a five-by-five slotted pegboard in an ordered fashion and the times for both dominant and non-dominant hands will be recorded Thermal Detection Thresholds—

The threshold for heat pain will be determined using the Marstock technique. A radiometer will be used at the outset of testing to ascertain the baseline skin temperature at all testing sites. All tests and measurements will be conducted at room temperature 22° C. Thermal ramps will be applied using a 3.6×3.6 cm Peltier thermode from a baseline temperature of 32° C. Skin heating will be at a ramp of 0.30° C./s, and skin cooling will be at a ramp of −0.5° C./s. Subjects will be instructed to signal when the stimulus is perceived as first becoming warmer and then painfully hot, or as first becoming cooler and then painfully cold. If a subject fails to reach a given threshold before the cutoff temperature of 51.5° C. for the ascending ramp or 3° C. held for 10 seconds in the cooling test, the cutoff values will be assigned for any that are not reached. The final threshold value for each skin sensation in each patient will be determined by averaging the results of three heating and cooling trials.

Statistical Analysis—

The thresholds for touch detection will be compared using nonparametric methods (Wilcoxon's test). The sharpness detection, thermal thresholds, and times in the grooved pegboard tests will be compared using analysis of variance and post hoc comparison of the means with Duncan's multiple range tests. Comparisons of mechanical and thermal thresholds will be performed between healthy subjects and patients for the different areas of the tested skin. Further analyses will be performed between glabrous and volar skin within the patient group. For every comparison performed in the present study, $p<0.05$ will be considered significant.

Following initial assessment of the above criteria, subjects will be divided into five groups:

a) Healthy controls
b) No treatment
c) Vehicle-only placebo, administered s.c., once daily for 14 days
d) MPP (or derivatives, analogues, or pharmaceutically acceptable salts thereof) alone, 10 mg/kg, administered s.c., once daily for 14 days
e) MPP (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH$_2$) 10 mg/kg, administered s.c., once daily for 14 days Following the 14 day treatment period, subjects will be re-assessed according to the above criteria, with statistical analysis as described above.

Results—

It is expected that neuropathy subjects administered the MPP (or derivatives, analogues, or pharmaceutically acceptable salts thereof) either alone or in combination with one or more active agents (e.g., any one or more of the peptides shown in Section II and/or Table 1 such as D-Arg-2'6'-Dmt-Lys-Phe-NH$_2$) for a period of 14 days will report a reduction in hyperalgesia compared to subjects administered a vehicle-only placebo. The reduction in hyperalgesia will be manifest in improved scoring for touch and sharpness detection thresholds, grooved pegboard tests, and thermal detection tests compared to control subjects. It is anticipated that treatment with the MPP along with the additional active agent(s) (e.g., an aromatic-cationic peptide) will show a synergistic effect compared to subjects that only receive the MPP.

These results will show that MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) are useful in the treatment of neuropathy-related hyperalgesia generally.

Example 71: Use of MPPs in the Prevention of Hyperalgesia in Humans

This example will demonstrate use of the methods and compositions of the present technology in the prevention of hyperalgesia. The example will demonstrate the use of MPPs (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH$_2$) in the prevention of hyperalgesia associated with peripheral neuropathy of various etiologies in humans.

Subjects at risk for developing hyperalgesia will be recruited as they present in clinic for the treatment of conditions associated with the development of peripheral neuropathy or hyperalgesia. Independent studies will address neuropathy and hyperalgesia resulting from, caused by, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. Subjects will be selected such that they are at risk for developing a single type of neuropathy or hyperalgesia, having no risk factors outside the scope of the study in which the subject is enrolled, and as yet not having symptoms associated with neuropathy or hyperalgesia. Subjects will be screened for their willingness to enroll in the study, and informed consent will be obtained. Healthy subjects will also be recruited for collection of comparison data.

After a focused interview about the medical history, baseline measurements of touch and sharpness detection thresholds, grooved pegboard tests, and thermal detection thresholds will be determined according to the methods described above, with statistical analysis as described above.

Following initial assessment of the above criteria, subjects will be divided into five groups:

a) Healthy controls
b) No treatment
c) Vehicle-only placebo, administered s.c., once daily
d) MPP (or derivatives, analogues, or pharmaceutically acceptable salts thereof) alone, 10 mg/kg, administered s.c., once daily
e) MPP (or derivatives, analogues, or pharmaceutically acceptable salts thereof) in combination with one or more active agents (e.g., any one or more of the peptides shown in Section II and/or Table 1 such as D-Arg-2'6'-Dmt-Lys-Phe-NH$_2$), 10 mg/kg, administered s.c., once daily Subjects will be evaluated weekly during the trial for sharpness detection thresholds, grooved pegboard tests, and thermal detection thresholds. The trial will continue for a period of 28 days, or until the no-treatment and placebo control groups display hyperalgesia according to the above criteria, at which point subjects will undergo a final assessment.

Results—

It is expected that at-risk subjects that are treated with the MPP (or derivatives, analogues, or pharmaceutically acceptable salts thereof) either alone or in combination with one or more active agents (e.g., any one or more of the peptides shown in Section II and/or Table 1 such as D-Arg-2'6'-Dmt-Lys-Phe-NH$_2$) will show attenuated development of neuropathy or hyperalgesia compared to untreated and placebo controls. It is anticipated that treatment with the MPP along with the additional active agent(s) (e.g., an aromatic-cationic peptide) will show a synergistic effect compared to subjects that only receive the MPP.

These results will show that MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) are useful in the prevention of neuropathy and hyperalgesia generally. The results will show that the methods and compositions described herein are useful in the prevention of neuropathy or hyperalgesia generally.

Example 72: MPP Translocation to the Mitochondria

This example will demonstrate the capacity of MPPs of the present technology to translocate to the mitochondria using solid-state NMR. In particular, it will demonstrate the capacity of the peptide Cha-Arg-Cha-Lys-NH$_2$ to translocate to the mitochondria using solid-state NMR.

Large unilamellar vesicles (LUVs) with a transmembrane gradient of about −180 mV are constructed, composed of a mixture of cardiolipin (CL, 10% mol), phosphatidylcholine (PC, 50% mol), and phosphatidylethanolamine (PE, 40% mol). An electrochemical gradient is incorporated because the transloation of MPPs is known to be highly dependent on electrochemical potential. Spectra from three different peptide-lipid systems are compared: Mn$^{2+}$ free, Mn$^{2+}$ bound to one side of the vesicle, and Mn$^{2+}$ bound to both the inside and outside of the vesicle.

It is expected that the results will show a sunstainable model of inner mitochondria membranes for ssNMR measurements and found that the MPP does not alter the bilayer integrity. At low peptide concentrations, the MPP is expected to bind to the outer leaflet only, whereas at high concentrations the MPP is exected to be distributed into both leaflets, following the electroporation model for translocation into the mitochondria.

Materials and Methods.

All lipid products used to form the model mitochondrial membranes are commercially available, including 1,1',2,2'- tetraoleoyl cardiolipin sodium salt (18:1 CL), 1-palmitoyl-2-linoleoyl-sn-glycero-3-phosphocholine (16:0-18:2 PC), and 1,2-distearoyl-sn-glycero-3-phosphoethanolamine (18:0 PE. The mitochondria-penetrating peptide (Cha-Arg-Cha-Lys) comprises uniformly labeled $^{13}$C, $^{15}$N residues at positions R2 and K4 at >95% purity.

Model Mitochondria Membrane Sample Preparation.

Large unilamellar vesicles (LUVs) are constructed that exhibit a transmembrane gradient according to two known protocols. A pH difference is used to establish a transmembrane gradient. The membrane encapsulates 300 mM pH 4 phosphate buffer inside the vesicle and 10 mM pH 7 phosphate buffer outside to establish an electrochemical potential of −177 mV, which is reflective of the biologically encountered mitochondrial gradient of −180 mV. The existence of a three unit pH gradient is confirmed by the fluorescence response of 9-aminoacridine as previously described.

Hydrated CL/PC/PE membranes are formed by dissolving the lipids in a 95:5 benzene:ethanol mixture at an appropriate molar ratio of 0.1/0.5/0.4, respectively. The lipid mixture is lyophilized overnight. The dried lipid cake is rehydrated with 300 mM phosphate buffer at pH 4 which is heated to 85° C. The rehydrated lipid sample is incubated for 2 hours at 85° C. and vortexed periodically to produce multilamellar vesicles (MLVs). The resulting MLVs are down-sized using a mini extruder (Avanti Polar Lipids, Inc.) and passed through a 100 nm polycarbonate membrane 21 times to produce LUVs of uniform diameter of 100 nm. The size of the vesicles is confirmed by dynamic light scattering on a ZetaPALS particle size analyzer. The LUVs are dialyzed for at least 8 hours using a Slide-A-Lyzer (Thermo Fisher Scientific) to remove the low pH, high salt buffer and replace it with 10 mM phosphate buffer at pH 7 for the exterior membrane environment.

After dialysis, the MPP is added at the appropriate molar ratio (P:L=1:10 or P:L=1:40) to the LUVs and incubated overnight. The MPP-lipid mixture is centrifuged at 160 000 g for 1.5 hours to yield a hydrated pellet, which is packed into a 200 μL MAS rotor. For the $Mn^{2+}$ containing samples, the $Mn^{2+}$ solution is prepared from $MnCl_2.4H2O$ and added at 8 mol % of the lipids. To obtain one side $Mn^{2+}$ bound vesicles, the $Mn^{2+}$ solution is either added after ultracentrifugation or during extrusion, producing outside-bound and inside-bound one side $Mn^{2+}$ bound samples. For two side $Mn^{2+}$ bound vesicles, the vesicles are extruded with the appropriate percentage of $Mn^{2+}$ and had $Mn^{2+}$ added after dialysis to replace the ions lost during this process.

NMR Spectroscopy.

All NMR measurements are performed on a Bruker Avance 500 (11.7 T) spectrometer operating at a resonant frequency of 500 MHz for $^1$H, 202 MHz for $^{31}$P, and 125 MHz for $^{13}$C, equipped with a BCU05 Variable Temperature Control Unit. Data is processed using Bruker Topspin 1.3 or iNMR software. All experiments are performed using a Bruker HXY broadband MAS probehead doubly tuned to $^1$H/$^{13}$C/Y or $^1$H/$^{31}$P/Y. $^{13}$C chemical shifts are externally referenced to adamantane at 38.5 ppm on the TMS scale. $^{31}$P chemical shifts are referenced to 85% phosphoric acid at 0.0 ppm. $^{15}$N chemical shifts are referenced to glycine at 109.4 ppm.

The spinning rate for all MAS experiments is 5 kHz, performed at 310 K. $^{13}$C direct polarization (DP) MAS NMR spectra is decoupled with two pulse phase modulation (TPPM) at $^1$H field strengths of 30 kHz. Typical radiofrequency (rf) pulse lengths are ~5 μs for $^{13}$C and ~2 μs for $^1$H. Static $^{31}$P spectra are decoupled with WALTZ-16 at $^1$H field strengths of 6 kHz. Typical rf pulse lengths are ~4 μs for $^{31}$P.

Results

Static $^{31}$P chemical shift anisotropy NMR measurements are conducted at variable temperatures (280 K-360 K) to determine if any changes in membrane morphology or lipid transition temperatures occurr upon peptide binding. The $^{31}$P NMR spectra of the model mitochondria membranes alone are recorded to provide a comparison to the peptide-bound membranes. The observed static $^{31}$P NMR lineshape is consistent with hydrated 100 nm unilamellar vesicles, as is the observed linewidth (~2 kHz), even at the highest temperature of 360 K. The alterations in $^{31}$P lineshape at each temperature are a reflection of the unique transition temperatures for each of the lipids, ranging from 264 K for PC to 347 K for PE, and the resulting mixed liquid crystalline and gel phases. For the peptide-containing samples, the MPP is added at a peptide to lipid ratio of P:L=1:12.5. This peptide concentration is sufficiently high to observe membrane defects, if they are present upon binding. No significant remodeling of the lipid bilayer is expected to be observed at any temperature, indicating that peptide insertion does disrupt the lamellarity of the bilayer. This observation will be consistent with the non-lytic nature of other penetrating peptides. Furthermore, no isotropic peak is expected to be observed, ruling out the possibility of the formation of inverse micelles to internalize the peptide.

To assess the remaining two mechanisms of translocation (electroporation and guanidinium-phosphate complexation), a $^{13}$C MAS NMR PRE method at 310 K is used. In order to assure asymmetric distribution of $Mn^{2+}$ paramagnetic ions with the new model inner mitochondrial membranes, the ion position is monitoted with the $^{31}$P NMR signal of the lipid heagroups. Without paramagnetic ions present, the entire signal is measured from all the phospholipid headgroups. The addition of $Mn^{2+}$ to the outside of the vesicles is expected to cause signal attenuation of about half the lipids, corresponding to dephasing of the outer leaflet. When the paramagnetic ions are on both sides of the bilayer, the entire $^{31}$P signal is expected to be killed because all lipid headgroups will be in close proximity to $Mn^{2+}$.

This experiment will show that $Mn^{2+}$ ions bind to lipid headgroups, but do not diffuse through the model inner mitochondria membranes, even in the presence of a negative transmembrane gradient, allowing asymmetric $Mn^{2+}$ distribution to probe insertion depth and determine bilayer sidedness, consistent with previously reported spectra in the absence of a transmembrane gradient. Since the addition of paramagnetic ions to the system may perturb the electrostatic interactions in subsequent membrane-peptide experiments, the minimal amount of $Mn^{2+}$ is added to achieve suitable signal attenuation, at 8 mol % of the lipid concentration. The peptide affinity for the membrane should not be affected by this minimal anionic phosphate charge neutralization of 8 mol %.

In order to determine whether peptide insertion is concentration dependent, the MPP is to the membranes at two difference concentrations. The $^{13}$C DP-MAS NMR results of the PRE effect of one and two side $Mn^{2+}$ bound membranes at both peptide concentrations is measured. The lipid peaks are expected to be attenuated in all samples. In the one side $Mn^{2+}$ bound sample at P:L-1:10, the peptide peaks are expectec to retain much of the signal intensity (~75%) when compared to the unbound sample. However, in the two side $Mn^{2+}$ bound spectra, much of the peptide peak intensity is expected to be dephased, with signal retention dropping to about 50%, on average. This will be consistent with the MPP partitioning into both leaflets of the bilayer at high concentration.

In order to compare between different samples, the NMR signal peak intensity is double-normalized, $(S/So)/(S/SO)$ max, where S is the signal of the $Mn^{2+}$ bound sample, So is the $Mn^{2+}$ free sample, and $(S/SO)$max is the normalized value of the lipid peak with the least attenuation. Error bars are obtained via error propagation of the signal to noise ratio of each peak. At low P:L=1:40, there is expected to be no change in signal intensity when comparing one side and two side $Mn^{2+}$ bound membranes, placing the peptide solely in the outer leaflet. At high P:L=1:10, the peptide is expected to retain much of its signal intensity in the one side $Mn^{2+}$ bound sample, while in the two side $Mn^{2+}$ bound sample, the signal intensity is expected to be significantly lowered. This will show that at low peptide concentrations, the MPP binds only to the outer leaflet while at high peptide concentrations the MPP is distributed in both the inner and outer leaflet of the bilayer.

Confirmation that the peptide is only bound to the outer leaflet of the bilayer will be achieved by constructing vesicles with $Mn^{2+}$ bound only to the inside of the vesicles with a P:L=1:40 and coparing the normalized signal intensities to P:L=1:40 with no $Mn^{2+}$, and P:L=1:40 with $Mn^{2+}$ bound only to the outside of the vesicles. If the peptide is bound to the outer leaflet of the vesicle, $Mn^{2+}$ ions on the inner leaflet only should have no effect of the peptide signal intensities. It is expected that the lipid Cy peak intensity wil be the same for both the inside $Mn^{2+}$ bound and outside$Mn^{2+}$ bound samples. The same vesicles will also be constructed to examine the P:L=1:1 sample. Nearly the same signal dephasing is expected to be observed for both one-sided $Mn^{2+}$ bound samples (inside and outside), confirming that the peptide is distributed into both the inner and outer leaflet, at approximately a 50/50 ratio.

In addition, $^{13}C$ MAS PRE data is used as a spectroscopic ruler to estimate the MPP location in the bilayer. Since the depth associated with the lipid peaks is known from the bilayer structure of the vesicles, the signal dephasing of the peptide can be compared to that of the lipids to estimate insertion depth. It is expected that at P:L=1:40, the MPP is inserted at approximately C1-C2, at the top of the acyl chain, in the interfacial region. It is further expected that a larger error associated with the low concentration peptide sample will suggest that the peptide may be closer to the surface of the bilayer than the high concentration sample, and the signal dephasing serves only as an approximation for insertion depth. It is further expected that even slight differences in insertion depth can result in larger signal dephasing since the spin-spin relaxation rate in the presence of paramagnetic ions is proportional to {6, where r is the distance between the paramagnetic center and the observed resonance.

It is expected that when the ratio is increased to P:L=1:10, the peptide will be distributed into both leaflets. Assuming that half of the peptide would be bound to the outer leaflet, and half would be bound to the inner leaflet, the data is expected to show that the MPP is inserted into both leaflets at C2. The peptide interaction at at the top of the acyl chain, near C1 (P:L=1:40) and C2 (P:L=1:10), will indicate stability at this position on the lipid acyl chain, which is expected to be due to the close proximity of the cationic peptide to the phospholipid headgroup.

In order to estimate the insertion depth, it will be assumed that the peptides are membranebound, and not exchanging with the solvent. In the rapid exchange regime, it is possible to estimate the mole fraction of peptide bound by varying the peptide to lipid ratio, and measuring the change in $^{13}C$ chemical shift as the peptide concentration increases. No change in $^{13}C$ chemical shift is expected to be observed between P:L=1:40 and P:L=1:10 for the peptide resonances, indicating that at both concentrations, the peptide is membrane-bound. This observation will be consistent with previous studies on short peptides reconstituted in model lipid systems that found over 90% of the peptides are membrane bound.

These results will show that the concentration-dependent peptide distribution in the inner and outer leaflets of the bilayer support the electroporation model of translocation. Once bound to the inner leaflet of the bilayer, the peptides can proceed to enter the matrix. The electroporation model provides an explanation as to how and why MPPs translocate through the dense, hydrophobic portion of the inner mitochondrial membrane. The threshold for a sufficient voltage to form pores of electroporation ranges from −250 to −550 mV. In the model membranes, there exists a transmembrane gradient of −180 mV that is equivalent to mitochondrial gradients encountered in biological systems. While this gradient alone is likely not enough to form transient pores, the accumulation of cationic peptides in the outer leaflet can induce an additional potential.

In the case of MPPs interacting with the model membranes, the electrostatic potential of a few peptides binding to the outer leaflet is not strong enough for electroporation because the charge is reduced by counterions on the phosphate headgroups. In particular, PC and PE are both zwitterionic lipids, whereas CL is anionic, with two negatively charged phosphate headgroups. In this case, the two positive charges from the Arg and Lys residues on the MPP are present at a 1:1 ratio with the negative charges on the cardiolipin headgroup. Given that the concentration of CL in the model membranes is 10%, to reflect the occurrence in mammalian mitochondria, peptide-to-lipid ratio of 1:40 would not fully neutralize the anionic charge in the outer leaflet, assuming an even distribution of anionic charge in both monolayers. Once an adequate amount of MPPs, the threshold concentration, also bind, the peptides provide enough surface charge density to attract additional anionic lipids in the inner leaflet to provide sufficient voltage to permit passage through the formation of transient pores. At a concentration of 1:10, the anionic character of the outer leaflet is fully saturated with cationic peptides, leading to an electroporation-like transfer of peptides to the inner leaflet, as revealed in the $^{13}C$ PRE NMR spectra.

The concentration dependence of translocation observed here is consistent with the electroporation model for interalization. The MPP is able to cross the high energy barrier of the hydrophobic bilayer core, in spite of membrane curvature, which can playa role in preventing penetrating-peptide translocation, and is likely stabilized by cardiolipin.

While hydrophobic interactions between the bilayer core and hydrophobic peptide residues are predicted to contribute to peptide translocation, several studies have found that the electrostatic attraction between negatively charged lipids and positively charged residues dominates the initial binding event. There is substantial evidence that the anionic phospholipid electrostatic contribution can be a minor compared to the total lipid population and still have an effect on penetrating-peptide binding and structural reorganization. Furthermore, the anionic phospholipid-cationic peptide interaction is predicted to be stronger for Arg residues than Lys residues, indicating the necessity of Arg residues to facilitate membrane insertion, especially into the plasma membrane. For MPPs, the presence of Arg clusters is predicted to increase transport across the plasma membrane, and result in a decrease in mitochondrial localization. Therefore, the requirement for mitochondrial membrane penetration is likely to be different than that of the plasma membrane, which is probably a delicate balance between electrostatic and hydrophobic interaction between the bilayer, peptides, and electrochemical gradient.

Similar NMR measurements were performed previously on a well known cell-penetrating peptide, penetratin. The translocation of penetratin was examined in lipid vesicles without a transmembrane gradient and that contained ~50% anionic character. Penetratin has seven cationic residues, and at both high (P:L=1:10) and low (P:L=1:40) concentrations was shown to distribute into both leaflets of the bilayer, even though the negatively charged phospholipid headgroups never become fully neutralized. This mechanism of internalization was attributed to a guanidinium-phosphate complexation that allowed the peptide to cross the hydrophobic portion of the bilayer without a high free-energy penalty, differing from the previously proposed models. The inner mitochondrial membranes presented here should allow easier translocation, due to the presence of a transmembrane gradient, as well as a lower anionic content, that would become saturated more quickly. Yet, a concentration dependent mode of translocation, consistent with the electroporation model is observed. This evidence suggests that different classes of penetrating peptides proceed with internalization via different mechanisms which may be lipid membrane and transmembrane gradient dependent.

Previous studies have implicated the importance of a transmembrane gradient to penetrating-peptide internalization, and since transmembrane potential was shown to be equally important for MPPs model membranes that exhibited a electrochemical gradient were generated. To examine the inflence of a transmembrane gradient on this system, the energy barriers the MPP had to overcome in order to go from the outer leaflet, through the hydrophobic center of the bilayer, to the inner leaflet of the bilayer will be evaluated. The energy cost of each step will be estimated using the Wimley-White interfacial hydrophobicity scale determined from measurements of short peptides partitioning into zwitterionic phosphatidylcholine (POPE) vesicles and n-octanol. For this system, a favorable, negative free energy change for insertion into the interfacial region will be estimated. The MPP then has to overcome an unfavorable, positive energy barrier to cross the bilayer core. Then, the peptide can fall back into the favorable interfacial region of the inner leaflet.

The force across the plasma membrane, F=12 kllmol (assuming the membrane potential is −60 mV), is sufficient to pull the cationic peptide across the free energy barrier in the hydrocarbon core and overcome the stabilizing forces present in the interfacial region to enter the cytosol. The OMM contains pore-like structures called porins, which allow the passage of small peptides. Here, the peptide can electrostatically interact with the anionic IMM. Because the IMM is anionic, rather than zwitterionic, the favorable free energy associated with the water-membrane interface will be lower than the calculated values. The IMM exhibits a transmembrane potential of −180 mY, providing a force of 36 kllmol. Assuming the transmembrane gradient is the only force acting on the peptide, if it is enough to pull the peptide over the high free energy barrier of the bilayer core (observing distribution in both leaflets at high peptide concentration), it should be enough to move the peptide from the interfacial region to the matrix, unless the peptide-lipid interaction provides enough stability to lock the MPP in the interfacial region. While it has been indicated that only a small percentage of peptides with similar amino acid sequences, SS tetrapeptides, reach the matrix, recent studies on several MPPs are consistent with matrix localization, suggesting these peptides undergo full internalization.

Results

This work will accurately models inner mitochondria membranes, exhibiting a transmembrane gradient of −180 mV that is suitable for the study of peptide-lipid interactions with ssNMR. The inner mitochondria membranes will be used to gain insight into the mechanism of translocation of a mitochondria-penetrating peptide. By using variable temperature static $^{31}$P NMR spectroscopy, it is expected to be determined that the peptide did not disrupt the lamellarity of the bilayer, nor did it affect the phase transition temperatures. It is further expected that the membranes are suitable for asymmetric insertion depth measurements, due to their non-permeable nature with respect to $Mn^{2+}$ ions, using $^{13}$C MAS PRE experiments. At low peptide concentrations, MPP is prediced to bind only to the outer leaflet of the bilayer, at C2 near the top of the lipid acyl chain. As the concentration is increased, the peptide is expected to pass through the hydrophobic core of the membrane and redistributes into both leaflets of the bilayer.

These results will show that the MPPs described herein, such as Cha-Arg-Cha-Lys-$NH_2$, and/or naturally or artificially occurring variants or analogues, or pharmaceutically acceptable salts thereof, alone or in combination with one or more active agents (e.g., an aromatic-cationic peptide such as D-Arg-2'6'-Dmt-Lys-Phe-$NH_2$) are useful for the delivery of therapeutic agents to the mitochondria. As such, the compositions described herein are useful in methods for prevention and/or treatment comprising the delivery of therapeutic agents to the mitochondria.

Example 73: Use of MPPs in Reducing Mitochondrial Fission

This example will demonstrate use of the methods and compositions of the present technology in the reduction of mitochondrial fission. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-$NH_2$) in the reduction of mitochondrial fission following exposure to mitochondrial stressors.

Cultured human SH-SY5Y neuronal cells are treated with buffer; 5 μM CCCP (carbonyl cyanide m-chloro phenyl hydrazone, a mitochondrial uncoupler); 5 μM CCCP and a MPP; and 5 μM CCCP, a MPP and an aromatic-cationic peptide for 30 minutes. The cells are then stained with anti-Tom20 antibody, a mitochondrial marker, and Hoechst stain. Mitochondrial morphology is analyzed using 63× oil immersion lens.

Results—

It is expected that control cells treated with CCCP will show extensive mitochondrial fragmentation as manifested by small, round or dot-like staining patterns. It is also anticipated that treatment with the MPP, alone and in combination with an aromatic-cationic peptide will result in significantly reduced mitochondrial fission compared to control cells that are only exposed to CCCP. It is anticipated that treatment with the MPP along with the aromatic-cationic peptide will show a synergistic effect.

These results will show that the MPPs (or derivatives, analogues, or pharmaceutically acceptable salts thereof), alone or in combination with an aromatic-cationic peptide, are useful in methods for reducing mitochondrial fission in mammalian subjects. The results will show that the methods and compositions described herein are useful in reducing mitochondrial fission generally.

Example 74: Use of MPPs to Increase Protein Expression Levels of Fully Assembled Complex I and Complex II in Cells Bearing Complex I Mutations This example will demonstrate use of the methods and compositions of the present technology to restore electron transport chain function in complex I mutant cells. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH2) in the elevation of Complex I and Complex II protein levels in Complex I mutant cells.

Experimental fibroblast cells are derived from patients with a mutation in different Complex I subunits. Control cells are human skin fibroblasts derived from healthy controls. Cultured Complex I mutant fibroblasts are incubated with buffer; a MPP; and a MPP and an aromatic-cationic peptide for up to 72 hours. The cells are then harvested by trypsinization and washed twice with ice-cold PBS. The cell suspensions are centrifuged for 5 minutes at 4° C. and the cell pellets are snap-frozen in liquid nitrogen. The cell pellets are subsequently thawed on ice and resuspended in 100 l of ice-cold PBS.

Isolation of OXPHOS complexes: The cell suspension is incubated with 100 µl (4 mg/ml) digitonin (Sigma, Zwijndrecht, Netherlands) on ice for 10 min. Digitonin dissociates membranes that contain cholesterol, thereby dissociating the cell membrane and the outer mitochondrial membrane, but not the inner mitochondrial membrane. Next, 1 ml ice-cold PBS is added to dilute the digitonin, followed by centrifugation (10 min; 15,600 xg; 4° C.). The resulting pellets contain a cell fraction which is enriched for mitoplasts. The supernatant is removed and the pellets are resuspended in 100 µl ice-cold PBS. 1 ml ice-cold PBS is then added and the suspension is centrifuged again (5 min; 15,600 xg; 4° C.), followed by removal of the supernatant and resuspension of the pellet in 100 µl ice-cold PBS. The supernatant is removed with a syringe and needle and the pellets containing the mitoplast fraction are stored overnight (−20° C.).

The complexes of the OXPHOS system are extracted from the inner membrane with β-lauryl maltoside and aminocaproic acid. The pellets are thawed on ice and solubilized in 100 µl ACBT buffer containing 1.5 M ε-aminocaproic acid (Serva, Amsterdam, Netherlands) and 75 mM Bis-Tris/HCl (pH 7.0) (Sigma). Subsequently 10 µl 20% (w/v) β-lauryl maltoside (Sigma) is added and the suspension is left on ice for 10 min. Next, the suspensions are centrifuged (30 min; 15,600×g; 4° C.) and the supernatants which contain the isolated complexes are transferred to a clean tube (L. G. Nijtmans et al., Methods 26 (4): 327-334 (2002)). The protein concentration of the isolated OXPHOS complexes is determined using a Biorad Protein Assay (Biorad, Veenendaal, Netherlands). Blue-native PAGE analysis of mitoplasts is performed as described in L. G. Nijtmans et al., Methods 26 (4): 327-334 (2002).

Complex I or complex II protein detection: To visualize the amount of complex I or complex II present in the BN-PAGE gels, the proteins are transferred to a PVDF membrane (Millipore, Amsterdam, Netherlands) using standard Western blotting techniques and detected by immunostaining. After the blotting and prior to blocking the PVDF membrane with 1:1 PBS-diluted Odyssey blocking buffer (Li-cor Biosciences, Cambridge, UK), the PVDF blot is stripped with stripping buffer for 15 min at 60° C. The stripping buffer consists of PBS, 0.1% Tween-20 (Sigma) and 2% SDS (Serva). A monoclonal primary antibody against NDUFA9 (39 kDa) (Molecular probes, Leiden, The Netherlands) is used for detection of Complex I. To detect Complex II, a monoclonal antibody against the 70 kDa subunit of complex II is used (Molecular probes). Both primary antibodies are diluted in PBS, 0.1% Tween-20 and 2.5% Protifar Plus (Nutricia, Cuijk, The Netherlands) and allowed to bind to the complex for 4 hours at room temperature or overnight at 4° C. The bound primary antibodies are subsequently detected by IRDye 800 CW conjugated anti-Mouse antibody (Li-cor Biosciences) at a final concentration of 0.1 µg/ml.

Results: It is expected that untreated Complex I mutant cells will show reduced protein expression levels of Complex I and Complex II compared to untreated control cells. It is also anticipated that treatment with the MPP, alone and in combination with an aromatic-cationic peptide will result in an increase in fully assembled complex I and complex II protein levels. It is anticipated that treatment with the MPP along with the aromatic-cationic peptide will show a synergistic effect.

These results will show that the MPPs (or derivatives, analogues, or pharmaceutically acceptable salts thereof), alone or in combination with an aromatic-cactionic peptide are useful in methods for elevating Complex I and Complex II protein levels in mammalian subjects. The results will show that the methods and compositions described herein are useful in promoting electron transport chain function generally.

Example 75: In Vivo Effect of MPPs on Grip Strength in Ndufs4 Knockout Mice

This example will demonstrate use of the methods and compositions of the present technology to improve grip strength in Ndufs4 knockout (Complex I deficient) mice. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) in improving grip strength in Complex I deficient subjects.

Animals and Treatments:

Ndufs4 knockout (KO) and wild-type (WT) mice are generated by crossing Ndufs4 heterozygote males and females (Kruse S E, et al., 2008, *Cell Metab* 7:312-320). Animals are divided into the following groups: Vehicle-WT; Vehicle-KO; MPP-KO; MPP and aromatic-cationic peptide-KO. Animals are tested at 3, 5 and 6 weeks of age. Animals will receive either vehicle (control) injections, consisting of sterile water, or a MPP, or a MPP in combination with an aromatic-cationic peptide. Animals are injected twice a day (about 2 ml/kg per injection). Injections begin during week 3 of life, and are continued daily until the conclusion of the experiment in week 6.

Data Analysis:

All data are expressed as mean+SEM. Data are analyzed using a oneway ANOVA in SPSS version 20.0. Significant overall effects (i.e. genotype, treatment and/or genotype treatment interaction) are further analyzed using Fisher's PLSD post-hoc analyses.

Grip Strength Paradigm:

The grip strength test is designed to measure muscular strength in rodents. The apparatus consists of a single bar, which the animal will grasp by instinct. Once the bar has been grasped, the experimenter gently retracts the animal until the animal is forced to release the bar. The amount of force exerted by the animal on the bar is measured in Pond (p) (1 p=1 gram). The grip strength test is repeated 5 times and the average force exerted is used as the quantitative readout. All measurements will be corrected for body weight, using the following equation:

$$\text{Grip Strength Score} = ((\text{week } X \text{ trials } 1+2+3+4+5)/5) / \text{Average Body Weight week } X \text{ (g) (Week } X = \text{week 3, 5 or 6)}$$

Testing Procedure: On testing days, animals will receive their morning injection 30 minutes prior to their testing time. After injections, the animals will be placed in the testing room for a 30 minute acclimation period.

Results:

It is expected that vehicle KO animals will show remarkably decreased grip strength compared to wild-type control animals. It is also anticipated that chronic treatment with the MPP, alone and in combination with an aromatic-cationic peptide will result in significantly improved grip strength in the knockout animals compared to vehicle knockouts. It is anticipated that treatment with the MPP along with the aromatic-cationic peptide will show a synergistic effect.

These results will show that the MPPs (or derivatives, analogues, or pharmaceutically acceptable salts thereof), alone or in combination with aromatic-cationic peptides, are useful in methods for improving grip strength in mammalian subjects. The results will show that the methods and compositions described herein are generally useful in treating neuromuscular defects in Complex I deficient subjects.

Example 76: Use of MPPs to Reduce Tumor Growth

This example will demonstrate use of the methods and compositions of the present technology to reduce the growth rate of implanted tumors. The example will demonstrate the use of MPPs (or derivatives, analogues, or pharmaceutically acceptable salts thereof) alone or in combination with one or more active agents (e.g., any one or more of the peptides shown in Section II and/or Table 1 such as D-Arg-2'6'-Dmt-Lys-Phe-NH$_2$) in reducing tumor growth.

A standard panel of 12 tumor cell lines will be used for the hollow fiber screening of the MPPs alone or in combination with an aromatic-cationic peptide. These include NCI-H23, NCI-H522, MDA-MB-231, MDA-MB-435, SW-620, COLO 205, LOX, UACC-62, OVCAR-3, OVCAR-5, U251 and SF-295. The cell lines are cultivated in RPMI-1640 containing 10% FBS and 2 mM glutamine. On the day preceding hollow fiber preparation, the cells are given a supplementation of fresh medium to maintain log phase growth. For fiber preparation, the cells are harvested by standard trypsinization technique and resuspended at the desired cell density (2-10×10$^6$ cells/ml). The cell suspension is then flushed into 1 mm (internal diameter) polyvinylidene fluoride hollow fibers with a molecular weight exclusion of 500,000 Da. The hollow fibers are heat-sealed at 2 cm intervals and the samples generated from these seals are placed into tissue culture medium and incubated at 37 in 5% CO$_2$ for 24-48 hours prior to implantation. A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line preparation are quantitated for viable cell mass by a stable endpoint MTT assay so that the time zero cell mass is known. Mice are treated with MPPs alone or in combination with an aromatic-cationic peptide starting on day 3 or 4 following fiber implantation and continuing daily for 4 days. Control animals receive the tumor implants and are treated with only the empty vehicle. The therapeutic compositions are administered by intraperitoneal injection at 2 dose levels. The doses are based on the maximum tolerated dose (MTD) determined during prior toxicity testing. The fibers are collected from the mice on the day following the fourth compound treatment and subjected to the stable endpoint MTT assay. The optical density of each implanted tumor sample is determined spectrophotometrically at 540 nm and the mean of each treatment group is calculated. The percent net growth for each cell line in each treatment group is calculated and compared to the percent net growth in the vehicle treated controls. A 50% or greater reduction in percent net growth in the treated samples compared to the vehicle control samples is considered a positive result. Each positive result is given a score of 2 and all of the scores are totaled for a given MPP (either alone or in combination with an aromatic-cationic peptide. The maximum possible score for an agent is 96 (12 cell lines×2 sites×2 dose levels×2 [score]). A compound is considered for xenograft testing if it has a combined ip+sc score of 20 or greater, a sc score of 8 or greater, or produces cell kill of any cell line at either dose level evaluated.

Results:

It is expected that vehicle treated controls will show an increase in tumor net growth after 4 days. It is also anticipated that treatment with the MPP, alone and in combination with an aromatic-cationic peptide will result in significantly reduced tumor net growth compared to vehicle treated controls. It is anticipated that treatment with the MPP along with the aromatic-cationic peptide will show a synergistic effect.

These results will show that the MPPs (or derivatives, analogues, or pharmaceutically acceptable salts thereof), alone or in combination with aromatic-cationic peptides, are useful in methods for reducing tumor growth in mammalian subjects. The results will show that the methods and compositions described herein are generally useful in treating a neoplastic disease.

Example 77: MPPs Restore Motor and Cognitive Function in an In Vivo Huntington's Disease (HD) Animal Model This example will show that MPPs (alone or in combination with an aromatic-cationic peptide) of the present technology reduce neurological defects associated with HD.

R6/2 mice, expressing exon 1 of the human HD gene carrying more than 120 CAG repeats, exhibit progressive neurological phenotypes that mimic the features of HD in humans. The mice develop progressive neurological phenotypes gradually with mild phenotype (e.g., resting tremor) as early as 5 weeks of age and severe symptoms (including reduced mobility and seizures) at 9-11 weeks, with many of the mice dying by 14 weeks.

R6/2 HD transgenic mice are treated with an empty vehicle; a MPP; or a MPP and an aromatic-cationic peptide, using Alzet osmotic mini-pumps (delivering 3 mg/kg/day) from age 5 weeks to 13 weeks. These animals will be subjected to a number of behavioral assessments to study motor and cognitive function. Rotor-rod and mobility in an activity chamber are used for assessment of motor function, and the Y-maze is used for assessment of working memory.

Results—

It is anticipated that vehicle-treated R6/2 mice will display major motor deficits such as a reduced ability to stand on their rear limbs and increased periods of immobility compared to wild-type controls. It is further anticipated that treatment with the MPP, alone and in combination with an aromatic-cationic peptide will restore motor activity and improve cognitive function (as demonstrated by the animals' performance in the Y-maze test). It is anticipated that treatment with the MPP along with the aromatic-cationic peptide will show a synergistic effect.

These results will show that the MPPs (or derivatives, analogues, or pharmaceutically acceptable salts thereof), alone or in combination with aromatic-cationic peptides, are useful in methods for restoring cognitive and motor function in mammals suffering from HD. The results will show that the methods and compositions described herein are generally useful in treating symptoms associated with neurodegenerative diseases.

Example 78: Use of MPPs to Suppress Aβ-Mediated Toxicity in the Brain

This example will demonstrate use of the methods and compositions of the present technology to treat or ameliorate the toxic effects of Aβ accumulation in brain tissue. The example will demonstrate the use of MPPs (or derivatives, analogues, or pharmaceutically acceptable salts thereof) alone or in combination with one or more active agents (e.g., an aromatic-cationic peptide such as D-Arg-2'6'-Dmt-Lys-Phe-NH$_2$) in reducing the synaptic dysfunction and memory loss caused by Aβ accumulation.

Rats are treated with saline; a MPP; or a MPP and an aromatic-cationic peptide (0.5-2 tmol/kg body weight, n=12). The compositions are injected intraperitoneally into the animal 24 hours before hippocampal slices are obtained to measure long-term potentiation (LTP). Brain slices from each group are incubated with Aβ for 15 min before evaluating LTP.

Results—

It is expected that brain slices recovered from saline-treated controls will show impaired LTP post Aβ treatment. It is also anticipated that treatment with the MPP, alone and in combination with an aromatic-cationic peptide will suppress Aβ-mediated impairment of LTP. It is anticipated that treatment with the MPP along with the aromatic-cationic peptide will show a synergistic effect.

These results will show that the MPPs (or derivatives, analogues, or pharmaceutically acceptable salts thereof), alone or in combination with aromatic-cationic peptides, are useful in methods for treating or ameliorating Aβ-mediated toxicity in brain tissue. The results will show that the methods and compositions described herein are useful in reducing the synaptic dysfunction and memory loss caused by Aβ accumulation generally.

Example 79: Use of MPPs to Delay Ageing

This example will demonstrate use of the methods and compositions of the present technology to reduce the frequency and/or severity of age-related symptoms. The example will demonstrate the use of MPPs (or derivatives, analogues, or pharmaceutically acceptable salts thereof) alone or in combination with one or more active agents (e.g., an aromatic-cationic peptide such as D-Arg-2'6'-Dmt-Lys-Phe-NH$_2$) in delaying ageing.

Ercc1$^{-/\Delta}$ progeroid mice are treated with (1) a MPP; or (2) a MPP and an aromatic-cationic peptide three times per week over an 18-21 week period (i.p. about 0.5-2 mg/kg in sunflower oil carrier). Control animals are Ercc1$^{-/\Delta}$ progeroid mice that receive sunflower seed oil according to the same schedule. The treated and control mice are monitored twice a week for weight and symptom/sign development. Symptoms include dystonia, trembling, kyphosis, ataxia, wasting, priapism, decreased activity, incontinence, and vision loss. The rate of deterioration of intervertebral discs (an index of degenerative disease of the vertebra) is assessed by measuring the level of glycosaminoglycan in the discs in treated and control mice.

Results—

It is expected that treatment with the MPP, alone and in combination with an aromatic-cationic peptide will result in a significant delay in onset of age-related degeneration compared to controls treated with vehicle only. It is also anticipated that the intervertebral discs of mice treated with the MPP, alone and in combination with an aromatic-cationic peptide will contain more glycosaminoglycan relative to control mice, indicating inhibition of disc degeneration. It is further anticipated that treatment with the MPP along with the aromatic-cationic peptide will show a synergistic effect.

These results will show that the MPPs (or derivatives, analogues, or pharmaceutically acceptable salts thereof), alone or in combination with aromatic-cationic peptides, are useful in methods for reducing the frequency and/or severity of age-related symptoms. The results will show that the methods and compositions described herein are useful in delaying ageing generally.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A composition comprising the mitochondria penetrating peptide (MPP) Cha-Arg-Cha-Lys-NH$_2$ alone or in combination with one or more aromatic-cationic peptides selected from the group consisting of:

2'6'-Dmp-D-Arg-2'6'-Dmt-Lys-NH$_2$;
2',6'-Dmt-D-Arg-Phe-Lys-NH$_2$;
2'6'-Dmp-D-Arg-Phe-Lys-NH$_2$;

2'6'-Dmt-D-Arg-PheOrn-NH$_2$;
2'6'-Dmt-D-Arg-Phe-Ahp(2-aminoheptanoicacid)-NH$_2$;
2'6'-Dmt-D-Arg-Phe-Lys-NH$_2$;
2'6'-Dmt-D-Cit-PheLys-NH$_2$;
Ala-D-Phe-D-Arg-Tyr-Lys-D-Trp-His-D-Tyr-Gly-Phe;
Arg-D-Dmt-Arg-NH$_2$;
Arg-D-Dmt-Lys-NH$_2$;
Arg-D-Dmt-NH$_2$;
Arg-D-Leu-D-Tyr-Phe-Lys-Glu-D-Lys-Arg-D-Trp-Lys-D-Phe-Tyr-D-Arg-Gly;
Arg-D-Tyr-Arg-NH$_2$;
Arg-D-Tyr-Lys-NH$_2$;
Arg-D-Tyr-NH$_2$;
Asp-Arg-D-Phe-Cys-Phe-D-Arg-D-Lys-Tyr-Arg-D-Tyr-Trp-D-His-Tyr-D-Phe-Lys-Phe;
Asp-D-Trp-Lys-Tyr-D-His-Phe-Arg-D-Gly-Lys-NH$_2$;
D-Arg-2'6'-Dmt-Lys-Phe-NH$_2$;
D-Arg-Arg-Dmt-Phe-NH$_2$;
D-Arg-Arg-Tyr-Phe-NH$_2$;
D-Arg-Cha-Lys-Cha-NH$_2$;
D-Arg-Cha-Lys-NH$_2$;
D-Arg-D-Dmt-NH$_2$;
D-Arg-Dmt-D-Lys-Phe-NH$_2$;
D-Arg-Dmt-Lys-Dmt-Lys-Met-NH$_2$;
D-Arg-Dmt-Lys-Dmt-Lys-Trp-NH$_2$;
D-Arg-Dmt-Lys-D-Phe-NH$_2$;
D-Arg-Dmt-Lys-NH$_2$;
D-Arg-Dmt-Lys-Phe-Lys-Met-NH$_2$;
D-Arg-Dmt-Lys-Phe-Lys-Trp-NH$_2$;
D-Arg-Dmt-Lys-Phe-Met-NH$_2$;
D-Arg-Dmt-Lys-Trp-NH$_2$;
D-Arg-Dmt-NH$_2$;
D-Arg-Dmt-Phe-NH$_2$;
D-Arg-D-Tyr-D-Lys-D-Phe-NH$_2$;
D-Arg-D-Tyr-Lys-Phe-NH$_2$;
D-Arg-D-Tyr-NH$_2$;
D-Arg-Phe-Lys-NH$_2$;
D-Arg-Trp-Lys-NH$_2$;
D-Arg-Trp-Lys-Trp-NH$_2$;
D-Arg-Tyr-D-Lys-Phe-NH$_2$;
D-Arg-Tyr-Lys-D-Phe-NH$_2$;
D-Arg-Tyr-Lys-NH$_2$;
D-Arg-Tyr-Lys-Phe-NH$_2$;
D-Arg-Tyr-NH$_2$;
D-Arg-Tyr-Phe-NH$_2$;
D-Dmt-Arg-NH$_2$;
D-Glu-Asp-Lys-D-Arg-D-His-Phe-Phe-D-Val-Tyr-Arg-Tyr-D-Tyr-Arg-His-Phe-NH$_2$;
D-His-Glu-Lys-Tyr-D-Phe-Arg;
D-His-Lys-Tyr-D-Phe-Glu-D-Asp-D-Asp-D-His-D-Lys-Arg-Trp-NH$_2$;
Dmt-D-Arg-NH$_2$;
Dmt-D-Phe-Arg-Lys-NH$_2$;
Dmt-Lys-D-Phe-NH$_2$;
Dmt-Lys-NH$_2$;
Dmt-Lys-Phe-NH$_2$;
D-Nle-Cha-Ahe-Cha-NH$_2$;
D-Nle-Dmt-Ahe-Phe-NH$_2$;
D-Phe-D-Arg-D-Phe-D-Lys-NH$_2$;
D-Tyr-Arg-NH$_2$;
D-Tyr-Trp-Lys-NH$_2$;
Glu-Arg-D-Lys-Tyr-D-Val-Phe-D-His-Trp-Arg-D-Gly-Tyr-Arg-D-Met-NH$_2$;
Gly-Ala-Lys-Phe-D-Lys-Glu-Arg-Tyr-His-D-Arg-D-Arg-Asp-Tyr-Trp-D-His-Trp-His-D-Lys-Asp;
Gly-D-Phe-Lys-His-D-Arg-Tyr-NH$_2$;
H-D-Arg(NαMe)-Dmt(NMe)-Lys(NαMe)-Phe(NMe)-NH$_2$;
H-D-Arg-Dmt-Lys(NαMe)-Phe(NMe)-NH$_2$;
H-D-Arg-Dmt-Lys(NαMe)-Phe-NH$_2$;
H-D-Arg-Dmt-Lys-Phe(NMe)-NH$_2$;
H-D-Arg-Dmt-Lys-Phe-Sar-Gly-Cys-NH$_2$;
H-D-Arg-Dmt-LysΨ[CH2-NH]Phe-NH$_2$;
H-D-Arg-Dmt-Ψ[CH2-NH]Lys-Phe-NH$_2$;
H-D-Arg-Dmt-Ψ[CH2-NH]Lys-Ψ[CH2-NH]Phe-NH$_2$;
H-D-Arg-Ψ[CH2-NH]Dmt-Lys-Phe-NH$_2$;
His-Tyr-D-Arg-Trp-Lys-Phe-D-Asp-Ala-Arg-Cys-D-Tyr-His-Phe-D-Lys-Tyr-His-Ser-NH$_2$;
Lys-D-Arg-Tyr-NH$_2$;
Lys-D-Gln-Tyr-Arg-D-Phe-Trp-NH$_2$;
Lys-Dmt-D-Arg-NH$_2$;
Lys-D-Phe-Arg-Dmt-NH$_2$;
Lys-D-Phe-Arg-Tyr-NH$_2$;
Lys-Phe-NH$_2$;
Lys-Trp-D-Tyr-Arg-Asn-Phe-Tyr-D-His-NH$_2$;
Met-Tyr-D-Arg-Phe-Arg-NH$_2$;
Met-Tyr-D-Lys-Phe-Arg;
Phe-Arg-D-His-Asp;
Phe-D-Arg-2'6'-Dmt-Lys-NH$_2$;
Phe-D-Arg-D-Phe-Lys-NH$_2$;
Phe-D-Arg-His;
Phe-D-Arg-Lys-Trp-Tyr-D-Arg-His;
Phe-D-Arg-Phe-D-Lys-NH$_2$;
Phe-D-Arg-Phe-Lys-NH$_2$;
Phe-D-Dmt-Arg-Lys-NH$_2$;
Phe-D-Tyr-Arg-Lys-NH$_2$;
Phe-Lys-Dmt-NH$_2$;
Phe-Phe-D-Tyr-Arg-Glu-Asp-D-Lys-Arg-D-Arg-His-Phe-NH$_2$;
Phe-Tyr-Lys-D-Arg-Trp-His-D-Lys-D-Lys-Glu-Arg-D-Tyr-Thr;
Thr-Gly-Tyr-Arg-D-His-Phe-Trp-D-His-Lys;
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$;
Trp-D-Lys-Tyr-Arg-NH$_2$;
Trp-Lys-Phe-D-Asp-Arg-Tyr-D-His-Lys;
Tyr-Asp-D-Lys-Tyr-Phe-D-Lys-D-Arg-Phe-Pro-D-Tyr-His-Lys;
Tyr-D-Arg-NH$_2$;
Tyr-D-Arg-Phe-Lys-Glu-NH$_2$;
Tyr-D-Arg-Phe-Lys-NH$_2$;
Tyr-D-His-Phe-D-Arg-Asp-Lys-D-Arg-His-Trp-D-His-Phe;
Tyr-D-Phe-Arg-Lys-NH$_2$;
Tyr-His-D-Gly-Met; and
Val-D-Lys-His-Tyr-D-Phe-Ser-Tyr-Arg-NH$_2$,
and further comprising one or more additional active agents selected from the group consisting of cyclosporine, a cardiac drug, an anti-inflammatory, an anti-hypertensive drug, an antibody, an ophthalmic drug, an antioxidant, a metal complexer, and an antihistamine.

2. The composition of claim 1, wherein the MPP further comprises a modification selected from the group consisting of inclusion of one or more D-amino acids, inclusion of one or more sites of N-methylation, and inclusion of one or more reduced amide bonds (Ψ[CH2-NH]).

3. The composition of claim 1, further comprising at least one pharmaceutically acceptable pH-lowering agent and at least one absorption enhancer comprising an absorbable or biodegradable surface active agent selected from the group consisting of an acylcarnitine, a phospholipid, a bile acid, and a sucrose ester.

4. The composition of claim 3, wherein the pH-lowering agent is selected from the group consisting of citric acid, tartaric acid, and an acid salt of an amino acid.

5. The composition of claim 3, wherein the composition comprises a lamination having a first layer comprising the at least one pharmaceutically acceptable pH-lowering agent and a second layer comprising the MPP alone or in combination with one or more aromatic-cationic peptides and further comprising the at least one absorption enhancer, wherein the first and second layers are united with each other, but wherein the layers prevent interaction between the pH-lowering agent and the peptide(s).

* * * * *